(12) United States Patent
Koshy et al.

(10) Patent No.: US 11,786,457 B2
(45) Date of Patent: Oct. 17, 2023

(54) PERITUMORAL AND INTRATUMORAL MATERIALS FOR CANCER THERAPY

(71) Applicant: President and Fellows of Harvard College, Cambridge, MA (US)

(72) Inventors: Sandeep T. Koshy, Boston, MA (US); David J. Mooney, Sudbury, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/546,852

(22) PCT Filed: Jan. 29, 2016

(86) PCT No.: PCT/US2016/015825
§ 371 (c)(1),
(2) Date: Jul. 27, 2017

(87) PCT Pub. No.: WO2016/123573
PCT Pub. Date: Aug. 4, 2016

(65) Prior Publication Data
US 2018/0021253 A1 Jan. 25, 2018

Related U.S. Application Data

(60) Provisional application No. 62/110,203, filed on Jan. 30, 2015.

(51) Int. Cl.
| | |
|---|---|
| *A61K 9/00* | (2006.01) |
| *A61K 47/36* | (2006.01) |
| *A61K 31/4745* | (2006.01) |
| *A61K 31/704* | (2006.01) |
| *A61K 47/42* | (2017.01) |
| *A61K 31/4725* | (2006.01) |
| *A61K 39/39* | (2006.01) |
| *A61K 38/08* | (2019.01) |
| *A61K 38/19* | (2006.01) |
| *A61K 9/06* | (2006.01) |

(52) U.S. Cl.
CPC .......... *A61K 9/0024* (2013.01); *A61K 9/0019* (2013.01); *A61K 9/06* (2013.01); *A61K 31/4725* (2013.01); *A61K 31/4745* (2013.01); *A61K 31/704* (2013.01); *A61K 38/08* (2013.01); *A61K 38/19* (2013.01); *A61K 38/193* (2013.01); *A61K 39/39* (2013.01); *A61K 47/36* (2013.01); *A61K 47/42* (2013.01)

(58) Field of Classification Search
CPC ............................ A61K 9/0024; A61K 9/0019
See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |
| 5,951,976 A | 9/1999 | Segal |
| 6,129,716 A | 10/2000 | Steer |
| 6,160,084 A | 12/2000 | Langer et al. |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,352,694 B1 | 3/2002 | June et al. |
| 6,403,374 B1 | 6/2002 | Tsien et al. |
| 6,429,199 B1 | 8/2002 | Krieg et al. |
| 6,511,511 B1 | 1/2003 | Slivka et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 6,858,222 B2 | 2/2005 | Nelson et al. |
| 6,974,698 B1 | 12/2005 | Miller et al. |
| 7,015,205 B1 | 3/2006 | Wallack et al. |
| 7,157,566 B2 | 1/2007 | Tsien et al. |
| 7,186,413 B2 | 3/2007 | Bouhadir et al. |

(Continued)

FOREIGN PATENT DOCUMENTS

| | | |
|---|---|---|
| AU | 2014200405 A1 | 2/2014 |
| AU | 2018201930 A1 | 4/2018 |

(Continued)

OTHER PUBLICATIONS

Mangsbo et al. (J. Immunotherapy Apr. 2010 33 (3): 225-235 (Year: 2010).*
Nivolumab (MeSH-NCBI https://www.ncbi.nlm.nih.gov/mesh/?term=nivolumab 2010, downloaded Mar. 8, 2019). (Year: 2010).*
Furqan et al., STAT inhibitors for cancer therapy. J Hematol Oncol. Dec. 5, 2013;6:90.
Ichida et al., A small-molecule inhibitor of tgf-Beta signaling replaces sox2 in reprogramming by inducing nanog. Cell Stem Cell. Nov. 6, 2009;5(5):491-503.
Kyi et al., Checkpoint blocking antibodies in cancer immunotherapy. FEBS Lett. Jan. 21, 2014;588(2):368-76.

(Continued)

*Primary Examiner* — Peter J Reddig
(74) *Attorney, Agent, or Firm* — McCarter & English, LLP; Maria Laccotripe Zacharakis; Maneesh Gulati

(57) ABSTRACT

The invention provides methods and compositions for reducing tumor-mediated immune evasion and inducing patient-specific immunization.

26 Claims, 37 Drawing Sheets

Specification includes a Sequence Listing.

(56) References Cited

U.S. PATENT DOCUMENTS

| | | | |
|---|---|---|---|
| 7,192,693 B2 | 3/2007 | Bryant et al. | |
| 7,244,714 B1 | 7/2007 | Gonda et al. | |
| 7,357,936 B1 | 4/2008 | Garcon | |
| 7,410,953 B2 | 8/2008 | Kawasaki | |
| 7,427,602 B1 | 9/2008 | Shea et al. | |
| 7,569,850 B2 | 8/2009 | Noy et al. | |
| 7,575,759 B2 | 8/2009 | Murphy et al. | |
| 7,687,241 B2 | 3/2010 | Chen | |
| 7,709,458 B2 | 5/2010 | Karaolis et al. | |
| 7,790,699 B2 | 9/2010 | Melvik et al. | |
| 8,067,237 B2 | 11/2011 | Mooney et al. | |
| 8,188,058 B2 | 5/2012 | Hackam et al. | |
| 8,273,373 B2 | 9/2012 | Aisberg et al. | |
| 8,354,119 B2 | 1/2013 | Geistiich et al. | |
| 8,367,628 B2 | 2/2013 | Goodwin et al. | |
| 8,535,719 B2 | 9/2013 | Badylak et al. | |
| 8,709,464 B2 | 4/2014 | Ma et al. | |
| 8,728,456 B2 | 5/2014 | Sands et al. | |
| 8,883,308 B2 | 11/2014 | Polshettiwar et al. | |
| 8,932,583 B2 | 1/2015 | Mooney et al. | |
| 9,012,399 B2 | 4/2015 | Cao et al. | |
| 9,132,210 B2 | 9/2015 | Mooney et al. | |
| 9,139,809 B2 | 9/2015 | Porcelli et al. | |
| 9,150,631 B2 | 10/2015 | Super et al. | |
| 9,370,558 B2 | 6/2016 | Ali et al. | |
| 9,381,235 B2 | 7/2016 | Sands et al. | |
| 9,446,107 B2 | 9/2016 | Mooney et al. | |
| 9,486,512 B2 | 11/2016 | Kim et al. | |
| 9,591,360 B2 | 3/2017 | Jennings et al. | |
| 9,675,561 B2 | 6/2017 | Bencherif et al. | |
| 9,770,535 B2 | 9/2017 | Mooney et al. | |
| 9,821,045 B2 | 11/2017 | Ali et al. | |
| 9,937,249 B2 | 4/2018 | Kim et al. | |
| 10,045,947 B2 | 8/2018 | Bencherif et al. | |
| 10,080,789 B2 | 9/2018 | Sands et al. | |
| 10,137,184 B2 | 11/2018 | Mooney | |
| 10,149,897 B2 | 12/2018 | Mooney et al. | |
| 2002/0045672 A1 | 4/2002 | Harris et al. | |
| 2002/0131853 A1 | 9/2002 | Nagasawa | |
| 2002/0131953 A1 | 9/2002 | Takashima et al. | |
| 2002/0150604 A1 | 10/2002 | Yi et al. | |
| 2003/0075822 A1 | 4/2003 | Slivka et al. | |
| 2003/0082806 A1 | 5/2003 | Berenson et al. | |
| 2003/0095994 A1 | 5/2003 | Geistlich et al. | |
| 2003/0100527 A1 | 5/2003 | Krieg et al. | |
| 2003/0194397 A1 | 10/2003 | Mishra | |
| 2003/0232895 A1 | 12/2003 | Omidian et al. | |
| 2004/0028745 A1* | 2/2004 | Bouhadir | A61K 47/595 424/488 |
| 2004/0043034 A1 | 3/2004 | Jensenius et al. | |
| 2004/0058883 A1 | 3/2004 | Phillips et al. | |
| 2004/0063206 A1 | 4/2004 | Rowley et al. | |
| 2004/0136968 A1 | 7/2004 | Zheng et al. | |
| 2004/0151764 A1 | 8/2004 | Zamora | |
| 2004/0213795 A1 | 10/2004 | Collins et al. | |
| 2004/0220111 A1 | 11/2004 | Kleinman et al. | |
| 2004/0228858 A1 | 11/2004 | Hanson et al. | |
| 2004/0242469 A1 | 12/2004 | Lee et al. | |
| 2004/0242482 A1 | 12/2004 | Gehring et al. | |
| 2005/0002915 A1 | 1/2005 | Atala et al. | |
| 2005/0037330 A1 | 2/2005 | Fischer et al. | |
| 2005/0053667 A1 | 3/2005 | Irvine et al. | |
| 2005/0079159 A1 | 4/2005 | Shastri et al. | |
| 2005/0090008 A1 | 4/2005 | Segura et al. | |
| 2005/0106211 A1 | 5/2005 | Nelson et al. | |
| 2005/0154376 A1 | 7/2005 | Riviere et al. | |
| 2005/0177249 A1 | 8/2005 | Kladakis et al. | |
| 2005/0202394 A1 | 9/2005 | Dobson | |
| 2006/0083712 A1 | 4/2006 | Anversa | |
| 2006/0141018 A1 | 6/2006 | Cochrum et al. | |
| 2006/0264380 A1 | 11/2006 | Hellstrom et al. | |
| 2006/0292134 A1 | 12/2006 | Stohs | |
| 2007/0003595 A1 | 1/2007 | Wang et al. | |
| 2007/0020232 A1 | 1/2007 | Rossignol et al. | |
| 2007/0026518 A1 | 2/2007 | Healy et al. | |
| 2007/0081972 A1 | 4/2007 | Sandler et al. | |
| 2007/0116680 A1 | 5/2007 | Stegemann et al. | |
| 2007/0178159 A1 | 8/2007 | Chen et al. | |
| 2007/0190646 A1 | 8/2007 | Engler et al. | |
| 2008/0044900 A1* | 2/2008 | Mooney | A61K 38/1866 435/375 |
| 2008/0044990 A1 | 2/2008 | Lee | |
| 2008/0051490 A1 | 2/2008 | Williams et al. | |
| 2008/0113929 A1 | 5/2008 | Lipford et al. | |
| 2008/0138416 A1 | 6/2008 | Rauh et al. | |
| 2008/0152624 A1 | 6/2008 | Paludan et al. | |
| 2008/0206308 A1 | 8/2008 | Jabbari et al. | |
| 2008/0233181 A1 | 9/2008 | Nagy et al. | |
| 2008/0268019 A1 | 10/2008 | Badylak et al. | |
| 2008/0268052 A1 | 10/2008 | Voytik-Harbin et al. | |
| 2009/0017096 A1 | 1/2009 | Lowman et al. | |
| 2009/0041825 A1 | 2/2009 | Kotov et al. | |
| 2009/0192079 A1 | 7/2009 | Santos et al. | |
| 2009/0238853 A1 | 9/2009 | Liu et al. | |
| 2009/0252752 A1 | 10/2009 | Tahara et al. | |
| 2009/0297551 A1 | 12/2009 | Sattentau et al. | |
| 2009/0297579 A1 | 12/2009 | Semino et al. | |
| 2009/0305983 A1 | 12/2009 | Ying et al. | |
| 2010/0015709 A1 | 1/2010 | Rehfeldt et al. | |
| 2010/0055102 A1* | 3/2010 | Langermann | A61K 31/675 424/134.1 |
| 2010/0055186 A1 | 3/2010 | Dadsetan et al. | |
| 2010/0080816 A1 | 4/2010 | Hadeiba et al. | |
| 2010/0129422 A1 | 5/2010 | Han et al. | |
| 2010/0159008 A1 | 6/2010 | Barron et al. | |
| 2010/0189760 A1 | 7/2010 | Schaffer et al. | |
| 2010/0190741 A1 | 7/2010 | Cohen et al. | |
| 2010/0272771 A1 | 10/2010 | Harlow et al. | |
| 2011/0008443 A1 | 1/2011 | Alsberg et al. | |
| 2011/0020216 A1 | 1/2011 | Mooney et al. | |
| 2011/0117170 A1 | 5/2011 | Cao et al. | |
| 2011/0207166 A1 | 8/2011 | Vaiselbuh | |
| 2011/0223255 A1 | 9/2011 | Thiesen et al. | |
| 2011/0253643 A1 | 10/2011 | Polshettiwar et al. | |
| 2011/0256184 A1 | 10/2011 | Lei et al. | |
| 2011/0300186 A1 | 12/2011 | Hellstrom et al. | |
| 2012/0100182 A1 | 4/2012 | Mooney et al. | |
| 2012/0121539 A1 | 5/2012 | Sands et al. | |
| 2012/0122218 A1 | 5/2012 | Huebsch et al. | |
| 2012/0134967 A1 | 5/2012 | Mooney et al. | |
| 2012/0256336 A1 | 10/2012 | Yano et al. | |
| 2012/0264599 A1 | 10/2012 | Komatsu et al. | |
| 2012/0294888 A1 | 11/2012 | Kishimoto et al. | |
| 2012/0329791 A1 | 12/2012 | Ashwell et al. | |
| 2013/0029030 A1 | 1/2013 | Larsen | |
| 2013/0035283 A1 | 2/2013 | Super et al. | |
| 2013/0045246 A1 | 2/2013 | Edwards et al. | |
| 2013/0052117 A1 | 2/2013 | Imai et al. | |
| 2013/0072547 A1 | 3/2013 | Hackam et al. | |
| 2013/0145488 A1 | 6/2013 | Wang et al. | |
| 2013/0177536 A1 | 7/2013 | Mooney et al. | |
| 2013/0202707 A1 | 8/2013 | Ali et al. | |
| 2013/0302396 A1 | 11/2013 | Mooney et al. | |
| 2013/0331343 A1 | 12/2013 | Cao et al. | |
| 2014/0072510 A1 | 3/2014 | Shea et al. | |
| 2014/0079752 A1 | 3/2014 | Huebsch et al. | |
| 2014/0112990 A1 | 4/2014 | Bencherif et al. | |
| 2014/0178964 A1 | 6/2014 | Mooney et al. | |
| 2014/0193488 A1 | 7/2014 | Kim et al. | |
| 2014/0227327 A1 | 8/2014 | Bencherif et al. | |
| 2014/0227723 A1 | 8/2014 | Ingber et al. | |
| 2014/0234423 A1 | 8/2014 | Sands et al. | |
| 2015/0024026 A1 | 1/2015 | Mooney et al. | |
| 2015/0030669 A1 | 1/2015 | Platscher et al. | |
| 2015/0072009 A1 | 3/2015 | Kim et al. | |
| 2015/0094518 A1* | 4/2015 | Wu | A61K 9/06 600/1 |
| 2015/0359928 A1 | 12/2015 | Gu et al. | |
| 2015/0366956 A1 | 12/2015 | Mooney et al. | |
| 2016/0033511 A1 | 2/2016 | Pannell et al. | |
| 2016/0129053 A1 | 5/2016 | Brass et al. | |
| 2016/0220667 A1 | 8/2016 | Mooney et al. | |
| 2016/0220668 A1 | 8/2016 | Mooney et al. | |
| 2016/0228543 A1 | 8/2016 | Mooney et al. | |

(56) References Cited

U.S. PATENT DOCUMENTS

| | | |
|---|---|---|
| 2016/0271298 A1 | 9/2016 | Mooney et al. |
| 2016/0279219 A1 | 9/2016 | Mooney et al. |
| 2016/0279220 A1 | 9/2016 | Mooney et al. |
| 2016/0296611 A1 | 10/2016 | Ali et al. |
| 2017/0042995 A1 | 2/2017 | Ali et al. |
| 2017/0182138 A1 | 6/2017 | Kim et al. |
| 2017/0246281 A1 | 8/2017 | Super et al. |
| 2017/0362307 A1 | 12/2017 | Ingber et al. |
| 2018/0117171 A1 | 5/2018 | Mooney et al. |
| 2018/0164298 A1 | 6/2018 | All et al. |
| 2018/0243231 A1 | 8/2018 | Bencherif et al. |
| 2018/0289789 A1 | 10/2018 | Ali et al. |
| 2018/0320157 A1 | 11/2018 | Super et al. |
| 2018/0344821 A1 | 12/2018 | Kim et al. |
| 2018/0371058 A1 | 12/2018 | Watters et al. |
| 2019/0060525 A1 | 2/2019 | Shah et al. |
| 2019/0076373 A1 | 3/2019 | Bencherif et al. |
| 2019/0125849 A1 | 5/2019 | Mooney et al. |
| 2019/0183992 A1 | 6/2019 | Sands et al. |
| 2019/0216910 A1 | 7/2019 | Mooney et al. |
| 2019/0292517 A1 | 9/2019 | Cheung et al. |
| 2020/0276290 A1 | 9/2020 | Ali et al. |
| 2021/0170007 A1 | 6/2021 | Super et al. |
| 2021/0205233 A1 | 7/2021 | Bencherif et al. |

FOREIGN PATENT DOCUMENTS

| | | | | |
|---|---|---|---|---|
| CN | 1487839 | A | 4/2004 | |
| CN | 1757662 | A | 4/2006 | |
| CN | 101584612 | A | 11/2009 | |
| CN | 101655611 | A | 2/2010 | |
| CN | 101829361 | A | 9/2010 | |
| CN | 102000689 | A | 4/2011 | |
| CN | 102947341 | A | 2/2013 | |
| CN | 103237885 | A | 8/2013 | |
| EP | 0562862 | A1 | 9/1993 | |
| EP | 1452191 | A2 | 9/2004 | |
| EP | 1561481 | A2 | 8/2005 | |
| EP | 1712238 | A1 * | 10/2006 | ......... A61K 39/0011 |
| EP | 1975230 | A1 | 10/2008 | |
| JP | 2000-503884 | A | 4/2000 | |
| JP | 2001-049018 | A | 2/2001 | |
| JP | 2001-524136 | A | 11/2001 | |
| JP | 2003-506401 | A | 2/2003 | |
| JP | 2003-180815 | A | 7/2003 | |
| JP | 2004-159849 | A | 6/2004 | |
| JP | 2004-520043 | A | 7/2004 | |
| JP | 2005-160669 | A | 6/2005 | |
| JP | 2005-168760 | A | 6/2005 | |
| JP | 2005-170816 | A | 6/2005 | |
| JP | 2005-528401 | A | 9/2005 | |
| JP | 2007-500673 | A | 1/2007 | |
| JP | 2007-503881 | A | 3/2007 | |
| JP | 2007-505827 | A | 3/2007 | |
| JP | 2007-528848 | A | 10/2007 | |
| JP | 2008-515503 | A | 5/2008 | |
| JP | 2008-528114 | A | 7/2008 | |
| JP | 2009-519042 | A | 5/2009 | |
| JP | 2009-521406 | A | 6/2009 | |
| JP | 2009-540921 | A | 11/2009 | |
| JP | 2010-502824 | A | 1/2010 | |
| JP | 2010-508976 | A | 3/2010 | |
| JP | 2010-227012 | A | 10/2010 | |
| JP | 2010-227012 | A | 10/2010 | |
| JP | 2011-511684 | A | 4/2011 | |
| JP | 2011-511834 | A | 4/2011 | |
| JP | 2013-531043 | A | 8/2013 | |
| JP | 2015-503626 | A | 2/2015 | |
| JP | 2015-516398 | A | 6/2015 | |
| WO | WO-1996/02555 | A1 | 2/1996 | |
| WO | WO-1996/16086 | A1 | 5/1996 | |
| WO | WO-1998/12228 | A1 | 3/1998 | |
| WO | WO-1998/16266 | A1 | 4/1998 | |
| WO | WO-1999/44583 | A2 | 9/1999 | |
| WO | 1999/52356 | A1 | 10/1999 | |
| WO | WO-1999/51259 | A2 | 10/1999 | |
| WO | WO-2000/50006 | A2 | 8/2000 | |
| WO | WO-2001/10421 | A1 | 2/2001 | |
| WO | WO-2001/35932 | A2 | 5/2001 | |
| WO | WO-2001/37810 | A2 | 5/2001 | |
| WO | WO-2002/16557 | A2 | 2/2002 | |
| WO | WO-2002/40071 | A1 | 5/2002 | |
| WO | WO-2002/058723 | A2 | 8/2002 | |
| WO | WO-2002/092054 | A2 | 11/2002 | |
| WO | WO-2003/020161 | A2 | 3/2003 | |
| WO | WO-2003/020884 | A2 | 3/2003 | |
| WO | 2003/070291 | A1 | 8/2003 | |
| WO | WO-2003/088905 | A2 | 10/2003 | |
| WO | WO-2004/006990 | A2 | 1/2004 | |
| WO | WO-2004/029230 | A2 | 4/2004 | |
| WO | WO-2004/030706 | A2 | 4/2004 | |
| WO | WO-2004/031371 | A2 | 4/2004 | |
| WO | WO-2004/089413 | A1 | 10/2004 | |
| WO | WO-2005/013896 | A2 | 2/2005 | |
| WO | WO-2005/013933 | A1 | 2/2005 | |
| WO | WO-2005/020849 | A2 | 3/2005 | |
| WO | WO-2005/025614 | A2 | 3/2005 | |
| WO | WO-2005/026318 | A2 | 3/2005 | |
| WO | WO-2005/037190 | A2 | 4/2005 | |
| WO | WO-2005/037293 | A1 | 4/2005 | |
| WO | WO-2005/046748 | A1 | 5/2005 | |
| WO | WO-2005/072088 | A2 | 8/2005 | |
| WO | WO-2005/104755 | A2 | 11/2005 | |
| WO | WO-2006/039045 | A2 | 4/2006 | |
| WO | WO-2006/040128 | A1 | 4/2006 | |
| WO | WO-2006/078987 | A2 | 7/2006 | |
| WO | WO-2006/113407 | A2 | 10/2006 | |
| WO | WO-2006/119619 | A1 | 11/2006 | |
| WO | WO-2006/136905 | A2 | 12/2006 | |
| WO | 2007/001332 | A2 | 1/2007 | |
| WO | WO-2007/030901 | A1 | 3/2007 | |
| WO | WO-2007/039150 | A2 | 4/2007 | |
| WO | WO-2007/042554 | A2 | 4/2007 | |
| WO | 2007/051120 | A2 | 5/2007 | |
| WO | 2007/068489 | A2 | 6/2007 | |
| WO | WO-2007/063075 | A1 | 6/2007 | |
| WO | WO-2007/064152 | A1 | 6/2007 | |
| WO | WO-2007/070660 | A2 | 6/2007 | |
| WO | WO-2007/078196 | A1 | 7/2007 | |
| WO | WO-2007/087585 | A1 | 8/2007 | |
| WO | WO-2007/089870 | A2 | 8/2007 | |
| WO | WO-2007/107739 | A1 | 9/2007 | |
| WO | WO-2007/149161 | A2 | 12/2007 | |
| WO | WO-2007/150020 | A1 | 12/2007 | |
| WO | 2008/008266 | A2 | 1/2008 | |
| WO | WO-2008/018707 | A1 | 2/2008 | |
| WO | WO-2008/031525 | A1 | 3/2008 | |
| WO | WO-2008/043157 | A1 | 4/2008 | |
| WO | WO-2008/057600 | A2 | 5/2008 | |
| WO | WO-2008/109852 | A2 | 9/2008 | |
| WO | WO-2008/114149 | A2 | 9/2008 | |
| WO | WO-2008/148761 | A1 | 12/2008 | |
| WO | WO-2008/157394 | A2 | 12/2008 | |
| WO | WO-2009/002401 | A2 | 12/2008 | |
| WO | WO-2009/005769 | A2 | 1/2009 | |
| WO | 2009/024775 | A1 | 2/2009 | |
| WO | WO-2009/018500 | A1 | 2/2009 | |
| WO | WO-2009/072767 | A2 | 6/2009 | |
| WO | WO-2009/074341 | A1 | 6/2009 | |
| WO | WO-2009/100716 | A2 | 8/2009 | |
| WO | WO-2009/102465 | A2 | 8/2009 | |
| WO | WO-2009/146456 | A1 | 12/2009 | |
| WO | WO-2009/155583 | A1 | 12/2009 | |
| WO | WO-2010/078209 | A2 | 7/2010 | |
| WO | WO-2010/120749 | A2 | 10/2010 | |
| WO | WO-2011/014871 | A1 | 2/2011 | |
| WO | 2011/043834 | A1 | 4/2011 | |
| WO | 2011/043835 | A1 | 4/2011 | |
| WO | WO-2011/063336 | A2 | 5/2011 | |
| WO | WO-2011/109834 | A2 | 9/2011 | |
| WO | WO-2011/130753 | A2 | 10/2011 | |
| WO | WO-2011/150240 | A1 | 12/2011 | |
| WO | WO-2011/151431 | A1 | 12/2011 | |
| WO | WO-2011/163669 | A2 | 12/2011 | |

(56) References Cited

FOREIGN PATENT DOCUMENTS

| WO | WO-2012/009611 A2 | 1/2012 | |
|---|---|---|---|
| WO | WO-2012/019049 A1 | 2/2012 | |
| WO | WO-2012/048165 A2 | 4/2012 | |
| WO | WO-2012/064697 A2 | 5/2012 | |
| WO | WO-2012/148684 A1 | 11/2012 | |
| WO | WO-2012/149358 A1 | 11/2012 | |
| WO | WO-2012/167230 A1 | 12/2012 | |
| WO | WO-2012167230 A1 * | 12/2012 | ............. A61P 35/04 |
| WO | 2013/012924 A2 | 1/2013 | |
| WO | WO-2013/106852 A1 | 7/2013 | |
| WO | WO-2013/158673 A1 | 10/2013 | |
| WO | WO-2013/172967 A1 | 11/2013 | |
| WO | 2013/190555 A1 | 12/2013 | |
| WO | WO-2014/063128 A1 | 4/2014 | |
| WO | 2014/189805 A1 | 11/2014 | |
| WO | 2014/190229 A1 | 11/2014 | |
| WO | 2015/066535 A1 | 5/2015 | |
| WO | 2015/154078 A1 | 10/2015 | |
| WO | WO-2015/168379 A2 | 11/2015 | |
| WO | 2016/004068 A1 | 1/2016 | |
| WO | WO-2016/123573 A1 | 8/2016 | |
| WO | WO-2016/161372 A1 | 10/2016 | |
| WO | 2017/136837 A1 | 8/2017 | |
| WO | 2017/143024 A2 | 8/2017 | |
| WO | 2018/013797 A1 | 1/2018 | |
| WO | 2018/026884 A1 | 2/2018 | |

OTHER PUBLICATIONS

Li et al., pH sensitive Laponite/alginate hybrid hydrogels: swelling behaviour and release mechanism. Soft Matter. Jun. 2, 2011;7(13):6231-6238.
Liu et al., Selective inhibition of IDO1 effectively regulates mediators of antitumor immunity. Blood. Apr. 29, 2010;115(17):3520-30.
Flatten et al., Cancer Immunotherapy by Targeting IDO1/TDO and Their Downstream Effectors. Front Immunol. Jan. 12, 2015;5:673.
Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.
Tang et al., Combining radiation and immunotherapy: a new systemic therapy for solid tumors? Cancer Immunol Res. Sep. 2014;2(9):831-8.
Xiong et al., Transcription Factor STAT3 as a Novel Molecular Target for Cancer Prevention. Cancers (Basel). Apr. 16, 2014;6(2):926-57.
Zhao et al., A cell-permeable Stat3 SH2 domain mimetic inhibits Stat3 activation and induces antitumor cell effects in vitro. J Biol Chem. Nov. 12, 2010;285(46):35855-65.
Abrahams et al., Expression and secretion of antiviral factors by trophoblast cells following stimulation by the TLR-3 agonist, Poly(I:C). Hum Reprod. Sep. 2006;21(9):2432-9.
Agache et al., Mechanical properties and Young's modulus of human skin in vivo. Arch Dermatol Res. 1980;269(3):221-32.
Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.
Aguado et al., Improving viability of stem cells during syringe needle flow through the design of hydrogel cell carriers. Tissue Eng Part A. Apr. 2012;18(7-8):806-15.
Akira et al., Pathogen recognition and innate immunity. Cell. Feb. 24, 2006;124(4):783-801.
Akira et al., Toll-like receptors: critical proteins linking innate and acquired immunity. Nat Immunol. Aug. 2001;2(8):675-80.
Akpalo et al., Fibrin-polyethylene oxide interpenetrating polymer networks: new self-supported biomaterials combining the properties of both protein gel and synthetic polymer. Acta Biomater. Jun. 2011;7(6):2418-27.

Aldhous, Print Me a Heart and a Set of Arteries. New Scientist. 2006:2547:19.
Ali et al., Biomaterial-based vaccine induces regression of established intracranial glioma in rats. Pharm Res. May 2011;28(5):1074-80.
Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.
Ali et al., Converging Cell Therapy with Biomateriais. Cell Transplantation from Laboratory to Clinic. 2006:591-609.
Ali et al., Identification of immune factors regulating antitumor immunity using polymeric vaccines with multiple adjuvants. Cancer Res. Mar. 15, 2014;74(6):1670-81.
Ali et al., In situ regulation of DC subsets and T cells mediates tumor regression in mice. Sci Transl Med. Nov. 25, 2009;1(8):1-10.
Ali et al., Infection-mimicking materials to proaram dendritic cells in situ. Nat Mater. Feb. 2009;8(2):151-8.
Ali et al., Sustained GM-CSF and PEI condensed pDNA presentation increases the level and duration of gene expression in dendritic cells. J Control Release. Dec. 18, 2008;132(3):273-8.
Ali et al., The efficacy of intracranial PLG-based vaccines is dependent on direct implantation into brain tissue. J Control Release. Sep. 25, 2011;154(3):249-57.
Allen et al., Regulation of satellite cells during skeletal muscle growth and development. Proc Soc Exp Biol Med. Jun. 1990;194(2):81-6.
Allen et al., Regulation of skeletal muscle satellite cell proliferation by bovine pituitary fibroblast growth factor. Exp Cell Res. May 1984;152(1):154-60.
Almarza et al., Evaluation of three growth factors in combinations of two for temporomandibular joint disc tissue engineering. Arch Oral Biol. Mar. 2006;51(3):215-21.
Alsberg et al., Cell-interactive alginate hydrogels for bone tissue engineering. J Dent Res. Nov. 2001;80(11):2025-9.
Alsberg et al., Engineerina growing tissues. Proc Natl Acad Sci U S A. Sep. 17, 2002;99(19):12025-30.
Alsberg et al., Regulating bone formation via controlled scaffold degradation. J Dent Res. Nov. 2003;82(11):903-8.
Ambrosini et al., Astrocytes produce dendritic cell-attracting chemokines in vitro and in multiple sclerosis lesions. J Neuropathol Exp Neurol. Aug. 2005;64(8):706-15.
American Diabetes Association, Standards of Medical Care in Diabetes—2013. Diabetes Care. 2013;36(S1):S11-S66.
Anderson et al., Biomaterial microarrays: rapid, microscale screening of polymer-cell interaction. Biomateriais. Aug. 2005;26(23):4892-7.
Anderson et al., Nanoliter-scale synthesis of arrayed biomateriais and application to human embryonic stem ceils. Nat Biotechnol. Jul. 2004;22(7):863-6.
Anderson et al., The NOD mouse: a model of immune dysregulation. Annu Rev Immunol. 2005;23:447-85.
Anderson, A role for nitric oxide in muscle repair: nitric oxide-mediated activation of muscle satellite cells. Mol Biol Cell. May 2000; 11(5):1859-74.
Annual Review. 2008:122-131.
Arany et al., At the edge of translation—materials to proaram cells for directed differentiation. Oral Dis. Apr. 2011;17(3):241-51.
Aschner et al., Metabolic memory for vascular disease in diabetes. Diabetes Technol Ther. Jun. 2012:14 Suppl 1:S68-74.
Atala et al., Endoscopic treatment of vesicoureteral reflux with a chondrocyte-alginate suspension. J Urol. Aug. 1994;152(2 Pt2):641-3.
Aubin et al., Directed 3D cell alignment and elongation in microengineered hydrogels. Biomaterials. Sep. 2010;31(27):6941-6951.
Augst et al., Alginate hydrogels as biomateriais. Macromol Biosci. Aug. 7, 2006;6(8):623-33.
Babensee et al., Host response to tissue engineered devices. Advanced Drug Delivery Reviews. Aug. 3, 1998;33(1-2):111-139.

(56) References Cited

OTHER PUBLICATIONS

Bachelder et al., Acid-degradable polyurethane particles for protein-based vaccines: biological evaluation and in vitro analysis of particle degradation products. Mol Pharm. Sep.-Oct. 2008;5(5):876-84.
Bachem et al., Superior antigen cross-presentation and XCR1 expression define human CD11c+CD141+ cells as homologues of mouse CD8+ dendritic cells. J Exp Med. Jun. 7, 2010;207(6):1273-81.
Badovinac et al., Regulation of CD8+ T cells undergoing primary and secondary responses to infection in the same host. J Immunol. May 15, 2003;170(10):4933-42.
Bakri et al., Pharmacokinetics of intravitreal bevacizumab (Avastin). Ophthalmology. May 2007; 114(5):855-9.
Balakrishna et al., Structural correlates of antibacterial and membrane-permeabilizing activities in acylpolyamines. Antimicrob Agents Chemother. Mar. 2006;50(3):852-61.
Banchereau et al., Dendritic cells and the control of immunity. Nature. Mar. 19, 1998;392(6673):245-52.
Bar-Cohen et al., Electroactive Polymer Actuators and Sensors. MRS Bullet. 2008;33(3):173-181.
Bar-Or et al., Induction of antigen-specific tolerance in multiple sclerosis after immunization with DNA encoding myelin basic protein in a randomized, placebo-controlled phase 1/2 trial. Arch Neurol. Oct. 2007;64(10):1407-15.
Barbero et al., Growth factor supplemented matrigel improves ectopic skeletal muscle formation—a cell therapy approach. J Cell Physiol. Feb. 2001;186(2):183-92.
Barbucci et al., Hyaluronic acid hydrogel in the treatment of osteoarthritis. Biomateriais. Dec. 2002;23(23):4503-13.
Barrio et al., A two-dimensional numerical study of spatial pattern formation in interacting Turing systems. Bull Math Biol. May 1999;61(3):483-505.
Bates, Improved muscle regeneration by combining VEGF with IGF1. Regen Med. Nov. 2010;5(6):853-4.
Beaucage et al., The Functionalization of Oligonucleotides via Phosphoramidite Derivatives. Tetrahedron. Mar. 5, 1993;49(10):1925-1963.
Beauchamp et al., Dynamics of myoblast transplantation reveal a discrete minority of precursors with stem cell-like properties as the myogenic source. J Cell Biol. Mar. 22, 1999;144(6):1113-22.
Becker et al., Cytological demonstration of the clonal nature of spleen colonies derived from transplanted mouse marrow cells. Nature. Feb. 2, 1963;197:452-4.
Beebe et al., Functional hydrogel structures for autonomous flow control inside microfiuidic channels. Nature. Apr. 6, 2000:404(6778):588-90.
Bekiari et al, Study of poly(N,N-dimethylacrylainide)/CdS nanocomposite organic/inorganic gels. Langmuir. Sep. 14, 2004;20(19):7972-5.
Bell, Models for the specific adhesion of cells to cells. Science. May 12, 1978;200(4342):618-27.
Bencherif et al., End-group effects on the properties of PEG-co-PGA hydrogels. Acta Biomater. Jul. 2009;5(6):1872-83.
Bencherif et al., Influence of cross-linker chemistry on release kinetics of PEG-co-PGA hydrogels. J Biomed Mater Res A. Jul. 2009;90(1):142-53.
Bencherif et al., Influence of the degree of methacrylation on hyaluronic acid hydrogels properties. Biomateriais. Apr. 2008;29(12):1739-49.
Bencherif et al., Injectable preformed scaffolds with shape-memory properties. Proc Natl Acad Sci U S A. Nov. 27, 2012;109(48):19590-5.
Bencherif et al., Nanostructured hybrid hydrogels prepared by a combination of atom transfer radical polymerization and free radical polymerization. Biomaterials. Oct. 2009;30(29):5270-8.
Bencherif et al., Synthesis by AGET ATRP of degradable nanogei precursors for in situ formation of nanostructured hyaluronic acid hydrogel. Biomacromoiecuies. Sep. 14, 2009;10(9):2499-507.

Benton et al., Photocrosslinking of gelatin macromers to synthesize porous hydrogels that promote valvular interstitial cell function. Tissue Eng Part A. Nov. 2009;15(11):3221-30.
Berg et al., Il-10 is a central regulator of cyclooxygenase-2 expression and prostaglandin production. J Immunol. Feb. 15, 2001;166(4):2674-80.
Bergstraesser et al., Stimulation and inhibition of human mammary epithelial cell duct morphogenesis in vitro. Proc Assoc Am Physicians. Mar. 1996;108(2):140-54.
Bianco et al., The meaning, the sense and the significance: translating the science of mesenchymal stem cells into medicine. Nat Med. Jan. 2013;19(1):35-42.
Bilodeau et al., Regular Pyramid Punch Problem, J Appl Mech. 1992;59(3):519-523.
Bischoff, Proliferation of muscle satellite cells on intact myofibers in culture. Dev Biol. May 1986;115(1):129-39.
Blanas et al., Induction of autoimmune diabetes by oral administration of autoantigen. Science. Dec. 6, 1996;274(5293):1707-9.
Blumenthal et al., Polyurethane scatfolds seeded with genetically engineered skeletal myoblasts: a promising tool to regenerate myocardial function. Artif Organs. Feb. 2010;34(2):E46-54.
Boateng et al., Wound healing dressings and drug delivery systems: a review. J Pharm Sci. Aug. 2008;97(8):2892-923.
Boerckel et al., Mechanical regulation of vascular growth and tissue regeneration in vivo. Proc Natl Acad Sci U S A. Sep. 13, 2011;108(37):E674-80.
Bohl et al., Role of synthetic extracellular matrix in development of engineered dental pulp. J Biomater Sci Polym Ed. 1998;9(7):749-64.
Bonauer et al., MicroRNA-92a controls angiogenesis and functional recovery of ischemic tissues in mice. Science. Jun. 26, 2009;324(5935):1710-3.
Boontheekul et al., Controlling alginate gel degradation utilizing partial oxidation and bimodal molecular weight distribution. Biomateriais. May 2005;26(15):2455-65.
Boontheekul et al., Regulating myoblast phenotype through controlled gel stiffness and degradation. Tissue Eng. Jul. 2007;13(7):1431-42.
Borselli et al., Functional muscle regeneration with combined delivery of angiogenesis and myogenesis factors. Proc Natl Acad Sci U S A. Feb. 23, 2010;107(8):3287-92.
Bouhadir et al., Degradation of partially oxidized alginate and its potential application for tissue engineering. Biotechnoi Prog. Sep.-Oct. 2001;17(5):945-50.
Bouhadir et al., Synthesis of Cross-Linked Poly(aldehyde guluronate) Hydrogels, Polymer. Jun. 1999;40(12):3575-3584.
Bowne et al., Injection of DNA encoding granulocyte-macrophage colony-stimulating factor recruits dendritic cells for immune adjuvant effects. Cytokines Cell Mol Ther. Dec. 1999;5(4):217-25.
Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.
Brinkman et al., Photo-cross-linking of type I collagen gels in the presence of smooth muscle cells: mechanical properties, cell viability, and function. Biomacromoiecuies. Jul.-Aug. 2003;4(4):890-5.
Brinkmann et al., Neutrophil extracellular traps kill bacteria. Science. Mar. 5, 2004;303(5663):1532-5.
Bristol-Myers Squibb, Investigational Anti-PD-1 immunotherapy BMS-936558 Showed Clinical Activity in Phase 1 Trial of Patients with Previously-Treated non-Small-Cell Lung Cancer, Metastatic Melanoma adn Renal Ceil Cancer. Financial Times. 3 pages, Jun. 2, 2012.
Brouwers et al., Can the growth factors PTHrP, Ihh and VEGF, together regulate the development of a long bone? J Biomech. 2006;39(15):2774-82.
Broxmeyer, Insights into the biology of cord blood stem/progenitor cells. Cell Prolif. Apr. 2011;44 Suppl 1:55-9.
Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.

(56) References Cited

OTHER PUBLICATIONS

Bryant et al., Photo-patterning of porous hydrogels for tissue engineering. Biomateriais. Jul. 2007;28(19):2978-86.

Buckwalter et al., Form of Antigen Dictates immunity: Irradiated Cell vs. Whole Cell Lysate Vaccination. J Immunol. Apr. 1, 2007;178(1 Suppl):S77.

Bullard et al., Fetal wound healing: current biology. World J Surg. Jan. 2003;27(1):54-61.

Buonaguro et al., Translating tumor antigens into cancer vaccines. Clin Vaccine Immunol. Jan. 2011;18(1):23-34.

Burdick et al., Controlled degradation and mechanical behavior of photopolymerized hyaluronic acid networks. Biomacromolecules. Jan.-Feb. 2005;6(1):386-91.

Burdick et al., Photoencapsulation of osteoblasts in injectable RGD-modified PEG hydrogels for bone tissue engineering. Biomaterials. Nov. 2002;23(22):4315-23.

Burdick et al., Stimulation of neurite outgrowth by neurotrophins delivered from degradable hydrogels. Biomaterials. Jan. 2006;27(3):452-9.

Burger et al., Effect of VEGF and its receptor antagonist SU-5416, an inhibitor of angiogenesis, on processing ofthe beta-amyloid precursor protein in primary neuronal cells derived from brain tissue of Tg2576 mice. Int J Dev Neurosci. Nov. 2010;28(7):597-604.

Béguéet al., Vaccination against human papillomavirus, implementation and efficacy against cervical cancer control. Bull Acad Natl Med. Dec. 2007;191(9):1805-16.

Callahan et al., At the bedside: CTLA-4- and PD-1-blocking antibodies in cancer immunotherapy. J Leukoc Biol. Jul. 2013;94(1):41-53.

Calvert, Eiectroactive Polymer Gels. Electroactive Polymer (EAP) Acutators as Artificial Muscle: Reality, Potential, and Challenges. Bar-Cohen. (Ed.). Spie Press, Bellingham. WA. 151-170. (2004).

Calvert, Gel Sensors and Actuators. MRS Bullet. 2008;33(3):207-212.

Cameron et al., The influence of substrate creep on mesenchymal stem ceil behaviour and phenotype. Biomateriais. Sep. 2011;32(26):5979-93.

Cao et al., Promoting angiogenesis via manipulation of VEGF responsiveness with notch signaling. Biomateriais. Sep. 2009;30(25):4085-93.

Carlson et al., Notch signaling pathway and tissue engineering. Front Biosci. Sep. 1, 2007;12:5143-56.

Carmeliet et al., Angiogenesis in cancer and other diseases. Nature. Sep. 14, 2000;407(6801):249-57.

Carmeliet, Mechanisms of angiogenesis and arteriogenesis. Nat Med. Apr. 2000;6(4):389-95.

Caulfield et al., Regulation of major histocompatibility complex class II antigens on human alveolar macrophages by granulocyte-macrophage colonv-stimulating factor in the presence of glucocorticoids. Immunology. Sep. 1999;98(1):104-10.

Ceriello et al., Clinical review 2: The "metabolic memory": is more than just tight glucose control necessary to prevent diabetic complications? J Clin Endocrinol Metab. Feb. 2009;94(2):410-5.

Ceriello et al., The emerging challenge in diabetes: the "metabolic memory", Vascul Pharmacol, Nov.-Dec. 2012;57(5-6): 133-8.

Champion et al., Shape induced inhibition of phagocytosis of polymer particles. Pharm Res. Jan. 2009;26(1):244-9.

Chan et al., Antifibrotic effects of suramin in injured skeletal muscle after laceration. J Appl Physiol. Sep. 2003;95(2):771-80.

Chan et al., Helix induction in antimicrobial peptides by alginate in biofilms. J Biol Chem. Sep. 10, 2004;279(37):38749-54.

Chan et al., Traction dynamics of filopodia on compliant substrates. Science. Dec. 12, 2008;322(5908):1687-91.

Chang, Mouse models for studies of retinal degeneration and diseases. Methods Mol Biol. 2013;935:27-39.

Chen et al., Adipogenic differentiation of adipose tissue-derived human mesenchymal stem ceils: effect of gastric bypass surgery. Surg Endosc. Dec. 2012;26(12):3449-56.

Chen et al., Functional Human Vascular Network Generated in Photocrosslinkable Gelatin Methacrylate Hydrogels. Adv Funct Mater. May 23, 2012;22(10):2027-2039.

Chen et al., Integrated approach to designing growth factor delivery systems. FASEB J. Dec. 2007;21(14):3896-903.

Chen et al., Polymeric growth factor delivery strategies for tissue engineering. Pharm Res. Aug. 2003;20(8):1103-12.

Chen et al., Skeletal muscle stem cells. Reprod Biol Endocrinol. Nov. 13, 2003;1:101. 7 pages.

Chen et al., Spatio-temporal VEGF and PDGF delivery patterns blood vessel formation and maturation. Pharm Res. Feb. 2007;24(2):258-64.

Chiang et al., Whole tumor antigen vaccines. Semin Immunol. Jun. 2010;22(3):132-43.

Choi et al., In vitro mineralization by preosteoblasts in poly(DL-lactide-co-glycolide) inverse opal scaffolds reinforced with hydroxyapatite nanoparticies, Langmuir. Jul. 20, 2010;26(14):12126-31.

Choi et al., Three-dimensional scaffolds for tissue engineering: the importance of uniformity in pore size and structure. Langmuir. Dec. 21, 2010;26(24):19001-6.

Choi, Replacement Organs, Hot off the Press. New Scientist. 2003; 177(2379):16.

Chou et al., Characterization of Photocross Linked Alginate Hydrogels for Nucleus Pulposus Cell Encapsulation. J Biomed Mater Res A. 2009;91A(1):187-194.

Chromiak et al., Bioreactor perfusion system for the long-term maintenance of tissue-engineered skeletal muscle organoids. In Vitro Cell Dev Biol Anim. Oct. 1998;34(9):694-703.

Clark et al., Myosin II and mechanotransduction: a balancing act. Trends Cell Biol. Apr. 2007; 17(4):178-86.

Clauss et al., Interstitial transport of rabbit and sheep antibodies in normal and neoplastic tissues. Cancer Res. Jun. 15, 1990;50(12):3487-92.

ClinicalTrials.gov, NCT00729664, Multiple Ascending Dose (MDX1105-01)(Anti-PDL1). 4 pages, Sep. 3, 2015.

ClinicalTrials.gov, NCT00730639, A Phase 1 Study of Nivolumab (BMS-936558) in Subjects with Advanced or Recurrent Malignancies (MDX1106-03). 5 pages, Mar. 24, 2016.

ClinicalTrials.gov, NCT01352884, Study to Assess the Safety, and Pharmacokinetics of AMP-224 in Patients with Advanced Cancer. 3 pages, Sep. 2, 2016.

ClinicalTrials.gov, NCT01391143, Safety Study of MGA271 in Refractory Cancer. 4 pages, Sep. 28, 2016.

Cohen et al., Controlled delivery systems for proteins based on poly(lactic/glycolic acid) microspheres. Pharm Res. Jun. 1991;8(6):713-20.

Comisar et al., Engineering RGD nanopatterned hydrogels to control preosteoblast behavior: a combined computational and experimental approach. Biomaterials. Oct. 2007;28(30):4409-17.

Conboy et al., The regulation of Notch signaling controls satellite cell activation and cell fate determination in postnatal myogenesis. Dev Cell, Sep. 2002;3(3):397-409.

Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.

Conn et al., Purification of a glycoprotein vascular endothelial cell mitogen from a rat glioma-derived cell line. Proc Natl Acad Sci U S A. Feb. 1990;87(4):1323-7.

Cook et al., A sialomucopeptide liberated by trypsin from the human erythrocyte. Nature. Dec. 17, 1960;188:1011-2.

Cooper et al., Extended amplification in vitro and replicative senescence: key factors implicated in the success of human myoblast transplantation. Hum Gene Ther. Aug. 10, 2003;14(12):1169-79.

Cooper, Metabolic memory: implications for diabetic vascular complications. Pediatr Diabetes. Aug. 2009;10(5):343-6.

Corcione et al., CCL19 and CXCL12 trigger in vitro chemotaxis of human mantle cell lymphoma B cells. Clin Cancer Res. Feb. 1, 2004;10(3):964-71.

Cornelison et al., Single-cell analysis of regulatory gene expression in quiescent and activated mouse skeletal muscle satellite cells. Dev Biol. Nov. 15, 1997;191(2):270-83.

(56) References Cited

OTHER PUBLICATIONS

Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.
Coulson et al., Flow of Fluids through Granular Beds and Packed Columns. Chemical Engineering, vol. 2. Third Edition. Pergamon Press. Chapter 4, pp. 125-171, (1978).
Crameri et al., Improved areen fluorescent protein by molecular evolution using DNA shuffling. Nat Biotechnol. Mar. 1996;14(3):315-9.
Cuda et al., In vitro actin filament sliding velocities produced by mixtures of different types of myosin. Biophys J. Apr. 1997;72(4):1767-79.
Cukierman et al., Taking cell-matrix adhesions to the third dimension. Science. Nov. 23, 2001;294(5547):1708-12.
Cullen et al., Investigation of vascular endothelial growth factor effects on pulmonary endothelial monolayer permeability and neutrophil transmigration. Gen Pharmacol. Sep. 2000;35(3):149-57.
Curiel et al., Tumor immunotherapy: inchina toward the finish line. J Clin Invest. Feb. 2002;109(3):311-2.
Curran et al., PD-1 and CTLA-4 combination blockade expands infiltrating T cells and reduces reaulatory T and myeloid cells within B16 melanoma tumors. Proc Natl Acad Sci U S A. Mar. 2, 2010;107(9):4275-80.
D'Amico et al., The early progenitors of mouse dendritic cells and plasmacytoid predendritic cells are within the bone marrow hemopoietic precursors expressing Fit3. J Exp Med, Jul. 21, 2003;198(2):293-303.
Dainiak et al., Gelatin-fibrinogen cryogel dermal matrices for wound repair: preparation, optimisation and in vitro study. Biomaterials, Jan. 2010;31(1):67-76.
Dar et al., Optimization of cardiac cell seeding and distribution in 3D porous alginate scaffolds. Biotechnol Bioeng. Nov. 5, 2002;80(3):305-12.
Daro et al., Polyethylene glycol-modified GM-CSF expands CD11b(high)CD11c(high) but not CD11b(low)CD11c(high) murine dendritic cells in vivo: a comparative analysis with Fit3 ligand. J Immunol. Jul. 1, 2000;165(1):49-58.
David et al., The in vitro Desensitization of Sensitive Ceils by Trypsin. J Exp Med. Dec. 1, 1964;120:1189-200.
Davies et al., Antibody-antigen complexes. Annu Rev Biochem. 1990;59:439-73.
De Jong et al., Regulation of Notch signaling genes during BMP2-induced differentiation of osteoblast precursor ceils. Biochem Biophys Res Commun. Jul. 16, 2004;320(1):100-7.
De Temmerman et al., Particulate vaccines: on the quest for optimal delivery and immune response. Drug Discov Today. Jul. 2011;16(13-14):569-82.
Dembo et al., Stresses at the cell-to-substrate interface during locomotion of fibroblasts, Biophys J. Apr. 1999;76(4):2307-16.
Den Haan et al., CD8(+) but not CD8(−) dendritic cells cross-prime cytotoxic T cells in vivo, J Exp Med. Dec. 18, 2000;192(12):1685-96.
Dennis et al., Excitability and contractility of skeletal muscle engineered from primary cultures and cell lines. Am J Physiol Cell Physiol. Feb. 2001;280(2):C288-95.
Dennis et al., Excitability and isometric contractile properties of mammalian skeletal muscle constructs engineered in vitro. In Vitro Ceil Dev Biol Anim. May 2000;36(5):327-35.
Deshmane et al., Monocyte chemoattractant protein-1 (MCP-1): an overview. J Interferon Cytokine Res. Jun. 2009;29(6):313-26.
Dexter et al., Conditions controlling the proliferation of haemopoietic stem cells in vitro. J Cell Physiol. Jun. 1977;91(3):335-44.
Di Nicola et al., Human bone marrow stromal ceils suppress T-lymphocyte proliferation induced by cellular or nonspecific mitogenic stimuli. Blood. May 15, 2002;99(10):3838-43.
Diduch et al., Two cell lines from bone marrow that differ in terms of collagen synthesis, osteogenic characteristics, and matrix mineralization. J Bone Joint Surg Am. Jan. 1993;75(1):92-105.

Dieu et al., Selective recruitment of immature and mature dendritic cells by distinct chemokines expressed in different anatomic sites. J Exp Med. Jul. 20, 1998;188(2):373-86.
Diridollou et al., Skin ageing: changes of physical properties of human skin in vivo. Int J Cosmet Sci. Dec. 2001;23(6):353-62.
Discher et al., Tissue cells feel and respond to the stiffness of their substrate. Science. Nov. 18, 2005;310(5751):1139-43.
Disis et al., Granulocyte-macrophage colony-stimulating factor: an effective adjuvant for protein and peptide-based vaccines. Blood. Jul. 1, 1996;88(1):202-10.
Doan et al., Antigens and Receptors. Lippincott's Illustrated Reviews: Immunology. Wolters Kluwer/Lippincott Williams & Wilsons, Philadelphia. Chapter 12, pp. 11-23, (2008).
Doan et al., Subcellular localization of a sporulation membrane protein is achieved through a network of interactions along and across the septum. Mol Microbiol. Mar. 2005;55(6):1767-81.
Donati et al., New hypothesis on the role of alternating sequences in calcium-alginate gels. Biomacromolecules. Mar.-Apr. 2005;6(2):1031-40.
Dong et al., Antitumor effect of secreted Flt3-ligand can act at distant tumor sites in a murine model of head and neck cancer. Cancer Gene Ther. Feb. 2003;10(2):96-104.
Dor et al., Making vascular networks in the adult: branching morphogenesis without a roadmap. Trends Cell Biol. Mar. 2003;13(3):131-6.
Douay et al., Ex vivo production of human red blood cells from hematopoietic stem cells: what is the future in transfusion? Transfus Med Rev. Apr. 2007;21(2):91-100.
Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.
Dranoff, Cytokines in cancer pathogenesis and cancer therapy. Nat Rev Cancer. Jan. 2004;4(1):11-22.
Dranoff, GM-CSF-based cancer vaccines. Immunol Rev. Oct. 2002;188:147-54.
Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.
Dufort et al., Balancing forces: architectural control of mechanotransduction. Nat Rev Mol Cell Biol. May 2011;12(5):308-19.
Dupont et al., Role of YAP/TAZ in mechanotransduction. Nature. Jun. 8, 2011;474(7350):179-83.
Duraiswamy et al., Dual blockade of PD-1 and CTLA-4 combined with tumor vaccine effectively restores T-cell rejection function in tumors—response. Cancer Res. Jan. 15, 2014;74(2):633-4.
Duraiswamy et al., Dual blockade of PD-1 and CTLA-4 combined with tumor vaccine effectively restores T-cell rejection function in tumors. Cancer Res. Jun. 15, 2013;73(12):3591-603.
Edwards et al., Evaluation of biomechanical properties of human skin. Clin Dermatol, Jul.-Aug. 1995;13(4):375-80.
Egholm et al., Peptide Nucleic Acids (PNA). Oligonucleotide Analogues with an Achiral Peptide Backbone. J Am Chem Soc. 1992;114(5):1895-1897.
Egholm et al., PNA hybridizes to complementary oligonucleotides obeying the Watson-Crick hydrogen-bonding rules. Nature. Oct. 7, 1993;365(6446):566-8.
Ehrbar et al., Endothelial cell proliferation and progenitor maturation by fibrin-bound VEGF variants with differential susceptibilities to local cellular activity. J Control Release. Jan. 3, 2005;101(1-3):93-109.
Eiselt et al., Porous carriers for biomedical applications based on alginate hydrogels. Biomaterials. Oct. 2000;21(19):1921-7.
El-Backly et al., Regeneration of dentine/puip-like tissue using a dental pulp stem cell/poly(lactic-co-glycolic) acid scaffold construct in New Zealand white rabbits. Aust Endod J. Aug. 2008;34(2):52-67.
Eldar et al., Elucidating mechanisms underlying robustness of morphogen gradients. Curr Opin Genet Dev. Aug. 2004;14(4):435-9.
Eldar et al., Robustness of the BMP morphogen gradient in *Drosophila* embryonic patterning. Nature. Sep. 19, 2002;419(6904):304-8.

(56) References Cited

OTHER PUBLICATIONS

Eldar et al., Self-enhanced ligand degradation underlies robustness of morphogen gradients. Dev Cell. Oct. 2003;5(4):635-46.
Eming et al., Inflammation in wound repair: molecular and cellular mechanisms. J Invest Dermatol. Mar. 2007;127(3):514-25.
Engler et al., Matrix elasticity directs stem cell lineage specification. Cell. Aug. 25, 2006;126(4):677-89.
Engler et al., Microtissue elasticity: measurements by atomic force microscopy and its influence on cell differentiation. Methods Cell Biol. 2007;83:521-45.
Engler et al., Substrate compliance versus liaand density in cell on gel responses. Biophys J. Jan. 2004;86(1 Pt 1):617-28.
Ennett et al., Temporally regulated delivery of VEGF in vitro and in vivo. J Biomed Mater Res A. Oct. 2006;79(1):176-84.
Exposito et al., The fibrillar collagen family. Int J Mol Sci. Jan. 28, 2010;11(2):407-26.
Faissner et al., Boundaries and inhibitory molecules in developing neural tissues. Glia. Apr. 1995;13(4):233-54.
Falanga, Wound healing and its impairment in the diabetic foot. Lancet. Nov. 12, 2005;366(9498):1736-43.
Falsey et al., Peptide and small molecule microarray for high throughput cell adhesion and functional assays. Bioconjug Chem. May-Jun. 2001;12(3):346-53.
Farrar et al., T helper subset development: roles of instruction, selection, and transcription. J Clin Invest. Feb. 2002;109(4):431-5.
Fauquemberque et al., HLA-A*0201-restricted CEA-derived peptide CAP1 is not a suitable target for T-celi-based immunotherapy. J Immunother. May 2010;33(4):402-13.
Ferrara et al., Angiogenesis as a therapeutic target. Nature. Dec. 15, 2005;438(7070):967-74.
Ferrara et al., Discovery and development of bevacizumab, an anti-VEGF antibody for treating cancer. Nat Rev Drug Discov. May 2004;3(5):391-400.
Fischbach et al., Polymeric Systems for Bioinspired Delivery of Angiogenic Molecules. Adv Polym Sci. 2006;203:191-221.
Fischer et al., A brilliant monomeric red fluorescent protein to visualize cytoskeleton dynamics in Dictyosteiium. FEBS Lett. Nov. 5, 2004;577(1-2):227-32.
Fischer et al., Visualizing cytoskeleton dynamics in mammalian cells using a humanized variant of monomeric red fluorescent protein. FEBS Lett. May 1, 2006;580(10):2495-502.
Fisher et al., The study of protein mechanics with the atomic force microscope. Trends Biochem Sci. Oct. 1999;24(10):379-84.
Folkman, Angiogenesis. Annu Rev Med. 2006;57:1-18.
Fonseca et al., Capitalizing on the immunogenicity of dying tumor cells. Ciin Cancer Res. Mar. 15, 2008; 14(6):1603-8.
Fontaine et al., Surgical treatment of peripheral circulation disorders. Helv Chir Acta. Dec. 1954;21(5-6):499-533.
Fox, Management of worsening multiple sclerosis with mitoxantrone: a review. Clin Ther. Apr. 2006;28(4):461-74.
Fransen et al., Local Immunomodulation for cancer therapy: Providing treatment where needed. Oncoimmunology. Nov. 1, 2013;2(11):e26493.
Fritdenstein et al., Fibroblast precursors in normal and irradiated mouse hematopoietic organs. Exp Hematol. Sep. 1976;4(5):267-74.
Friedrich et al., Promoter traps in embryonic stem cells: a genetic screen to identify and mutate developmental genes in mice. Genes Dev. Sep. 1991;5(9):1513-23.
Fukushima et al., The use of an antifibrosis agent to improve muscle recovery after laceration. Am J Sports Med. Jul.-Aug. 2001;29(4):394-402.
Gamvrellis et al., Vaccines that facilitate antigen entry into dendritic ceils. Immunoi Cell Biol. Oct. 2004;82(5):506-16.
Gardel et al., Traction stress in focal adhesions correlates biphasically with actin retrograde flow speed. J Cell Biol. Dec. 15, 2008;183(6):999-1005.
Gasic et al., Removal and regeneration of the ceil coating in tumour cells. Nature. Oct. 13, 1962;196:170.
Gauthier et al., Temporary increase in plasma membrane tension coordinates the activation of exocytosis and contraction during cell spreading. Proc Natl Acad Sci U S A. Aug. 30, 2011;108(35):14467-72.
Geerligs et al., Linear viscoelastic behavior of subcutaneous adipose tissue. Biorheology. 2008;45(6):677-88.
GenBank Accession No. 000082.2, May 10, 2014.
GenBank Accession No. 000091.4, May 10, 2014.
GenBank Accession No. 000230.2, Dec. 17, 2012.
GenBank Accession No. 000514.3, Aug. 19, 2012.
GenBank Accession No. 000572.2, May 18, 2014.
GenBank Accession No. 000601.4, Nov. 25, 2012.
GenBank Accession No. 000614.3, Sep. 9, 2012.
GenBank Accession No. 000629.3, May 4, 2014.
GenBank Accession No. 000638.3, May 4, 2014.
GenBank Accession No. 000660.4, Dec. 9, 2012.
GenBank Accession No. 000749.2, May 4, 2014.
GenBank Accession No. 000758.3, May 4, 2014.
GenBank Accession No. 000800.3, Mar. 4, 2012.
GenBank Accession No. 000876.3, Apr. 13, 2014.
GenBank Accession No. 000885.4, Apr. 13, 2014.
GenBank Accession No. 000954.1, Jun. 13, 2014.
GenBank Accession No. 000963.3, Jun. 13, 2014.
GenBank Accession No. 001001522.1, May 18, 2014.
GenBank Accession No. 001096124.1, Dec. 16, 2012.
GenBank Accession No. 001102654.1, Dec. 16, 2012.
GenBank Accession No. 001111283.1, Dec. 9, 2012.
GenBank Accession No. 001171630.1, Dec. 9, 2012.
GenBank Accession No. 001202.3, Nov. 18, 2012.
GenBank Accession No. 001836.2, May 3, 2014.
GenBank Accession No. 001845.4, May 3, 2014.
GenBank Accession No. 001892.1, May 18, 2014.
GenBank Accession No. 001901.2, May 18, 2014.
GenBank Accession No. 002010.2, Dec. 9, 2012.
GenBank Accession No. 002421.3, May 11, 2014.
GenBank Accession No. 002506.2, Dec. 9, 2012.
GenBank Accession No. 002632.4, May 4, 2011.
GenBank Accession No. 002973.1, May 3, 2014.
GenBank Accession No. 002982.3, May 3, 2014.
GenBank Accession No. 003236.2, Aug. 21, 2011.
GenBank Accession No. 003239.2, Feb. 18, 2014.
GenBank Accession No. 003254.2, Jan. 5, 2013.
GenBank Accession No. 003255.2, Jan. 6, 2013.
GenBank Accession No. 003259.2, Nov. 25, 2012.
GenBank Accession No. 003263.3, Jan. 5, 2013.
GenBank Accession No. 003264.3, Jan. 6, 2013.
GenBank Accession No. 003268.5, Nov. 25, 2012.
GenBank Accession No. 003368.1, May 5, 2014.
GenBank Accession No. 003377.4, May 5, 2014.
GenBank Accession No. 003383.2, May 5, 2014.
GenBank Accession No. 003392.4, May 5, 2014.
GenBank Accession No. 004460.1, May 25, 2014.
GenBank Accession No. 004469.4, May 25, 2014.
GenBank Accession No. 005420.1, May 11, 2014.
GenBank Accession No. 005429.3, Mar. 31, 2014.
GenBank Accession No. 006059.2, Oct. 28, 2012.
GenBank Accession No. 006068.4, Oct. 28, 2012.
GenBank Accession No. 015719.3, Feb. 26, 2014.
GenBank Accession No. 016562.3, Jan. 6, 2013.
GenBank Accession No. 030956.3, Oct. 28, 2012.
GenBank Accession No. 033023.4, Nov. 18, 2012.
GenBank Accession No. 056534.2, Feb. 26, 2014.
GenBank Accession No. 057646.1, Jan. 6, 2013.
GenBank Accession No. 112218.2, Oct. 28, 2012.
GenBank Accession No. 138554.4, Dec. 29, 2012.
GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.

(56) References Cited

OTHER PUBLICATIONS

GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56/38.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010,.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. P49771.1, Jan. 9, 2013.
GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angioaenic sprouting utilizing endothelial tip cell filopodia. J Cell Biol. Jun. 23, 2003;161(6):1163-77.
Gilboa, DC-based cancer vaccines. J Clin Invest. May 2007; 117(5):1195-203.
Glasbey et al., Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 2010;16(4):382-91.
Godbey et al. Tracking the intracellular path of poly(ethylenimine)/DNA complexes for gene delivery. Proc Natl Acad Sci U S A. Apr. 27, 1999;96(9):5177-81.
Godbey et al., Size matters: molecular weight affects theefficiency of poly(ethylenimine) as a gene delivery vehicle. J Biomed Mater Res. Jun. 5, 1999;45(3):268-75.
Goddard et al., Polymer surface modification for the attachment of bioactive compounds. Progress in Polymer Science. Jul. 2007;32(7):698-725.
Gospodarowicz et al., Effect of fibroblast growth factor on the division and fusion of bovine myoblasts. J Cell Biol. Aug. 1976;70(2 pt 1):395-405.
Gratssley, Entangled Linear, Branched and Network Polymer Systems—Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004;130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.
Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.
Gussoni et al., Dystrophin expression in the mdx mouse restored by stem cell transplantation. Nature. Sep. 23, 1999;401(6751):390-4.
Halim et al., Biologic and synthetic skin substitutes: An overview. Indian J Plast Surg. Sep. 2010;43(Suppl):S23-8.
Hamby et al., Small molecule inhibitors of tumor-promoted angiogenesis, including protein tyrosine kinase inhibitors. Pharmacol Ther. May-Jun. 1999;82(2-3):169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Hanada, Efficacy of rehabilitative therapy in regional musculoskeletal conditions. Best Pract Res Clin Rheumatol. Feb. 2003;17(1):151-66.
Hansen et al., Comparison of clinical grade type 1 polarized and standard matured dendritic cells for cancer immunotherapy. Vaccine. Jan. 11, 2013;31(4):639-46.
Hansen et al., Integrin binding and ceil spreading on extracellular matrix act at different points in the cell cycle to promote hepatocyte growth. Mol Biol Cell. Sep. 1994;5(9):967-75.
Harris et al., Open pore biodearadabie matrices formed with gas foaming. J Biomed Mater Res. Dec. 5, 1998:42(3):396-402.
Harris, Classification, Diagnostic Criteria, and Screening for Diabetes, Diabetes in America, NIH Publication No. 95-1468. Chapter 2. (1995):15-36.
Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of seif-assembling materials. Proc Natl Acad Sci U S A. Apr. 16, 2002;99(8):5133-8.
Hartmann et al., CpG DNA: a potent signal for growth, activation, and maturation of human dendritic cells. Proc Natl Acad Sci U S A. Aug. 3, 1999;96(16):9305-10.
Hashimoto et al., Development of alginate wound dressings linked with hybrid peptides derived from laminin and elastin. Biomateriais. Mar.-Apr. 25, 2004;(7-8):1407-14.
Hawke et al., Myogenic satellite cells: physiology to molecular biology. J Appl Physiol (1985). Aug. 2001;91(2):534-51.
Heath, Cells for tissue engineering. Trends Biotechnol. Jan. 2000;18(1):17-9.
Helm et al., Synergy between interstitial flow and VEGF directs capillary morphogenesis in vitro throuah a gradient amplification mechanism. Proc Natl Acad Sci U S A. Nov. 1, 2005;102(44):15779-84.
Henry et al., VIVA investigators. The VIVA trial: Vascular endothelial growth factor in Ischemia for Vascular Angiogenesis. Circulation. Mar. 18, 2003;107(10):1359-65.

(56) References Cited

OTHER PUBLICATIONS

Hermanson, Bioconjugate Techniques. Academic Press, New York. pp. 152-186, (1996).

Heslop et al., Transplanted primary neonatal myoblasts can give rise io functional satellite cells as identified using the Myf5nlacZl+ mouse. Gene Ther. May 2001;8(10):778-83.

Hildner et al., Batf3 deficiency reveals a critical role for CD8alpha+ dendritic cells in cytotoxic T cell immunity. Science. Nov. 14, 2008;322(5904):1097-100.

Hill et al., Designing scaffolds to enhance transplanted myoblast survival and migration. Tissue Eng. May 2006;12(5):1295-304.

Hill et al., Muscle satellite (stem) cell activation during local tissue injury and repair. J Anat. Jul. 2003;203(1):89-99.

Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.

Hirano et al., Peptide and Protein Presenting Materials for Tissue Enaineering. Adv Mat. Jan. 16, 2004;16(1):17-25.

Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.

Hodi et al., Immunologic and clinical effects of antibody blockade of cytotoxic T lymphocyte-associated antigen 4 in previously vaccinated cancer patients. Proc Natl Acad Sci U S A. Feb. 26, 2008;105(8):3005-10.

Hodi et al., Improved survival with ipilimumab in patients with metastatic melanoma. N Engl J Med. Aug. 19, 2010;363(8):711-23.

Holland et al., Dual growth factor delivery from degradable oligo(poly(ethylene glycol) fumarate) hydrogel scaffolds for cartilage tissue enaineering. Journal of Controlled Release. 2005;101:111-125.

Holland et al., Transforming growth factor-beta 1 release from oligo(poly(ethylene glycol) fumarate) hydrogels in conditions that model the cartilage wound healing environment. J Control Release. Jan. 8, 2004;94(1):101-14.

Horsley et al., IL-4 acts as a myoblast recruitment factor during mammalian muscle growth. Cell. May 16, 2003;113(4):483-94.

Hsiong et al., Differentiation stage alters matrix control of stem cells. J Biomed Mater Res A. Apr. 2008;85A(1):145-56.

Huang et al., Fabrication and in vitro Testing of Polymeric Delivery Systems for Condensed DNA. J Biomed Mater Res. 2003;67:1384-1392.

Huang et al., Long-Term In Vivo Gene Expression via Delivery of PEL-DNA Condensates From Porous Polymer Scaffolds. Hum Gene Ther. 2005;16(5):609-617.

Hubbell et al., Materials Engineering for Immunomodulation. Nature. 2009;462:449-460.

Hubbell, Biomateriais in tissue engineering. Biotechnology (N Y). Jun. 13, 1995;(6):565-76.

Huebsch et al., Harnessing traction-mediated manipulation of the cell/matrix interface to control stem-cell fate. Nat Mater. Jun. 2010;9(6):518-26.

Humphries et al., Integrin ligands at a glance. J Cell Sci. Oct. 1, 2006;119(Pt 19):3901-3.

Huston et al., Protein engineering of antibody binding sites: recovery of specific activity in an anti-digoxin sinqle-chain Fv analogue produced in *Escherichia coli*. Proc Natl Acad Sci U S A. Aug. 1988;85(16):5879-83.

Hutson et al., Synthesis and characterization of tunable poly(ethylene glycol): gelatin methacrylate composite hydrogels. Tissue Eng Part A, Jul. 2011;17(13-14):1713-23.

Hwang et al., Fabrication of three-dimensional porous cell-laden hydrogel for tissue engineering. Biofabrication. Sep. 2010;2(3):035003. 12 pages.

Iellem et al., Unique chemotactic response profile and specific expression of chemokine receptors CCR4 and CCR8 by CD4(+)CD25(+) regulatory T cells. J Exp Med. Sep. 17, 2001;194(6):847-53.

Ihnat et al., Hypothesis: the 'metabolic memory', the new challenge of diabetes. Diabet Med. Jun. 2007;24(6):582-6.

Ii et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.

Irintchev et al., Formation of Skeletal Muscle After Subcutaneous implantation of Cultured Myoblasts. Bio/Technology. p. 366, Abstract 153.06, Jun. 1995.

Irvine et al., Engineering synthetic vaccines using cues from natural immunity. Nat Mater. Nov. 2013;12(11):978-90.

Isern et al., Self-renewing human bone marrow mesenspheres promote hematopoietic stem cell expansion. Cell Rep. May 30, 2013;3(5):1714-24.

Ishihara et al., Roles of bradykinin in vascular permeability and angiogenesis in solid tumor. Int Immunopharmacol. Mar. 2002;2(4):499-509.

Iwamoto et al., Preparation of an Ionic Polymer Gel Microactuator and Measurement of its Periodic Motions. Nippon Kagaku Kaishi. 1997;9:609-614.

Jain, Molecular Regeneration of Vessel Maturation. Nat Med. Jun. 1, 2003;9:685-693.

Jain, The manufacturing techniques of various drug loaded biodegradable poly(lactide-co-glycolide) (PLGA) devices. Biomateriais. Dec. 2000;21(23):2475-90.

Jankovic et al., In the absence of IL-12, CD4(+) T cell responses to intracellular pathogens fail to default to a Th2 pattern and are host protective in an IL-10(−/−) setting. Immunity. Mar. 2002;16(3):429-39.

Janmey et al., From tissue mechanics to transcription factors. Differentiation. Oct. 2013;86(3):112-20.

Jego et al., Plasmacytoid dendritic cells induce plasma cell differentiation through type I interferon and interleukin 6. Immunity. Aug. 2003;19(2):225-34.

Jiang et al. Two-piconewton slip bond between fibronectin and the cytoskeleton depends on talin. Nature. Jul. 17, 2003;424(6946):334-7.

Jiang et al., Click hydrogels, microgels and nanogels: emerging platforms for drug delivery and tissue engineering. Biomaterials. Jun. 2014;35(18):4969-85.

Jiang et al., Self-organization of periodic patterns by dissociated feather mesenchymal ceils and the regulation of size, number and spacing of primordia. Development. Nov. 1999;126(22):4997-5009.

Jinushi et al., Enhancing the clinical activity of granulocyte-macrophage colony-stimulating factor-secreting tumor cell vaccines. Immunol Rev. Apr. 2008;222:287-98.

Jinushi et al., MFG-E8-mediated uptake of apoptotic ceils by APCs links the pro- and antiinflammatory activities of GM-CSF. J Clin Invest. Jul. 2007;117(7):1902-13.

Johnson et al., Activation of skeletal muscle satellite cells and the role of fibroblast growth factor receptors. Exp Cell Res. Aug. 1995;219(2):449-53.

Jokinen et al., Integrin-mediated cell adhesion to type I collagen fibrils. J Biol Chem. Jul. 23, 2004;279(30):31956-63.

Jugdutt et al., Aging and defective healing, adverse remodeling, and blunted postconditioning in the reperfused wounded heart. J Am Coll Cardiol. Apr. 8, 2008;51(14):1399-403.

Juntanon et al., Electrically controlled release of sulfosalicylic acid from crosslinked poly(vinyl alcohol) hydrogel. Int J Pharm. May 22, 2008;356(1-2):1-11.

Kang et al., Effect of Porous Structure on the Degradation of breeze-Dried Gelatin Hydrogels. J Bioact Compat Poly. Jul. 1, 1999;14(4):331-343.

Kanzler et al., Therapeutic targeting of innate immunity with Toll-like receptor agonists and antagonists. Nat Med. May 2007;13(5):552-9.

Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.

Katayama et al., Integrated analysis of the genome and the transcriptome by FANTOM. Brief Bioinform. Sep. 2004;5(3):249-58.

(56) References Cited

OTHER PUBLICATIONS

Kathuria et al., Synthesis and characterization of elastic and macroporous chitosan-gelatin cryogels for tissue engineering. Acta Biomater. Jan. 2009;5(1):406-18.
Kawai et al., Innate immune recognition of viral infection. Nat Immunol. Feb. 2006;7(2):131-7.
Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.
Kearney et al., Macroscale delivery systems for molecular and cellular payloads. Nat Mater. Nov. 2013;12(11):1004-17.
Kennedy et al., Rapid and extensive collapse from electrically responsive macroporous hydrogels. Adv Healthc Mater. Apr. 2014;3(4):500-7.
Khetan et al., Degradation-mediated cellular traction directs stem cell fate in covalently crosslinked three-dimensional hydrogels. Nat Mater. May 2013;12(5):458-65.
Khownium et al., Novel endotoxin-sequestering compounds with terephthaiaidehyde-bis-guanyihydrazone scaffolds. Bioorg Med Chem Lett. Mar. 1, 2006:16(5):1305-8.
Kim et al., An overview of cartilage tissue engineering. Yonsei Med J. Dec. 2000;41(6):766-73.
Kim et al., Injectable, spontaneously assembling, inorganic scaffolds modulate immune cells in vivo and increase vaccine efficacy. Nat Biotechnol. Jan. 2015;33(1):64-72.
Kim et al., Multifunctional capsule-in-capsules for immunoprotection and trimodal imaging. Angew Chem Int Ed Engl. Mar. 1, 2011;50(10):2317-21.
Kim et al., The effect of VEGF on the myogenic differentiation of adipose tissue derived stem ceiis within thermosensitive hydrogel matrices, Biomateriais. Feb. 2010;31(6):1213-8.
Kinoshita et al., Successive injections in mdx mice of myoblasts grown with bFGF. Neuromuscul Disord. May 1996;6(3):187-93.
Kisak et al. The vesosome—a muiticompartment drug delivery vehicle. Curr Med Chem. Jan. 2004;11(2):199-219.
Klebanoff et al., CD8+ T-cell memory in tumor immunology and immunotherapy. Immunol Rev. Jun. 2006;211:214-24.
Klein et al., Cell-Cycle Control by Physiological Matrix Elasticity and In Viivo Tissue Stiffening. Curr Biol. 2009 Sep. 29;19:1511-1518.
Klinman, Immunotherapeutic uses of CpG oligodeoxynucieotides. Nat Rev Immunol. Apr. 2004;4(4):249-58.
Kohane, Microparticles and nanoparticles for drug delivery. Biotechnol Bioeng. Feb. 1, 2007;96(2):203-9.
Kondo et al., A reaction-diffusion wave on the skin of the marine angelfish *Pomacanthus*. Nature. Aug. 31, 1995;376(6543):765-8.
Kong et al., Controlling Degradation of Hydrogels via the Size of Cross-Linked Junctions. Adv Mater. Nov. 30, 2004;16(21):1917-1921.
Kong et al., Controlling rigidity and degradation of alginate hydrogels via molecular weight distribution. Biomacromoiecuies. Sep.-Oct. 2004;5(5):1720-7.
Kong et al., Decoupling the Dependence of Rheoiogical/Mechanical Properties of Hydrogels from Solids Concentration. Polymer. 2002;43(23):6239-6246.
Kong et al., Design of biodegradable hydrogel for the local and sustained delivery of angiogenic plasmid DNA. Pharm Res. May 2008;25(5):1230-8.
Kong et al., Designing alginate hydrogels to maintain viability of immobilized cells. Biomaterials. Oct. 2003;24(22):4023-9.
Kong et al., FRET measurements of cell-traction forces and nanoscale clustering of adhesion ligands varied by substrate stiffness. Proc Natl Acad Sci U S A. Mar. 22, 2005;102(12):4300-5.
Kong et al., Non-viral gene delivery regulated by stiffness of cell adhesion substrates. Nat Mater. Jun. 2005;4(6):460-4.
Kratky et al., Direct activation of antigen-presenting cells is required for CD8+ T-cell priming and tumor vaccination. Proc Natl Acad Sci U S A. Oct. 18, 2011;108(42):17414-9.

Krieg, Development of TLR9 agonists for cancer therapy. J Clin Invest. May 2007;117(5):1184-94.
Krishnamachari et al., PLGA Microparticles that Co-deliver Antigen and Toll Like Receptor Ligand Adjuvants for Applications in Cancer Immunotherapy. AAPS Annual Meeting and Exposition. Nov. 9, 2009. 1 page.
Kumamoto et al., Induction of tumor-specific protective immunity by in situ Langerhans cell vaccine. Nat Biotechnol. Jan. 2002;20(1):64-9.
Kumar et al., Toll-like receptors and innate immunity. Biochem Biophys Res Commun. Oct. 30, 2009;388(4):621-5.
Kurts et al., CD8 T cell ignorance or tolerance to islet antiaens depends on antigen dose. Proc Natl Acad Sci U S A. Oct. 26, 1999;96(22):12703-7.
Kuwahara et al., Cell delivery using an injectable and adhesive transglutaminase-gelatin gel. Tissue Eng Part C Methods. Aug. 2010;16(4):609-18.
Kwon et al., Electrically erodible polymer gel for controlled release of drugs. Nature. Nov. 28, 1991;354(6351):291-3.
Kwon et al., In vivo targeting of dendritic cells for activation of cellular immunity using vaccine carriers based on pH-responsive microparticles. Proc Natl Acad Sci U S A. Dec. 20, 2005;102(51):18264-8.
Langenkamp et al., Kinetics of dendritic cell activation: impact on priming of TH1, TH2 and nonpolarized T cells. Nat Immunol. Oct. 2000;1(4):311-6.
Langer et al., Tissue engineering. Science. May 14, 1993;260(5110):920-6.
Lanzavecchia et al., Regulation of T cell immunity by dendritic cells. Cell. Aug. 10, 2001;106(3):263-6.
Lao et al., Magnetic and hydrogel composite materials for hyperthermia applications. J Mater Sci Mater Med. Oct. 2004;15(10):1061-4.
Latorre et al., Applications of magnetic nanoparticies in medicine: magnetic fluid hyperthermia. P R Health Sci J. Sep. 2009;28(3):227-38.
Latz et al., TLR9 signals after translocating from the ER to CpG DNA in the lysosome. Nat Immunol. Feb. 2004;5(2):190-8.
Lauterbach et al., Mouse CD8alpha+ DCs and human BDCA3+ DCs are major producers of IFN-lambda in response to poly IC. J Exp Med. Nov. 22, 2010;207(12):2703-17.
Leach et al., Coating of VEGF-releasing scaffolds with bioactive glass for angiogenesis and bone regeneration. Biomateriais. Jun. 2006;27(17):3249-55.
Lee et al., Controlling Mechanical and Swelling Properties of Alginate Hydrogels Independently by Cross-Linker Type and Cross-Linking Density. Macromolecules. Apr. 2000;33(11):4291-4294.
Lee et al., Engineering liver tissue spheroids with inverted colloidal crystal scaffolds. Biomateriais. Sep. 2009;30(27):4687-94.
Lee et al., Hydrogel Formation via Vell Crosslinking. Advanced Materials. Nov. 2003;15(21):1828-1832.
Lee et al., Hydrogels for tissue engineering. Chem Rev. Jul. 2001;101(7):1869-79.
Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.
Lefaucheur et al., The cellular events of injured muscle regeneration depend on the nature of the injury. Neuromuscul Disord. Nov. 1995;5(6):501-9.
Lele et al., Investigating complexity of protein-protein interactions in focal adhesions. Biochem Biophys Res Commun, May 9, 2008;369(3):929-34.
Lensch et al., Scientific and clinical opportunities for modeling blood disorders with embryonic stem cells. Blood. Apr. 1, 2006;107(7):2605-12.
Leor et al., Cells, scaffolds, and molecules for myocardial tissue engineering. Pharmacol Ther. Feb. 2005;105(2):151-63.
Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.
Letsinger et al., Phosphoramidate analogs of oligonucleotides. J Org Chem. Nov. 1970;35(11):3800-3.

(56) References Cited

OTHER PUBLICATIONS

Levental et al., Soft biological materials and their impact on cell function. Soft Matter. 2007;3:299-306.
Li et al., Effect of growth factors and extracellular matrix materials on the proliferation and differentiation of microencapsulated myoblasts. J Biomater Sci Polym Ed. 2003;14(6):533-49.
Li et al., Effects of Three-Dimensional Scaffolds on Cell Organization and Tissue Development. Biotechnology and Bioprocess Engineering. Oct. 2001;6(5):311-325.
Li et al., Purified hybrid cells from dendritic cell and tumor cell fusions are superior activators of antitumor immunity. Cancer Immunol Immunother. Nov. 2001;50(9):456-62.
Li, TNF-alpha is a mitogen in skeletal muscle. Am J Physiol Cell Physiol. Aug. 2003;285(2):C370-6.
Lin et al., Transdermal regulation of vascular network bioengineering using a photopolymerizable methacrylated gelatin hydrogel. Biomaterials. Sep. 2013;34(28):6785-96.
Lipton et al., Developmental fate of skeletal muscle satellite cells. Science. Sep. 21, 1979;205(4412):1292-4.
Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.
Liu et al., Immunostimulatory CpG oligodeoxynucieotides enhance the immune response to vaccine strategies involvina granulocyte-macrophage colony-stimulating factor. Blood. Nov. 15, 1998;92(10):3730-6.
Liu et al., Nanostructured materials designed for cell binding and transduction. Biomacromolecules. 2001 Summer;2(2):362-8.
Liu et al., On the viscoelastic character of liver tissue: experiments and modelling of the linear behaviour. Biorheology, 2000;37(3):191-201.
Liu et al., Preparation of uniform calcium alginate gel beads by membrane emulsification coupled with internal gelation. Journal of Applied Polymer Science. Nov. 22, 2002;87(5):848-852.
Liu, Dendritic cell subsets and lineages, and their functions in innate and adaptive immunity. Cell. Aug. 10, 2001;106(3):259-62.
Lo et al., Cell movement is guided by the rigidity of the substrate. Biophys J. Jul. 2000;79(1):144-52.
Lodish et al., Collagen: The Fibrous Proteins of the Matrix. Molecular Cell Biology. W.H. Freeman, New York. 2000;Section 22.3:979-985.
Lopez et al., Magnetic Applications of Polymer Gels. Macromol Symp. 2001;166(1):173-178.
Lu et al., Muscle-derived stem cells seeded into acellular scaffolds develop calcium-dependent contractile activity that is modulated by nicotinic receptors. Uroloay. Jun. 2003;61(6):1285-91.
Lubeck, The costs of musculoskeletal disease: health needs assessment and health economics. Best Pract Res Clin Rheumatol. Jun. 2003;17(3):529-39.
Ludewig et al., Immunotherapy with dendritic cells directed against tumor antigens shared with normal host cells results in severe autoimmune disease, J Exp Med. Mar. 6, 2000;191(5):795-804.
Lumelsky et al., Differentiation of embryonic stem cells to insulin-secreting structures similar to pancreatic islets. Science. May 18, 2001;292(5520):1389-94.
Lutolf et al., Repair of bone defects using synthetic mimetics of collagenous extracellular matrices. Nat Biotechnol. May 2003;21(5):513-8.
Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.
Magram et al., IL-12-deficient mice are defective but not devoid of type 1 cytokine responses. Ann N Y Acad Sci. Oct. 31, 1996;795:60-70.
Maini, Spatial and spatio-temporal patterns in a cell-haptotaxis model. J Math Biol. 1989;27(5):507-22.
Majeti et al., Identification of a hierarchy of multipotent hematopoietic progenitors in human cord blood. Cell Stem Cell. Dec. 13, 2007;1(6):635-45.
Maldonado et al., How tolerogenic dendritic cells induce regulatory T cells. Adv Immunol. 2010;108:111-65.
Maley et al., Extracellular matrix, growth factors,genetics: their influence on cell proliferation and myotube formation in primary cultures of adult mouse skeletal muscle. Exp Cell Res. Jul. 1995;219(1):169-79.
Malhotra et al., Use of an oncolytic virus secreting GM-CSF as combined oncolytic and immunotherapy for treatment of colorectal and hepatic adenocarcinomas. Surgery. Apr. 2007;141(4):520-9.
Malmqvist, Biospecific interaction analysis using biosensor technology. Nature. Jan. 14, 1993;361(6408):186-7.
Mammoto et al., Mechanical control of tissue and organ development. Development. May 2010;137(9):1407-20.
Manavski et al., Vascular niche controls organ regeneration. Circ Res. Mar. 28, 2014; 114(7):1077-9.
Mansoor et al., Engineering T cells for cancer therapy. Br J Cancer. Nov. 14, 2005;93(10):1085-91.
Martinsen et al., Alginate as immobilization material: I. Correlation between chemical and physical properties of alginate gel beads. Biotechnol Bioeng. Jan. 5, 1989;33(1):79-89.
Marui et al., Simultaneous application of basic fibroblast growth factor and hepatocyte growth factor to enhance the blood vessels formation. J Vasc Surg. Jan. 2005;41(1):82-90.
Masedunskas et al., Role for the actomyosin complex in regulated exocytosis revealed by intravital microscopy. Proc Natl Acad Sci U S A. Aug. 16, 2011;108(33):13552-7.
Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.
Matthew et al., Subperiosteal behaviour of alginate and cellulose wound dressing materials. Biomateriais. Mar. 1995;16(4):275-8.
McColl, Chemokines and dendritic cells: a crucial alliance. Immunol Cell Biol. Oct. 2002;80(5):489-96.
McConnell et al., Vaccination with outer membrane complexes elicits rapid protective immunity to multidrug-resistant Acinetobacter baumannii. Infect Immun. Jan. 2011;79(1):518-26.
McDonald et al., Early fracture callus displays smooth muscle-like viscoelastic properties ex vivo: implications for fracture healing. J Orthop Res. Nov. 2009;27(11):1508-13.
McKinney-Freeman et al., Muscle-derived hematopoietic stem cells are hematopoietic in origin. Proc Natl Acad Sci U S A. Feb. 5, 2002;99(3):1341-6.
McKinnon et al., Biophysically defined and cytocompatible covalently adaptable networks as viscoelastic 3D cell culture systems. Adv Mater. Feb. 12, 2014;26(6):865-72.
McPherron et al., Regulation of skeletal muscle mass in mice by a new TGF-beta superfamily member. Nature. May 1, 1997;387(6628):83-90.
McWhorter et al., Modulation of macrophage phenotype by cell shape. Proc Natl Acad Sci U S A. Oct. 22, 2013;110(43):17253-8.
Meier et al., Peptide Nucleic Acids(PNAs)—Unusual Properties of Noionic Oligonucleotide Analogues. Angewandte Chemie, Int'l Edition. Aug. 1992;31(8):1008-1010.
Melero-Martin et al., Engineering robust and functional vascular networks in vivo with human adult and cord blood-derived progenitor cells. Circ Res. Jul. 18, 2008; 103(2):194-202. Includes supplementary materials.
Melief et al., Immunotherapy of established (pre)malignant disease by synthetic long peptide vaccines. Nat Rev Cancer. May 2008;8(5):351-60.
Mellman et al., Dendritic cells: specialized and regulated antigen processing machines. Cell. Aug. 10, 2001;106(3):255-8.
Menetry et al., Suturing Versus Immobilization of a Muscle Laceration: A Morphological and Functional Study in a Mouse Model. Am J Sports Med. 1999;27(2):222-229.
Meraz et al., Mesoporous Silicon Particles for the Presentation of Tumor Antigens and Adjuvant for Anti-Cancer immunity. Cancer Res. 2011;71(S24):159s-160s, Abstract #P1-01-12.

(56) References Cited

OTHER PUBLICATIONS

Merck, Merck Announces Presentation of Interim Data from Phase 1B Study of MK-3475, investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.
Merkel et al., Using mechanobiological mimicry of red blood cells to extend circulation times of hydrogel microparticles. Proc Natl Acad Sci U S A. Jan. 11, 2011;108(2):586-91.
Merriam-Webster, Transient. Merriam-Webster Dictionary. Web. Jul. 18, 2014. www.merriam-webster.com/dictionary/transient. 3 pages.
Metters et al., Fundamental studies of biodegradable hydrogels as cartilage replacement materials. Biomed Sci Instrum. 1999;35:33-8.
Meyer et al., Clinical investigations of Toll-like receptor agonists. Expert Opin Investig Drugs. Jul. 2008;17(7):1051-65.
Meylan et al., Intracellular pattern recognition receptors in the host response. Nature. Jul. 6, 2006;442(7098):39-44.
MGI, Mouse Facts. Retrieved online at: http://www.informatics.jax.org/mgihome/other/mouse_facts1.shtml. 2 pages. Jul. 31, 2018.
Miljkovic et al., Chondrogenesis, bone morphogenetic protein-4 and mesenchymal stem cells. Osteoarthritis Cartilage. Oct. 2008;16(10):1121-30.
Miller et al., Hepatocyte growth factor affects satellite cell activation and differentiation in regenerating skeletal muscle. Am J Physiol Cell Physiol. Jan. 2000;278(1):C174-81.
Miller et al., Lipopolysaccharide sequestrants: structural correlates of activity and toxicity in novel acyl homospermines. J Med Chem. Apr. 7, 2005;48(7):2589-99.
Miller et al., Melanoma. N Engl J Med. Jul. 6, 2006,355(1):51-65.
Miralles et al., Actin dynamics control SRF activity by regulation of its coactivator MAL. Cell. May 2, 2003;113(3):329-42.
Mitchell et al., The exogenous administration of basic fibroblast growth factor to regenerating skeletal muscle in mice does not enhance the process of regeneration. Growth Factors. 1996;13(1-2):37-55.
Miyata et al., Biomolecule-sensitive hydrogels. Adv Drug Deliv Rev. Jan. 17, 2002;54(1):79-98.
Mohan et al., Novel Porous, Polysaccharide Scaffolds for Tissue Engineering Applications. Trends Biomater Artif Organs. 2005; 18(2):21 9-224.
Moioli et al., Matrices and scaffolds for drug delivery in dental, oral and craniofacial tissue engineering. Adv Drug Deliv Rev. May 30, 2007;59(4-5):308-24.
Molinari et al., Modification of surface membrane antigens by trypsin. Proc Soc Exp Biol Med. Apr. 1975;148(4):991-4.
Molloy et al., Movement and force produced by a single myosin head. Nature. Nov. 9, 1995;378(6553):209-12.
Mooney et al., Cytoskeletal filament assembly and the control of cell spreading and function by extracellular matrix. J Cell Sci. Jun. 1995;108 (Pt 6):2311-20.
Mooney et al., Switching from differentiation to growth in hepatocytes: control by extracellular matrix. J Cell Physiol. Jun. 1992;151(3):497-505.
Moser et al., Dendritic cell reaulation of TH1-TH2 development. Nat Immunol. Sep. 2000;1(3):199-205.
Mulder et al., Wound Management: Past, Present, and Future. Clinicians' Pocket Guide to Chronic Wound Repair. Springhouse Corporation, Springhouse, Pennsylvania. 1998:85-90.
Muralidharan-Chari et al., ARF6-regulated shedding of tumor cell-derived plasma membrane microvesicles. Curr Biol. Dec. 1, 2009;19(22):1875-85.
Murdan, Electro-responsive drug delivery from hydrogels. J Control Release. Sep. 19, 2003;92(1-2):1-17.
Nagai et al., A variant of yellow fluorescent protein with fast and efficient maturation for cell-biological applications. Nat Biotechnol. Jan. 2002;20(1):87-90.
Naik et al., Development of plasmacytoid and conventional dendritic cell subtypes from single precursor cells derived in vitro and in vivo. Nat Immunol. Nov. 2007;8(11):1217-26.

Nair et al., Polymers as biomateriais for tissue engineering and controlled drug delivery. Adv Biochem Eng Biotechnol. 2006;102:47-90.
NCBI Accession No. 000749.2, Apr. 1, 2012.
NCBI Accession No. 000758, Apr. 1, 2012.
NCBI Accession No. 001020537, Jan. 30, 2011.
NCBI Accession No. 001020538, Jan. 30, 2011.
NCBi Accession No. 001020539, Jan. 30, 2011.
NCBI Accession No. 001020540, Jan. 30, 2011.
NCBI Accession No. 001028928, Jan. 30, 2011.
NCBI Accession No. 001193, May 3, 2014.
NCBI Accession No. 001552.2, Mar. 16, 2014.
NCBi Accession No. 001561,5, Mar. 16, 2014.
NCBI Accession No. 003237.2, May 25, 2014.
NCBI Accession No. 003265, Dec. 30, 2012.
NCBI Accession No. 003318.1, May 4, 2014.
NCBI Accession No. 003327.3, May 4, 2014.
NCBi Accession No. 003367, Jan. 30, 2011.
NCBI Accession No. 004119, Apr. 14, 2013.
NCBI Accession No. 004448.3, Apr. 23, 2014.
NCBI Accession No. 005009.2, Apr. 27, 2014.
NCBi Accession No. 005018.2, Apr. 27, 2014.
NCBI Accession No. 006274.2, Mar. 31, 2013.
NCBI Accession No. 017442, Apr. 14, 2012.
NCBI Accession No. 059138, Apr. 14, 2012.
NCBI Accession No. 181780.3, Jan. 27, 2014.
NCBI Accession No. 861445.3, Jan. 27, 2014.
Nehls et al., A novel, microcarrier-based in vitro assay for rapid and reliable quantification of three-dimensional cell migration and angiogenesis. Microvasc Res. Nov. 1995;50(3):311-22.
Nestle et al., Vaccination of melanoma patients with peptide- or tumorlysate-pulsed dendritic ceils. Nature Medicine. Mar. 1, 1998;4(3):328-32.
Niamlang et al., Electrically controlled release of salicylic acid from poly(p-phenylene vinylene)/polyacrylamide hydrogels. Int J Pharm. Apr. 17, 2009;371(1-2):126-33.
Nichol et al., Cell-laden microengineered gelatin methacrylate hydrogels. Biomateriais. Jul. 2010;31(21):5536-44.
Nicodemus et al., Cell encapsulation in biodegradable hydrogels for tissue engineering applications. Tissue Eng Part B Rev. Jun. 2008;14(2):149-65.
Niessen et al., The alpha 6 beta 4 inteqrin is a receptor for both laminin and kalinin. Exp Cell Res. Apr. 1994;211(2):360-7.
Noguera-Troise et al., Blockade of DII4 inhibits tumour growth by promoting nonproductive angiogenesis. Nature. Dec. 21, 2006;444(7122):1032-7.
Ní Annaidh et al., Characterization of the anisotropic mechanical properties of excised human skin. J Mech Behav Biomed Mater. Jan. 2012;5(1):139-48.
O'Garra et al., Are dendritic cells afraid of commitment? Nat Immunol. Dec. 2004;5(12):1206-8.
O'Shea et al., Type 1 IFNs and regulation of TH1 responses: enigmas both resolved and emerge. Nat Immunol. Jul. 2000;(1):17-9.
Ohashi et al., Surgical excision combined with autologous whole tumor cell vaccination is an effective therapy for murine neuroblastoma. J Pediatr Surg. Aug. 2006;41(8):1361-8.
Ohlstein et al., The stem cell niche: theme and variations. Curr Opin Cell Biol. Dec. 2004;16(6):693-9.
Oldenburg et al., TLR13 recognizes bacterial 23S rRNA devoid of erythromycin resistanceforming modification. Science. Aug. 31, 2012;337(6098):1111-5.
Oldenhove et al., Decrease of Foxp3+ Treg cell number and acquisition of effector cell phenotype during lethal infection. Immunity. Nov. 20, 2009;31(5):772-86.
Orner et al., Arrays for the combinatorial exploration of cell adhesion, J Am Chem Soc. Sep. 8, 2004;126(35):10808-9.
Osunkoya et al., Synthesis and fate of immunological surface receptors on cultured Burkitt lymphoma cells. Int J Cancer. Mar. 15, 1969;4(2):159-65.
Ota et al., Percutaneous subxiphoid access to the epicardium using a miniature crawling robotic device. Innovations (Phila). 2006 Fall;1(5):227-31.

(56) References Cited

OTHER PUBLICATIONS

Overwijk et al., Tumor regression and autoimmunity after reversal of a functionally tolerant state of self-reactive CD8+ T cells. J Exp Med. Aug. 18, 2003;198(4):569-80.
Ozawa et al., Microenvironmental VEGF concentration, not total dose, determines a threshold between normal and aberrant angiogenesis. J Clin invest. Feb. 2004;113(4):516-27.
Padilla et al., Insufficient TLR activation contributes to the slow development of CD8+ T cell responses in Trypanosoma cruzi infection. J Immunol. Jul. 15, 2009;183(2):1245-52.
Page-McCaw et al., Matrix metalloproteinases and the regulation of tissue remodelling. Nat Rev Mol Cell Biol. Mar. 2007;8(3):221-33.
Pailler-Maitei et al., In vivo measurements of the elastic mechanical properties or human skin by indentation tests. Med Eng Phys. Jun. 2008;30(5):599-606.
Pajonk et al., From sol-gel to aerogels and cryogels. J Non Cryst Solids. May 1990;121(1-3):66-67.
Palacio et al., Interleukin 10 and tumor necrosis factor alpha gene expression in respiratory and peripheral muscles. Relation to sarcolemmal damage. Arch Bronconeumol. Jul. 2002;38(7):311-6.
Paradee et al., Effects of crosslinking ratio, model drugs, and electric field strength on electrically controlled release for aiginate-based hydrogel. J Mater Sci Mater Med. Apr. 2012;23(4):999-1010.
Pardoll, The blockade of immune checkpoints in cancer immunotherapy. Nat Rev Cancer. Mar. 22, 2012;12(4):252-64.
Parekh et al., Modulus-driven differentiation of marrow stromal cells in 3D scaffolds that is independent of myosin-based cytoskeletal tension. Biomateriais, Mar. 2011;32(9):2256-64.
Parekkadan et al., Mesenchymal stem cell-derived molecules reverse fulminant hepatic failure. PLoS One. Sep. 26, 2007;2(9):e941.
Park et al., Photopolymerized hyaluronic acid-based hydrogels and interpenetrating networks. Biomaterials. Mar. 2003;24(6):893-900.
Parker et al., Effect of mitoxantrone on outcome of children with first relapse of acute lymphoblastic leukaemia (ALL R3): an open-label randomised trial. Lancet. Dec. 11, 2010;376(9757):2009-17.
Partridge et al., Conversion of mdx myofibres from dystrophin-negative to -positive by injection of normal myoblasts. Nature. Jan. 12, 1989;337(6203):176-9.
Patterson et al., Differential binding of chemokines to macrophages and neutrophils in the human inflamed synovium. Arthritis Res, 2002;4(3):209-14.
Pawlaczyk et al., Age-dependent biomechanical properties of the skin. Postepy Dermatol Alergol. Oct. 2013;30(5):302-6.
Pedersen et al., Induction of regulatory dendritic cells by dexamethasone and 1 alpha,25-Dihydroxyvitamin D(3). Immunol Lett. Jan. 30, 2004;91(1):63-9.
Pek et al., The effect of matrix stiffness on mesenchymal stem cell differentiation in a 3D thixotropic gel. Biomateriais. Jan. 2010;31(3):385-91.
Pelinkovic et al., Tissue engineering and gene therapy of the musculoskeletal system with muscle cells. Z Orthop Ihre Grenzgeb, Sep.-Oct. 2000;138(5):402-6.
Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.
Peters et al., Engineering vascular networks in porous polymer matrices. J Biomed Mater Res. Jun. 15, 2002;60(4):668-78.
Peyton et al., The use of poly(ethylene glycol) hydrogels to investigate the impact of ECM chemistry and mechanics on smooth muscle cells. Biomateriais. Oct. 2006;27(28):4881-93.
Phillippi, Patternina of Multiple Cell Lineages from a Sinaie Stem Cell Population. Annual Meeting of the American Society for Cell Biology. Dec. 10, 2006.
Pinho et al., PDGFRa and CD51 mark human nestin sphere-forming mesenchymal stem cells capable of hematopoietic progenitor cell expansion. J Exp Med. Jul. 1, 2013;210(7):1351-67.
Pluen et al., Role of tumor-host interactions in interstitial diffusion of macromolecules: cranial vs. subcutaneous tumors. Proc Natl Acad Sci U S A. Apr. 10, 2001;98(8):4628-33.

Pooyan et al., Conjugates bearing multiple formyl-methionyl peptides display enhanced binding to but not activation of phagocytic cells. Bioconjug Chem. Mar.-Apr. 2002;13(2):216-23.
Pope et al., Organ-specific regulation of the CD8 T cell response to Listeria monocytogenes infection. J Immunol. Mar. 1, 2001;166(5):3402-9.
Porter et al., Separation of Natural Populations of Coliform Bacteria from Freshwater and Sewage by Magnetic-Bead Cell Sorting. J Microbiol Meth. 1998;33(3):221-226.
Pouzet et al., Factors affecting functional outcome after autologous skeletal myoblast transplantation. Ann Thorac Surg. Mar. 2001;71(3):844-50; discussion 850-1.
PRNewsWire, GlaxoSmithKline and Amplimmune Form Global Strategic Collaboration. Alliance to Focus on AMP-224 for Cancer and Other Diseases. 3 pages, Aug. 4, 2010.
Pulendran et al., Fit3-ligand and granulocyte colony-stimulating factor mobilize distinct human dendritic cell subsets in vivo. J Immunol. Jul. 1, 2000;165(1):566-72.
Qi et al., Patterned differentiation of individual embryoid bodies in spatially organized 3D hybrid microgels. Adv Mater. Dec. 7, 2010;22(46):5276-81.
Qin et al., Soft lithography for micro- and nanoscaie patternina. Nat Protoc. Mar. 2010;5(3):491-502.
Qiu et al., Environment-sensitive hydrogels for drug delivery. Adv Drug Deliv Rev. Dec. 31, 2001;53(3):321-39.
Qu et al., Development of approaches to improve cell survival in myoblast transfer therapy. J Cell Biol. Sep. 7, 1998;142(5):1257-67.
Qu-Petersen et al., Identification of a novel population of muscle stem cells in mice: potential for muscle regeneration. J Cell Biol. May 27, 2002;157(5):851-64.
Quezada et al., CTLA4 blockade and GM-CSF combination immunotherapy alters the intratumor balance of effector and regulatory T cells. J Clin Invest. Jul. 2006; 116(7):1935-45.
Quintana et al., Autoantibody patterns in diabetes-prone NOD mice and in standard C57BL/6 mice. J Autoimmun. Nov. 2001;17(3):191-7.
Raeber et al., Molecularly engineered PEG hydrogels: a novel model system for proteolytically mediated cell migration. Biophys J. Aug. 2005;89(2):1374-88.
Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.
Ramón-Azcón et al., Gelatin methacrylate as a promising hydrogel for 3D microscale organization and proliferation of dielectrophoretically patterned cells. Lab on a Chip. Aug. 21, 2012;12(16):2959-69.
Randolph et al., Migration of dendritic cell subsets and their precursors. Annu Rev Immunol. 2008;26:293-316.
Ranganath et al., Harnessing the mesenchymal stem cell secretome for the treatment of cardiovascular disease. Cell Stem Cell. Mar. 2, 2012;10(3):244-58.
Raposo et al., Extracellular vesicles: exosomes, microvesicles, and friends. J Cell Biol. Feb. 18, 2013;200(4):373-83.
Rappolee et al. Macrophage-derived growth factors. Curr Top Microbiol Immunol. 1992;181:87-140.
Rapraeger, Syndecan-regulated receptor signaling. J Cell Biol. May 29, 2000;149(5):995-8.
Reddy et al., Exploiting lymphatic transport and complement activation in nanoparticle vaccines, Nat Biotechnol, Oct. 2007;25(10):1159-64.
Reimann et al., Satellite Cells in Normal and Regenerated Soleus Muscles of mdx and Control Mice. Eur J Neurosci. 1998;10:366, Abstract No. 153.07.
Reis E Sousa., Activation of dendritic cells: translating innate into adaptive immunity. Curr Opin Immunol. Feb. 2004;16(1):21-5.
Research Results of National institute of Advanced Industrial Science and Technology, retrieved online at: http://www.aist.go.jp/aist_j/press_release/pr2006/pr20060719.html. 4 pages, (2006).
Rhoads et al., Satellite cell-mediated angiogenesis in vitro coincides with a functional hypoxia-inducible factor pathway. Am J Physiol Cell Physiol. Jun. 2009;296(6):C1321-8.

(56) References Cited

OTHER PUBLICATIONS

Ribas et al., Phase III randomized clinical trial comparing tremelimumab with standard-of-care chemotherapy in patients with advanced melanoma. J Clin Oncol. Feb. 10, 2013;31(5):616-22.
Richards Grayson et al., Multi-pulse drug delivery from a resorbable polymeric microchip device. Nat Mater. Nov. 2003;2(11):767-72.
Richardson et al., Polymeric system for dual growth factor delivery. Nat Biotechnol. Nov. 2001;19(11):1029-34.
Riddle et al., Role of poly(lactide-co-glycolide) particle size on gas-foamed scaffolds. J Biomater Sci Polym Ed. 2004;15(12):1561-70.
Ridgway et al., Inhibition of Dll4 signalling inhibits tumour growth by deregulating angiogenesis. Nature. Dec. 21, 2006;444(7122):1083-7.
Rinderknecht et al., The amino acid sequence of human insulin-like growth factor I and its structural homology with proinsulin. J Biol Chem. Apr. 25, 1978;253(8):2769-76.
Rizzo et al., An improved cyan fluorescent protein variant useful for FRET. Nat Biotechnol. Apr. 2004;22(4):445-9.
Roccaro et al., BM mesenchymal stromal cell-derived exosomes facilitate multiple myeloma progression. J Clin Invest. Apr. 2013;123(4):1542-55.
Rodriguez et al., Minimal "Self" peptides that inhibit phagocytic clearance and enhance delivery of nanoparticies. Science. Feb. 22, 2013;339(6122):971-5.
Rosenberg et al., Cancer immunotherapy: moving beyond current vaccines. Nat Med. Sep. 2004;10(9):909-15.
Roth et al., SC68896, a novel small molecule proteasome inhibitor, exerts antiglioma activity in vitro and in vivo. Clin Cancer Res. Nov. 1, 2009;15(21):6609-18.
Rowlands et al., Directing osteogenic and myogenic differentiation of MSCs: interplay of stiffness and adhesive ligand presentation. Am J Physiol Cell Physiol. Oct. 2008;295(4):C1037-44.
Rowley et al. Alginate hydrogels as synthetic extracellular matrix materials. Biomaterials. Jan. 1999;20(1):45-53.
Rowley et al. Alginate type and RGD density control myoblast phenotype. J Biomed Mater Res. May 2002;60(2):217-23.
Rowley et al., Biomaterials to Spatially Regulate Cell Fate. Adv Mater. Jun. 2002;14(12):886-889.
Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.
Ryten et al., ATP regulates the differentiation of mammalian skeletal muscle by activation of a P2X5 receptor on satellite cells. J Cell Biol. Jul. 22, 2002:158(2):345-55.
Ryu et al., The construction of three-dimensional micro-fluidic scaffolds of biodegradable polymers by solvent vapor based bonding of micro-molded layers. Biomaterials. Feb. 2007:28(6):1174-84.
Sacchetti et al., Self-renewing osteoprogenitors in bone marrow sinusoids can organize a hematopoietic microenvironment. Cell. Oct. 19, 2007;131(2):324-36.
Sakai et al., An injectable, in situ enzymatically gellable, gelatin derivative for drug delivery and tissue engineering. Biomaterials. Jul. 2009;30(20):3371-7.
Salem et al., Defining the antigen-specific T-cell response to vaccination and poly(I:C)/TLR3 signaling: evidence of enhanced primary and memory CD8 T-cell responses and antitumor immunity. J Immunother. May-Jun. 2005;28(3):220-8.
Salvador et al., Combination of immune stimulating adjuvants with poly(lactide-co-giycolide) microspheres enhances the immune response of vaccines. Vaccine. Jan. 11, 2012;30(3):589-96.
Salvay et al., Inductive tissue engineering with protein and DNA-releasing scaffolds. Mol Biosyst. Jan. 2006;2(1):36-48.
Sano et al., Swift development of protective effector functions in naive CD8(+) T cells against malaria liver stages. J Exp Med. Jul. 16, 2001; 194(2):173-9.
Sansonetti, The innate signaling of dangers and the dangers of innate signaling. Nat Immunol. Dec. 2006;7(12):1237-42.

Sarkar et al., Condensation of oligonucleotides assembled into nicked and gapped duplexes: potential structures for oligonucleotide delivery. Nucleic Acids Res. Jan. 7, 2005;33(1):143-51.
Sato, Human dendritic cells. Biotherapy. Nov. 2004;18(6):467-77.
Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, Integrins and extracellular matrix in mechanotransduction. Cold Spring Harb Perspect Biol. Dec. 2010;2(12):a005066.
Seale et al., Pax7 is required for the specification of myogenic satellite cells. Cell. Sep. 15, 2000;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnoi. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI usina micron-sized iron oxide particles. Magn Reson Med. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheridan et al., Bioabsorbable polymer scaffolds for tissue engineering capable of sustained growth factor delivery. J Control Release, Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colonv-stimulating factor (GM-CSF) and T-cell responses: what we do and don't know. Cell Res. Feb. 2006; 16(2):126-33.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult human hematopoietic cells. Proc Natl Acad Sci U S A. Nov. 19, 2013;110(47):18892-7.
Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnoi Bioeng. May 20, 1996;50(4):374-81.
Shortman et al., Steady-state and inflammatory dendritic-cell development. Nat Rev Immunol. Jan. 2007;7(1):19-30.
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-

(56) References Cited

OTHER PUBLICATIONS 2-methylene-1,3-dioxepane)-based polymers and crosslinked gels, J Biomed Mater Res A. Nov. 2008;87(2):345-58.
Silva et al., Effects of VEGF temporal and spatial presentation on angiogenesis. Biomaterials. Feb. 2010;31(6):1235-41.
Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Simpson et al., FC-dependent depletion of tumor-infiltrating regulatory T cells co-defines the efficacy of anti-CTLA-4 therapy against melanoma. J Exp Med. Aug. 26, 2013;210(9):1695-710.
Singer et al., Cutaneous wound healing. N Engl J Med. Sep. 2, 1999;341(10):738-46.
Skokos et al., CD8-DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Smidsød et al., Alginate as immobilization matrix for cells. Trends Biotechnol. Mar. 1990;8(3):71-8.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Sonawane et al., Chloride accumulation and swelling in endosomes enhances DNA transfer by polyamine-DNA polyplexes. J Biol Chem. Nov. 7, 2003;278(45):44826-31.
Stachowiak et al., Inverse opal hydrogel-collagen composite scaffolds as a supportive microenvironment for immune cell migration. J Biomed Mater Res A. Jun. 1, 2008;85(3):815-28.
Steinman et al., Taking dendritic cells into medicine. Nature. Sep. 27, 2007;449(7161):419-26.
Storrie et al., Sustained delivery of plasmid DNA from polymeric scaffolds for tissue engineering. Adv Drug Deliv Rev. Jul. 7, 2006;58(4):500-14.
Straub et al., Animal models for muscular dystrophy show different patterns of sarcolemmal disruption. J Cell Biol. 1997 Oct. 20;139(2):375-85.
Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.
Sun et al., Highly stretchable and tough hydrogels. Nature. Sep. 6, 2012;489(7414):133-6.
Sun et al., Sustained vascular endothelial growth factor delivery enhances angiogenesis and perfusion in ischemic hind limb. Pharm Res. Jul. 2005;22(7):1110-6.
Suri et al., Photopatterned collagen-hyaluronic acid interpenetrating polymer network hydrogels. Acta Biomater. Sep. 2009;5(7):2385-97.
Swift et al., Nuclear lamin-A scales with tissue stiffness and enhances matrix-directed differentiation. Science. Aug. 30, 2013;341(6149):1240104. 17 pages.
Syed et al., Stem cell therapy market. Nat Rev Drug Discov. Mar. 2013;12(3):185-6.
Tabata et al., Enhanced Vascularization and Tissue Granulation by Basic Fibroblast Growth Factor impregnated in Gelatin Hydrogels. Journal of Controlled Release. Sep. 1994:31(2):189-199.
Takahashi et al., Induction of pluripotent stem cells from adult human fibroblasts by defined factors. Cell. Nov. 30, 2007;131(5):861-72.

Takeshita et al., Therapeutic angiogenesis. A single intraarterial bolus of vascular endothelial growth factor augments revascularization in a rabbit ischemic hind limb model. J Clin Invest. Feb. 1994;93(2):662-70.
Tamura et al., Immunotherapy of tumors with autologous tumor-derived heat shock protein preparations. Science. Oct. 3, 1997;278(5335):117-20.
Tanaka et al., Collapse of gels in an electric field. Science. Oct. 29, 1982;218(4571):467-9.
Tannous, Gaussia luciferase reporter assay for monitoring biological processes in culture and in vivo. Nat Protoc, 2009;4(4):582-91.
Tatsumi et al., HGF/SF is present in normal adult skeletal muscle and is capable of activating satellite cells. Dev Biol. Feb. 1, 1998;194(1):114-28.
Ten Duke et al., Growth Factors for Wound Healing. Nat Biotechnol. 1989;7:793-798.
Thelin et al., In Vivo Enrichment of Diabetogenic T Cells. Diabetes. Aug. 2017;66(8):2220-2229.
Thomas et al., Intravenous infusion of bone marrow in patients receiving radiation and chemotherapy. N Engl J Med. Sep. 12, 1957;257(11):491-6.
Thornton et al., Shape retaining injectable hydrogels for minimally invasive bulking. J Urol. Aug. 2004;172(2):763-8.
Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.
Thurston et al., The Delta paradox: DLL4 blockade leads to more tumour vessels but less tumour growth. Nat Rev Cancer. May 2007;7(5):327-31.
Tidball, Inflammatorvcell response to acute muscle injury. Med Sci Sports Exerc. Jul. 1995;27(7):1022-32.
Tomer et al., Electrically Controlled Release of Macromolecules from Cross-Linked Hyaluronic Acid Hydrogels. Journal of Controlled Release. Mar. 1995:33(3):405-413.
Tong et al., Engineering interpenetrating network hydrogels as biomimetic cell niche with independently tunable biochemical and mechanical properties. Biomaterials. Feb. 2014;35(6):1807-15.
Tourniaire et al., Polymer microarrays for cellular adhesion. Chem Commun (Camb). May 28, 2006;(20):2118-20.
Trappmann et al., Extracellular-matrix tethering regulates stem-cell fate. Nat Mater. May 27, 2012;11(7):642-9.
Trappmann et al., How cells sense extracellular matrix stiffness: a material's perspective. Curr Opin Biotechnol. Oct. 2013;24(5):948-53.
Tripathi et al., Elastic and macroporous agarose-gelatin cryogels with isotropic and anisotropic porosity for tissue engineering. J Biomed Mater Res A. Sep. 1, 2009;90(3):680-94.
Tsien, The green fluorescent protein. Annu Rev Biochem. 1998;67:509-44.
Turing, Discussion: Turing's Theory of Morphogenesis—Its Influence on Modelling Biological Pattern and Form. Bull Math Biol. 1990;52(1-2):119-159.
Turing, The Chemical Basis of Morphogenesis. Philosophical Transactions of the Royal Society of London. Series B. 1952;237(641):37-72.
Uchida et al., Immunization by particle bombardment of antigen-loaded poly-(DL-lactide-co-glycolide) microspheres in mice. Vaccine. Mar. 15, 2006;24(12):2120-30.
Ugarte et al., Notch signaling enhances osteogenic differentiation while inhibiting adipogenesis in primary human bone marrow stromal cells. Exp Hematol. Jul. 2009;37(7):867-875.
Uhlenbruck, Action of proteolytic enzymes on the human erythrocyte surface. Nature. Apr. 8, 1961;190:181.
Ulrich et al., Probing cellular mechanobiology in three-dimensional culture with collagenagarose matrices. Biomaterials. Mar. 2010;31(7):1875-84.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.

(56) References Cited

OTHER PUBLICATIONS

UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014,.
UniProtKB/Swiss-Prot Accession No. Q9NZQ7.1, Apr. 16, 2014.
Urbanek et al. Stem cell niches in the adult mouse heart. Proc Natl Acad Sci U S A. Jun. 13, 2006;103(24):9226-31.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1):49-55.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Vandenburgh et al., Tissue-engineered skeletal muscle organoids for reversible gene therapy. Hum Gene Ther. Nov. 10, 1996;7(17):2195-200.
Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.
Villadangos, Presentation of antigens by MHC class II molecules: getting the most out of them. Mol immunoi. Sep. 2001;38(5):329-46.
Vincent et al., Stem cell differentiation: Post-degradation forces kick in. Nat Mater. May 2013;12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
W.H.O., World Health Organization, Global Burden of Musculoskeletal Disease Revealed in new WHO Report. Bull World Health Organ. 2003;81(11):853-854.
W.H.O., World Health Organization, The World Health Report 2004: Changing History. The World Health Report, 2004:1-169.
Wakim et al., Dendritic cell-induced memory T cell activation in nonlymphoid tissues. Science. Jan. 11, 2008;319(5860):198-202.

Waldron-Lynch et al., Advances in Type 1 diabetes therapeutics: immunomodulation and beta-cell salvage. Endocrinol Metab Clin North Am. Jun. 2009;38(2):303-17.
Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Evolution of new nonantibody proteins via iterative somatic hypermutation. Proc Natl Acad Sci U S A. Nov. 30, 2004;101(48):16745-9.
Wang et al., Mechanotransduction at a distance: mechanically coupling the extracellular matrix with the nucleus. Nat Rev Mol Cell Biol. Jan. 2009;10(1):75-82.
Wang et al., Photothermal effects of supramoieculariy assembled gold nanoparticies for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Weeks et al., The effects of chemokine, adhesion and extracellular matrix molecules on binding of mesenchymal stromal cells to poly(l-lactic acid). Cytotherapy. Oct. 2012;14(9):1080-8.
Wei et al., Global mapping of H3K4me3 and H3K27me3 reveals specificity and plasticity in lineage fate determination of differentiating CD4+ T cells. Immunity. Jan. 16, 2009;30(1):155-67.
Weiner et al., Immunostimulatory oligodeoxynucieotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform, Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.
Wernig et al., Function of skeletal muscle tissue formed after myoblast transplantation into irradiated mouse muscles. J Physiol. Jan. 15, 2000;522 Pt 2:333-45.
White et al., Leukemia inhibitory factor enhances regeneration in skeletal muscles after myoblast transplantation. Muscle Nerve. May 2001;24(5):695-7.
Wieland et al., Engineering molecular circuits using synthetic biology in mammalian cells. Annu Rev Chem Biomol Eng. 2012;3:209-34.
Wipff et al., Myofibroblast contraction activates latent TGF-beta1 from the extracellular matrix. J Cell Biol. Dec. 17, 2007;179(6):1311-23.
Wong et al., Focal adhesion kinase links mechanical force to skin fibrosis via inflammatory signaling. Nat Med. Dec. 11, 2011;18(1):148-52.
Wong et al., Mechanical force prolongs acute inflammation via T-cell-dependent pathways during scar formation. FASEB J. Dec. 2011;25(12):4498-510.
Wong et al., Pushing back: wound mechanotransduction in repair and regeneration. J Invest Dermatol. Nov. 2011;131(11):2186-96.
Wozniak et al., Mechanotransduction in development: a growing role for contractility. Nat Rev Mol Cell Biol. Jan. 2009;10(1):34-43.
Wright et al., Muscle-based gene therapy and tissue engineering for the musculoskeletal system. Drug Discov Today. Jul. 1, 2000;6(14):728-733.
Wu et al., Intraperitoneal administration of poly(I:C) with polyethylenimine leads to significant antitumor immunity against murine ovarian tumors. Cancer Immunol Immunother. Aug. 2011;60(8):1085-96.

(56) References Cited

OTHER PUBLICATIONS

Xie et al., Preparation and Application of Surface-Coated Superparamagnetic Nanobeads in the Isolation of Genomic DNA. J Magn Magnetic Mater. Jun. 2004;277(1-2):16-23.
Yamazaki et al., CD8+ CD205+ splenic dendritic cells are specialized to induce Foxp3+ regulatory T cells. J Immunol. Nov. 15, 2008;181(10):6923-33.
Yancopoulos et al., Vascular-specific growth factors and blood vessel formation. Nature. Sep. 14, 2000;407(6801):242-8.
Yang et al., The effect of incorporating RGD adhesive peptide in polyethylene glycol diacrylate hydrogel on osteogenesis of bone marrow stromal cells. Biomateriais. Oct. 2005;26(30):5991-8.
Yeung et al., Effects of substrate stiffness on cell morphology, cytoskeletal structure, and adhesion. Cell Motil Cytoskeleton, Jan. 2005;60(1):24-34.
Yoo et al., Bio-inspired, bioengineered and biomimetic drug delivery carriers. Nat Rev Drug Discov. Jul. 1, 2011;10(7):521-35.
Yoon, Hidden Markov Models and their Applications in Biological Sequence Analysis. Curr Genomics. Sep. 2009;10(6):402-15.
Young et al., Gelatin as a delivery vehicle for the controlled release of bioactive molecules. J Control Release. Dec. 5, 2005;109(1-3):256-74.
Yu et al., Induced pluripotent stem cell lines derived from human somatic cells. Science, Dec. 21, 2007;318(5858):1917-20.
Yuen et al., Mimicking nature by codelivery of stimulant and inhibitor to create temporally stable and spatially restricted angiogenic zones. Proc Natl Acad Sci U S A. Oct. 19, 2010; 107(42):17933-8.
Yuk et al., Electric current-sensitive drug delivery systems using sodium alginate/polyacrylic acid composites. Pharm Res. Jul. 1992;9(7):955-7.
Zammit et al., Kinetics of myoblast proliferation show that resident satellite cells are competent to fully regenerate skeletal muscle fibers. Exp Cell Res. Nov. 15, 2002;281(1):39-49.
Zammit et al., Muscle satellite cells adopt divergent fates: a mechanism for self-renewal? J Cell Biol. Aug. 2, 2004;166(3):347-57.
Zeltinger et al., Effect of pore size and void fraction on cellular adhesion, proliferation, and matrix deposition. Tissue Eng. Oct. 2001;7(5):557-72.
Zemel et al., Optimal matrix rigidity for stress fiber polarization in stem cells. Nat Phys. Jun. 1, 2010;6(6):468-473.
Zhang et al., A comparative study of the antigen-specific immune response induced by codelivery of CpG ODN and antigen using fusion molecules or biodegradable microparticles. J Pharm Sci. Dec. 2007;96(12):3283-92.
Zhang et al., A tension-induced mechanotransduction pathway promotes epithelial morphogenesis. Nature. Mar. 3, 2011;471(7336):99-103.
Zhang et al., Generation of a syngeneic mouse model to study the effects of vascular endothelial growth factor in ovarian carcinoma. Am J Pathol. Dec. 2002;161(6):2295-309.
Zhang et al., Talin depletion reveals independence of initial cell spreading from integrin activation and traction. Nat Cell Biol. Sep. 2008;10(9):1062-8.
Zhao et al., Active scaffolds for on-demand drug and cell delivery. Proc Natl Acad Sci U S A. Jan. 4, 2011;108(1):67-72.
Zhao et al., Directed cell migration via chemoattractants released from degradable microspheres. Biomaterials. Aug. 2005;26(24):5048-63.
Zhao et al., Stress-relaxation behavior in gels with ionic and covalent crosslinks. J Appl Phys. Mar. 15, 2010;107(6):63509.
Zhou et al., Instability of the transcription factor Foxp3 leads to the generation of pathogenic memory T cells in vivo. Nat Immunol. Sep. 2009;10(9):1000-7.
Zhou et al., Microstructure and Mechanical Properties of Poly(L-lactide) Scaffolds Fabricated by Gelatin Particle Leaching Method. J Appl Polymer Sci. Nov. 5, 2005;98(3):1373-1379.
Zizzari et al., The Macrophage Galactose-Type C-Type Lectin (MGL) Modulates Regulatory T Cell Functions. PLoS One. Jul. 6, 2015;10(7):e0132617. 12 pages.

U.S. Appl. No. 13/386,950, Jan. 25, 2012, filed U.S. Pat. No. 8,728,456, Issued.
U.S. Appl. No. 16/170,313, filed Oct. 25, 2018, Pending.
U.S. Appl. No. 16/033,025, filed Jul. 11, 2018, Pending.
U.S. Appl. No. 12/867,426, filed Jan. 13, 2012, 2012-0100182, Published.
U.S. Appl. No. 15/135,255, filed Apr. 21, 2016, 2016-0220667, Allowed.
U.S. Appl. No. 15/345,131, filed Nov. 7, 2016, 2017-0182138, Published.
U.S. Appl. No. 16/121,988, filed Sep. 5, 2018, Pending.
U.S. Appl. No. 14/122,096, filed Dec. 27, 2013, U.S. Pat. No. 10,045,947, Issued.
U.S. Appl. No. 16/263,098, filed Jan. 31, 2019, Pending.
U.S. Appl. No. 12/867,426, filed Jan. 13, 2012, 2012-0100182, Allowed.
U.S. Appl. No. 15/345,131, filed Nov. 7, 2016, 2017-0182138, Allowed.
Ali et al., Inflammatory cytokines presented from polymer matrices differentially generate and activate DCs in situ.. Adv Funct Mater. Aug. 1, 2013;23(36):4621-4628.
Ali et al., Relationship of vaccine efficacy to the kinetics of DC and T-cell responses induced by PLG-based cancer vaccines. Biomater. 2011;1(1):66-75.
Annabi et al., Controlling the porosity and microarchitecture of hydrogels fortissue engineering. Tissue Eng Part B Rev. Aug. 2010;16(4):371-83.
Baskin et al., Copper-free click chemistry for dynamic in vivo imaging. Proc Natl Acad Sci U S A. Oct. 23, 2007;104(43):16793-7.
Bjork et al., Tuning the shape of mesoporous silica particles by alterations in parameter space: from rods to platelets. Langmuir. Nov. 5, 2013;29(44):13551-61.
Bojarova et al., Sugared biomaterial binding lectins: achievements and perspectives Biomater Sci. Jul. 19, 2016;4(8):1142-60.
care.diabetesjournals.org, Standards of Medical Care in Diabetes. Diabetes Care. Jan. 2013;36(Suppl 1):S1-S2.
Chapman, Endosomal proteases in antigen presentation. Curr Opin Immunol. Feb. 2006;18(1):78-84.
El-Behi et al., The encephalitogenicity of T(H)17 cells is dependent on IL-1- and IL-23-induced production of the cytokine GM-CSF. Nat Immunol. Jun. 2011;12(6):568-75.
Koo et al., Bioorthogonal copper-free click chemistry in vivo for tumor-targeted delivery of nanoparticles. Angew Chem Int Ed Engl. Nov. 19, 2012;51(47):11836-40.
Kratz, Albumin as a drug carrier: design of prodrugs, drug conjugates and nanoparticles. J Control Release. Dec. 18, 2008; 132(3):171-83.
Kupferschmidt et al., Mesoporous silica particles potentiate antigen-specific T-cell responses. Nanomedicine (Lond). 2014;9(12):1835-46.
Li et al., Mesoporous silica nanoparticles in biomedical applications. Chem Soc Rev. Apr. 7, 2012;41(7):2590-605.
Li et al., Recent advances of biomaterials in biotherapy. Regen Biomater. Jun. 2016;3(2):99-105.
Liederer et al., Enzymes involved in the bioconversion of ester-based prodrugs. J Pharm Sci. Jun. 2006;95(6):1177-95.
Lutterotti et al., Antigen-specific tolerance by autologous myelin peptide-coupled cells: a phase 1 trial in multiple sclerosis. Sci Transl Med. Jun. 5, 2013;5(188):188ra75.
Mahony et al., Mesoporous silica nanoparticles act as a self-adjuvant for ovalbumin model antigen in mice. Small. Sep. 23, 2013;9(18):3138-46.
McKay et al., Click chemistry in complex mixtures: bioorthogonal bioconjugation. Chem Biol. Sep. 18, 2014,21(9):1075-101.
McQualter et al., Granulocyte macrophage colony-stimulating factor: a new putative therapeutic target in multiple sclerosis. J Exp Med. Oct. 1, 2001;194(7):873-82.
Mehta et al., Engineering New Approaches to Cancer Vaccines. Cancer Immunol Res. Aug. 2015;3(8):836-43.
NIH—National Cancer Institute, AMP-224, anti-PD-1 fusion protein AMP-224. Retrieved online at: https://www.cancer/gov/publications/dictionaries/cancer-drug/def/anti-pd-1-fusion-protein-amp-224. 1 page, (2019).

(56) References Cited

OTHER PUBLICATIONS

Nuttelman et al., Dexamethasone-functionalized gels induce osteogenic differentiation of encapsulated hMSCs. J Biomed Mater Res A Jan. 2006;76(1):183-95.
Oneto et al., Implantable biomaterial based on click chemistry for targeting small molecules. Acta Biomaterialia. 2014;10:5099-5105.
Sheppard et al., Polyethyleneimine is a potent systemic adjuvant for glycoprotein antigens. Int Immunol. Oct. 2014;26(10):531-8.
Simmons et al., GM-CSF as a systemic adjuvant in a phase II prostate cancer vaccine trial. Prostate. Jun. 1, 1999;39(4):291-7.
Sletten et al., A hydrophilic azacyclooctyne for Cu-free click chemistry. Org Lett. Jul. 17, 2008;10(14):3097-9.
Stockmann et al., Exploring isonitrile-based click chemistry for ligation with biomolecules. Organic & Biomolecular Chemistry. 2011;9:7300-7302.
Udono, Cancer immunotherapy with blocking of immune checkpoint. Journal of Okayama Medical Association. Apr. 2013;125:13-18.
Van Berkel et al., Metal-free triazole formation as a tool for bioconjugation. Chembiochem. Sep. 3, 2007;8(13):1504-8.
Wegmann et al., Polyethyleneimine is a potent mucosal adjuvant for viral glycoprotein antigens. Nat Biotechnol. Sep. 2012;30(9):883-8.
Japanese Office Action for Application No. 2016-565339, dated Jan. 8, 2019. 9 pages.
Anderson et al., Crosslinking CD3 with CD2 using sepharose-immobilized antibodies enhances T lymphocyte proliferation. Cell Immunol. Sep. 1988;115(2):246-56.
Baroja et al., The anti-T cell monoclonal antibody 9.3 (anti-CD28) provides a helper signal and bypasses the need for accessory cells in T cell activation with immobilized anti-CD3 and mitogens. Cell Immunol. Apr. 15, 1989;120(1):205-17.
Bierer et al., T cell receptors: adhesion and signaling. Adv Cancer Res. 1991;56:49-76.
Brodie et al., In vivo migration and function of transferred HIV-1-specific cytotoxic T cells. Nat Med. Jan. 1999;5(1):34-41.
Che et al., Synthesis and characterization of chiral mesoporous silica. Nature. May 20, 2004;429(6989):281-4.
Chen et al., Morphological control of mesoporous silica SBA-15 synthesized at low temperature without additives. J Porous Mater. 2011;18:211-6.
Choi et al., Facile synthesis of high quality mesoporous SBA-15 with enhanced control of the porous network connectivity and wall thickness. Chem Commun (Camb). Jun. 21, 2003;(12):1340-1.
Cooper, A Genetic Pathogen Capture Technology for Sepsis Diagnosis. Submitted to the Department of Chemical Engineering in Partial Fulfillment of the Requirements for the Degree of Doctor of Philosophy in Medical and Engineering Physics at the Massachusetts Institute of Technology. 130 pages, May 1, 2013.
Damle et al., Stimulation via the CD3 and CD28 molecules induces responsiveness to IL-4 in CD4+CD29+CD45R-memory T lymphocytes. J Immunol. Sep. 15, 1989;143(6):1761-7.
Drury et al., Hydrogels for tissue engineering: scaffold design variables and applications. Biomaterials. Nov. 2003;24(24):4337-51.
Dudley et al., CD8+ enriched "young" tumor infiltrating lymphocytes can mediate regression of metastatic melanoma Clin Cancer Res. Dec. 15, 2010;16(24):6122-31.
Fadel et al., A carbon nanotube-polymer composite for T-cell therapy. Nat Nanotechnol. Aug. 2014;9(8):639-47.
Fadel et al., Enhanced cellular activation with single walled carbon nanotube bundles presenting antibody stimuli. Nano Lett. Jul. 2008;8(7):2070-6.
Fesnak et al., Engineered T cells: the promise and challenges of cancer immunotherapy. Nat Rev Cancer. Aug. 23, 2016;16(9):566-81.
Gao et al., Immune cell recruitment and cell-based system for cancer therapy. Pharm Res. Apr. 2008;25(4):752-68.
Garlie et al., T cells coactivated with immobilized anti-CD3 and anti-CD28 as potential immunotherapy for cancer. J Immunother. Jul. 1999;22(4):336-45.

Gimmi et al., B-cell surface antigen B7 provides a costimulatory signal that induces T cells to proliferate and secrete Interleukin 2. Proc Natl Acad Sci U S A. Aug. 1, 1991;88(15):6575-9.
Han et al., Synthesis of rod-like mesoporous silica using mixed surfactants of cetyltrimethylammonium bromide and cetyltrimethylammonium chloride as templates. Materials Letters. 2003;57:4520-4.
Harding et al., CD28-mediated signalling co-stimulates murine T cells and prevents induction of anergy in T-cell clones. Nature. Apr. 16, 1992;356(6370):607-9.
Hasan et al., Artificial Antigen Presenting Cells: An off the Shelf Approach for Generation of Desirable T-Cell Populations for Broad Application of Adoptive Immunotherapy. Advancements in Genetic Engineering. 2015;4(3):1-10.
Haso et al., Anti-CD22-chimeric antigen receptors targeting B-cell precursor acute lymphoblastic leukemia. Blood. Feb. 14, 2013;121(7):1165-74.
Hollyman et al., Manufacturing validation of biologically functional T cells targeted to CD19 antigen for autologous adoptive cell therapy. J Immunother. Feb.-Mar. 2009;32(2):169-80.
Huppa et al., T-cell-antigen recognition and the immunological synapse. Nat Rev Immunol. Dec. 2003;3(12):973-83.
Johansson, Controlling the Pore Size and Morphology of Mesoporous Silica. Linkoping Studies in Science and Technology Licentiate Thesis No. 1451, 53 pages, (2010).
June et al., Adoptive cellular therapy: a race to the finish line. Sci Transl Med. Mar. 25, 2015;7(280):280ps7.
June et al., The B7 and CD28 receptor families. Immunol Today. Jul. 1994;15(7):321-31.
Kosuge et al., Morphological Control of Rod- and Fiberlike SBA-15 Type Mesoporous Silica Using Water-Soluble Sodium Silicate Chem Mater. 2004;16:899-905.
Lee et al., The immunological synapse balances T cell receptor signaling and degradation. Science. Nov. 14, 2003;302(5648):1218-22.
Levine et al., Effects of CD28 costimulation on long-term proliferation of CD4+ T cells in the absence of exogenous feeder cells. J Immunol. Dec. 15, 1997;159(12):5921-30.
Li et al., The effect of surface modification of mesoporous silica micro-rod scaffold on immune cell activation and infiltration. Biomaterials. Mar. 2016;83:249-56.
Liao et al., Synthesis of mesoporous silica nanoparticle-encapsulated alginate microparticles for sustained release and targeting therapy. J Biomed Mater Res B Appl Biomater. Feb. 2014;102(2):293-302.
Lindstein et al., Regulation of lymphokine messenger RNA stability by a surface-mediated T cell activation pathway. Science. Apr. 21, 1989;244(4902):339-43.
Linsley et al., The role of the CD28 receptor during T cell responses to antigen. Annu Rev Immunol. 1993;11:191-212.
Mandal et al., Polymer-based synthetic dendritic cells for tailoring robust and multifunctional T cell responses. ACS Chem Biol. Feb. 20, 2015;10(2):485-92.
Maus et al., Ex vivo expansion of polyclonal and antigen-specific cytotoxic T lymphocytes by artificial APCs expressing ligands for the T-cell receptor, CD28 and 4-1BB. Nat Biotechnol Feb. 2002;20(2):143-8.
Melief et al., T-cell immunotherapy of tumors by adoptive transfer of cytotoxic T lymphocytes and by vaccination with minimal essential epitopes. Immunol Rev. Jun. 1995;145:167-77.
Weng et al.. Use of a lipid-coated mesoporous silica nanoparticle platform for synergistic gemcitabine and paclitaxel delivery to human pancreatic cancer in mice. ACS Nano. 2015;9(4):3540-57.
Meyer et al., Biodegradable nanoellipsoidal artificial antigen presenting cells for antigen specific T-cell activation. Small. Apr. 2015;11(13):1519-25.
NCBI, MeSH. Nivolumab. Retrieved online at: https:/fwww.ncbi.nlm.nih/gov/mesh/?term=nivolumab. 3 pages, (2010).
Perica et al., Enrichment and Expansion with Nanoscale Artificial Antigen Presenting Cells for Adoptive Immunotherapy. ACS Nano Jul. 28, 2015;9(7):6861-71.
Qiao et al., Synthesis and Bio-adsorptive Properties of Large-Pore Periodic Mesoporous Organosilica Rods. Chem Mater. 2005;17:6172-6.

(56) References Cited

OTHER PUBLICATIONS

Qin et al., CD22-Targeted Chimeric Antigen Receptor (CAR) T Cells Containing the 4-1BB Costimulatory Domain Demonstrate Enhanced Persistence and Superior Efficacy Against B-Cell Precursor Acute Lymphoblastic Leukemia (ALL) Compared to Those Containing CD28. Blood. 2013;122:1431.
Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.
Riddell et al., Principles for adoptive T cell therapy of human viral diseases. Annu Rev Immunol. 1995;13:545-86.
Riddell et al., Restoration of viral immunity in immunodeficient humans by the adoptive transfer of T cell clones. Science Jul. 10, 1992;257(5067)238-41.
Riddell et al., The use of anti-CD3 and anti-CD28 monoclonal antibodies to clone and expand human antigenspecific T cells. J Immunol Methods Apr. 17, 1990;128(2):189-201.
Rosenberg et al., Adoptive cell transfer as personalized immunotherapy for human cancer. Science. Apr. 3, 2015;348(6230):62-8.
Rosenberg et al., Durable complete responses in heavily pretreated patients with metastatic melanoma using T-cell transfer immunotherapy. Clin Cancer Res. Jul. 1, 2011;17(13):4550-7.
Rubbi et al., Evidence of surface antigen detachment during incubation of cells with immunomagnetic beads. J Immunol Methods. Dec. 3, 1993;166(2)233-41.
Schwartz, A cell culture model for T lymphocyte clonal anergy. Science. Jun. 15, 1990;248(4961):1349-56.
U.S. Appl. No. 15/434,781, filed Feb. 16, 2017, 2017-0246281, Published.
U.S. Appl. No. 15/564,905, filed Oct. 6, 2017, 2018-0164298, Published.
U.S. Appl. No. 15/303,985, filed Oct. 13, 2016, 2017-0042995, Published.
U.S. Appl. No. 15/818,509, filed Nov. 20, 2017, 2018-0289789, Published.
U.S. Appl. No. 15/563,878, filed Oct. 2, 2017, 2018-0117171, Published.
Shibuya et al., Anti-CD3/anti-CD28 bead stimulation overcomes CD3 unresponsiveness in patients with head and neck squamous cell carcinoma. Arch Otolaryngol Head Neck Surg. Apr. 2000;126(4):473-9.
Singh et al., Hydrogels and scaffolds for immunomodulation. Adv Mater. Oct. 2014;26(38):6530-41.
Springer et al., The lymphocyte function-associated LFA-1, CD2, and LFA-3 molecules: cell adhesion receptors of the immune system. Annu Rev Immunol. 1987;5:223-52.
Steenblock et al., A comprehensive platform for ex vivo T-cell expansion based on biodegradable polymeric artificial antigen-presenting cells. Mol Ther. Apr. 2008;16(4):765-72.
Steenblock et al., An artificial antigen-presenting cell with paracrine delivery of IL-2 impacts the magnitude and direction of the T cell response. J Biol Chem. Oct. 7, 2011;286(40):34883-92.
Sunshine et al., Particle shape dependence of CD8+ T cell activation by artificial antigen presenting cells. Biomaterials. Jan. 2014;35(1):269-277.
Thielemann et al., Pore structure and surface area of silica SBA-15: influence of washing and scale-up. Beilstein J Nanotechnol. 2011;2:110-8.
Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. 2015;126:184.
Turtle et al., CD19 Car-T cells of defined CD4+:CD8+ composition in adult B cell ALL patients. J Clin Invest. Jun. 1, 2016;126(6):2123-38.
Wang et al., Mouse CD229 Ligation Co-stimulates T Cell Activation. The Journal of Immunology. May 2012;188(suppl 1):176.7.

Yee et al., Melanocyte destruction after antigen-specific immunotherapy of melanoma: direct evidence of t cell-mediated vitiligo. J Exp Med Dec. 4, 2000;192(11):1637-44.
Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.
U.S. Appl. No. 15/434,781, filed Feb. 16, 2017, 2017-0246281, Allowed.
U.S. Appl. No. 17/015,177, filed Sep. 9, 2020, Pending.
U.S. Appl. No. 15/546,905, filed Oct. 6, 2017, 2018-0164298, Published.
U.S. Appl. No. 13/638,796, filed Dec. 13, 2006, U.S. Pat. No. 8,067,237, Issued.
U.S. Appl. No. 15/135,207, filed Apr. 21, 2016, 10,149,897, Issued.
U.S. Appl. No. 16/170,313, filed Oct. 25, 2018, 2019-0125849, Published.
U.S. Appl. No. 15/617,837, filed Jun. 8, 2017, 2018-0243231, Published.
Andersson et al., HSP70 promoter-driven activation of gene expression for immunotherapy using gold nanorods and near infrared light. Vaccines (Basel). Mar. 25, 2014;2(2):216-27.
Bhardwaj et al., TLR Agonists: Are They Good Adjuvants? Cancer J. 2010;16(4):382-391.
Casanova et al., Human Mannose-binding Lectin in Immunity: Friend, Foe, or Both?. J Exp Med. 2004;199(10):1295-1299.
Chao et al., Morphological control on SBA-15 mesoporous silicas via a slow self-assembling rate. J Mater Sci. 2009;44:6453-62.
Chen et al., Enhanced humoral and cell-mediated immune responses generated by cationic polymer-coated PLA microspheres with adsorbed HBsAg. Mol Pharm. Jun. 2, 2014;11(6):1772-84.
Chen et al., Quantitative proteomic profiling of pancreatic cancer juice. Proteomics. Jul. 2006;6(13):3871-9.
Cheung et al., Engineered Materials for Cancer Immunotherapy. Nano Today. Aug. 1, 2015;10(4):511-531.
Cheung et al., Scaffolds that mimic antigen-presenting cells enable ex vivo expansion of primary T cells. Nat Biotechnol. Feb. 2018;36(2):160-169.
Del Chiaro et al., Early detection and prevention of pancreatic cancer: is it really possible today? World J Gastroenterol. Sep. 14, 2014;20(34):12118-31.
Dengler et al., Mesoporous silica-supported lipid bilayers (protocells) for DNA cargo delivery to the spinal cord. J Control Release. Jun. 10, 2013;168(2):209-24.
Egea et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.
Eggermont et al., Towards efficient cancer immunotherapy: advances in developing artificial antigen-presenting cells. Trends Biotechnol. Sep. 2014;32(9):456-65.
Grabowska et al., Systemic in vivo delivery of siRNA to tumours using combination of polyethyleneimine and transferrin-polyethyleneimine conjugates. Biomater Sci. Nov. 2015;3(11):1439-48.
Jiang, Application of polymers in nucleic acid delivery. Thesis in partial fulfillment of the requirements for the Doctor of Philosophy degree in Pharmacy in the Graduate College of the University of Iowa. 138 pages, Dec. 2011.
John et al., Passive and active mechanisms trap activated CD8+ T cells in the liver. J Immunol. May 1, 2004;172(9):5222-9.
Lacy et al., Cytokine release from innate immune cells: association with diverse membrane trafficking pathways. Blood. 2011;118(1):9-18.
Liu et al., Fecal markers, intestinal inflammation and inflammatory enteritis. Clinical Journal of Digestive Disease. 2003;15(6):275-7.
Liu et al., Porous nanoparticle supported lipid bilayers (protocells) as delivery vehicles. J Am Chem Soc. Feb. 4, 2009;131(4):1354-5.
Millar et al., Prediction of local recurrence, distant metastases, and death after breast-conserving therapy in early-stage invasive breast cancer using a five-biomarker panel. J Clin Oncol. Oct. 1, 2009;27(28):4701-8.

(56) References Cited

OTHER PUBLICATIONS

Milone et al., Powered and controlled T-cell production. Nat Biomed Eng. Mar. 2018;2(3):148-150.
Mu et al., Identification and characterization of a mannose-binding lectin from Nile tilapia (*Oreochromis niloticus*). Fish Shellfish Immunol. 2017;67:244-253.
Stanley et al., Transjugular intrahepatic portosystemic shunt as a treatment for protein-losing enteropathy caused by portal hypertension. Gastroenterology. Dec. 1996;111(6):1679-82.
Stephen et al., Biopolymer implants enhance the efficacy of adoptive T-cell therapy. Nat Biotechnol. Jan. 2015;33(1):97-101.
Sunshine et al., Nanoengineering approaches to the design of artificial antigen-presenting cells. Nanomedicine. 2013;8(7):1173-89.
Takamura et al., Regulatory role of lymphoid chemokine CCL19 and CCL21 in the control of allergic rhinitis. J Immunol. 2007;179(9):5897-5906.
Yu, Designed synthesis of mono-dispersed silica-based nanostructures and their applications in drug/gene delivery. A thesis submitted for the degree of Doctor of Philosophy at the University of Queensland in 2014, 196 pages.
U.S. Appl. No. 15/434,781, filed Feb. 16, 2017, U.S. Pat. No. 10,813,988, Issued.
U.S. Appl. No. 17/015,177, filed Sep. 9, 2020, 2021-0170007, Published.
U.S. Appl. No. 13/386,950, filed Jan. 25, 2012, U.S. Pat. No. 8,728,456, Issued.
U.S. Appl. No. 14/185,494, filed Feb. 20, 2014, U.S. Pat. No. 9,381,235, Issued.
U.S. Appl. No. 15/147,442, filed May 5, 2016, U.S. Pat. No. 10,080,789, Issued.
U.S. Appl. No. 16/121,988, filed Sep. 5, 2018, 2019-0183992, Published.
U.S. Appl. No. 15/564,905, filed Oct. 6, 2017, 2018-0164298, Allowed.
U.S. Appl. No. 16/316,778, filed Jan. 10, 2019, 2019-0292517, Published.
U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,213, filed Apr. 21, 2016, U.S. Pat. No. 10,137,184, Issued.
U.S. Appl. No. 16/170,313, filed Oct. 25, 2018, U.S. Pat. No. 11,096,997, Issued.
U.S. Appl. No. 17/381,031, filed Jul. 20, 2021, Pending.
U.S. Appl. No. 13/877,572, filed Nov. 19, 2013, 2014-0079752, Published.
U.S. Appl. No. 14/112,096, filed Dec. 27, 2013, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Abandoned.
U.S. Appl. No. 16/033,025, filed Jul. 11, 2018, 2019-0076373, Published.
U.S. Appl. No. 17/083,720, filed Oct. 29, 2020, 2021-0205233, Published.
U.S. Appl. No. 14/394,552, filed Oct. 15, 2014, U.S. Pat. No. 9,937,249, Issued.
U.S. Appl. No. 15/935,392, filed Mar. 26, 2018, 2018-0344821, Published.
U.S. Appl. No. 15/303,985, filed Oct. 13, 2016, U.S. Pat. no. 10,682,400, Issued.
U.S. Appl. No. 16/877,274, filed May 18, 2020, 2020-0276290, Published.
U.S. Appl. No. 16/263,098, filed Jan. 31, 2019, 2019-0216910, Published.
U.S. Appl. No. 12/867,426, filed Jan. 13, 2012, U.S. Pat. No. 10,328,133, Issued.
U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-0220668, Abandoned.
U.S. Appl. No. 13/510,356, filed May 17, 2012, Abandoned.
U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, U.S. Pat. No. 9,821,045, Issued.
U.S. Appl. No. 15/818,509, filed Nov. 20, 2017, U.S. Pat. No. 10,568,949, Issued.
U.S. Appl. No. 15/563,878, filed Oct. 2, 2017, 2018-0117171, Abandoned.
U.S. Appl. No. 16/075,937, filed Aug. 6, 2018, 2019-0060525, Published.
Ennett, Temporal Delivery of Multiple Growth Factors from Polymer Scaffolds to Enhance Neovascularization. A dissertation submitted in partial fulfillment of the requirements for the degree of Doctor of Philosophy (Biomedical Engineering) in the University of Michigan. 186 pages, (2004).
Kim et al., Galectin-3 binding protein promotes cell motility in colon cancer by stimulating the shedding of protein tyrosine phosphatase kappa by proprotein convertase 5. Biochem Biophys Res Commun. Jan. 7, 2011;404(1):96-102.
Lauw et al., Proinflammatory effects of IL-10 during human endotoxemia. J Immunol. Sep. 1, 2000;165(5):2783-9.
Veldhoen et al., TGFbetal, a "Jack of all trades": the link with pro-inflammatory IL-17-producing T cells. Trends Immunol. Aug. 2006;27(8):358-61.
Wegman et al., Combination of bone morphogenetic protein-2 plasmid DNA with chemokine CXCL12 creates an additive effect on bone formation onset and volume. Eur Cell Mater. Jul. 27, 2015;30:1-11.
Yu et al., Specific bone cells produce DLL4 to generate thymus-seeding progenitors from bone marrow. J Exp Med. May 4, 2015;212(5):759-74.

\* cited by examiner

GM-CSF

Scaffold
Nuclei
CD11c

Tumor growth curves

Flow cytometry plots of
CD8 T cell response
D21 after inoculation

PERITUMORAL AND INTRATUMORAL MATERIALS FOR CANCER THERAPY

CROSS-REFERENCE TO RELATED APPLICATIONS

This application is a national stage application filed under 35 U.S.C. § 371, of International Patent Application No. PCT/US2016/015825, filed on Jan. 29, 2016, which claims the benefit of and priority to U.S. Provisional Application No. 62/110,203, filed on Jan. 30, 2015, the entire contents of each of which are incorporated herein by reference.

STATEMENT REGARDING FEDERALLY SPONSORED RESEARCH OR DEVELOPMENT

This invention was made with government support under 5R01EB015498-02 awarded by the National Institutes of Health. The government has certain rights in the invention.

REFERENCE TO THE SEQUENCE LISTING

This application incorporates-by-reference nucleotide and/or amino acid sequences which are present in the file named "29297-127N01US SEQUENCE LISTING.txt" which is 53.9 kilobytes in size, and which was created Jul. 27, 2017 in the IBM-PC machine format, having an operating system compatibility with MS-Windows, which is contained in the text file filed Jul. 27, 2017 as part of this application.

BACKGROUND OF THE INVENTION

Traditional immune therapy for cancers has so far had limited success. Tumors can evade otherwise effective T cell responses by employing potent immunosuppressive mechanisms within their local environment. Both host- and tumor-related mechanisms can lead to a failure to mount a proper anti-tumor-specific immune response, and these are frequently key factors in limiting the success of cancer immunotherapy.

BRIEF SUMMARY OF THE INVENTION

The invention provides a solution to this longstanding problem in the field of cancer immunotherapy. A flexible injectable biomaterial cryogel or hydrogel (such as a click hydrogel) is administered into a tumor or to an anatomical location in the proximity of a tumor, e.g., in direct contact with the tumor/touching the tumor, within about 10, 9, 8, 7, 6, 5, 4, 3, 2, or 1 mm of a tumor, or into the tumor mass itself. to deliver immune modulating agents directly to the site of a growing tumor to facilitate cancer immunotherapy while bypassing systemic delivery (which can be associated with adverse side effects) and without loading a tumor antigen or tumor lysate into the delivery device prior to administration, e.g., injection, to a patient. Accordingly, the device (e.g., a cryogel or hydrogel) is administered in a peritumoral or intratumoral manner. Peritumoral delivery substantially surrounds (50, 75, 85, 95, 99-100% of the perimeter of a tumor mass) the tumor with the device/gel, either by direct physical contact or in close proximity to the tumor mass boundary. Intratumoral delivery is carried out by direct administration into a tumor mass through the boundary between tumor and normal tissue. For example, the biomaterial may be administered adjacent to but without compromising the integrity, e.g. piercing, of a tumor capsule, e.g., in the case of a solid tumor. Alternatively, the tumor capsule is compromised or pierced (intratumoral injection). In some embodiments, the tumor completely or partially envelopes a device or scaffold that is placed touching or proximal to the tumor. In such embodiments, the device or scaffold reshapes immune cell localization at or within the tumor. The present subject matter also relates to the administration of the biomaterial directly into the tumor (intratumoral), e.g., using a needle. Any tumor that can be diagnosed by taking a needle biopsy is treated in this manner. For example, tumors to be treated include breast, brain, lung, prostate, liver, bone, thyroid, skin, cervical, ovarian, endometrial, colon, bladder, and additional tumor types described below.

In various embodiments, the tumor is a solid tumor or a discrete tumor within defined, detectable boundaries. Accordingly, the present subject matter provides a method of reducing tumor-mediated immune evasion comprising administering to a tumor site (e.g., into a tumor (touching) or to a site adjacent to or in the proximity of a solid or discrete tumor mass) a biodegradable porous polymeric device comprising an inhibitor of T cell or dendritic cell suppression. For example, the inhibitor comprises a Transforming Growth Factor-Beta (TGF-β) pathway inhibitor, a Signal Transducer and Activator of Transcription 3 (STAT3) pathway inhibitor or an indoleamine-pyrrole 2,3-dioxygenase (IDO or INDO EC 1.13.11.52) inhibitor. In some examples, the inhibitor comprises at least one small molecule such as the TGF-β pathway inhibitor LY2157299, GW788388, LY364947, R268712, RepSox, SB525334, and SD208; and/or the STAT3 pathway inhibitor BP-1-102, S3I-M2001, STA-21, S3I-201, Stattic, Galiellalactone, a polypeptide having the sequence PY*LKTK (where Y* represents phosphotyrosine; SEQ ID NO: 1), and a polypeptide having the sequence Y*LPQTV (where Y* represents phosphotyrosine; SEQ ID NO: 2); and/or the IDO inhibitor INCB24360, NLG919 (also known as GDC-0919), Norharmane, Rosmarinic Acid, 1-Methyltryptophan, and indoximod. In another example, the inhibitor comprises a blocker of an immune checkpoint protein such as programmed cell death 1 protein (PD-1), PD-1 ligand 1 (PD-L1), Cytotoxic T-lymphocyte-associated antigen 4 (CTLA-4), lymphocyte activation gene-3 (LAG-3), Cluster of Differentiation 276 (CD276; also known as B7-H3), and/or T-cell immunoglobulin domain and mucin domain 3 (TIM3) inhibitors. In some embodiments, the inhibitor of an immune checkpoint protein includes an anti-PD-1 antibody, an anti-PD-L1 antibody, and/or an anti-CTLA-4 antibody. In preferred embodiments, the device does not comprise a tumor antigen, e.g., a patient-derived tumor antigen or tumor cell lysate (or other tumor antigen), prior to administration to the tumor location of a subject.

The device contains nanopores, micropores, macropores, or a combination thereof. The size of micropores and macropores permits cell migration or movement (e.g., immune cell, e.g., DC migration into and/or egress out of the delivery vehicle) through the micropores and macropores. For example, the composition comprises pores that are characterized by a diameter of 1-600 µm (e.g., 10-600 µm, 20-600 µm, 50-600 µm, 10-500 µm, 20-500 µm, 50-500 µm, or 10-300 µm).

In some situations, the device further comprises a chemotherapeutic agent that induces death, e.g., immunogenic cell death, of tumor cells. Immunogenic cell death is a form of cell death that is recognized by the immune system and results in immune activation (as opposed to apoptosis as seen with most other chemotherapeutics). In this form of cell death, calreticulin is presented on the surface of dying cells allowing tumor antigen to be engulfed; high mobility group box 1 protein (HMGB1) is released which results in toll-like receptor-4 (TLR-4) stimulation on dendritic cells to cause their maturation; and release of ATP from the dying cells resulting in recruitment of antigen presenting cells into the tumor bed. Such chemotherapeutic agents include members of the anthracycline class of compounds, e.g., doxorubicin, daunorubicin, epirubicin, idarubicin, and valrubicin as well as mitoxantrone, an anthracycline analog. This class of compounds is preferred due to their ability to activate the immune system, in addition to directly killing cancer cells. The agents oxaliplatin and cyclophosphamide also lead to immunogenic cell death. Other non-limiting examples of compounds that induce immunogenic cell death include shikonin, the proteasome inhibitor bortezomib, 7A7 (an epidermal growth factor receptor-specific antibody), cardiac glycosides, and vorinostat (a histone deacetylase inhibitor). See, e.g., H Inoue and K Tani (2014) Cell Death and Differentiation 21, 39-49, the entire content of which is hereby incorporated herein by reference. In addition to chemotherapy drugs, the device is utilized in combination with radiation therapy, which also leads to immunogenic cell death, as well as other approaches that kill tumor cells while activating immune responses to the tumor.

Optionally, the scaffold further comprises a hyperthermia-inducing composition. Suitable hyperthermia-inducing compositions include a magnetic nanoparticle or a near infrared (NIR) absorbing nanoparticle. In some cases, the nanoparticle is magnetic, and the method further comprises contacting the magnetic nanoparticle with an alternative magnetic field (AMF) to induce local hyperthermia in situ, thereby altering or disrupting the cancer cell and producing a processed tumor antigen. In another example, the method further comprises contacting the NIR nanoparticle with NIR radiation to induce local hyperthermia in situ, thereby altering or disrupting the cancer cell and producing a processed tumor antigen. Hyperthermia is characterized by a local temperature of greater than 37 degrees Celsius (° C.). For example, the temperature of the device is temporarily heated to about 40, 45, 50, 60, 70, 75, 80, 85, 90, 95° C. or more. In some embodiments, the hyperthermia-inducing composition is on the surface of a device or scaffold of the invention, e.g., the device of scaffold is coated with the hyperthermia-inducing composition. In various embodiments, the hyperthermia-inducing composition is within or throughout a device or scaffold.

In some embodiments, the scaffold further comprises a radioactive isotope. Suitable radioactive isotopes include iodine-131, iodine-125, rhenium-185, phosphorous-33, phosphorous-32, palladium-100, palladium-101, palladium-201, palladium-103, palladium-105, palladium-106, palladium-108, palladium-109, palladium-110, palladium-111, palladium-112, caesium-137, iridium-192, cobalt-60, lutetium-177, yttrium-90, thallium-201, gallium-67, technetium-99m, strontium-90, or strontium-89. In some embodiments, the radioactive isotope is on the surface of a device or scaffold of the invention, e.g., the device of scaffold is coated with the radioactive isotope. In various embodiments, the radioactive isotope composition is within or throughout a device or scaffold.

In some examples, the tumor comprises a discrete tumor with defined boundaries. In various embodiments, the tumor is a solid tumor or localized tumor mass. For example, the biomaterial-containing device is placed directly onto the tumor mass, into the tumor mass, or adjacent to the tumor mass (i.e., physically in contact with or in close proximity to) the tumor mass itself rather than at a site remote (e.g., more than 10 mm from) from the tumor mass, e.g., placed under the skin at a site remote from the tumor. Using the system described above, there is no need for patient-derived material, e.g., a patient-derived or biopsied tumor lysate or processed antigen, as a component of the device that serves as a tumor antigen, because dying tumor cells themselves provide any antigen required for generation of an adaptive immune cell response. In some embodiments, the scaffold or device does not comprise a tumor antigen prior to being administered to the subject.

Aspects of the present subject matter relate to the treatment of solid tumors. For example, the tumor is of a cancer that is other than a cancer of blood cells, such as leukemia. In certain embodiments, the cancer is metastatic. In various embodiments, the tumor is a skin cancer, such as melanoma. Implementations of the present subject matter relate to the treatment of cancer for which tumors may be biopsied (while avoiding the need for a biopsy to, e.g., produce a tumor antigen such as tumor cell lysate). In some embodiments, the tumor is a sarcoma or carcinoma tumor. Non-limiting tumors which may be targeted in embodiments of the present subject matter include breast cancer, testicular cancer, prostate cancer, ovarian cancer, pancreatic cancer, lung cancer, thyroid cancer, liver cancer (e.g., non-small cell lung cancer), colon, esophagus cancer, stomach cancer, cervical, brain cancer, renal cancer, retinoblastoma, osteosarcoma, osteosarcoma, chondroblastoma, chondrosarcoma, Ewing sarcoma, Wilms tumor, malignant rhabdoid, hepatoblastoma, hepatocellular carcinoma, neuroblastoma, medulloblastoma, glioblastoma, adrenocortical carcinoma, nasopharyngeal carcinoma, rhabdomyosarcoma, desmoid, fibrosarcoma, or liposarcoma tumor. In embodiments relating to the injection of a device of scaffold of the invention, the needle may be guided visually and/or with the assistance of an imaging device such as an X-ray (e.g., using a computerized tomography (CT) scan), ultrasound, endoscope, or laparoscope device.

The methods and biomaterial devices of the present subject matter are useful for treating any vertebrate subject who suffers from a tumor. In various embodiments, the subject is an amphibian, reptile, equine, mammal, rodent, canine, feline, avian, porcine, or primate subject. For example, human medical and veterinarian implementations of the present subject matter are provided. In certain embodiments, the subject is a dog, a cat (such as a domesticated cat or a cat such as a lion, a tiger, a leopard, or a cheetah), a guinea pig, a pig, a horse, a donkey, a mule, a mouse, a rat, a monkey, a chimpanzee, a gorilla, an orangutan, a bear (such as a panda bear), or a camel. The present subject also provides animals other than humans comprising a biomaterial device disclosed herein.

Also within the present subject matter is a biomaterial device comprising the active components described above. In some embodiments, the biomaterial device contains an immunostimulatory compound. In certain embodiments, the biomaterial further comprises one or more of (i) a compound that causes immunological cell death of a tumor cell; (ii) a compound that inhibits T cell or dendritic cell suppression; and (iii) a cytokine (e.g., a chemoattractant of immune cells, such as dendritic cells).

In some embodiments, the immunostimulatory compound is a CpG oligonucleotide, poly (I:C), monophosphoryl lipid A (MPLA), imiquimod, or a cyclic dinucleotide (such as a cyclic purine dinucleotide). Non-limiting examples of cyclic dinucleotides are described in U.S. Patent Application Publication No. 2014/0205653, published Jul. 24, 2014. Cyclic-di-nucleotides (CDNs) include, but are not limited to, c-diadenosine monophosphate (AMP), c-di-guanosine monophosphate (GMP), c-di-inosine monophosphate (IMP), c-AMP-GMP, c-AMP-IMP, and c-GMP-IMP, and analogs thereof including, but not limited to, phosphorothioate analogues, referred to herein as "thiophosphates". Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA Polymerase 1 exonuclease, nucleases 51 and P1, RNases, serum nucleases and snake venom phosphodiesterase. In addition, the potential for crossing the lipid bilayer increases. A phosphorothioate linkage in inherently chiral. The skilled artisan will recognize that the phosphates in this structure may each exist in R or S forms. Thus, Rp,Rp, Sp,Sp, and Rp,Sp forms are possible. In each case, preferred are substantially pure Rp,Rp and Rp,Sp diastereomers of these molecules. Examples of such CDN thiophosphate molecules include thiophosphate forms of Rp,Rp-c-di-adenosine monophosphate; Rp,Sp-c-di-adenosine monophosphate; Rp,Rp-c-di-guanosine monophosphate and Rp,Sp-c-di-guanosine monophosphate.

In some embodiments, the compound that causes immunological cell death is doxorubicin, mitoxantrone, oxaliplatin, or paclitaxel. In some embodiments, the compound that inhibits T cell or dendritic cell suppression is a TGF-β inhibitor, a STAT3 inhibitor, an IDO inhibitor, an anti-PD-1 antibody, or an anti-CTLA-4 antibody.

In some embodiments, the cytokine is GM-CSF, Flt3L, XCL1, IL-2, or IL-12.

In various embodiments, a device or scaffold of the present subject matter comprises a mRNA or expression vector that encodes a protein such as an immunostimulatory compound or a cytokine. The mRNA or expression vector may be combined in the device or scaffold with the polypeptide it encodes, or without the polypeptide it encodes. In some embodiments, a device or scaffold comprises a mRNA molecule or an expression vector that encodes a cytokine described herein, such as a cytokine that attracts a dendritic cell into the device or scaffold. In certain embodiments, the mRNA or expression vector is condensed to facilitate delivery to cells of the subject. In various embodiments, the mRNA or expression vector may be present in a device or scaffold with a transfection agent. For example, the mRNA or expression vector may be condensed with polyethylimine (PEI), poly-L-lysine (PLL), or a polyamidoamine (PAMAM) dendrimer. See, e.g., Huang et al. (2005) Human Gene Therapy 16:609-617. Additional non-limiting examples of transfection agents include liposomes (e.g., lipofectamine).

Aspects of the present subject matter provide a method of reducing tumor-mediated immune evasion comprising administering to a tumor site a biodegradable porous polymeric device comprising (a) an inhibitor of T cell or dendritic cell suppression or (b) an immunostimulatory compound, wherein said device lacks a tumor antigen prior to administration to a subject.

In some embodiments, the device comprises an inhibitor of T cell or dendritic cell suppression.

In some embodiments, the device comprises an immunostimulatory compound.

In some embodiments, said inhibitor comprises a transforming growth factor-beta (TGF-β) pathway inhibitor, or a signal transducer and activator of transcription 3 (STAT3) pathway inhibitor.

In some embodiments, said inhibitor comprises a small molecule, an aptamer, a protein, an RNAi molecule, an antibody, or an antibody fragment.

In some embodiments, the small molecule is an organic compound having a molecular weight less than 1000 Daltons.

In some embodiments, said TGF-β pathway inhibitor comprises LY2157299 GW788388, LY364947, R268712, RepSox, SB525334, or SD208 and said STAT3 pathway inhibitor comprises BP-1-102, S3I-M2001, STA-21, S3I-201, Stattic, Galiellalactone, a polypeptide having the sequence PY*LKTK (where Y* represents phosphotyrosine) (SEQ ID NO:1), and a polypeptide having the sequence Y*LPQTV (where Y* represents phosphotyrosine) (SEQ ID NO: 2).

In some embodiments, said inhibitor comprises an inhibitor of an immune checkpoint.

In some embodiments, the inhibitor of an immune checkpoint is a PD-1 pathway inhibitor, a LAG-3 pathway inhibitor, an IDO pathway inhibitor, a B7-H3 pathway inhibitor, or a TIM3 pathway inhibitor.

In some embodiments, said inhibitor is a small molecule, an aptamer, a protein, an RNAi molecule, an antibody, or an antibody fragment.

In some embodiments, the small molecule is an organic compound having a molecular weight less than 1000 Daltons.

In some embodiments, the inhibitor is an antibody.

In some embodiments, said antibody comprises an anti-PD-1 antibody, an anti-PD-L1 antibody, or an anti-CTLA-4 antibody.

In some embodiments, the anti-PD-1 antibody is nivolumab, pembrolizumab, or pidilizumab.

In some embodiments, the anti-PD-L1 antibody is BMS-936559 or MPDL3280A.

The method of claim 13, wherein the anti-CTLA-4 antibody is ipilimumab.

The method of claim 12, therein the antibody is a Fv, Fab, Fab', Fab'-SH, F (ab')2, diabody, a linear antibodies or a scFv.

In some embodiments, the antibody is a polyclonal antibody, a monoclonal antibody, a chimeric antibody, a humanized antibody, or a human antibody.

In some embodiments, said inhibitor is an IDO inhibitor.

In some embodiments, said IDO inhibitor is an IDO1 inhibitor.

In some embodiments, said inhibitor is a small molecule, an aptamer, a protein, a RNAi molecule, an antibody, or an antibody fragment.

In some embodiments, the small molecule is an organic compound having a molecular weight less than 1000 Daltons.

In some embodiments, the small molecule is INCB24360 or NLG919.

In some embodiments, said device further comprises an immunogenic cell death-inducing chemotherapeutic agent.

In some embodiments, said chemotherapeutic agent comprises a member of the anthracycline class of compounds.

In some embodiments, said chemotherapeutic agent comprises doxorubicin.

In some embodiments, said tumor comprises a solid tumor or localized tumor mass.

In some embodiments, said device does not comprise a purified tumor antigen or tumor cell lysate prior to administration to said tumor site.

In some embodiments, said device comprises a hydrogel.

In some embodiments, said device comprises a cryogel.

In some embodiments, said cryogel comprises pores.

In some embodiments, said device comprises a methacrylated gelatin cryogel or a click alginate cryogel.

In some embodiments, said device comprises an alginate hydrogel.

In some embodiments, the alginate hydrogel is an alginate cryogel.

In some embodiments, said alginate hydrogel comprises a click alginate.

In some embodiments, the device is administered via injection.

In some embodiments, the device is injected into the tumor.

In some embodiments, the device is injected to a site in the subject within about 0.1-10 mm from the tumor.

In some embodiments, the device further comprises a cytokine or a mRNA or expression vector encoding a cytokine.

In some embodiments, the cytokine is granulocyte macrophage colony-stimulating factor (GM-CSF), FMS-like tyrosine kinase 3 ligand (Flt3L), Chemokine (C-C Motif) Ligand 20 (CCL20), Interleukin 15 (IL-15), Chemokine (C Motif) Ligand 1 (XCL1), Chemokine (C-X-C Motif) Ligand 10 (CXCL10), Interferon Alpha 1 (IFN-alpha), Interferon Beta (IFN-beta), or Interleukin 12 (IL-12).

In some embodiments, the device further comprises an immunostimulatory compound.

In some embodiments, the immunostimulatory compound is CpG, polyinosine-polycytidylic acid (poly (I:C)) PEI-poly (I:C), polyadenylic-polyuridylic acid (poly (A:U)), PEI-poly (A:U), double stranded ribonucleic acid (RNA), monophosphoryl lipid A (MPLA), Imiquimod, or an immunostimulatory antibody.

In some embodiments, the device has a volume of about 50, 60, 70, 80, 90, 100, 200, 300, 400, 500, or 50-500 µl or less than about 50, 60, 70, 80, 90, 100, 200, 300, 400, 500, or 50-500 µl.

In some embodiments, said device further comprises laponite.

Aspects of the present subject matter provide a method of treating a subject afflicted with a tumor, comprising administering to a tumor site a biodegradable porous polymeric device comprising (a) an inhibitor of T cell or dendritic cell suppression or (b) and immunostimulatory compound, wherein said device lacks a tumor antigen prior to administration to a subject.

In some embodiments, the device comprises an inhibitor of T cell or dendritic cell suppression.

In some embodiments, the device comprises an immunostimulatory compound.

In some embodiments, treating the subject comprises (a) reducing the volume of the tumor; (b) reducing the growth of the tumor; (c) reducing metastasis of the tumor; (d) increasing the survival of the subject; (e) increasing the progression free survival of the subject; (f) increasing a T cell response to an antigen within the tumor; and/or (g) vaccinating the subject to an antigen within the tumor.

In some embodiments, treating the subject comprises reducing the volume of the tumor at least about 5, 10, 15, 20, 25, 30, 35, 40, 45, 50, 55, 60, 65, 70, 75, 80, 85, 90, 95, 96, 97, 98, 99, or 100%.

In some embodiments, treating the subject comprises reducing the volume of the tumor at least about 5, 10, 15, 20, 25, 30, 35, 40, 45, 50, 55, 60, 65, 70, 75, 80, 85, 90, 95, 96, 97, 98, 99, or 100% within about 1, 2, 3, 4, 5, 6, 7, 8, 9, 10, 14, 21, 28, 35, 41, 48, 180, 365 or 1-365 days or within about 1-12 months.

In some embodiments, (a) one such biodegradable porous polymeric device is administered to the subject; or (b) two such biodegradable porous polymeric devices are administered to the subject.

In some embodiments, said device comprises an alginate hydrogel.

In some embodiments, said alginate hydrogel comprises a click alginate.

In some embodiments, the device is administered via injection.

In some embodiments, the device is injected into the tumor.

In some embodiments, the device is injected to a site in the subject within about 0-10 mm from the tumor.

In some embodiments, the device further comprises a cytokine.

In some embodiments, the cytokine is granulocyte macrophage colony-stimulating factor (GM-CSF), FMS-like tyrosine kinase 3 ligand (Flt3L), Chemokine (C-C Motif) Ligand 20 (CCL20), Interleukin 15 (IL-15), Chemokine (C Motif) Ligand 1 (XCL1), Chemokine (C-X-C Motif) Ligand 10 (CXCL10), Interferon Alpha 1 (IFN-alpha), Interferon Beta (IFN-beta), or Interleukin 12 (IL-12).

In some embodiments, the device further comprises an immunostimulatory compound.

In some embodiments, the immunostimulatory compound is CpG, polyinosine-polycytidylic acid (poly (I:C)) PEI-poly (I:C), polyadenylic-polyuridylic acid (poly (A:U)), PEI-poly (A:U), double stranded ribonucleic acid (RNA), monophosphoryl lipid A (MPLA), or Imiquimod.

In some embodiments, the device has a volume of about 50, 60, 70, 80, 90, 100, 200, 300, 400, 500, or 50-500 µl or less than about 50, 60, 70, 80, 90, 100, 200, 300, 400, 500, or 50-500 µl.

In some embodiments, said subject has bene identified as comprising a solid tumor.

Aspects of the present subject matter provide a biodegradable porous polymeric device comprising at least two of (a) a compound that induces immunogenic cell death of a tumor cell; (b) a compound that attracts an immune cell to or into the device; (c) an immunostimulatory compound; and (d) a compound that inhibits tumor-mediated T cell or dendritic cell suppression.

In some embodiments, the device comprises an immunostimulatory compound.

In some embodiments, the immunostimulatory compound comprises a CpG oligonucleotide, poly (I:C), monophosphoryl lipid A (MPLA), imiquimod, or a cyclic dinucleotide.

In some embodiments, the device comprises a compound that induces immunogenic cell death of a tumor cell.

In some embodiments, the compound that induces immunogenic cell death of a tumor cell comprises doxorubicin, mitoxantrone, oxaliplatin, or paclitaxel.

In some embodiments, the device comprises a compound that attracts an immune cell to or into the device.

In some embodiments, compound that attracts an immune cell to or into the device is GM-CSF, Flt3L, XCL1, IL-2, or IL-12.

In some embodiments, the compound that attracts an immune cell to or into the device attracts a dendritic cell into the device.

In some embodiments, the device comprises a compound that inhibits tumor-mediated T cell or dendritic cell suppression.

In some embodiments, the compound that inhibits tumor-mediated T cell or dendritic cell suppression comprises a TGF-β inhibitor, a STAT5 inhibitor, an IDO inhibitor, an anti-PD-1 antibody, or an anti-CTLA-4 antibody.

In some embodiments, said device lacks a patient-derived tumor cell antigen prior to administration to a patient.

In some embodiments, the device has a volume of at least about 50, 60, 70, 80, 90, 100, 200, 300, 400, 500, or 50-500 μl or less than about 50, 60, 70, 80, 90, 100, 200, 300, 400, 500, or 50-500 μl.

Aspects of the present subject matter provide non-human mammal or a syringe comprising a device of the present subject matter. In some embodiments, the syringe is pre-loaded and packaged with a device.

In some embodiments, the tumor is contacted with radiation.

In some embodiments, a chemotherapeutic agent is administered systemically to the subject.

Each embodiment disclosed herein is contemplated as being applicable to each of the other disclosed embodiments. Thus, all combinations of the various elements described herein are within the scope of the invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIGS. 7-8 show that the biomaterial delivers immunostimulatory compounds in a sustained manner over time. Doing this in the tumor microenvironment stimulates maturation of recruited antigen-presenting cells (APCs) and results in antitumor immunity.

FIG. 10A is no nanoparticles, FIG. 10B is 1 mg/ml nanoparticles, and FIG. 10C is 0.1 mg/ml nanoparticles. Nanoparticles range in size from 10-5000 nm, e.g., 100-500 nm in size. Inhibitors of immune-suppressive factors found in the tumor microenvironment or chemotherapeutic agents (to generate tumor antigen) are delivered using these particles.

FIGS. 12-15 show data using Cryoclick gels. Using a click alginate cryogel, a number of cytokines and chemokines were placed under the skin and screened for resulting activity in terms of immune cell accumulation.

FIG. 13 is a series of photographs showing results using Chemokine (C motif) ligand (XCL1) (DC chemokine) leading to bright DC staining at gel periphery FIG. 14 is a series of photographs showing results using IL-15 (T cell/NK cell survival factor) causing accumulation of CD4 and CD8 T cells in the skin.

FIG. 15 is a series of photographs showing results using CCL20 (DC chemokine) leading to bright DC staining at gel periphery.

Local delivery to site of action
Sustained release of bioactive agents
Dose sparing
Reduced side effects
No tumor material/known tumor antigen required for vaccination
Avoid need for surgical implant.

Figure 1:
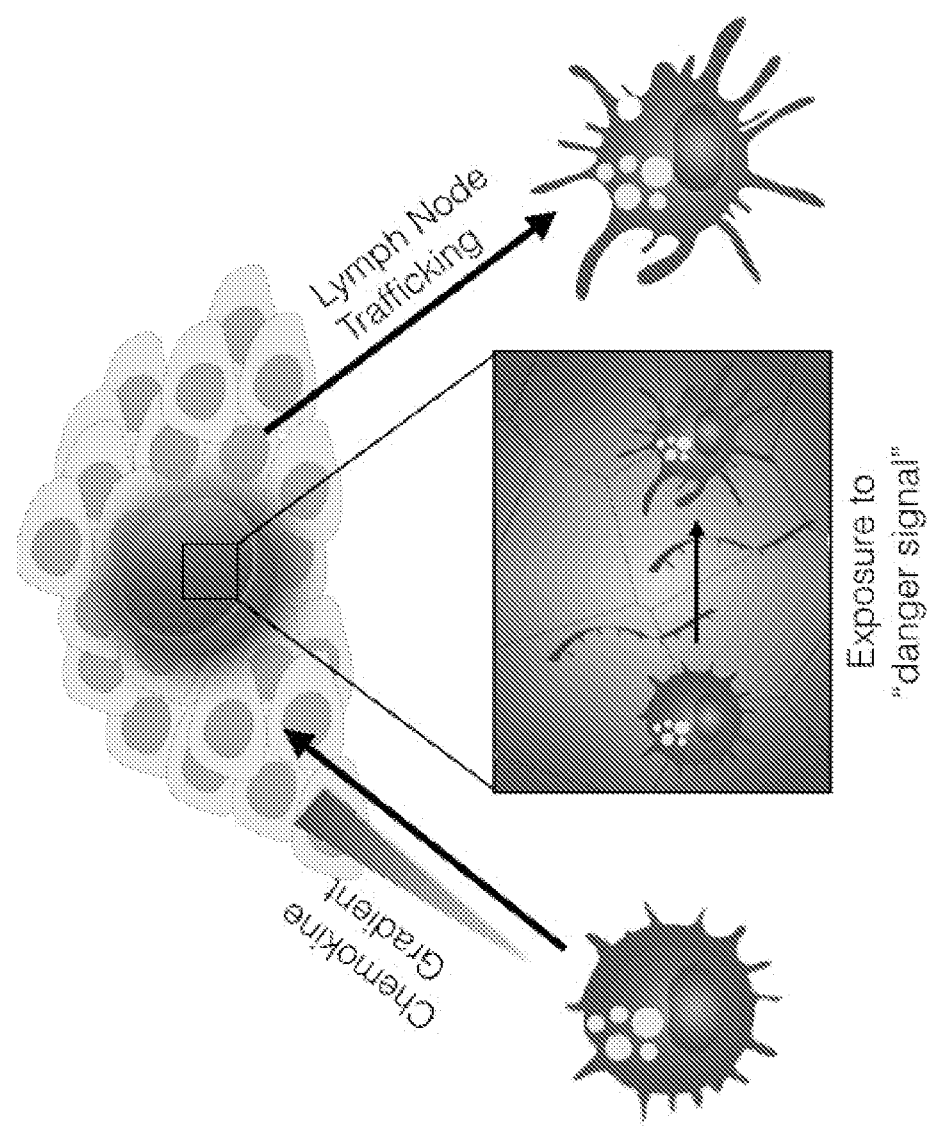
FIG. 1 is a diagram that shows bringing dendritic cells into the biomaterial cryogel that is placed within the tumor and stimulating their maturation so that they initiate responses against the tumor.
Figure 2:
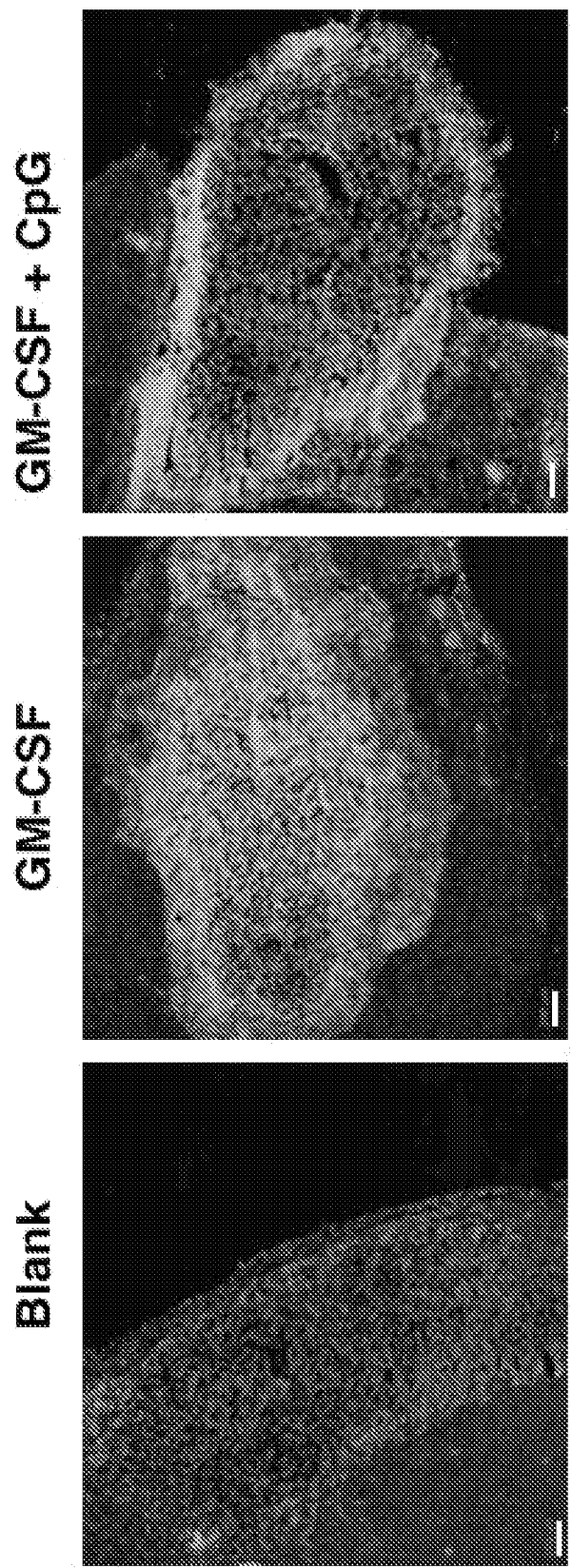
FIG. 2 is a series of photographs depicting immunofluorescence data and showing that scaffolds placed in the tumor accumulate immune cells around and within the scaffold within the tumor. The data shown in FIGS. 2-5 were generated following injection of the scaffold/cryogel device into, or on the periphery, of lung cancer tumors grown for 5 days in mice. The tumor and scaffolds were explanted and then sectioned evaluate immune cell accumulation. Scale bar shown in lower left hand corner of each panel is 200 μm.
Figure 3:
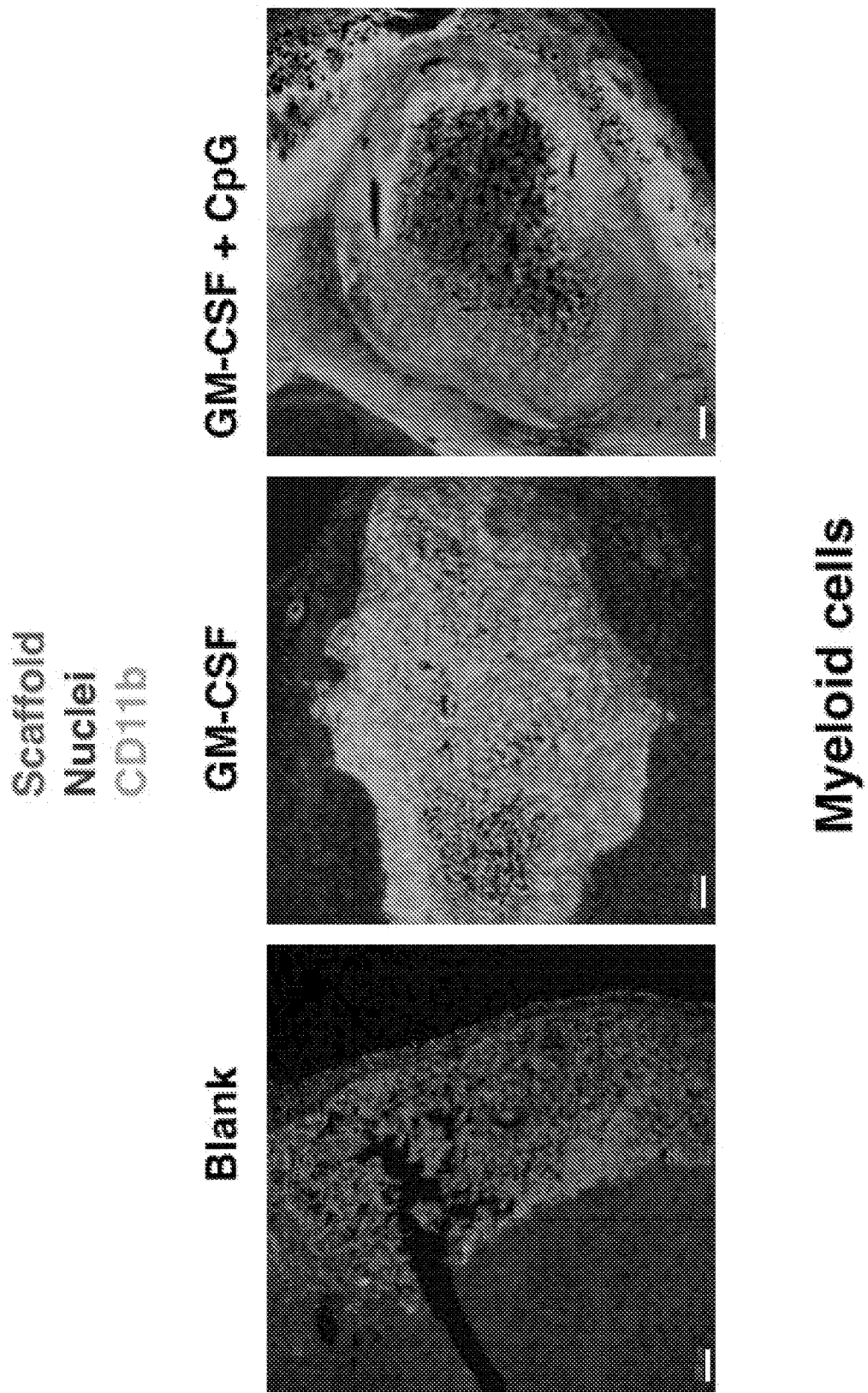
FIG. 3 is a series of photographs depicting immunofluorescence data and showing that scaffolds placed in the tumor accumulate cells of myeloid origin (which dendritic cells belong to) within the tumor. Scale bar shown in lower left hand corner of each panel is 200 μm.
Figure 4:
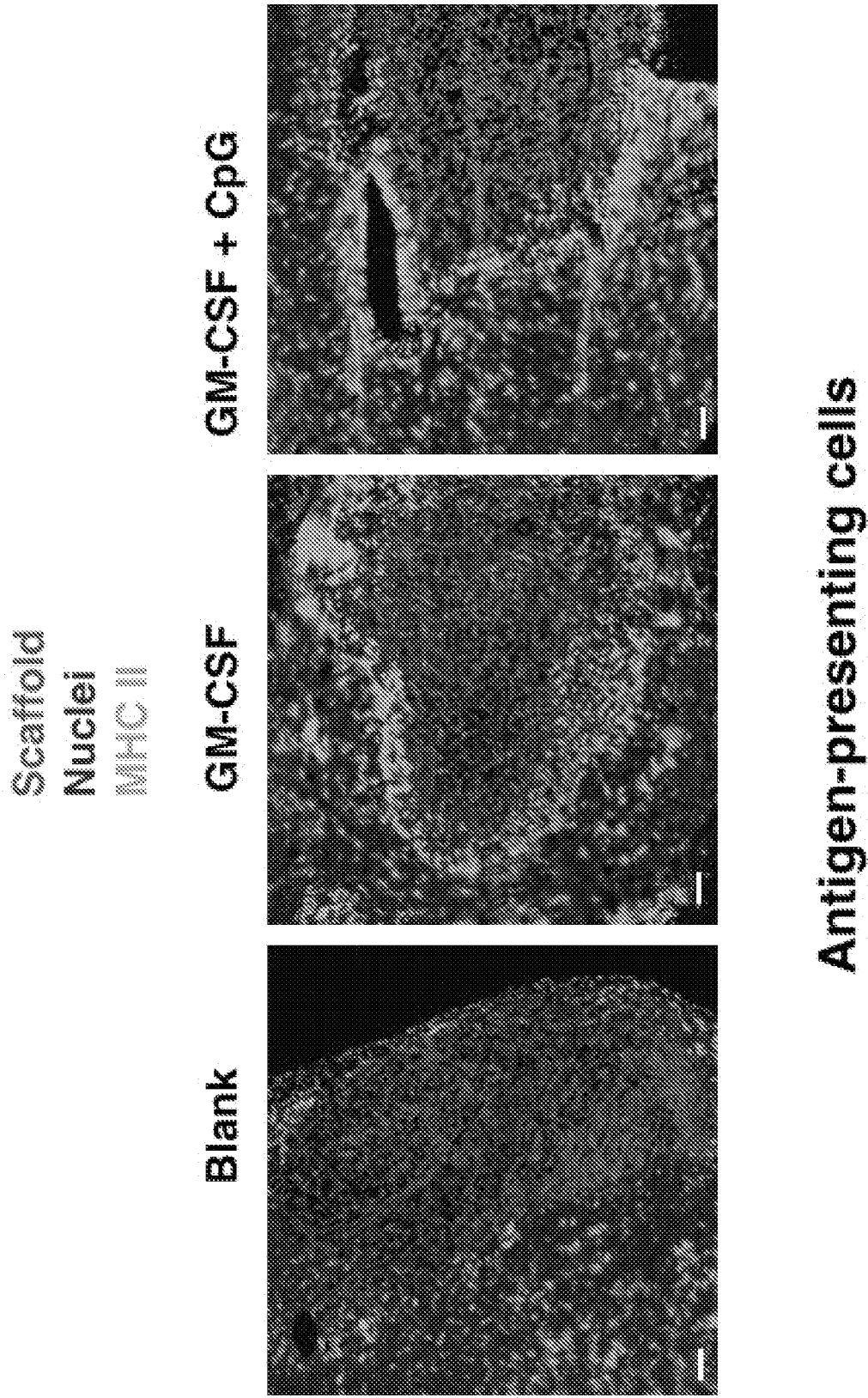
FIG. 4 is a series of photographs depicting immunofluorescence data and showing that scaffolds placed in the tumor accumulate and enrich antigen presenting cells at the scaffold within the tumor. Scale bar shown in lower left hand corner of each panel is 200 μm.
Figure 5:
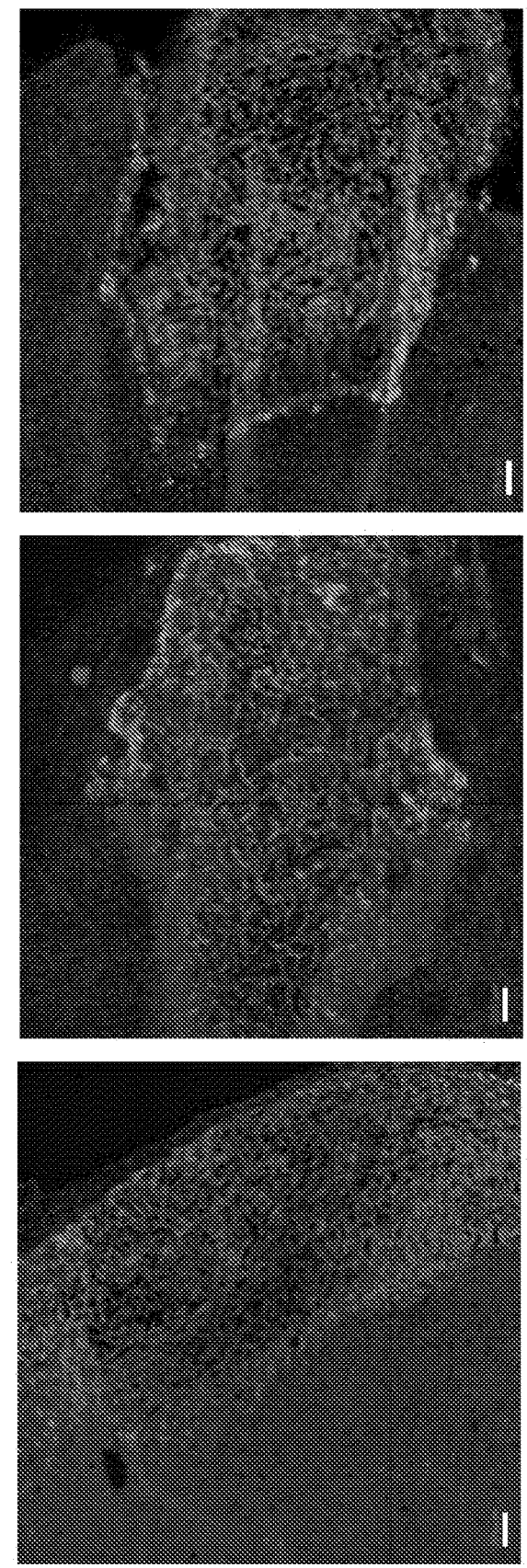
FIG. 5 is a series of photographs depicting immunofluorescence data and showing that scaffolds placed in the tumor accumulate dendritic cells (one target cell type) to the scaffold site within the tumor. Scale bar shown in lower left hand corner of each panel is 200 μm.
Figure 6:
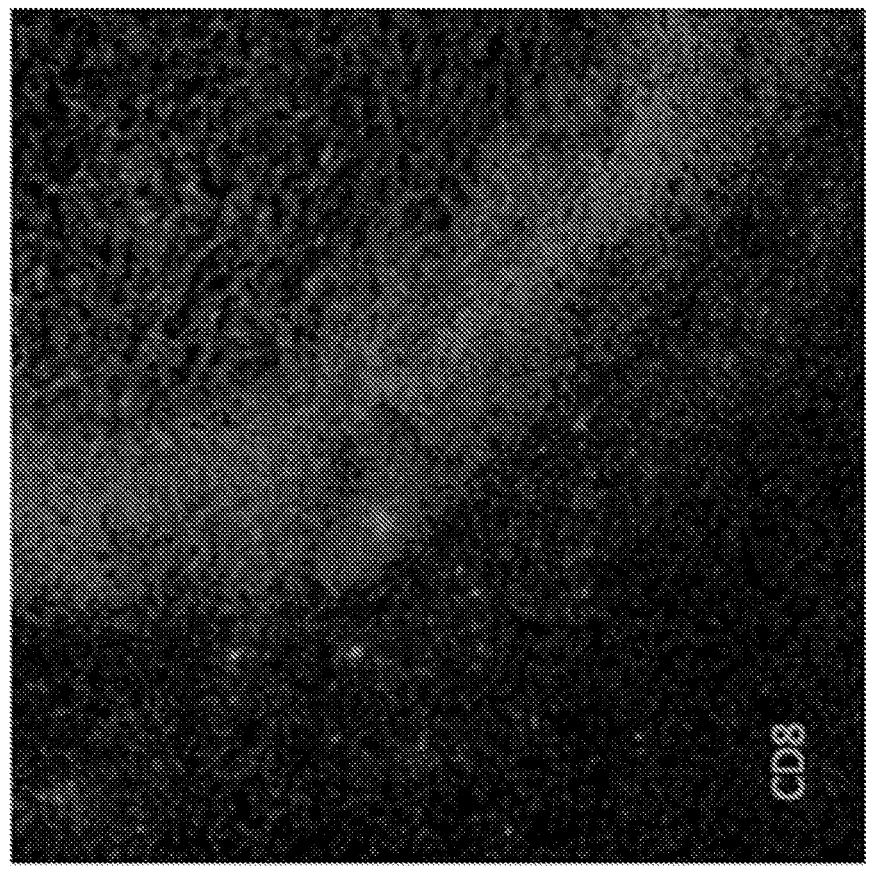
FIG. 6 is a pair of photographs depicting immunofluorescence data and showing that scaffolds placed in the tumor accumulate T cells near the placement site. The data in FIGS. 2-6 show that injecting this biomaterial into the tumor leads to immune cell localization. Attraction of immune cells are key to generating anti-tumor immune responses and this accumulation of immune cells generates an anti-tumor immune responses against established tumors.
Figure 6:
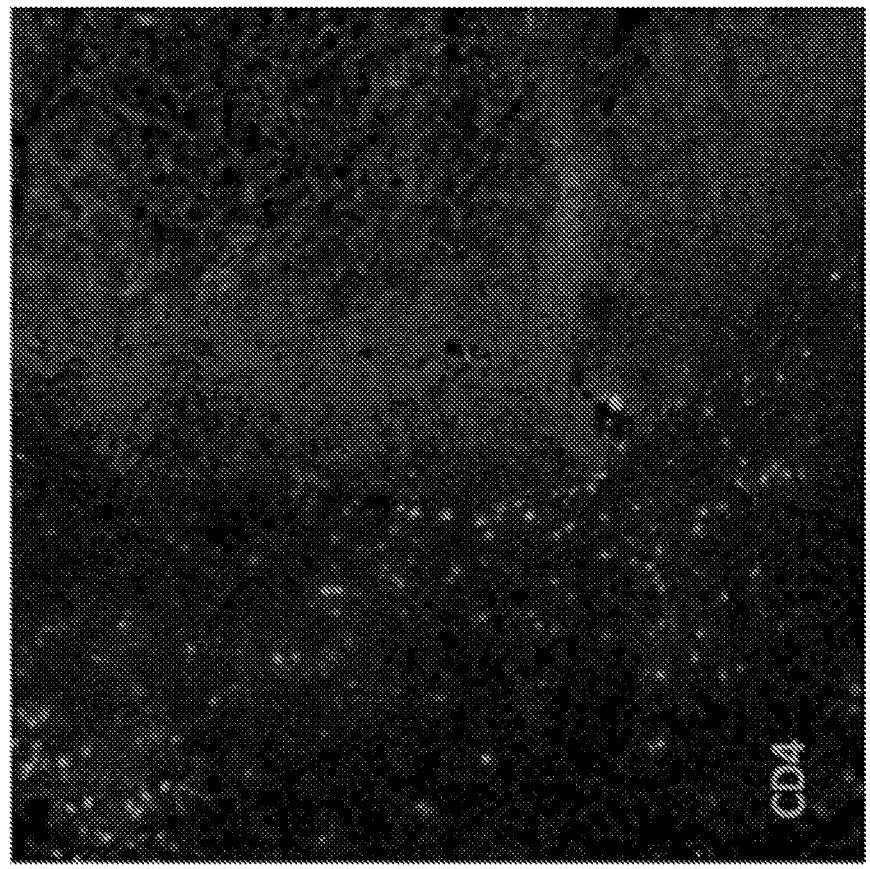
Figure 7:
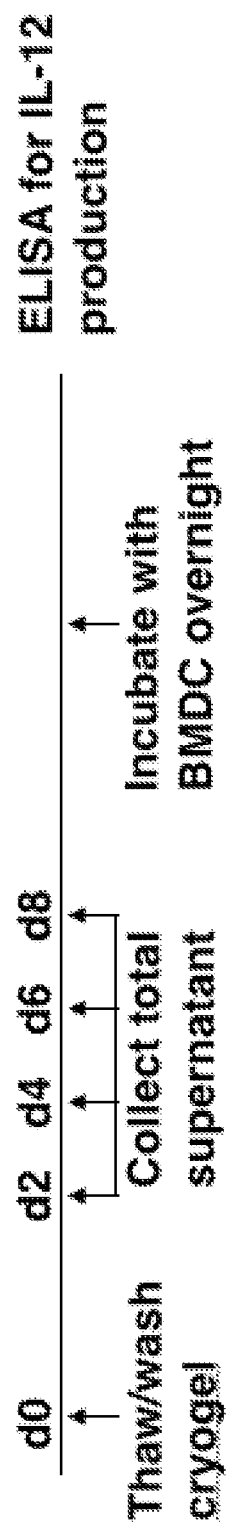
FIG. 7 is a line graph showing CryogelMA (methacrylated gelatin cryogel as used in FIGS. 2-5) CpG oligonucleotide release and bioactivity. In vitro, dendritic cells produce IL-12 (a cytokine indicative of maturation/activation) when exposed to supernatants from our material containing CpG oligonucleotide over the course of several days.
Figure 7:
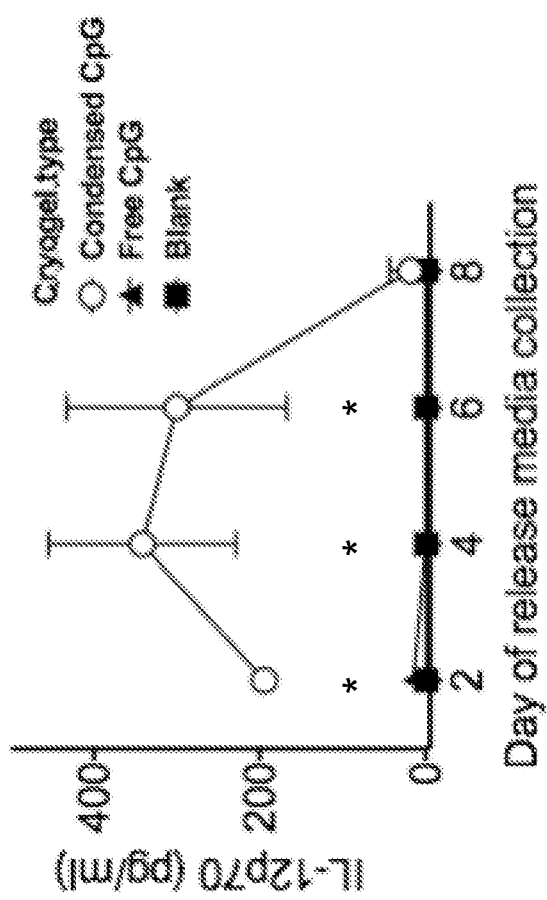
Figure 8:
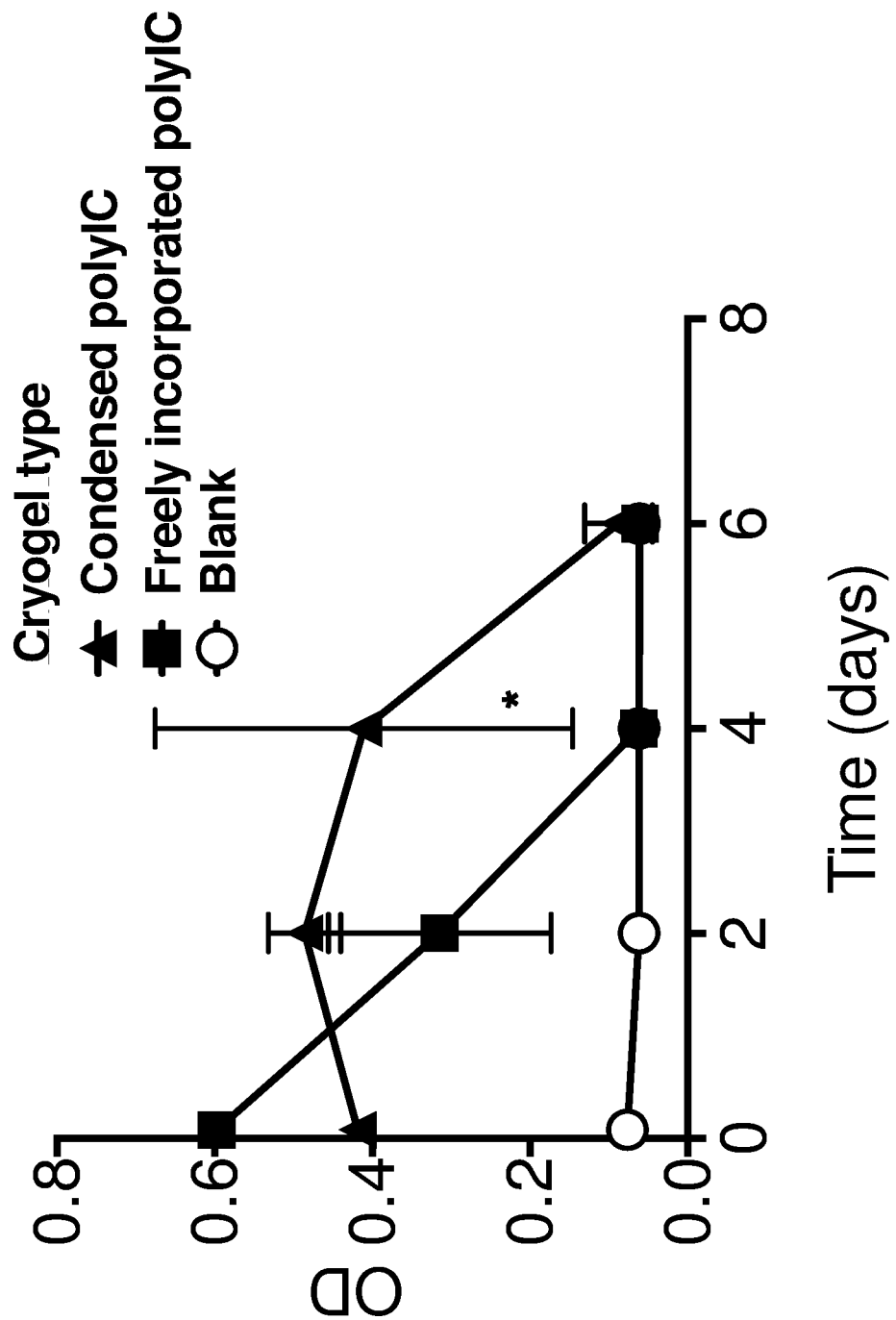
FIG. 8 is a line graph showing CryogelMA poly I:C release and bioactivity. In vitro, human embryonic kidney (HEK) toll-like receptor-3 (TLR3) cells (TLR3=receptor for poly I:C immunostimulatory compound) produce a response measured by absorbance when exposed to supernatants in vitro from the biomaterial containing polyinosine-polycytidylic acid (poly I:C) over the course of several days.
Figure 9:
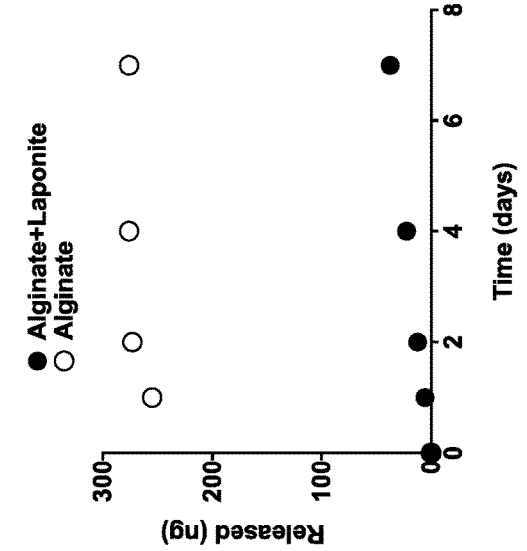
FIG. 9 is a series of graphs showing that by changing material formulation to click alginate for the cryogel and including clay nanoparticles, a variety of agents for dendritic cell recruitment and immune modulation were delivered in different temporal means to potentially produce distinct biological effects. Chemokine (C-C motif) ligand 20 (CCL20)—dendritic cell (DC) chemokine, FMS-like tyrosine kinase 3 ligand (Flt3L)—DC growth/differentiation factor, Granulocyte-macrophage colony-stimulating factor (GM-CSF)-DC growth/differentiation factor, interleukin-15 (IL-15)—T cell/Natural Killer (NK) cell survival factor.
Figure 9:
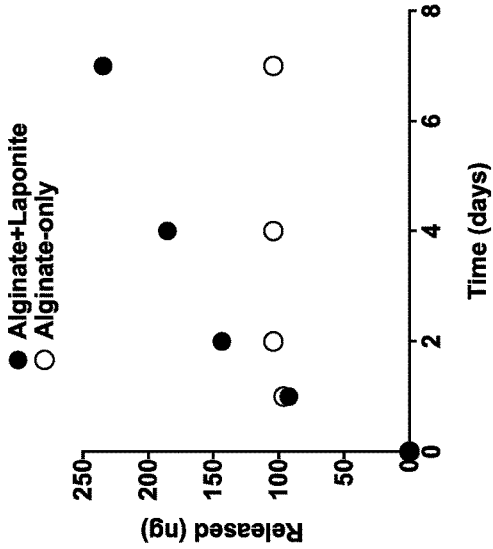
Figure 9:
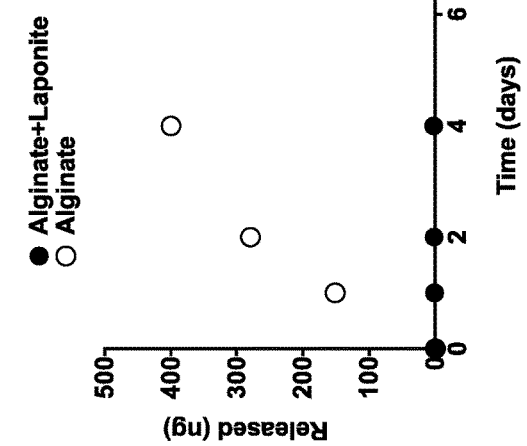
Figure 9:
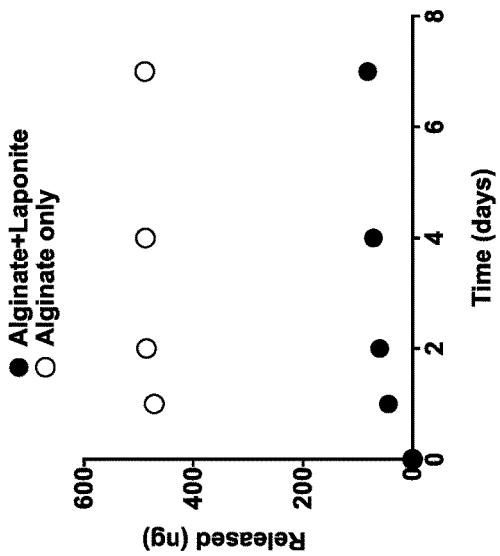
Figure 10A:
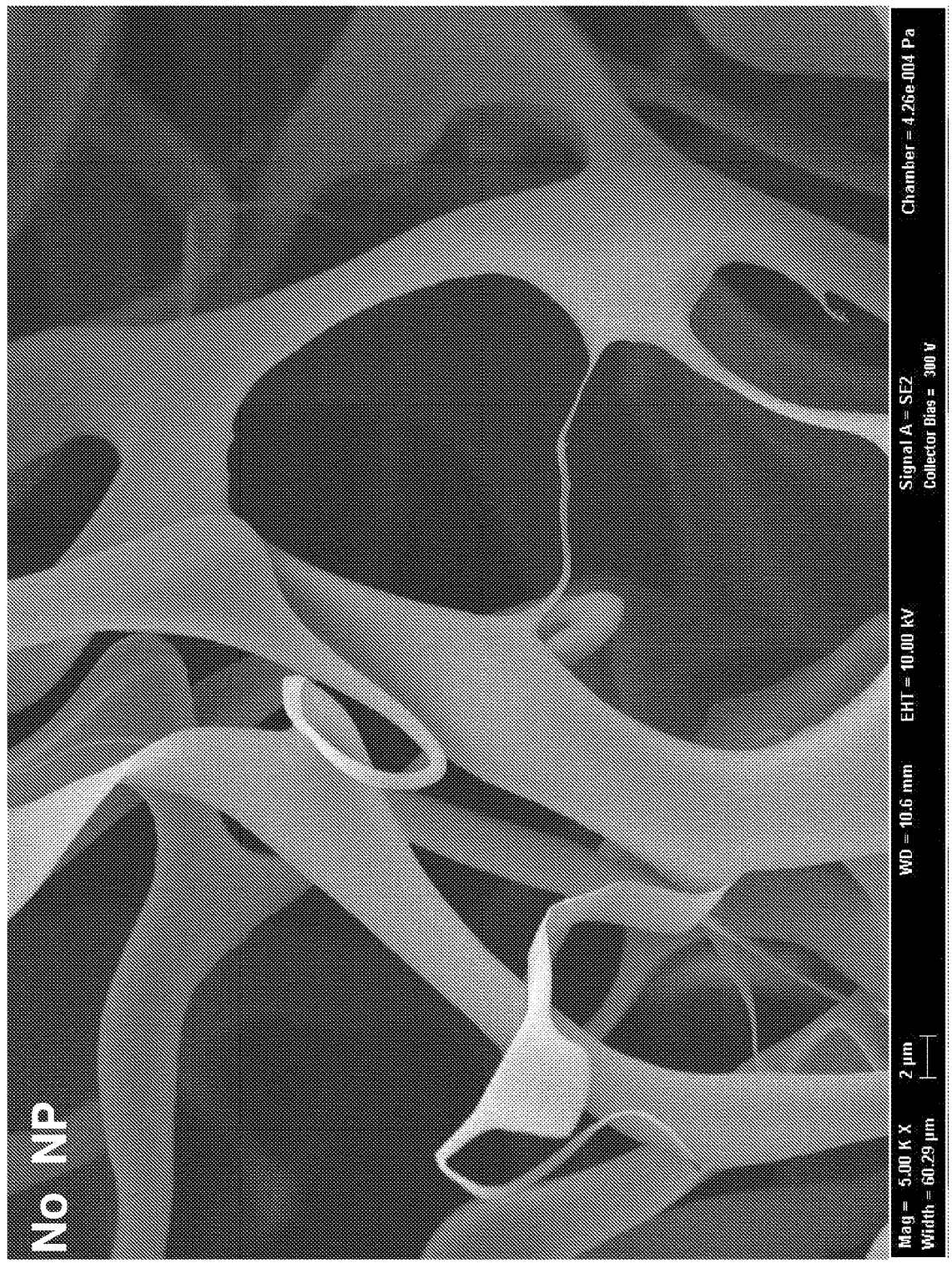
FIG. 10A-C are a series of scanning electron microscope (SEM) images showing that poly(lactide-co-glycolide) (PLGA) nanoparticles are incorporated into the cryogels to allow delivery of small molecules and hydrophobic compounds for immune modulation that could not be sustainably released using the cryogel alone.
Figure 10B:
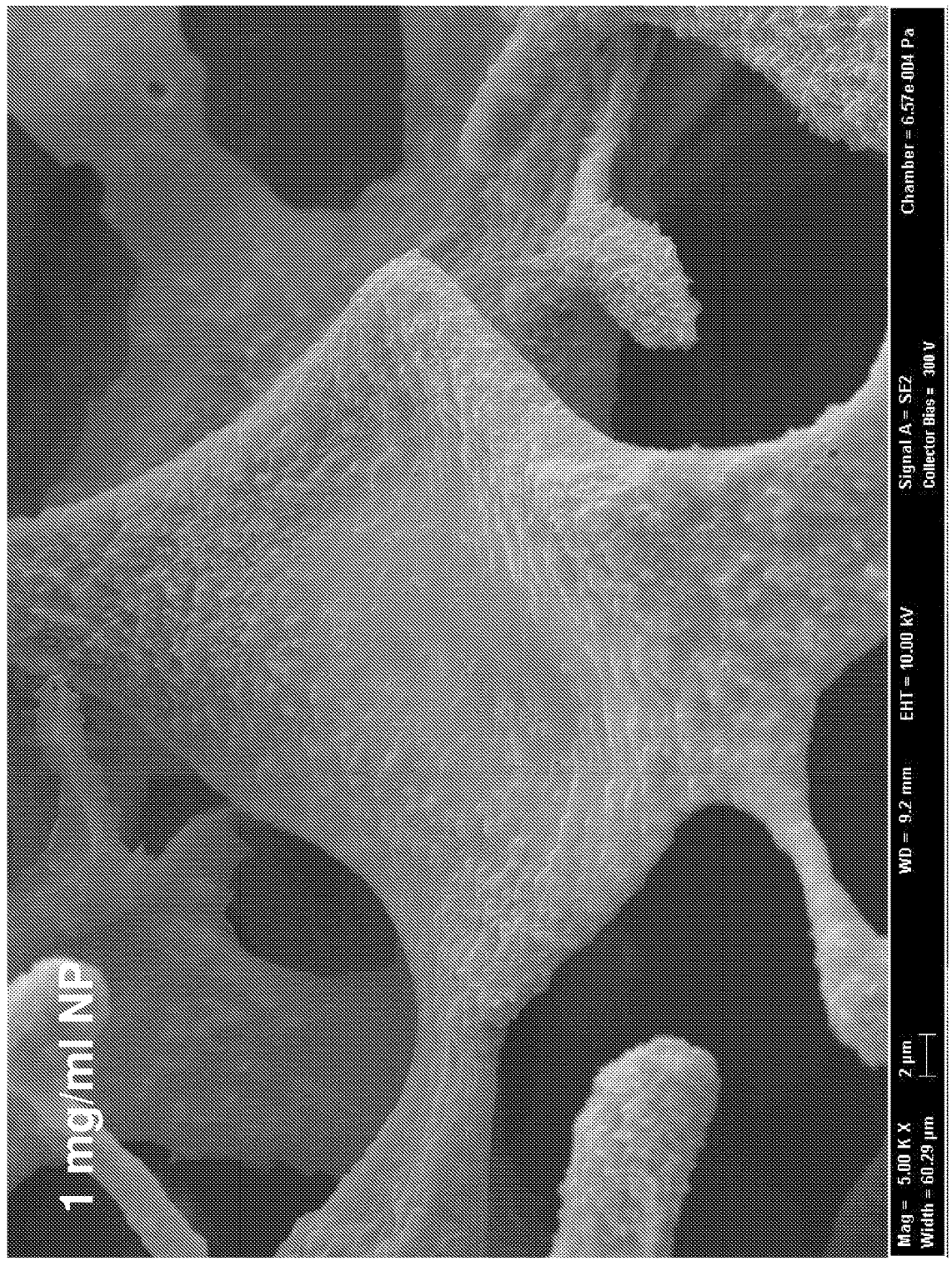
Figure 10C:
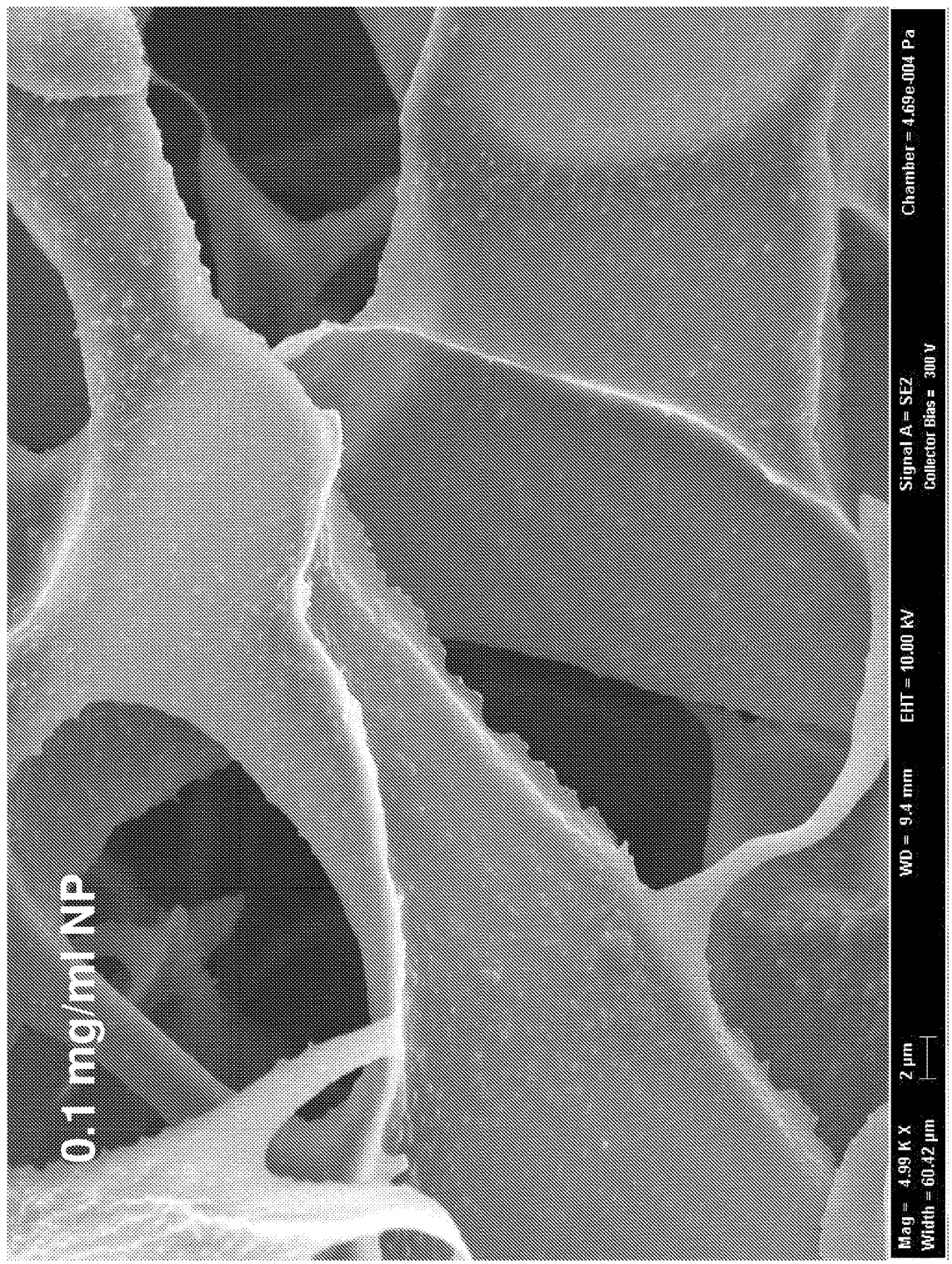
Figure 11:
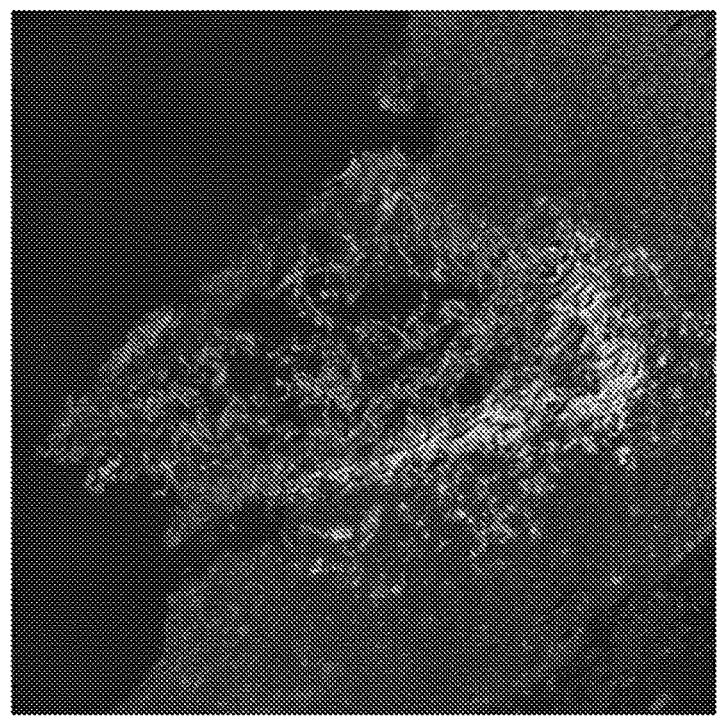
FIG. 11 is a series of photographs showing that by using the click alginate cryogel delivering GM-CSF, we can get substantial accumulation of dendritic cells within and around the material inside the tumor site, i.e., within the tumor microenvironment.
Figure 11:
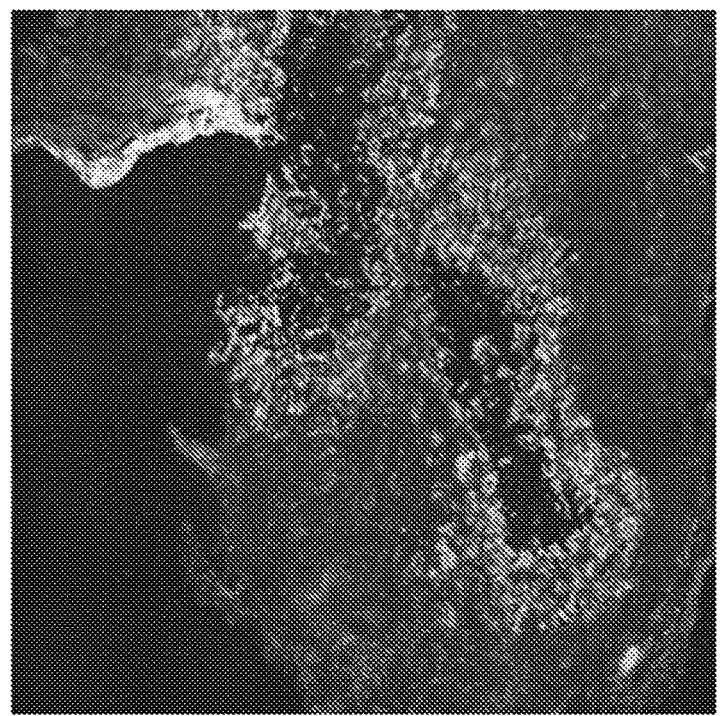
Figure 12:
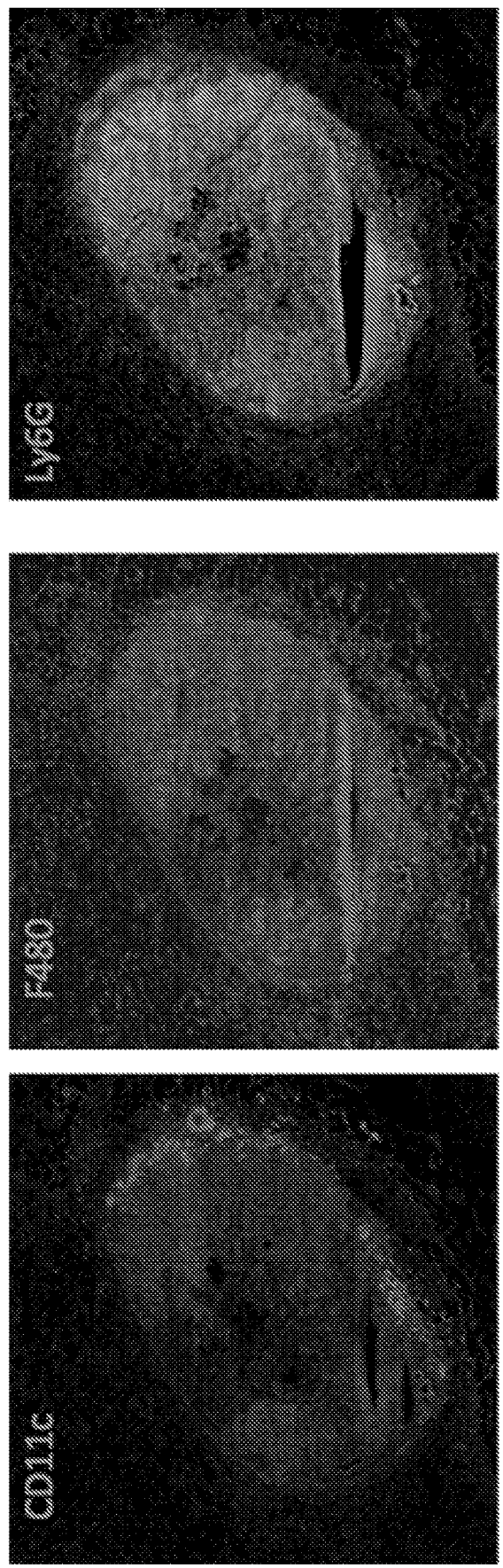
FIG. 12 is a series of photographs showing immune cell accumulation using GM-CSF—DC growth/differentiation factor in the device.
Figure 13:
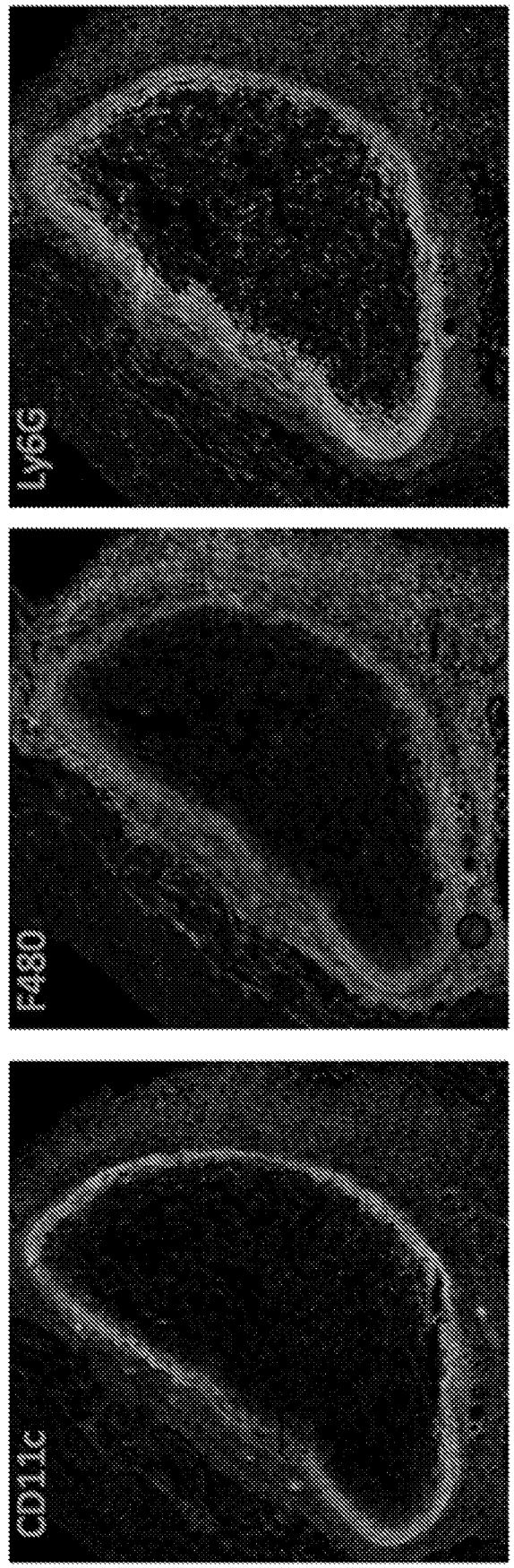
Figure 14:
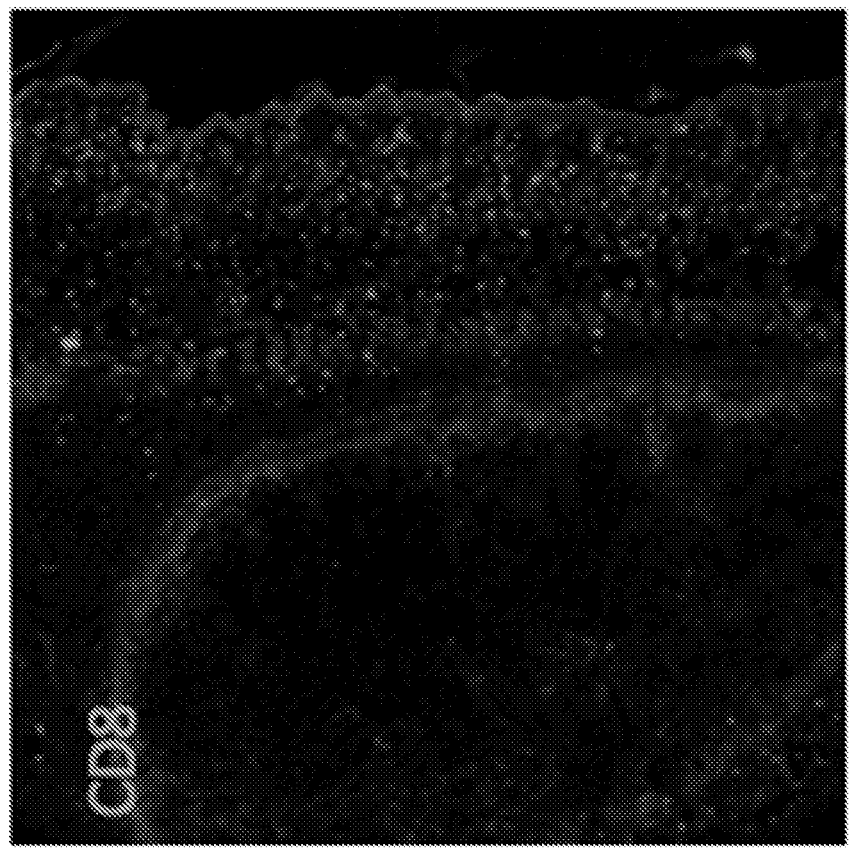
Figure 14:
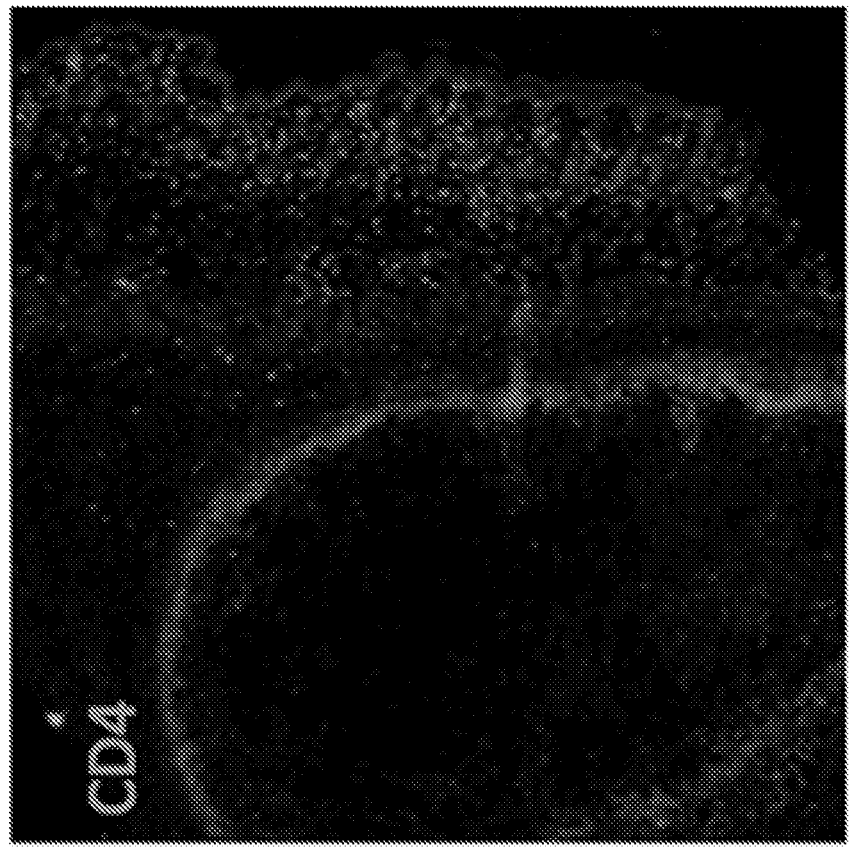
Figure 15:
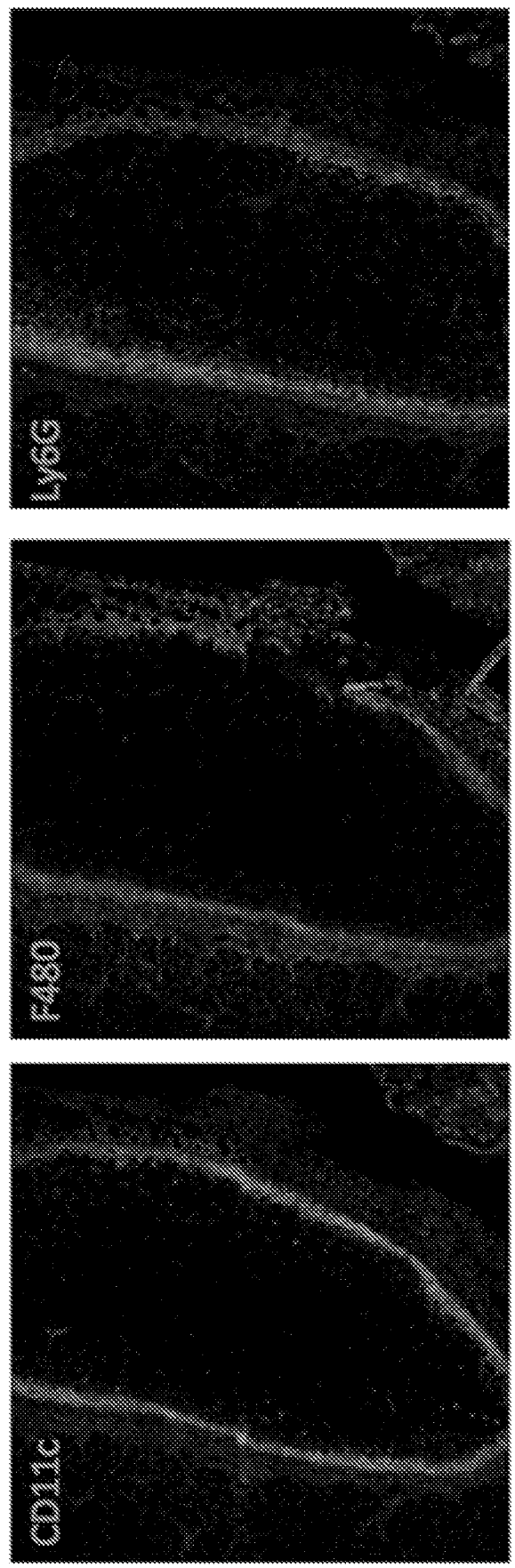
Figure 16:
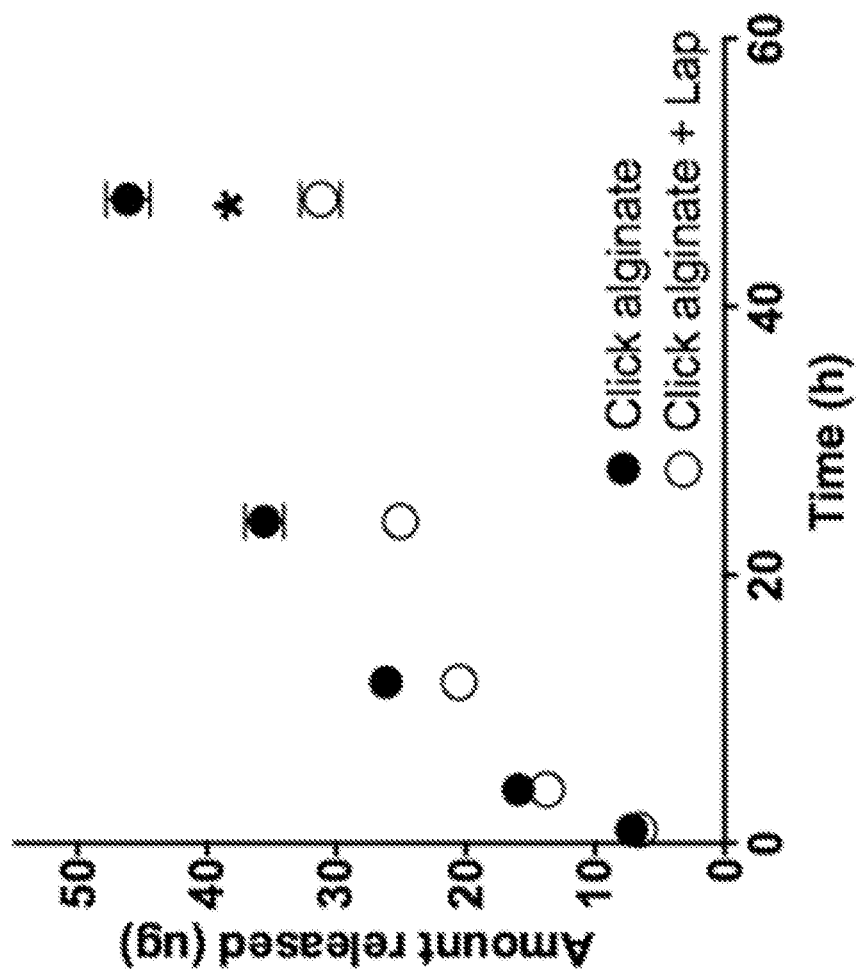
FIG. 16 is a graph showing release of a chemotherapeutic agent. ~100 μg of doxorubicin was loaded into the gels. The mechanism of action of doxorubicin also involves activating the immune system, in addition to directly killing cancer cells. The cryogel composition was the same as used for factor delivery in FIGS. 12-15. The data demonstrated sustained release of chemotherapeutic agent, e.g., doxorubicin, from the cryogels.
Figure 17:
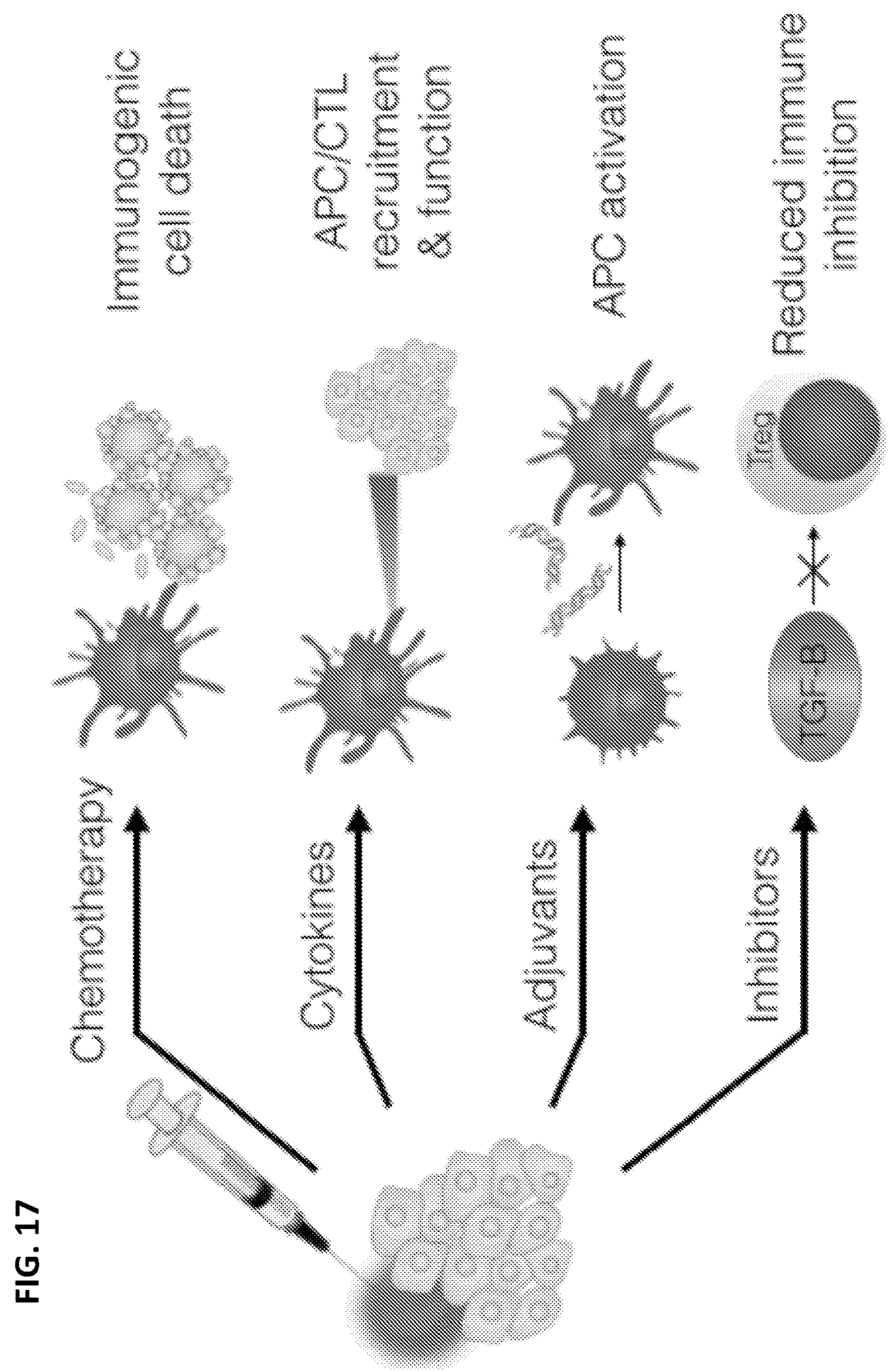
FIG. 17 is a diagram showing delivery of factors from an inert gel that is injected in a minimimally invasive way to the tumor site. Delivering immunomodulatory factors to the tumor site directly complements other therapies greatly by reducing the immunosuppressive environment at the tumor. Some potential advantages are listed below.
Figure 18A:
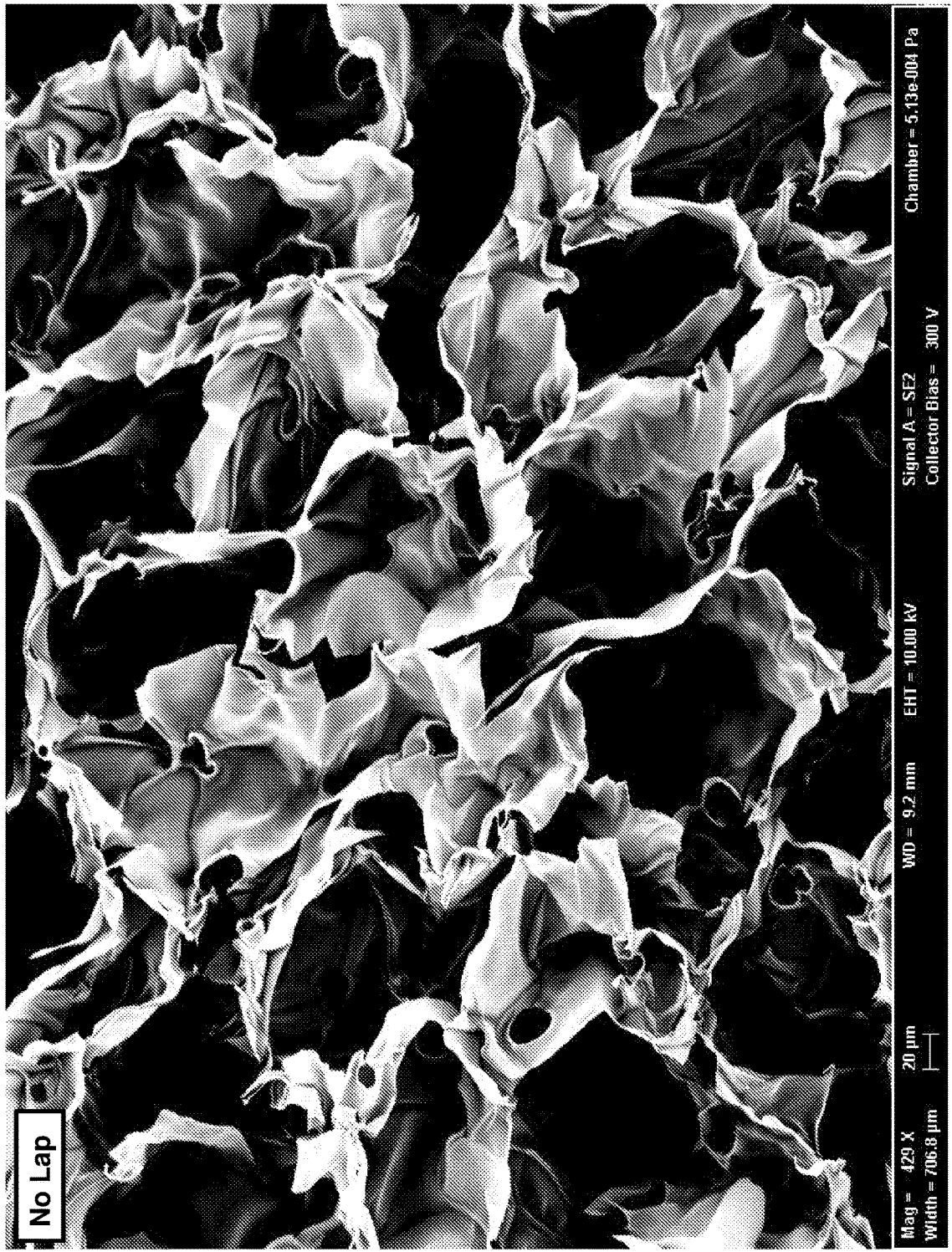
Figure 18B:
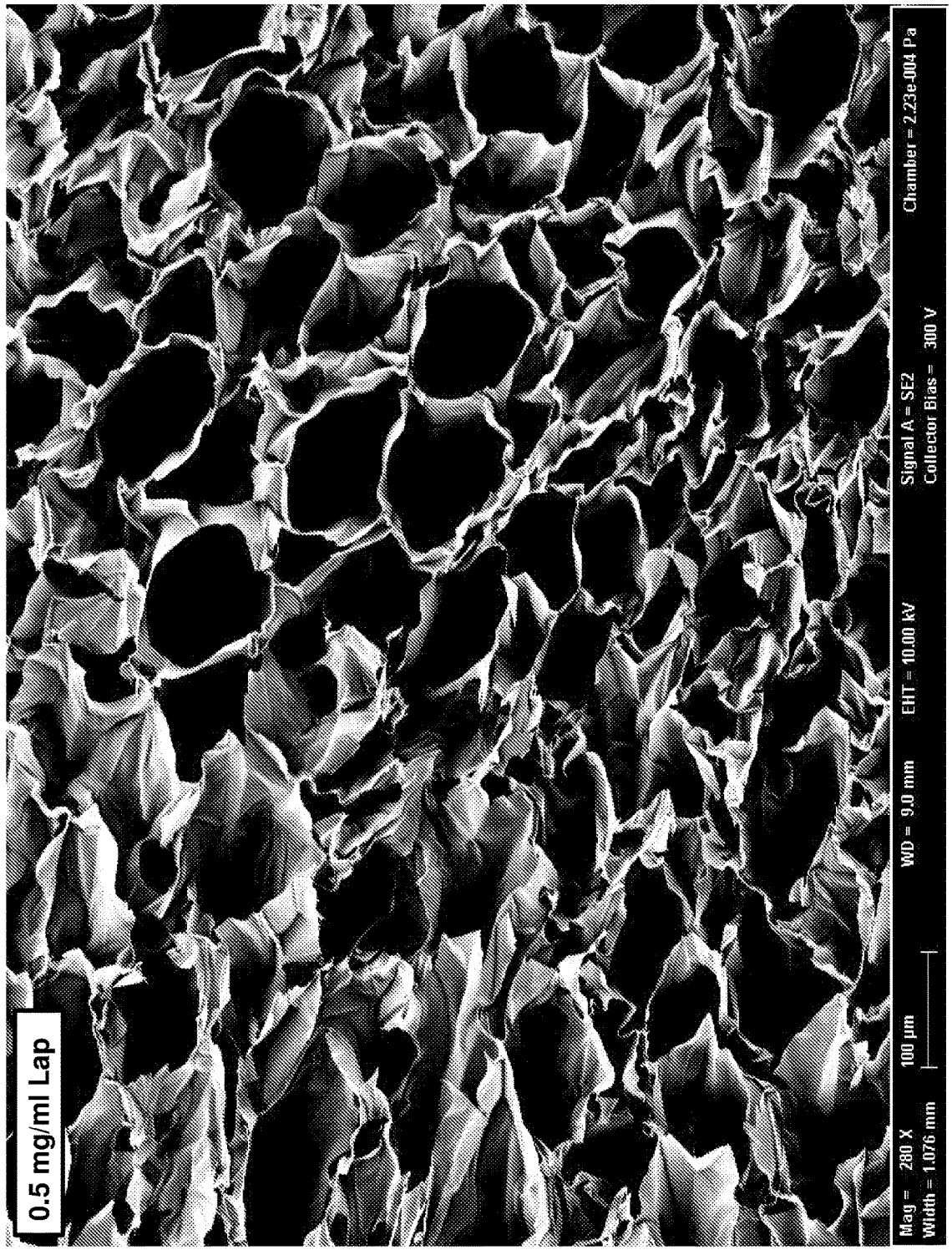
Figure 18C:
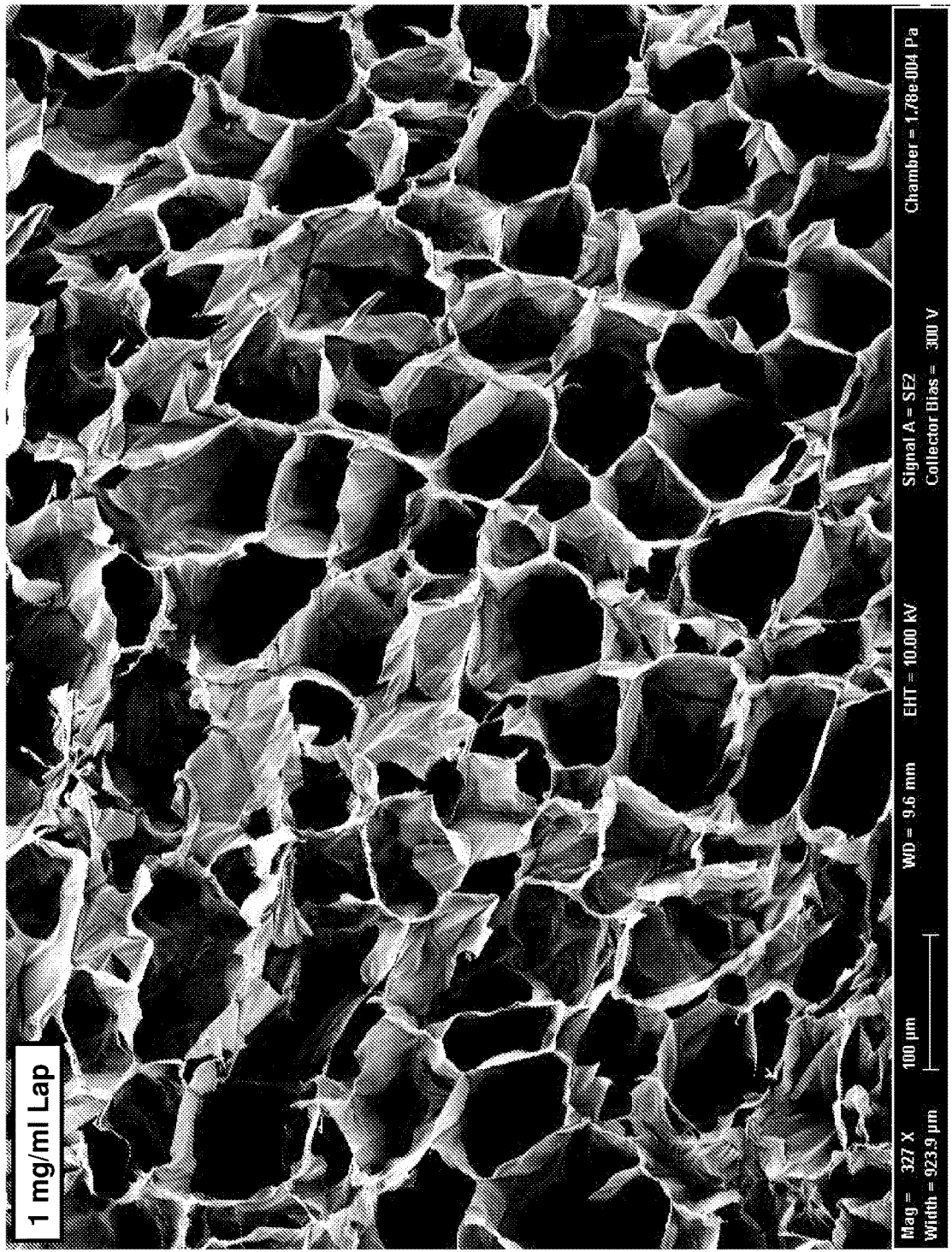
Figure 18D:
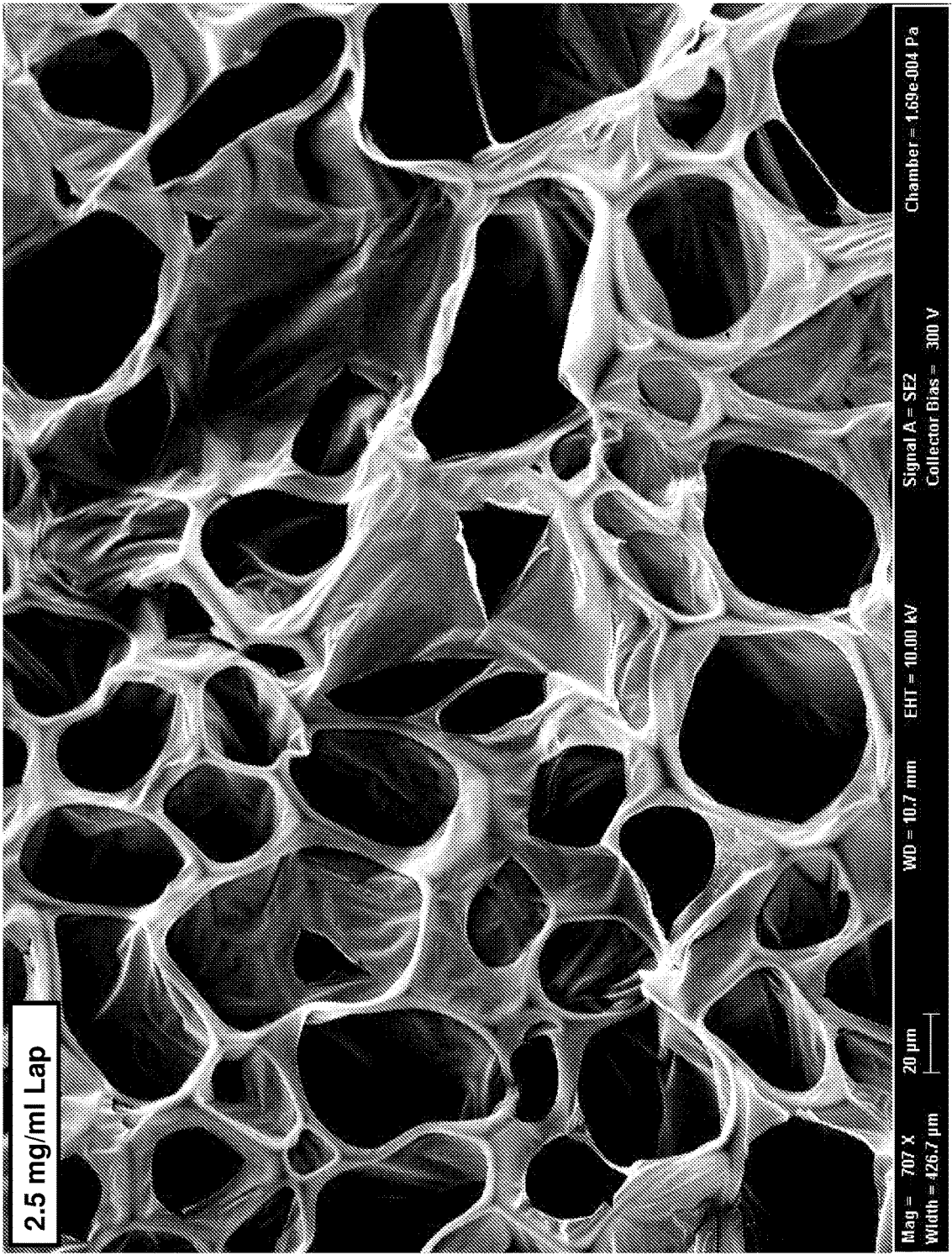

FIG. 18A-D are a series of SEM images showing the porous structure of CryoClick (click alginate) gels with various amounts of charged nanoparticles (laponite). FIG. 18A is no laponite, FIG. 18B is 0.5 mg/ml laponite, FIG. 18C is 1 mg/ml laponite, and FIG. 18D is 2.5 mg/ml laponite.

Figure 19:
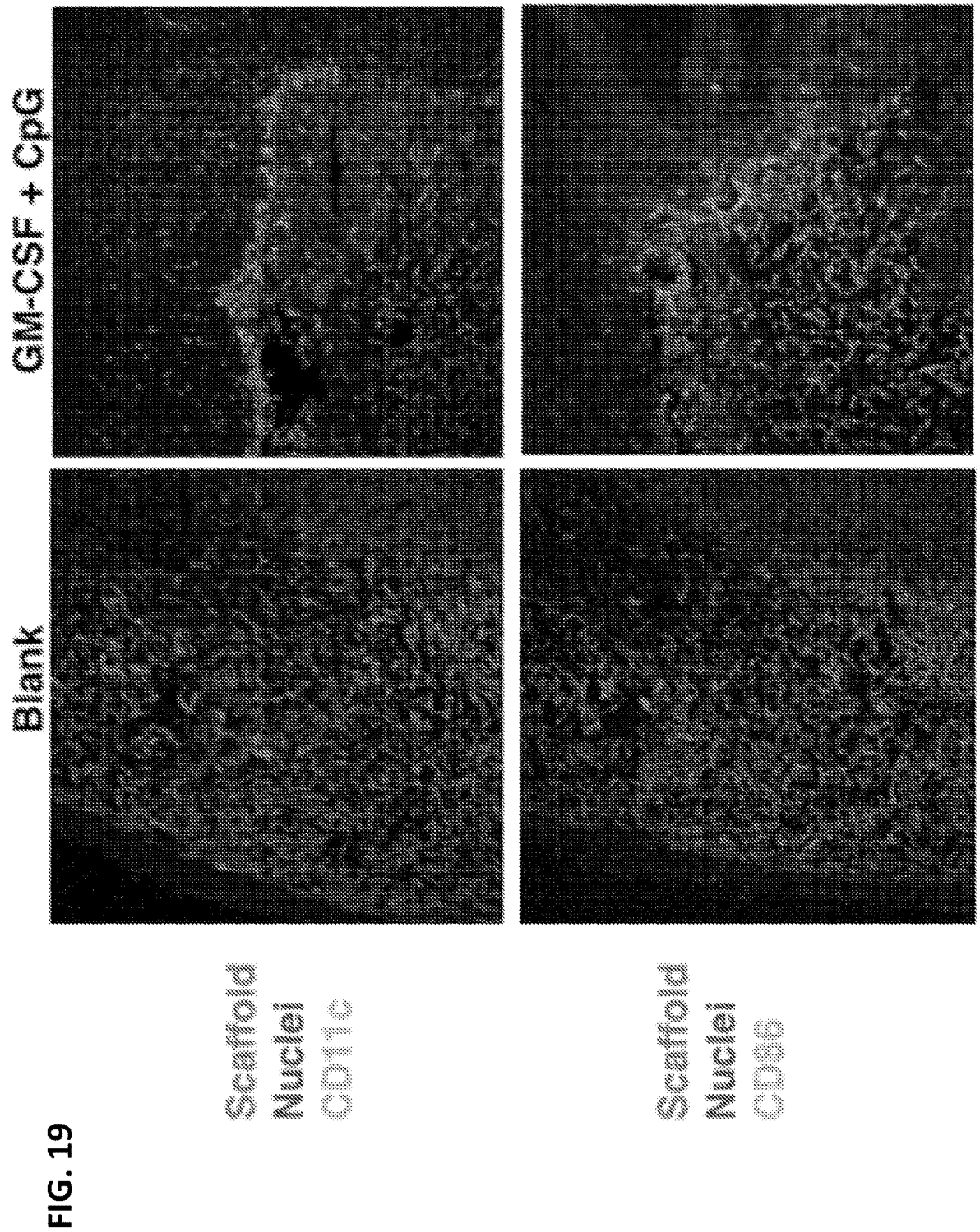

FIG. 19 is a series of photographs. The magnified images of cryoGelMA intratumorally injected above show that gels delivering GM-CSF and CpG oligonucleotide attract more CD11c DCs and show that cells that express Cluster of Differentiation 86 (CD86) (a marker of DC activation) are also enriched, relative to blank scaffolds.

Figure 20:
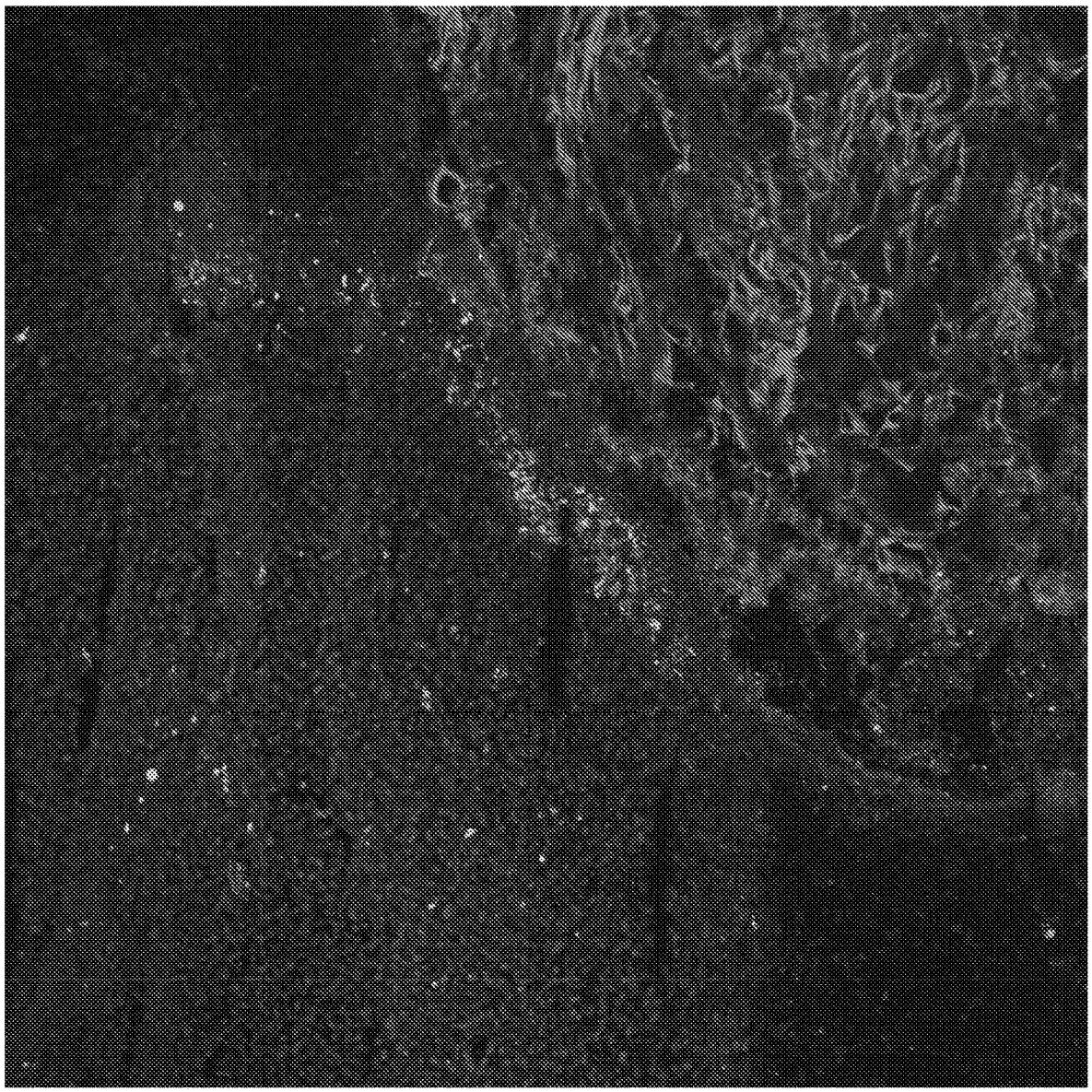
Figure 21:
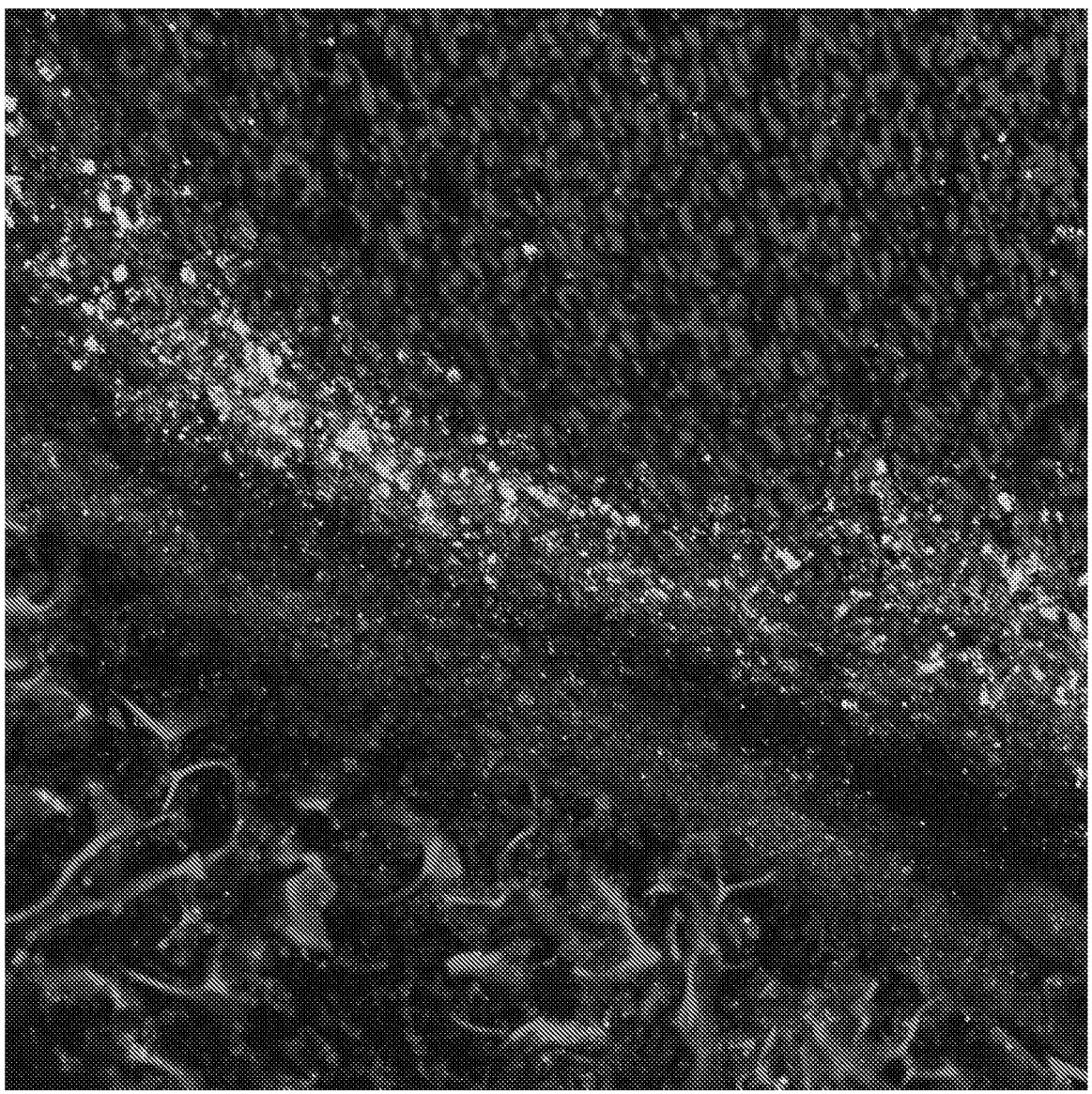
Figure 22:
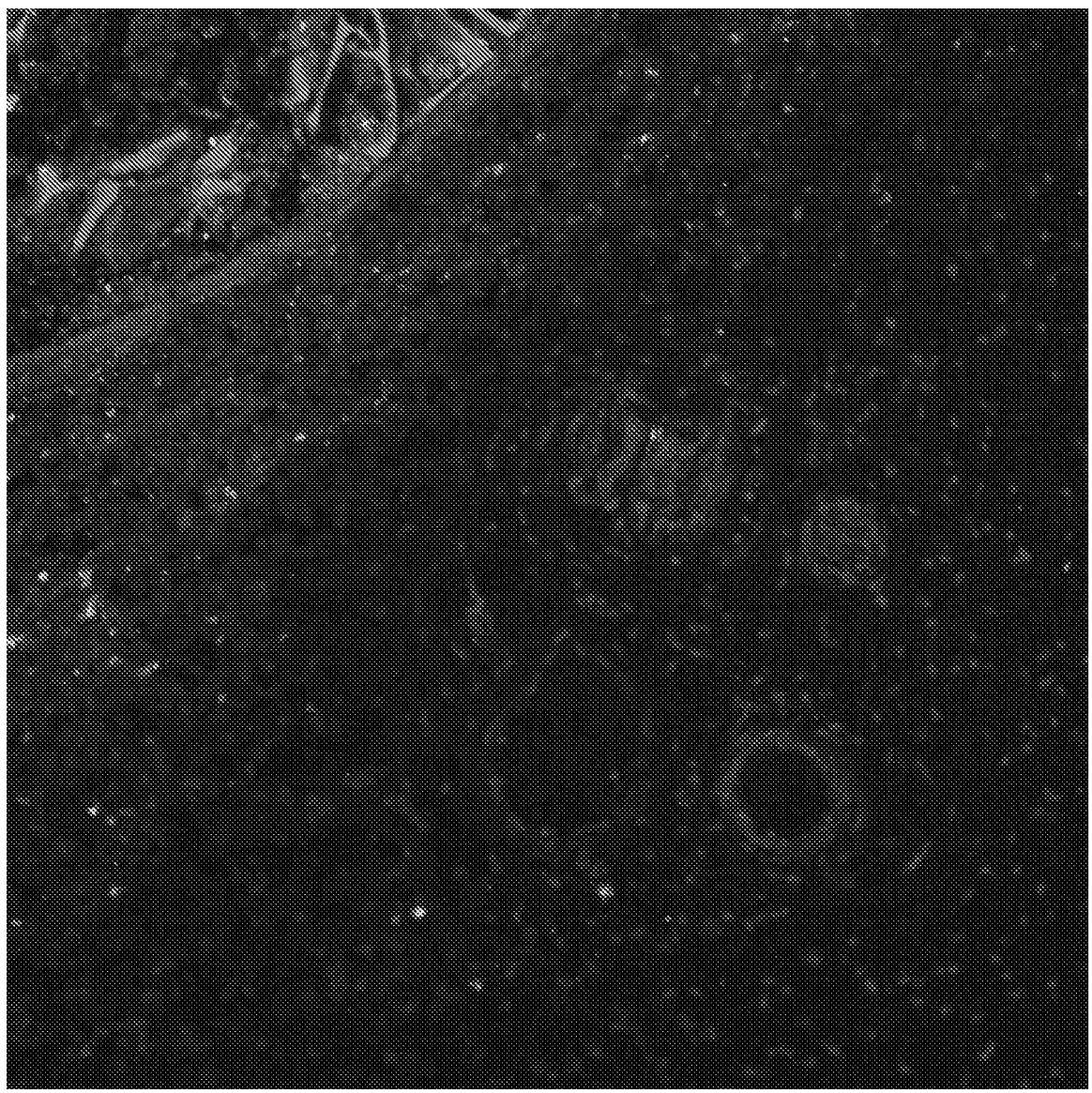

FIGS. 20-22 are photographs showing the effect of doxorubicin release from the gels. By releasing doxorubicin from the cryoClick gels, local cell death is induced at the tumor close to the scaffold border to generate antigen to be acquired by recruited antigen presenting cells. Immunofluorescence imaging from day 3 after peritumoral injection shows staining for cleaved-caspase 3 (a marker of apoptosis, green below) in cells adjacent to the injected cryoClick gel that releases doxorubicin. FIG. 20 shows that apoptotic cells appear only at the tumor border and not in the surrounding fat tissue. FIG. 21 is a higher magnification image showing dying tumor cells as a dox-releasing gel-tumor border. FIG. 22 is an image showing surrounding normal tissue is much less affected by the local delivery of doxorubicin from the gels.

Figure 23:
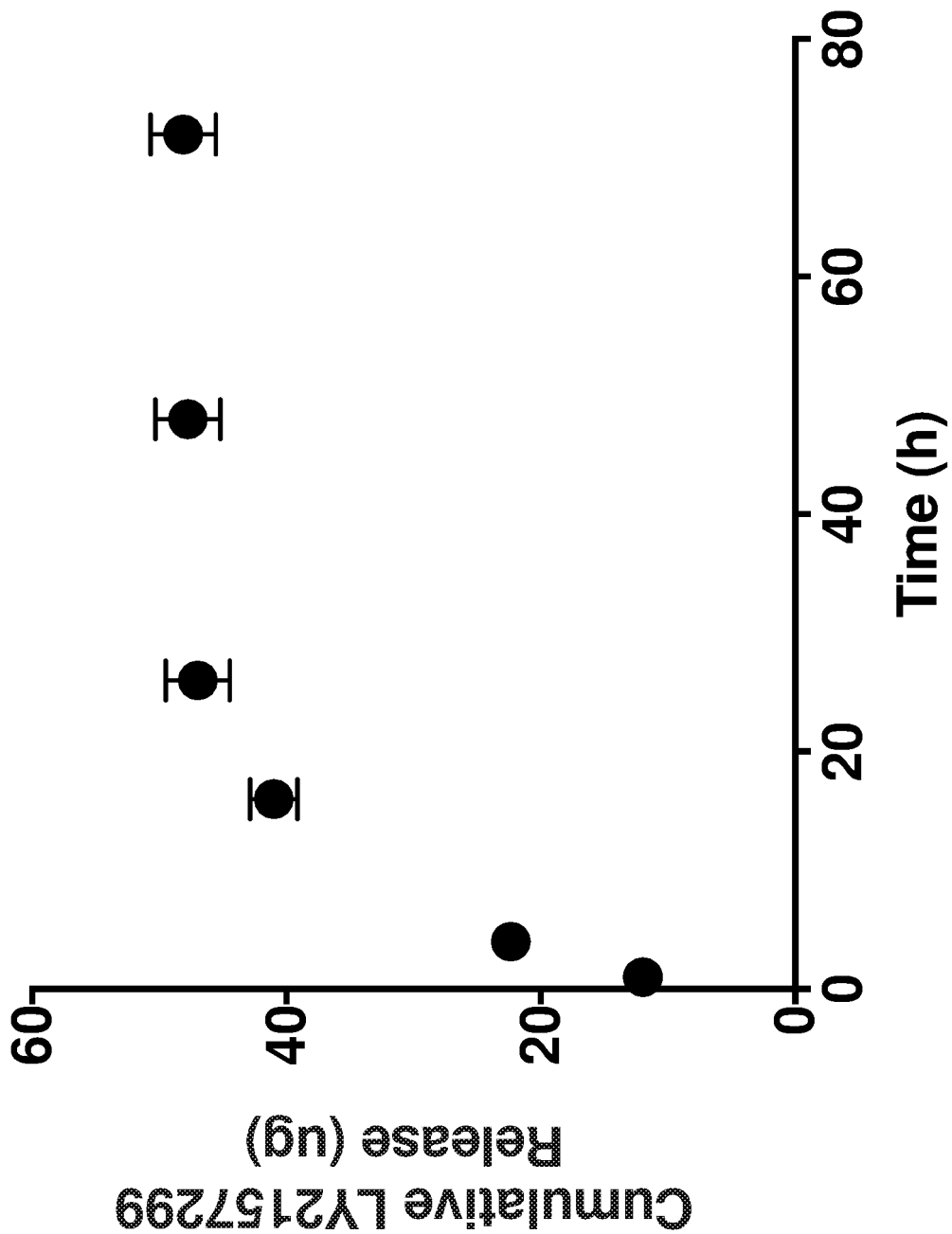

FIG. 23 is a graph showing Release of TGF-β inhibitor LY2157299 from cryoClick gels in vitro.

Figure 24B:
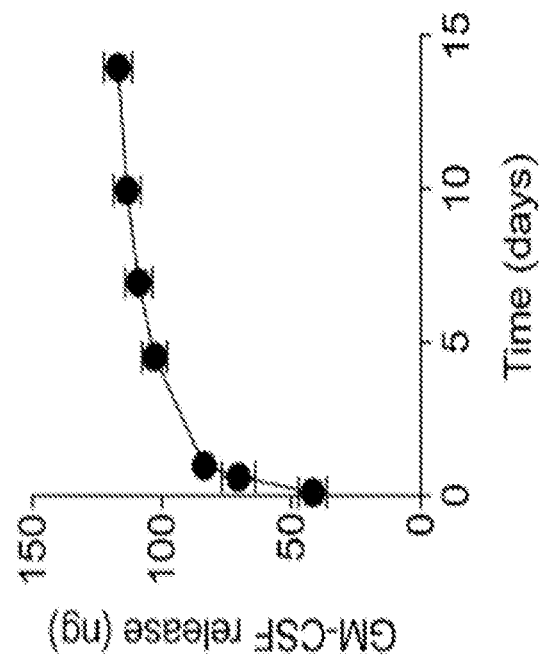
Figure 24D:
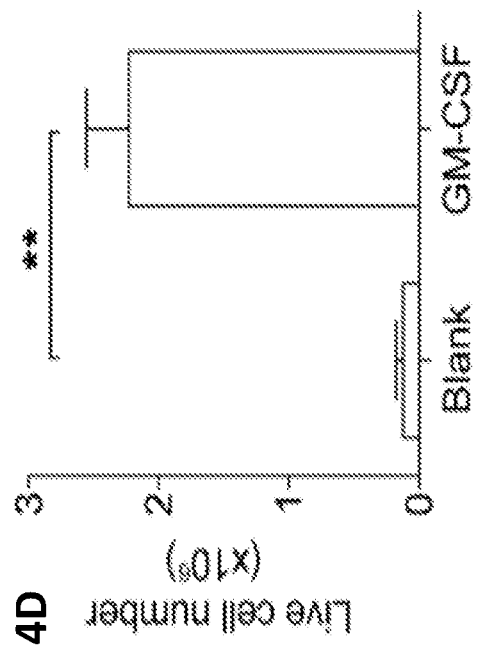
Figure 24A:
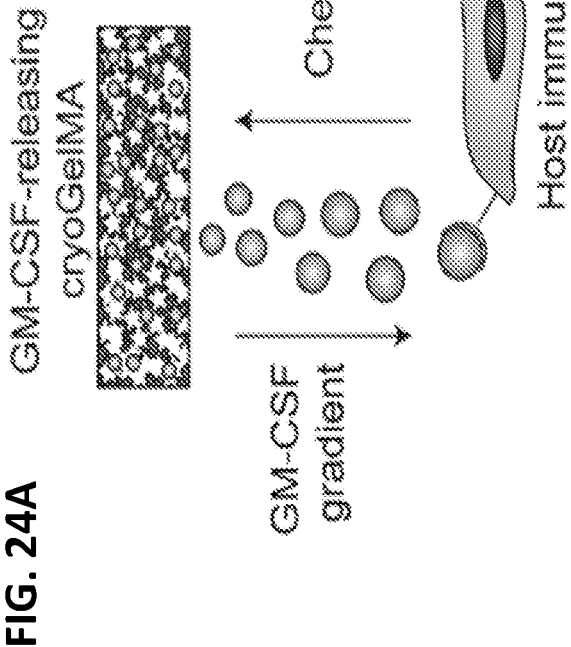
Figure 24C:
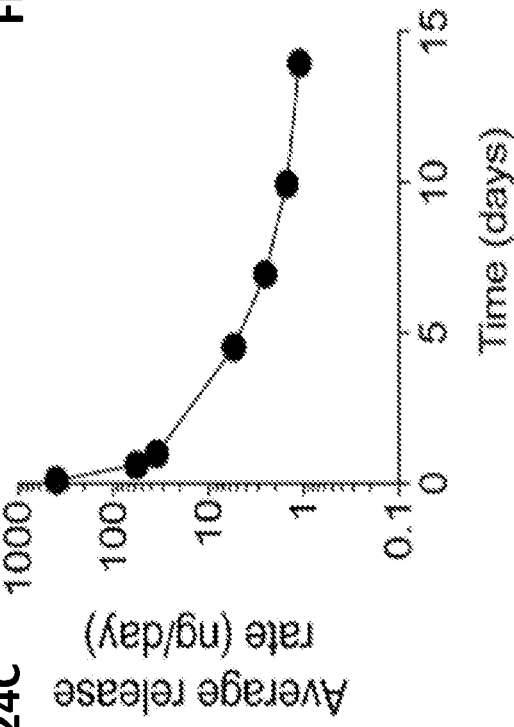
Figure 24:
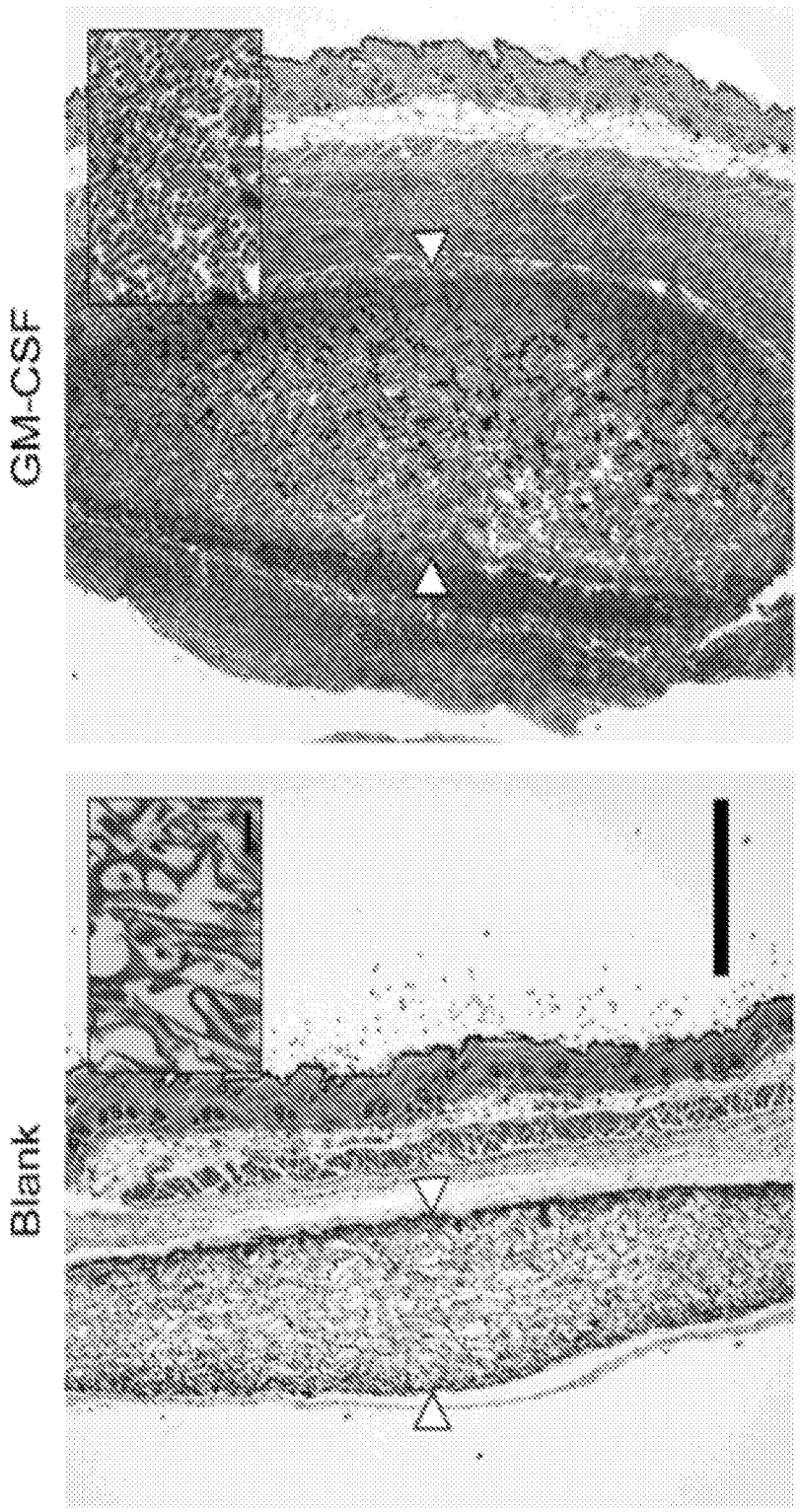
Figure 25A:
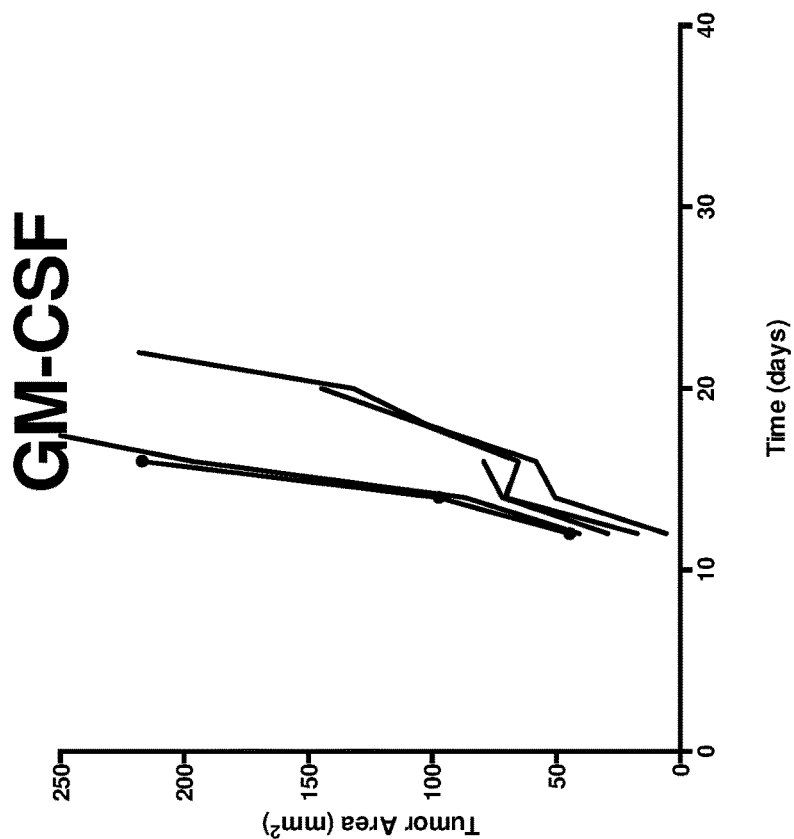
Figure 25B:
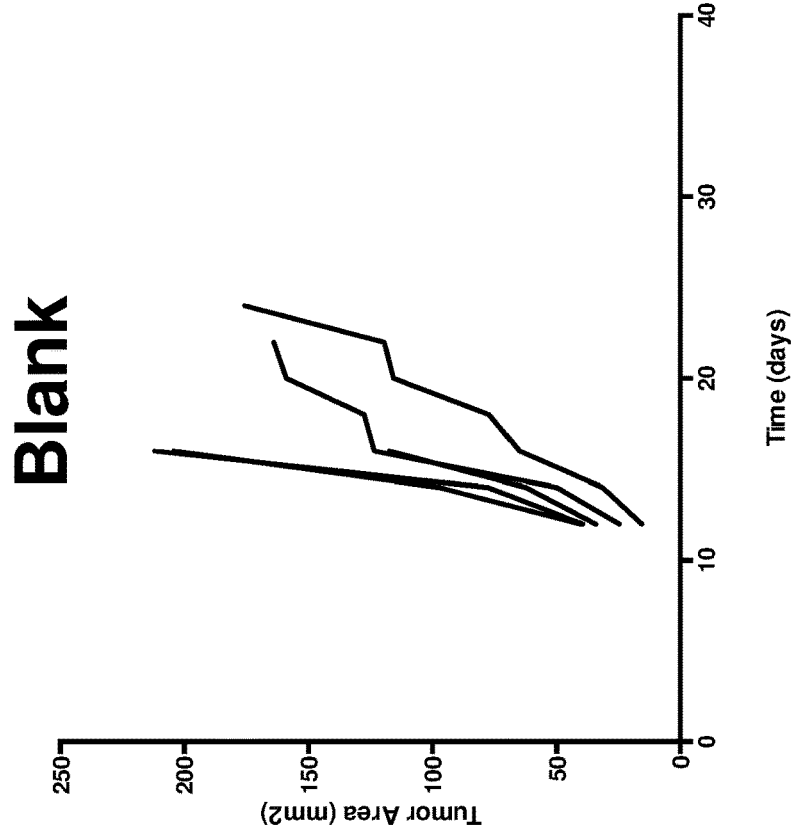
Figure 25D:
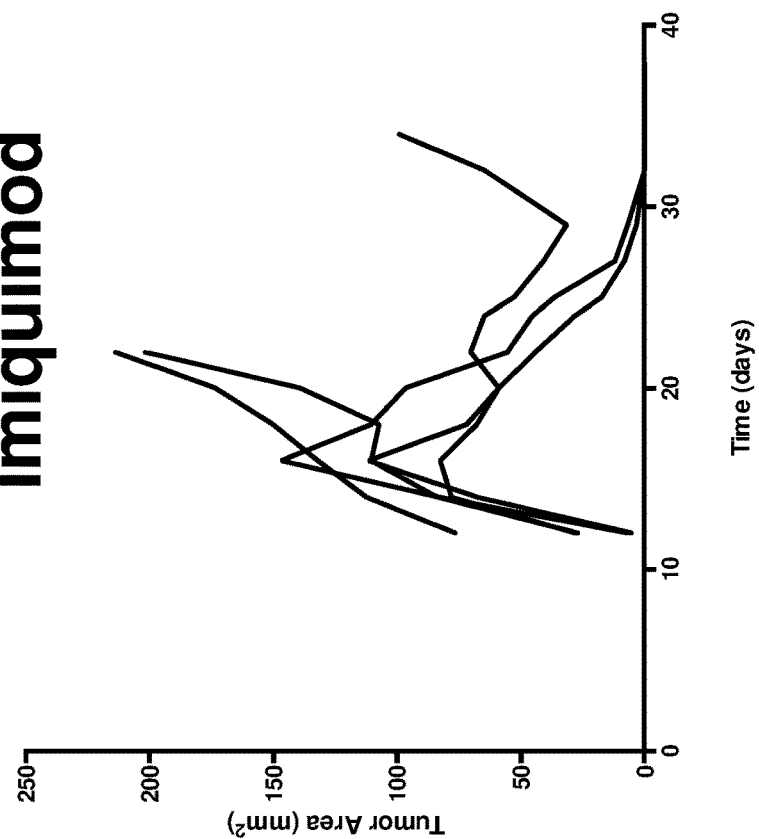
Figure 25C:
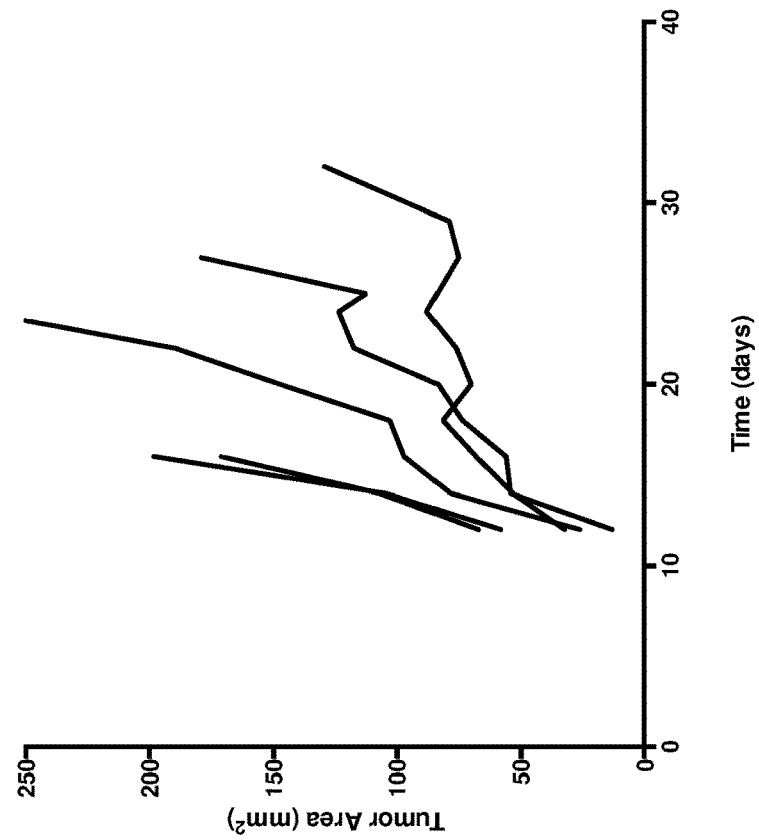

FIGS. 24A-E depicts in vivo cell recruitment to gelatin cryogels by sustained release of GM-CSF. FIG. 24A is a schematic of cell recruitment to GM-CSG-releasing gelatin cryogels. Sustained release of GM-CSF from the cryogel implant creates a chemoattractant gradient to attract host immune cells. FIG. 24B is a graph showing in vitro cumulative GM-CSF release from gelatin cryogels. FIG. 24C is a graph showing the average release rate of GM-CSF from gelatin cryogels. FIG. 24D is a graph showing recruited cell numbers in blank and GM-CSF-releasing gelatin cryogels at 14 d post-implant (Student's t-test, 1=3 mice, **p<0.01). FIG. 24E is a set of representative H&E staining from blank and GM-CSF-releasing cryogels 14 d after implantation in c57/B16J mice (n=3, scale bar=500m). Inset shows a magnified view of the scaffold interior (scale bar=20m). Arrows indicate the cryogel-tissue borders. Values respresent the mean and standard deviation in all plots.

FIG. 25A-D are graphs showing tumor growth and/or regression upon treatment with exemplary hydrogels. Mice injected with 2×10⁵ B16-mOVA cells (B16-F10 melanoma cells expressing inner cell membrane bound ovalbumin as a model antigen) were treated 11 and 13 days after tumor cell injection with click alginate hydrogels of the following compositions injected into the tumor: (A) Blank: hydrogel only; (B) GM-CSF: hydrogel containing 1 ug GM-CSF; (C) Imiquimod: hydrogel containing 1 mg imiquimod; (D) GM-CSF+Imiquimod: hydrogel containing 1 ug GM-CSF and 1 mg Imiquimod. Tumor dimensions were measured using calipers and used to calculate tumor area, which is plotted.

Figure 26:
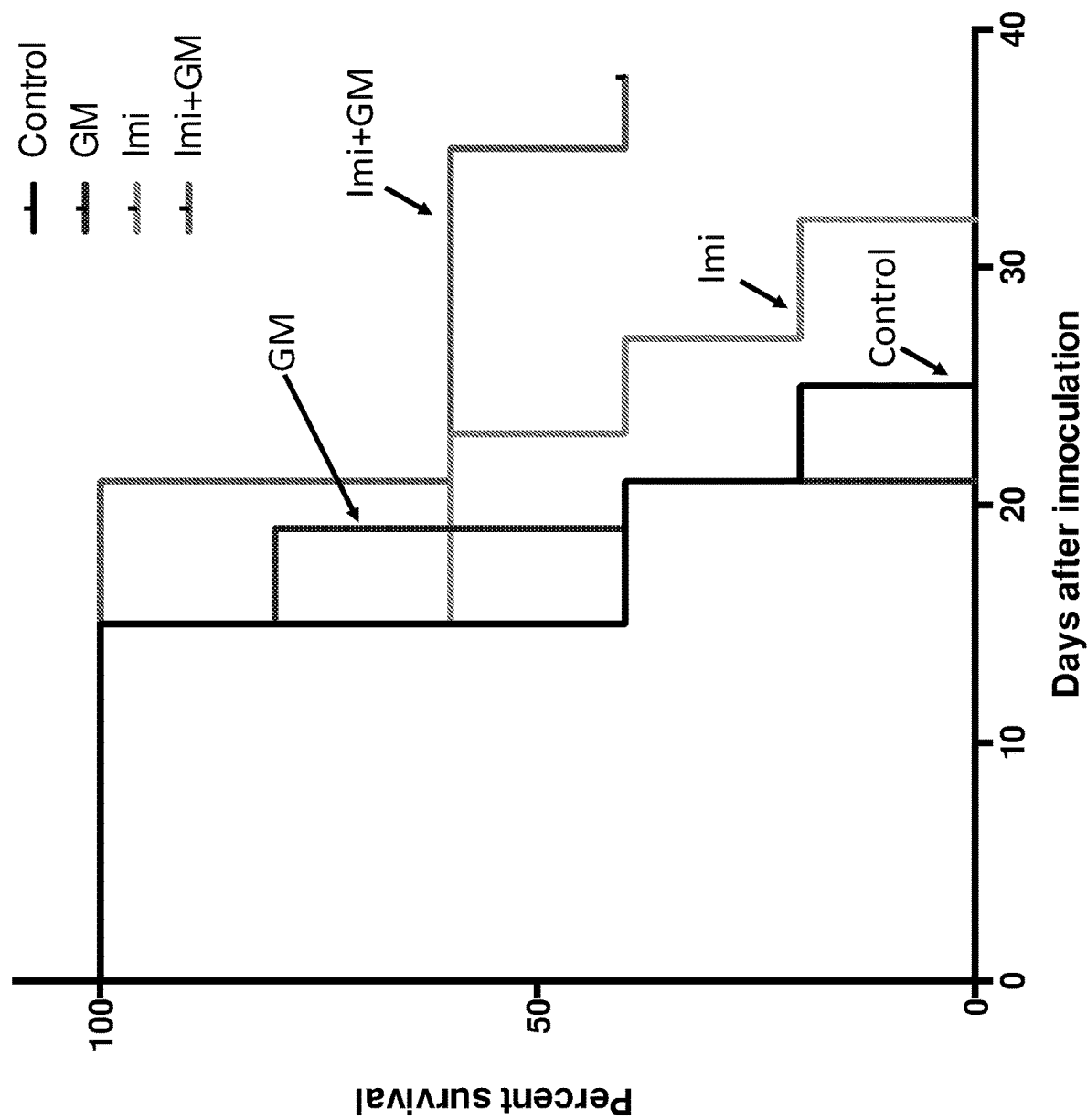

FIG. 26 is a graph illustrating survival data corresponding to the tumor growth curves shown in FIG. 25.

Figure 27:
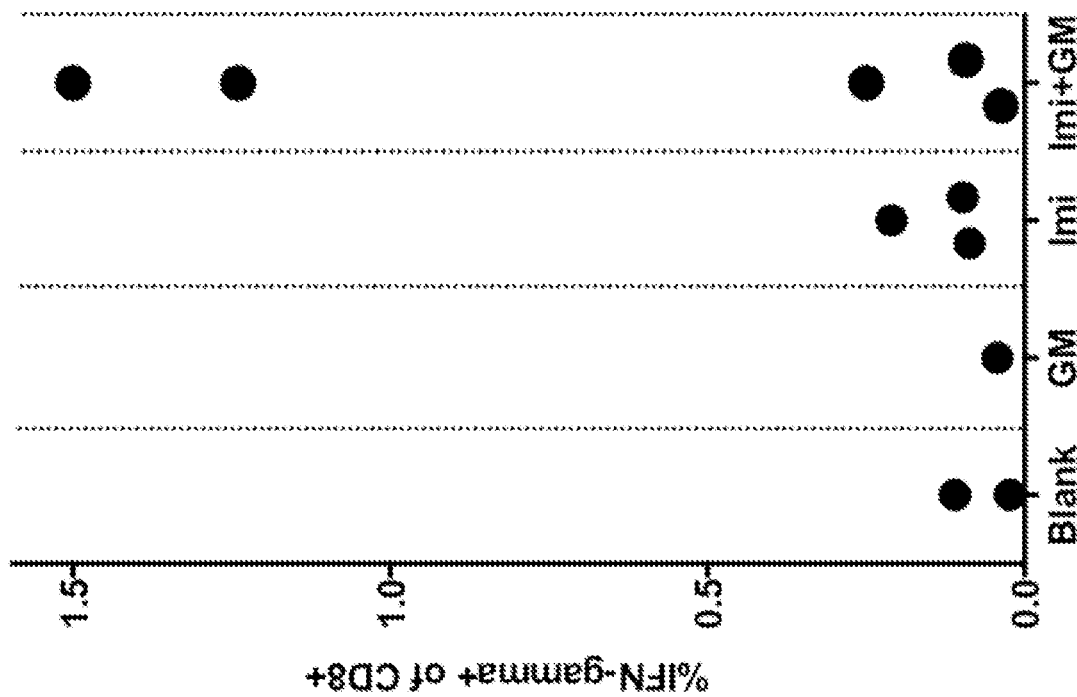

FIG. 27 is a graph showing the responses of T cells collected from treated mice upon stimulation with a peptide from ovalbumin. 21 days after tumor inoculation, peripheral blood was taken from mice that were surviving in each group. Cells were stimulated with a peptide from ovalbumin and the fraction of CD8+ T cells responding to the peptide was quantified using flow cytometry. The data indicate that in some mice, significant T cell responses are induced by peritumoral injection of gels containing GM-CSF and Imiquimod.

Figure 28A:
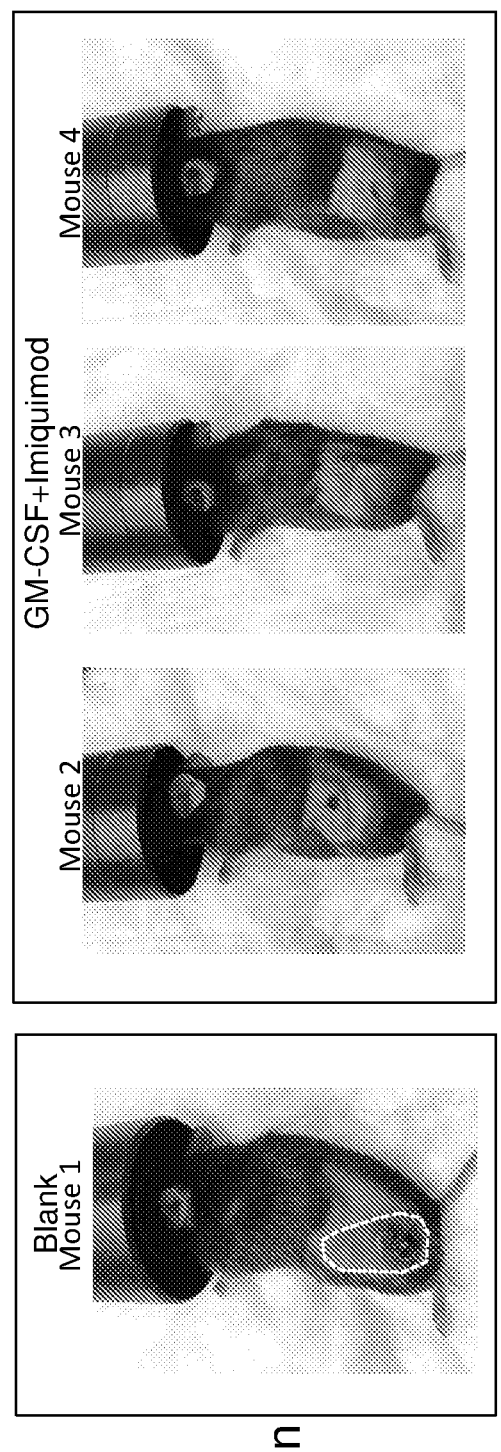
Figure 28B:
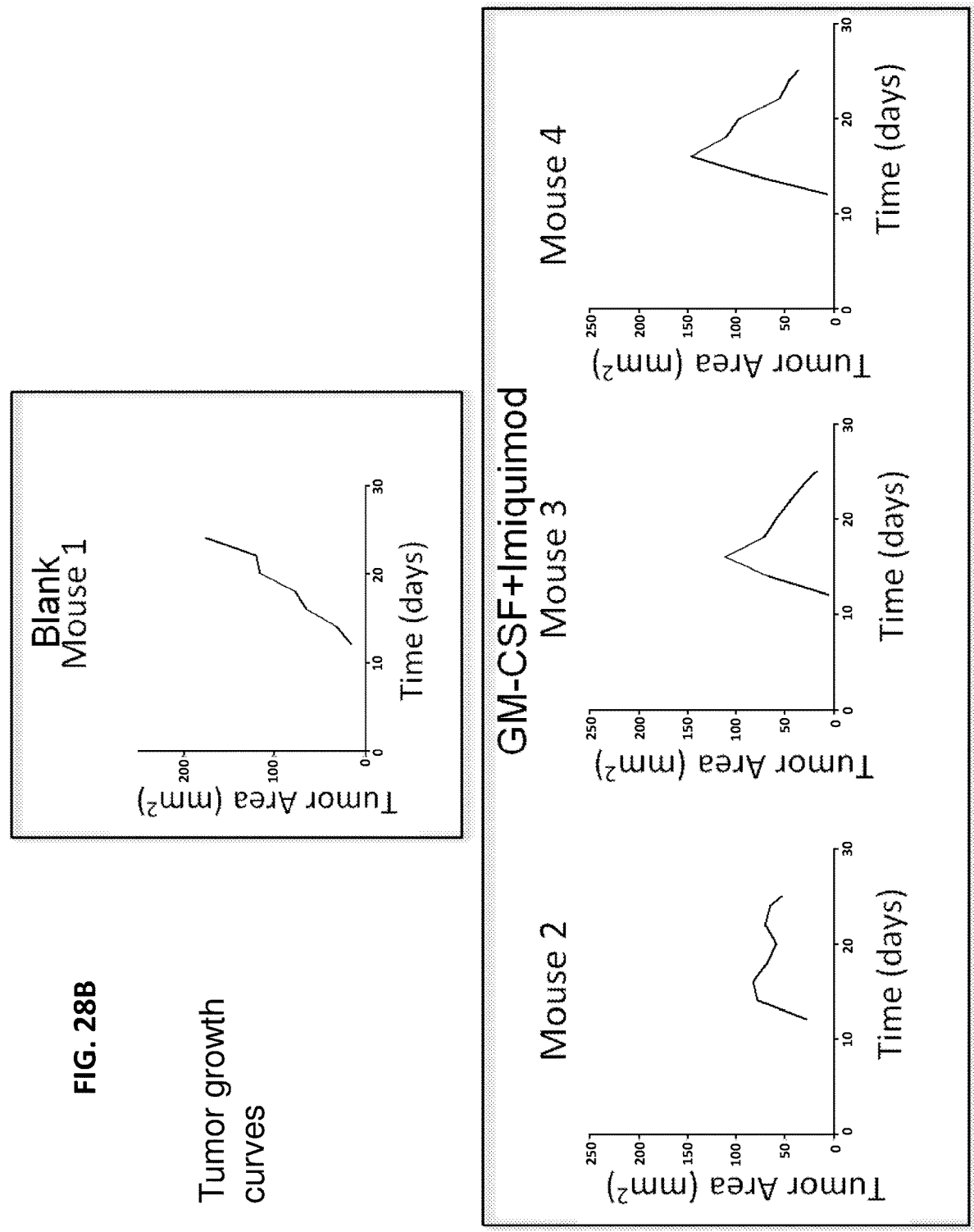
Figure 28C:
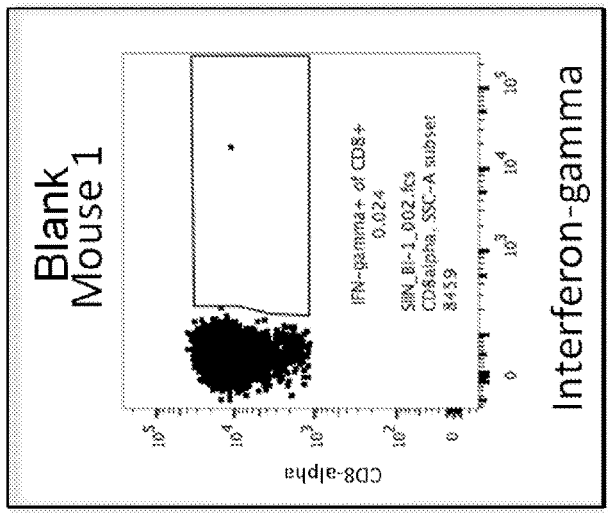
Figure 28C:
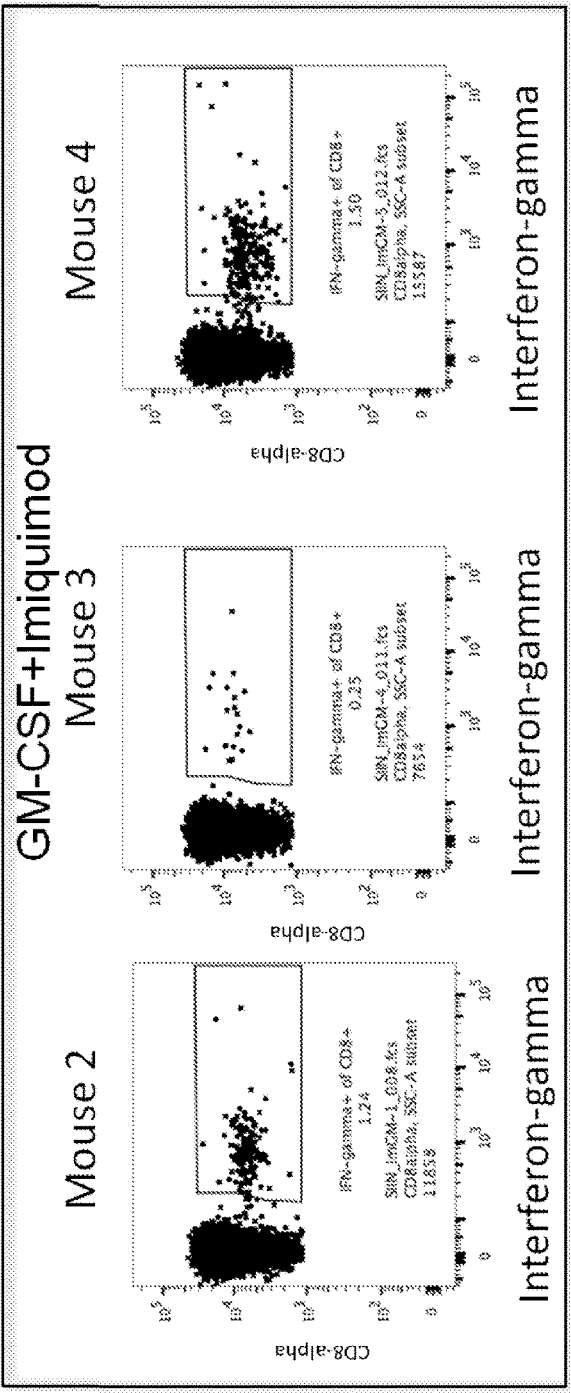

FIG. 28A-C is a set of images and graphs showing tumor size in treated mice, as well as flow cytometry plots showing CD8 T cell responses. The images and graphs provide exemplary data showing blank hydrogel treated mice and mice that showed regression in growing tumors in the GM-CSF+Imiquimod group. The data (FIGS. 28A and B) show a reduced tumor size in the GM-CSF+Imiquimod group relative to the blank hydrogel group. The flow cytometry plots (FIG. 28C) show significant CD8 T cell responses in the surviving GM-CSF+Imiquimod mice than in the lone surviving blank hydrogel mouse.

DETAILED DESCRIPTION OF THE INVENTION

The tumor microenvironment is highly immunosuppressive and prevents the activity of immune cells in generating and carrying out an anti-tumor immune response. Immunotherapy of cancer must do more than simply present antigens to the immune system—it must disrupt a pre-existing state of functional tolerance toward tumor antigens. This invention provides patient-specific immunization without antigen-loading of biomaterial (e.g., cryogel or hydrogel) delivery vehicle/device prior to administration to the patient. FIGS. 1-17 show delivery by a device, e.g., a cryogel or hydrogel (e.g., a click hydrogel), of a variety of immunomodulators to overcome immune inhibition in the tumor microenvironment.

An exemplary device for patient-specific immunization includes the one or more of the following components: an immune cell enrichment composition (e.g., GM-CSF for antigen presenting cells and/or a cytokine/chemoattractant for T cells or natural killer (NK) cells; a toll-like receptor (TLR) ligand (e.g., cytosine-guanosine oligonucleotide (CpG ODN) or poly I:C); an inducer of immunogenic cell death (e.g., a chemotherapeutic or cytotoxic agent) or means for generating radiation; immunomodulatory agent (e.g., inhibitor of tumor-mediated immune suppression). The device does not include a tumor antigen (such as a patient-derived tumor antigen or tumor cell lysate) prior to delivery to the patient, i.e., tumor antigens are generated in situ by virtue of administration of an inducer of immunogenic cell death, e.g., a device-delivered chemotherapeutic agent, or systemically delivered chemotherapeutic agent, or locally delivered chemotherapeutic agent, or delivery of tumor-killing radiation to the tumor itself. The factor-loaded cryogel or hydrogel devices alter the tumor microenvironment, modulate tolerance to tumor antigens, enrich the site for T cells, e.g., tumor-specific cytotoxic T cells, and enrich the tumor site with antigen presenting cells. For example, the device comprises a scaffold material—such as methacrylated gelatin or click alginate with or without particles to assist in or control release such as poly(lactide-co-glycolide) (PLGA) nanoparticles or encapsulated laponite nanoplatelets; agents to be released—1) chemotherapeutics, 2) cytokines—such as granulocyte-macrophage colony-stimulating factor (GM-CSF), FMS-like tyrosine kinase 3 ligand (Flt3L), Chemokine (C-C Motif) Ligand 20 (CCL20), Interleukin 15 (IL-15), Chemokine (C Motif) Ligand 1 (XCL1), Chemokine (C-X-C Motif) Ligand 10 (CXCL10), Interferon Alpha 1 (IFN-alpha), Interferon Beta (IFN-beta), and Interleukin 12 (IL-12) 3) immunostimulatory compounds—such as CpG oligonucleotide, polyinosine-polycytidylic acid (poly (I:C)) PEI-poly (I:C), polyadenylic-polyuridylic acid (poly (A:U)), PEI-poly (A:U), double stranded ribonucleic acid (RNA), monophosphoryl lipid A (MPLA), imiquimod, CRX-527, and OM-174; 4) small molecule immune suppression inhibitors—such as LY2157299, GW788388, LY364947, R268712, RepSox, SB525334, SD208, BP-1-102, S3I-M2001, STA-21, S3I-201, Stattic, Galiellalactone, INCB24360, NLG919, Norharmane, Rosmarinic Acid, 1-Methyltryptophan, and indoximod; and/or 5) antibodies that in inhibit immune suppression.

Non-liming examples of human amino acid sequences for isoforms of each of the cytokines listed above are publically available using the following accession numbers: GM-CSF—GenBank No: AAA52578.1 (SEQ ID NO: 3); Flt3L—UniProtKB/Swiss-Prot No: P49771.1 (SEQ ID NO: 4); CCL20—GenBank No: AAH20698.1 (SEQ ID NO: 5); IL-15—GenBank No: AAI00963.1 (SEQ ID NO: 6); XCL1—GenBank No: AAH69817.1 (SEQ ID NO: 7); CXCL10—GenBank No: EAX05693.1 (SEQ ID NO: 8); IFN-alpha—GenBank No: AAI12303.1 (SEQ ID NO: 9); IFN-beta—GenBank No: AAC41702.1 (SEQ ID NO: 10); and IL-12—NCBI Accession No. 1F45_A (Chain A) (SEQ ID NO: 11) and NCBI Accession No. 1F45_B (Chain B) (SEQ ID NO: 12).

One advantage of this patient-specific immunization system is reduced toxicity of immunomodulatory and/or chemotherapeutic agents, because the device delivers agents locally at the tumor site and/or permits the use of lower concentrations of the agents. Inducers of immunogenic cell death, e.g., chemotherapeutic/tumor cytotoxic agents synergize with the device-mediated immune modulation leading to improved tumor regression/reduction while reducing side effects. In one example, the cryogel or hydrogel includes an anthracycline or another immunogenic cell death inducer along with an immune cell enrichment composition, a toll-like receptor (TLR) ligand, and immunomodulatory agent (in the absence of tumor antigen prior to patient administration). In another example, the cryogel or hydrogel includes an immune cell enrichment composition, a TLR ligand, and an immunomodulatory agent (in the absence of tumor antigen prior to patient administration) without an anthracycline or other immunogenic cell death inducer with the anthracycline or other immunogenic cell death being administered to the patient systemically. In either case, the combination of components delivered to the patient in the context of the locally delivered device leads to a synergistic effect in tumor reduction and a clinical benefit to the cancer patient.

This approach complements other immunotherapy strategies by reducing the immunosuppressive environment at the tumor site. Advantages of using this biomaterial to deliver such immunomodulatory agents are listed below:

Local delivery to site of action—active agent to where it is needed.

Sustained release of bioactive agents—local high concentration for extended times unlike bolus injection that would be cleared rapidly.

Broader range of possible bioactive agents—agents, such as immunogenic cancer cell death inducers, immunostimulatory compounds, or immune cell enhancers that are not tolerable when administered systemically or as a bolus may be useful in devices of the invention. Thus, even agents that have been abandoned after clinical trials involving systemic or bolus administration are useful in the present subject matter.

Dose sparing—all drug to site of action so lower dose required than when delivered systemically.

Reduced side effects—these immunomodulatory agents can cause dose limiting toxicity when given systemically. This permits the use of compounds that are associated with adverse or dangerous side effects when administered systemically.

No tumor material/known tumor antigen required if performing vaccination—some other vaccine strategies require taking material from the patient or having a known tumor antigen Avoid need for surgical implant. In various embodiments in which a device or scaffold of the invention is administered without surgical implantation, the device or scaffold is injected using a needle. For example, the device or scaffold may be injected through a 16-gauge, an 18-gauge, a 20-gauge, a 22-gauge, a 24-gauge, a 26-gauge, a 28-gauge, a 30-gauge, a 32-gauge, or a 34-gauge needle.

As used herein, injection or other administration to a "tumor site" may mean placement of a device or scaffold of the invention such that (i) at least a portion of the device or scaffold is within the tumor, (ii) the entire device or scaffold is within the tumor, (iii) at least a portion of the device or scaffold contacts the tumor, or (iv) the device or scaffold is in the proximity of the tumor. In certain embodiments, the device or scaffold is administered such that it is peritumoral (i.e., in direct contact with or in close proximity to the tumor). Alternatively, the tumor capsule is punctured to deliver the device or scaffold directly into the tumor mass. In some embodiments, the tumor is not contacted with the device or scaffold. Various implementations of the present subject matter avoid puncturing or otherwise physically disrupting the tumor. Thus, aspects of the present invention relate to generating an immune response without physically interrupting or disrupting a tumor capsule. In non-limiting examples, the device or scaffold may be placed within 0 (i.e., touching the tumor) to 10 mm of a tumor. In various embodiments, the point of the device or scaffold that is closest to the tumor is about 0 (i.e., directly contacting tumor mass), 0.1, 0.5, 1, 2, 3, 4, 5, 6, 7, 8, 9, or 10 mm from the tumor mass boundary. In some embodiments, the point of the device or scaffold that is closest to the tumor is less than about 1, 2, 3, 4, 5, 6, 7, 8, 9, 10 mm from the tumor. In certain embodiments, the point of the device or scaffold that is closest to the tumor is at least about 1, 2, 3, or 5 mm and less than about 6, 7, 8, 9, or 10 mm from the tumor.

Embodiments of the present subject matter obviate the need for patient-derived material (e.g., patient-derived tumor antigens). Surprisingly, devices and scaffolds of the present subject matter that do not contain a tumor antigen (from a subject or another source) at the time of administration are effective at promoting an anti-tumor immune response in a subject. Anti-tumor vaccination may be achieved by inserting a device or scaffold into a tumor with, e.g., a needle, or by delivering a device or scaffold near a tumor without interrupting the tumor mass with the needle. Thus, aspects of the present invention relate to devices and scaffolds that promote immune activation against a tumor in vivo without (i) containing a tumor antigen when administered or (ii) disrupting a tumor capsule.

Delivery of immunomodulatory factors (e.g., agents that modulate targets in the T-cell checkpoint) to the tumor site directly reduces the immunosuppressive local microenvironment at/near the tumor.

Exemplary Compounds for Intratumoral or Peritumoral Delivery

Chemotherapy—Aspects of the present subject matter include compounds that induce immunogenic cell death. Such chemotherapeutic agents include members of the anthracycline class of compounds, e.g., doxorubicin, daunorubicin, epirubicin, idarubicin, and valrubicin as well as mitoxantrone, an anthracycline analog.

Chemotherapeutic agents may be used to generate antigen and prime the immune system. The anthracycline class of chemotherapeutic agents kill tumor cells in a way that causes priming of the immune system (immunogenic cell death). Anthracyclines are anticancer compounds that were originally derived from *Streptomyces* sp. Anthracyclines are red aromatic polyketides and occur in variety of forms due to the structural differences in the aglycone and the different attached sugar residues.

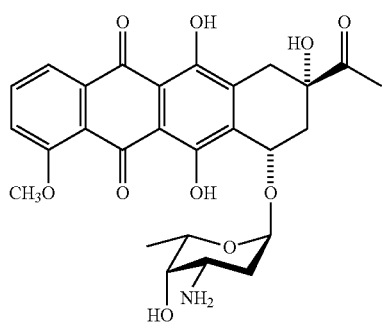

Daunorubicin, the prototypical anthracycline

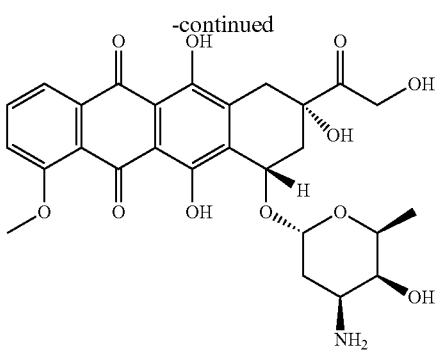

Doxorubicin

An exemplary chemotherapeutic agent that elicits immunogenic cell death is a tricyclic compound as shown below. In one embodiment, the present invention relates to a compound of formula (I):

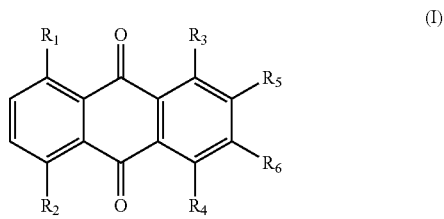

or a pharmaceutically acceptable salt, or solvate thereof, wherein $R_1$ and $R_2$ are independently selected from —OCH$_3$, —OH or —H; $R_3$ and $R_4$ are independently selected from —OH or —NHCH$_2$CH$_2$NHCH$_2$CH$_2$OH; $R_5$ and $R_6$ are selected from H or alternatively together form a six membered unsaturated carbocycle, substituted with $R_7$, $R_8$, and $R_9$; and $R_7$, $R_8$, and $R_9$ are independently selected from —OH, —C(=O)CH$_3$, —C(=O)CH$_2$OC(O)CH$_2$CH$_2$CH$_2$CH$_3$, —C(=O)CH$_2$OH,

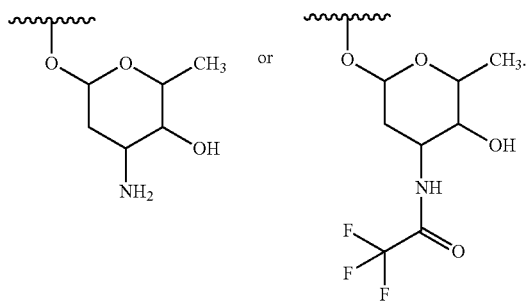 [SMILES: *OC1CC(N)C(O)C(C)O1 ; *OC1CC(NC(=O)C(F)(F)F)C(O)C(C)O1]

For example, one set of compounds of formula (I) includes those in which $R_3$ and $R_4$ are OH. Furthermore, this set of compounds can comprise a subset of compounds of formula (I), wherein $R_3$ and $R_4$ are OH and $R_1$ is H.

Another set of compounds of formula (I) includes those in which $R_1$ and $R_2$ are OH. This set of compounds can also comprise a subset of compounds of formula (I), wherein $R_1$ and $R_2$ are OH and $R_3$ and $R_4$ are NHCH$_2$CH$_2$NHCH$_2$CH$_2$OH. Another subset of compounds of formula (I) include those in which $R_1$ and $R_2$ are OH, $R_3$ and $R_4$ are NHCH$_2$CH$_2$NHCH$_2$CH$_2$OH, and $R_5$ and $R_6$ are H.

Another one embodiment, the present invention relates to a subset of compounds of formula (II):

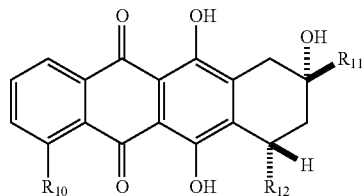

or a pharmaceutically acceptable salt, or solvate thereof, wherein $R_{10}$ is H or —OCH$_3$; $R_{11}$ is —C(=O), C(=O)CH$_2$OH or —C(=O)CH$_2$OC(=O)CH$_2$CH$_2$CH$_2$CH$_3$; and $R_{12}$ is

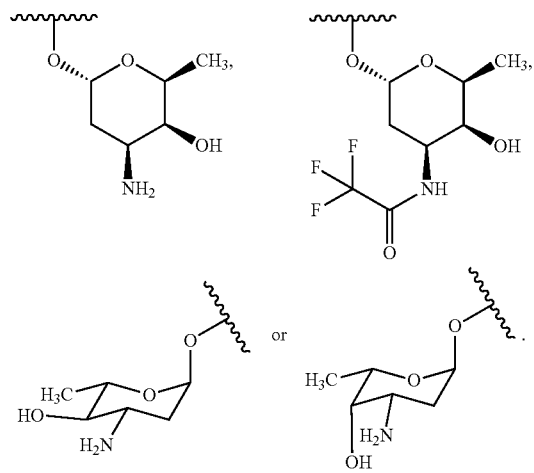

For example, one set of compounds of formula (II) includes those in which $R_{11}$ is OCH$_3$.

By "anthracycline" is meant a class of drugs that are commonly used as a chemotherapeutic agent. In embodiments, an anthracycline has a tricyclic core (e.g., Mitoxantrone) or a tetracyclic core. In embodiments, an anthracycline has a structure according to the following formula,

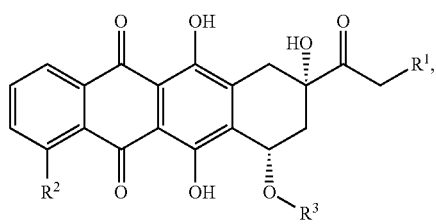

wherein $R^1$ is —H, —OH, or —O(C=O)(C$_1$-C$_6$ alkyl);

$R^2$ is —H or —OCH$_3$; and $R^3$ is an amino sugar. Exemplary anthracyclines doxorubicin, daunorubicin, epirubicin, idarubicin, and valrubicin are described in Table 1. Still further exemplary anthracyclines include those described as Formulas I and II of U.S. Pat. No. 9,107,962, herein incorporated by reference in its entirety.

| Anthracycline | $R^1$ | $R^2$ | $R^3$ |
|---|---|---|---|
| daunorubicin | —H | —OCH$_3$ | |
| doxorubicin | —OH | —OCH$_3$ | |
| epirubicin | —OH | —OCH$_3$ | |
| idarubicin | —H | —H | |
| valrubicin | —O(C=O)(C$_4$H$_9$) | —OCH$_3$ | |

Other classes of chemotherapeutic compounds that induce immunogenic cell death include alkylating agents such as platinum-containing anti-cancer drugs (e.g., cisplatin, oxaliplatin, and carboplatin), as well as (RS)—N,N-bis(2-chloroethyl)-1,3,2-oxazaphosphinan-2-amine 2-oxide (cyclophosphamide) and the related metabolite 4-hydroxy cyclophosphamide.

Immunogenic cell death may also be induced by cardiac glycosides such as oleandrin, ouabain, bufalin, digitoxin, digoxin, cinobufatalin, cinobufagin, and resibufogenin.

The activity of such inducers of immunogenic cell death results in antigen presenting cells being recruited to engulf dying tumor cells at the device injection site.

Cytokines—A variety of protein cytokines are used to recruit antigen presenting cells or cytotoxic lymphocytes to the material implant site and support their function there.

Immunostimulatory compounds—Immunostimulatory compounds are used to cause antigen presenting cell maturation.

Inhibitors—Inhibitors of a tumor-generated immunosuppressive microenvironment are used to downregulate immunosuppression at the tumor site, potentiating the action of the agents listed above. Inhibitors comprise proteins, peptides, antibodies, small molecules, or RNA interference (RNAi) molecules that reduce the expression of a target protein.

Many inhibitory pathways exist within tumors that suppress tumor antigen presentation and the anti-tumor immune response. For example, TGF-β dampens tumor immunosurveillance and polarizes innate immune cells towards an immature differentiation status that prevents optimal anti-tumor immunity. Additionally, the STAT3 pathway promotes the production of immune inhibitory cytokines within the tumor, dampens anti-tumor T-helper 1-mediated immunity, and inhibits dendritic cell maturation. Also, Indoleamine-pyrrole 2,3-dioxygenase (IDO or INDO EC 1.13.11.52). IDO is an enzyme that in humans is encoded by the IDO1 gene and catalyzes the degradation of the essential amino acid L-tryptophan to N-formylkynurenine. IDO can deplete tryptophan in the tumor microenvironment, inhibiting the activity of T cells and dendritic cells. Small molecule inhibitors of these (TGF-β, STAT3, and IDO) and other immunosuppressive pathways have been developed and are being tested clinically. Examples of such inhibitors include TGF-β pathway inhibitors (LY2157299), STAT3 pathway inhibitors (BP-1-102), IDO pathway inhibitors (NLG919); PD-1 pathway inhibitors, CTLA-4 pathway inhibitors, LAG-3 pathway inhibitors, B7-H3 pathway inhibitors, and/or TIM3 pathway inhibitors.

In addition to protein inhibitors and antibody-based inhibitors, small molecule inhibitors are loaded into or onto the device and are delivered to the location of a tumor/tumor site to inhibit the local tumor-mediated immunosuppression. Small molecules are compounds that have a molecular mass of a less than 1000 daltons, e.g., 500 daltons or less, 250 daltons or less, 100 daltons or less. Exemplary small molecule immunomodulatory compounds, e.g., inhibitors of immune suppression, are described below. Many are generally hydrophobic.

TGF-β Inhibitors

Non-limiting examples of TGF-β inhibitors include LY2157299, GW788388, LY364947, R268712, RepSox, SB525334, and SD208.

LY2157299 has the following structure:

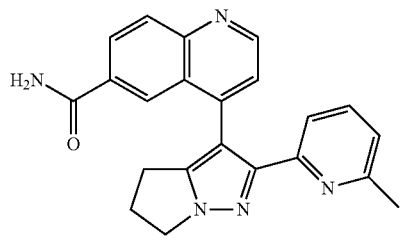 [SMILES: Cc1cccc(-c2nn3c(c2-c2ccnc4ccc(C(N)=O)cc24)CCC3)n1]

LY2157299 is also known as galunisertib and is described in Maier A, et al. (2015) Cell Oncol 38:131-144, the entire content of which is incorporated herein by reference. This compound has been used to treat solid tumors such as liver cancer (e.g. hepatocellular carcinoma) (clinicaltrials.gov/ct2/show/NCT02240433?term=LY2157299&rank=2) and has been used in combination with anti-PD-1 antibody from Bristol Meyers Squibb in advanced (metastatic and/or unresectable) glioblastoma, hepatocellular carcinoma and non-small cell lung cancer—news.bms.com/press-release/rd-news/bristol-myers-squibb-and-lilly-enter-clinical-collaboration-agreement-evaluate These and other non-limiting examples of TGF-β inhibitors are described in U.S. Pat. No. 7,265,225 issued Sep. 4, 2007; U.S. Pat. No. 7,834,029 issued Nov. 16, 2010; and U.S. Pat. No. 7,872,020 issued Jan. 8, 2011, the entire contents of each of which are incorporated herein by reference.

GW788388 has the following structure:

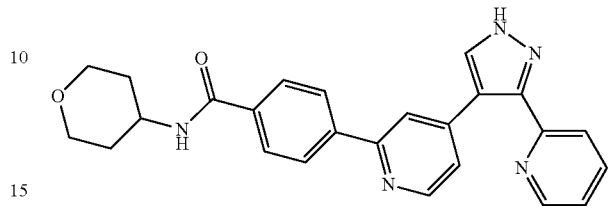

GW788388 is described in Gellibert et al (2006) Discovery of 4-{4-[3-(pyridin-2-yl)-1H-pyrazol-4-yl]pyridin-2-yl}-N-(tetrahydro-2H-pyran-4-yl)benzamide (GW788388): a potent, selective, and orally active transforming growth factor-β type I receptor inhibitor. J. Med. Chem. 49 2210, the entire content of which is incorporated herein by reference.

LY364947 has the following structure:

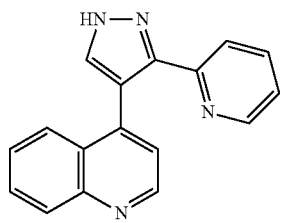 [SMILES: c1ccc(-c2n[nH]cc2-c2ccnc3ccccc23)nc1]

LY364947 is described in Sawyer et al (2003) Synthesis and activity of new aryl- and heteroaryl-substituted pyrazole inhibitors of the transforming growth factor-μ type I receptor kinase domain. Journal of Medicinal Chemistry, 46(19), 3953-3956, the entire content of which is incorporated herein by reference.

R268712 has the following structure:

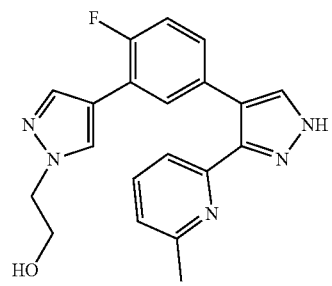

R268712 is described in Terashima et al (2014) R-268712, an orally active transforming growth factor-β type I receptor inhibitor, prevents glomerular sclerosis in a Thy1 nephritis model. Eur. J. Pharmacol. 734:60, the entire content of which is incorporated herein by reference.

RepSox has the following structure:

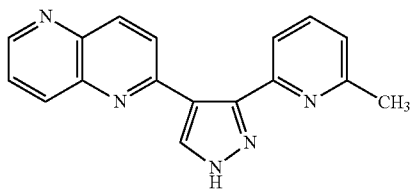 [SMILES: Cc1cccc(-c2n[nH]cc2-c2ccc3ncccc3n2)n1]

RepSox is also known as E-616452, SJN 2511, and ALK5 Inhibitor II. RepSox is described in Gellibert et al (2004) Identification of 1,5-naphthyridine derivatives as a novel series of potent and selective TGF-γ type I receptor inhibitors. J. Med. Chem. 47(18), 4494-4506, the entire content of which is incorporated herein by reference.

SB525334 has the following structure:

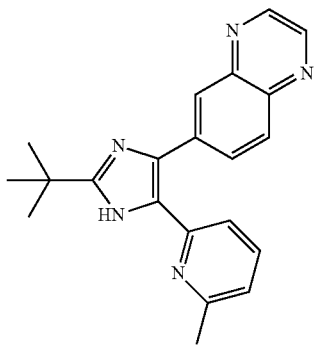 [SMILES: Cc1cccc(-c2[nH]c(C(C)(C)C)nc2-c2ccc3nccnc3c2)n1]

SB525334 is described in Grygielko et al (2005) Inhibition of gene markers of fibrosis with a novel inhibitor of transforming growth factor-β type I receptor kinase in puromycin-induced nephritis. J. Pharmacol. Exp. Ther. 313 943, the entire content of which is incorporated herein by reference.

SD208 has the following structure:

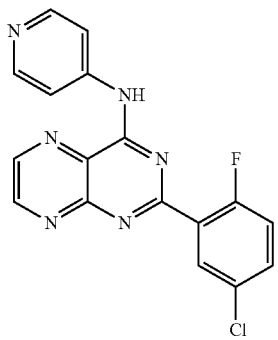 [SMILES: Fc1ccc(Cl)cc1-c1nc(Nc2ccncc2)c2nccnc2n1]

SD208 is described in Uhl et al (2004) SD-208, a novel transforming growth factor β feceptor I kinase inhibitor, inhibits growth and invasiveness and enhances immunogeneicity of murine and human glioma cells in vitro and in vivo. Cancer Res. 64(21), 7954-7961, the entire content of which is incorporated herein by reference.

Non-limiting examples of antibodies that antagonize TGF-0 include metelimumab (also known as CAT-192) and fresolimumab (also known as GC1008). Fresolimumab is described in Grater et al. (2008) "A cytokine-neutralizing antibody as a structural mimetic of 2 receptor interactions" Proceedings of the National Academy of Sciences 105 (51): 20251-20256, the entire content of which is incorporated herein by reference.

STAT3 Inhibitors

Non-limiting examples of STAT3 inhibitors include BP-1-102, S3I-M2001, STA-21, S3I-201, Stattic, Galiellalactone, a polypeptide having the sequence PY*LKTK (where Y* represents phosphotyrosine), and a polypeptide having the sequence Y*LPQTV (where Y* represents phosphotyrosine). Additional non-limiting examples of STAT3 inhibitors are described in Yue and Turkson Expert Opin Investig Drugs. 2009 January; 18(1): 45-56, the entire content of which is incorporated herein by reference.

S3I-M2001 has the following structure:

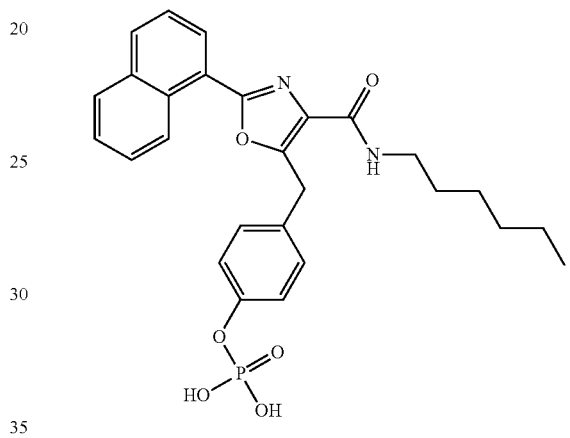

S3I-M2001 is described in U.S. Pat. No. 8,609,639, issued Dec. 17, 2013, the entire content of which is incorporated herein by reference.

STA-21 has the following structure:

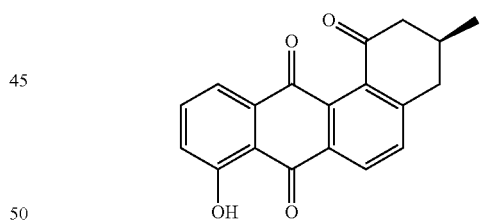

STA-21 is described in Miyoshi et al., J Invest Dermatol. 2011 January; 131(1):108-17, the entire content of which is incorporated herein by reference.

S3I-201 has the following structure:

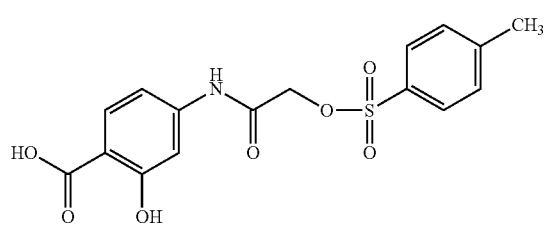 [SMILES: Cc1ccc(S(=O)(=O)OCC(=O)Nc2ccc(C(=O)O)c(O)c2)cc1]

S3I-201 is described in Siddiquee K, et al. Proc Natl Acad Sci USA, 2007, 104(18), 7391-7396, the entire content of which is incorporated herein by reference.

Stattic has the following structure:

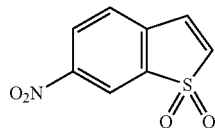 [SMILES: O=[N+]([O-])c1ccc2c(c1)S(=O)(=O)C=C2]

Stattic is described in Schust J, et al. Chem Biol, 2006, 13(11), 1235-1242, the entire content of which is incorporated herein by reference.

Galiellalactone has the following structure:

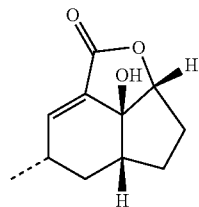

Galiellalactone is described in Don-Doncow et al., J Biol Chem. 2014 Jun. 6; 289(23):15969-78, the entire content of which is incorporated herein by reference.

BP-1-102 has the following structure:

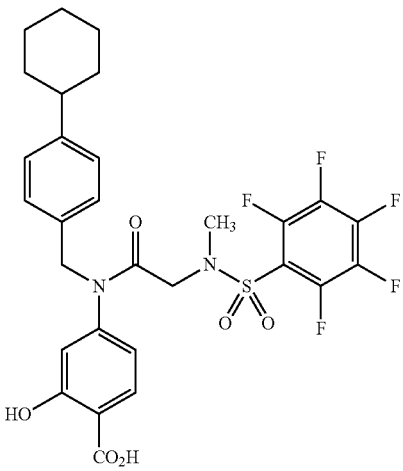 [SMILES: CN(CC(=O)N(Cc1ccc(C2CCCCC2)cc1)c1ccc(C(=O)O)c(O)c1)S(=O)(=O)c1c(F)c(F)c(F)c(F)c1F]

Signal transducer and activator of transcription 3 (STAT3) is a transcription factor which in humans is encoded by the STAT3 gene. The STAT3 inhibitor, BP-1-102 is active against tumors (e.g., solid tumors) such as human lung cancer and breast cancer in animals (PNAS 2012 109 (24) 9623-9628). Another small molecule STAT3 inhibitor is OPB-31121 (Cancer Lett. 2013 Jul. 10; 335(1):145-52. doi: 10.1016/j.canlet.2013.02.010. Epub 2013 Feb. 10).

Another non-limiting example is OPB-31121—clinicaltrials.gov/ct2/show/NCT00955812, clinicaltrials.gov/ct2/show/NCT01406574, OPB-31121 is an orally bioavailable inhibitor of STAT3, with antineoplastic activity. OPB-31121 inhibits the phosphorylation of STAT3, which prevents binding of STAT3 to DNA sequences on a variety of STAT3-responsive promoters and results in the inhibition of STAT3-mediated transcription and, potentially, the inhibition of tumor cell proliferation. STAT3 is constitutively activated in a variety of cancers, contributing to the loss of cell growth control and neoplastic transformation. OPB-31121 is described in Kim et al. (2013) OPB-31121, a novel small molecular inhibitor, disrupts the JAK2/STAT3 pathway and exhibits an antitumor activity in gastric cancer cells. Cancer Lett 335: 145-152, the entire content of which is incorporated herein by reference.

Other inhibitors are described in Miklossy et al., 2013 Nat. Rev. Drug Discov.12:611-629, the entire content of which is incorporated herein by reference.

IDO Inhibitors

IDO is expressed by cancer cells in a range of tumor types. High IDO expression correlates with poor outcome in a number of cancers, such as ovarian cancer, endometrial cancer, colon cancer, and melanoma. Non-limiting examples of IDO inhibitors include INCB24360, INCB24360 analogues, NLG919 (also known as GDC-0919), Norharmane, Rosmarinic Acid, 1-Methyltryptophan, and indoximod.

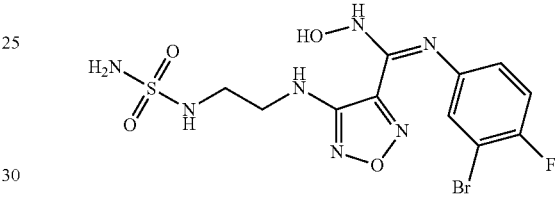

INCB24360

The structure of an INCB24360 analogue, which also inhibits IDO, has the following structure:

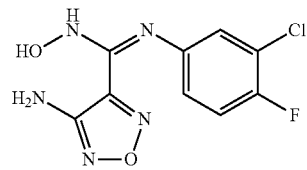 [SMILES: Nc1nonc1/C(=N\c1ccc(F)c(Cl)c1)NO]

This analogue is described in Yue et al. J Med Chem. 2009, 52(23), 7364-7367, the entire content of which is incorporated herein by reference.

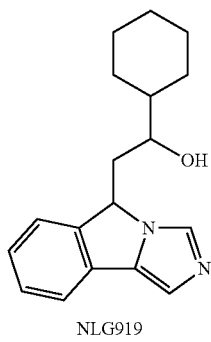 [SMILES: OC(CC1c2ccccc2-c2cncn21)C1CCCCC1]

NLG919

INCB24360, its analogue shown above, and NLG919 are IDO1 inhibitors. Selective inhibition of IDO1 effectively regulates mediators of antitumor immunity (Liu et al., Blood, 2010, 115: 3520-3530, incorporated herein by reference). These drugs are useful to inhibit tumor-mediated immune evasion or suppression and are optionally combined with immune checkpoint blockers such as antibody-based inhibitors, e.g., anti-PD1 (clinicaltrials.gov/ct2/show/NCT02327078, incorporated herein by reference).

Norharmane is another example of an IDO inhibitor, and has the following structure:

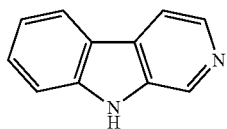 [SMILES: c1ccc2c(c1)[nH]c1cnccc12]

Norharmane is described in Chiarugi et al. (2000) Journal of Leukocyte Biology 68 (2): 260-6, the entire content of which is incorporated herein by reference.

Rosmarinic Acid is a further example of an IDO inhibitor, and has the following structure:

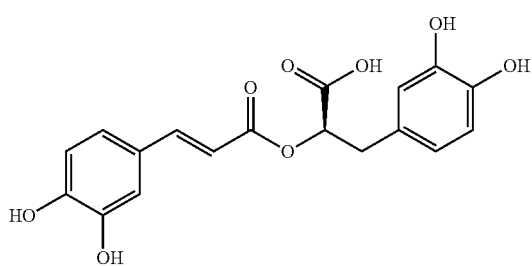 [SMILES: O=C(/C=C/c1ccc(O)c(O)c1)O[C@H](Cc1ccc(O)c(O)c1)C(=O)O]

Rosmarinic Acid is described in Lee et al. (2007) Biochemical Pharmacology 73 (9): 1412-21, the entire content of which is incorporated herein by reference.

1-Methyltryptophan is an additional example of an IDO inhibitor and has the following structure:

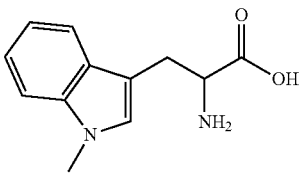 [SMILES: Cn1cc(CC(N)C(=O)O)c2ccccc21]

1-Methyltryptophan is described in Hou et al. (2007) Cancer Res. 67 (2): 792-801, the entire content of which is incorporated herein by reference.

The structure of indoximod is

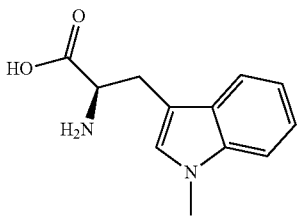 [SMILES: Cn1cc(C[C@@H](N)C(=O)O)c2ccccc21]

Indoximod is described in Soliman H H, Jackson E, Neuger T et al. A first in man phase I trial of the oral immunomodulator, indoximod, combined with docetaxel in patients with metastatic solid tumors. Oncotarget. 2014 Sep. 30; 5 (18):8136-46, the entire content of which is incorporated herein by reference.

Additional non-limiting examples of MO inhibitors are described in U.S. Patent Application Publication No. US 2014315962 published Oct. 23, 2014, the entire content of which is incorporated herein by reference.

PD-1 Pathway Inhibitors

PD-1 limits the activity of T cells in peripheral tissues at the time of an inflammatory response to infection and to limit autoimmunity PD-1 blockade in vitro enhances T-cell proliferation and cytokine production in response to a challenge by specific antigen targets or by allogeneic cells in mixed lymphocyte reactions. A strong correlation between PD-1 expression and response was shown with blockade of PD-1 (Pardoll, Nature Reviews Cancer, 12: 252-264, 2012). PD-1 blockade can be accomplished by a variety of mechanisms including antibodies that bind PD-1 or its ligand, PD-L1. Examples of PD-1 and PD-L1 blockers are described in U.S. Pat. Nos. 7,488,802; 7,943,743; 8,008,449; 8,168,757; 8,217,149, and PCT Published Patent Application Nos: WO03042402, WO2008156712, WO2010077634, WO2010089411, WO2010036959, WO2011066342, WO2011159877, WO2011082400, WO2011161699, and WO2013181452, the entire contents of each of which are incorporated herein by reference. In certain embodiments the PD-1 blockers include anti-PD-L1 antibodies.

Non-limiting examples of PD-1 pathway inhibitors include AMP-224, Nivolumab (also known as MDX-1106; ONO-4538), Pembrolizumab, Pidilizumab, BMS 936559 (also known as MDX-1105), MPDL3280A (also known as Atezolizumab), MEDI4736, and MSB0010718C. Non-limiting examples of PD-1 pathway inhibitors are also described in Dolan and Gupta Cancer Control. 2014 July; 21(3):231-7 the entire content of which is incorporated herein by reference.

AMP-224, also known as B7-DCIg, is a PD-L2-Fc fusion soluble receptor. AMP-224 is being used in U.S. National Institutes of Health (NIH) clinical trial number NCT02298946. AMP-224 is described in U.S. Patent Application Publication No. 2011/0223188, published Sep. 15, 2011; U.S. Patent Application Publication No. 2013/0017199, published Jan. 17, 2013; and Smothers et al., Ann Oncol (2013) 24 (suppl 1): i7, the entire contents of each of which are incorporated herein by reference.

Nivolumab is also known as ONO-4538, BMS-936558, MDX1106, and Opdivo. Nivolumab is described in U.S. Pat. No. 8,008,449, issued Aug. 30, 2011; and Sundar R, Cho B C, Brahmer J R, Soo R A (2015). "Nivolumab in NSCLC: latest evidence and clinical potential" Ther Adv Med Oncol 7 (2): 85-96, the entire contents of each of which are incorporated herein by reference.

Pembrolizumab is also known as MK-3475, lambrolizumab, and Keytruda. Pembrolizumab is also described in U.S. Pat. No. 8,952,136, issued Feb. 10, 2015; U.S. Pat. No. 8,168,757, issued May 1, 2012; and Hamid et al., (2013) "Safety and tumor responses with lambrolizumab (anti-PD-1) in melanoma" New England Journal of Medicine 369 (2): 134-44, the entire contents of each of which are hereby incorporated herein by reference.

Pidilizumab also known as CT-011 and is described in U.S. Pat. No. 8,747,847, issued Jun. 10, 2014; Westin et al. (2014) "Safety and Activity of PD1 Blockade by Pidilizumab in Combination with Rituximab in Patients with Relapsed Follicular Lymphoma: a Single Group, Open-label, Phase 2 Trial" Lancet Oncol. 15: 69-77, the entire contents of each of which are incorporated herein by reference.

BMS 936559 is also known as MDX-1105. BMS 936559 is described in U.S. Pat. No. 7,943,743, issued May 17, 2011; and Brahmer, J. R. et al. Safety and activity of anti-PD-L1 antibody in patients with advanced cancer. N. Engl. J. Med. 366, 2455-2465 (2012), the entire contents of each of which are incorporated herein by reference.

MPDL3280A is also known as Atezolizumab. MPDL3280A has the CAS Registry number 1422185-06-5. MPDL3280A is described in McDermott et al., Atezolizumab, an Anti-Programmed Death-Ligand 1 Antibody, in Metastatic Renal Cell Carcinoma: Long-Term Safety, Clinical Activity, and Immune Correlates From a Phase Ia Study, J Clin Oncol. 2016 Jan. 11. pii: JC0637421 (Epub ahead of print) PMID: 26755520.

MEDI4736 is described in U.S. Pat. No. 8,779,108, issued Jul. 15, 2014; and Ibrahim et al., Semin Oncol. 2015 June; 42(3):474-83, the entire contents of each of which are incorporated herein by reference.

MSB0010718C is also known as Avelumab. The CAS Registry number for MSB0010718C is 1537032-82-8. MSB0010718C is described in Boyerinas B, Jochems C, Fantini M, Heery C R, Gulley J L, Tsang K Y, Schlom J. Cancer Immunol Res. 2015 October; 3(10):1148-57, the entire content of which is incorporated herein by reference.

CTLA-4 Inhibitors

Non-limiting examples of CTLA-4 inhibitors include tremelimumab and ipilimumab. See, e.g., Pardoll D M (April 2012). "The blockade of immune checkpoints in cancer immunotherapy". Nat. Rev. Cancer 12 (4): 252-64, the entire content of which is incorporated herein by reference.

Tremelimumab is also known as ticilimumab and CP-675,206. Tremelimumab is described in Antoni Ribas (28 Jun. 2012). "Tumor immunotherapy directed at PD-1". New England Journal of Medicine 366 (26): 2517-9, the entire content of which is incorporated herein by reference.

Ipilimumab is also known as Yervoy, MDX-010, and MDX-101. Ipilimumab is described in Antoni Ribas (28 Jun. 2012). "Tumor immunotherapy directed at PD-1". New England Journal of Medicine 366 (26): 2517-9, the entire content of which is incorporated herein by reference.

LAG-3 Inhibitors

A non-limiting example of a LAG-3 inhibitor is IMP321. IMP321 is soluble version of the immune checkpoint molecule LAG-3, used to increase an immune response to tumors. IMP321 is described in Brignone et al. (2007) "IMP321 (sLAG-3), an immunopotentiator for T cell responses against a HBsAg antigen in healthy adults: a single blind randomised controlled phase I study" J Immune Based Ther Vaccines 5 (1): 5, the entire content of which is incorporated herein by reference.

Non-limiting examples of soluble fractions of the LAG-3 protein which may be useful in embodiments of the invention are described in U.S. Pat. No. 5,955,300, issued Sep. 21, 1999, the entire content of which is incorporated herein by reference.

Non-limiting examples of anti-LAG-3 antibodies include BMS-986016 and GSK2831781.

GSK2831781 is described in U.S. Patent Application Publication No. 2014/0286935, published Sep. 25, 2014, the entire content of which is incorporated herein by reference.

BMS-986016 is described in PCT International Patent Application No. WO 2015/042246, published Mar. 26, 2015, the entire content of which is incorporated herein by reference.

Non-limiting examples of anti-LAG-3 antibodies are described in U.S. Patent Application Publication No. 2014/0286935, published Sep. 25, 2014; U.S. Patent Application Publication No. 2015/0307609, published Oct. 29, 2015; PCT International Patent Application Publication No. WO2008132601, published Nov. 6, 2008, the entire contents of each of which are incorporated herein by reference.

B7-H3 Inhibitors

A non-limiting example of a B7-H3 inhibitor is the antibody known as MGA271. MGA271 is described in Loo et al. (2012) Cancer Res. 2012 Jul. 15; 18(14):3834-45, the entire content of which is incorporated herein by reference.

Additional non-limiting examples of anti-B7-H3 inhibitors are described in U.S. Pat. No. 8,802,091, issued Aug. 12, 2014, the entire content of which is incorporated herein by reference.

TIM3 Inhibitors

Non-limiting examples of TIM3 inhibitors include the antibodies described in U.S. Pat. No. 8,841,418, issued Sep. 23, 2014; and U.S. Pat. No. 8,552,156, issued Oct. 8, 2013, the entire contents of each of which are incorporated herein by reference.

Antibodies

The term "antibody" is used in the broadest sense and specifically covers monoclonal antibodies (including full length monoclonal antibodies), polyclonal antibodies, multispecific antibodies (e.g., bispecific antibodies), monovalent antibodies, multivalent antibodies, and antibody fragments so long as they exhibit the desired biological activity (e.g., Fab and/or single-armed antibodies).

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F (ab')$_2$; diabodies; linear antibodies; single-chain antibody molecules (e.g., scFv); and multispecific antibodies formed from antibody fragments.

The terms "full length antibody," "intact antibody," and "whole antibody" are used herein interchangeably to refer to an antibody having a structure substantially similar to a native antibody structure or having heavy chains that contain an Fc region.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three hypervariable regions (HVRs) of each variable domain interact to define an antigen binding site on the surface of the VH-VL dimer. Collectively, the six HVRs or a subset thereof confer antigen binding specificity to the antibody. However, even a single variable domain (or half of an Fv comprising only three HVRs specific for an antigen) has the ability to recognize and bind antigen, although usually at a lower affinity than the entire binding site.

A "Fab" fragment contains a variable and constant domain of the light chain and a variable domain and the first constant domain (CHI) of the heavy chain. F(ab') 2 antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the VH and VL domains of an antibody, wherein these domains are present in a single polypeptide chain. Generally the Fv polypeptide further comprises a polypeptide linker between the VH and L domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-31S (1994), the entire content of which is incorporated herein by reference.

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, BP 404,097; WO 93/11161; and Hollinger et al., Proc. Natl. Acad. Sci. USA, 90:6444-6448 (1993), the entire content of which is incorporated herein by reference.

The expression "linear antibodies" refers to the antibodies described in Zapata et al., Protein Eng., 8 (10): 1057-1062 (1995), the entire content of which is incorporated herein by reference. Briefly, these antibodies comprise a pair of tandem Fd segments (V.sub.H-C.sub.H1-V.sub.H-C.sub.H1) which, together with complementary light chain polypeptides, form a pair of antigen binding regions. Linear antibodies can be bispecific or monospecific.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

RNA Interference

As used herein, "RNA interference inducing compound" or "RNAi compound" refers to a compound capable of inducing RNA interference or "RNAi" of protein expression, depending on the context. RNAi involves mRNA degradation, but many of the biochemical mechanisms underlying this interference are unknown. The use of RNAi has been described in Fire et al., 1998, Carthew et al., 2001, and Elbashir et al., 2001, the contents of which are incorporated herein by reference.

Isolated RNA molecules can mediate RNAi. That is, the isolated RNA molecules of the present invention mediate degradation or block expression of mRNA that is the transcriptional product of the gene, which is also referred to as a target gene. For convenience, such mRNA may also be referred to herein as mRNA to be degraded. The terms RNA, RNA molecule (s), RNA segment(s) and RNA fragment(s) may be used interchangeably to refer to RNA that mediates RNA interference. These terms include double-stranded RNA, small interfering RNA (siRNA), hairpin RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the RNA molecules of the present invention can also comprise nonstandard nucleotides, including non-naturally occurring nucleotides or deoxyribonucleotides. Collectively, all such altered RNAi molecules are referred to as analogs or analogs of naturally-occurring RNA. RNA of the present invention need only be sufficiently similar to natural RNA that it has the ability to mediate RNAi.

As used herein the phrase "mediate RNAi" refers to and indicates the ability to distinguish which mRNA molecules are to be afflicted with the RNAi machinery or process. RNA that mediates RNAi interacts with the RNAi machinery such that it directs the machinery to degrade particular mRNAs or to otherwise reduce the expression of the target protein. In one embodiment, the present invention relates to RNA molecules that direct cleavage of specific mRNA to which their sequence corresponds. It is not necessary that there be perfect correspondence of the sequences, but the correspondence must be sufficient to enable the RNA to direct RNAi inhibition by cleavage or blocking expression of the target mRNA.

As noted above, the RNA molecules of the present invention in general comprise an RNA portion and some additional portion, for example a deoxyribonucleotide portion. In some embodiments, an RNAi molecules comprises about 10, 11, 12, 13, 14, 15, 16, 17, 18, 19, 20, 21, 22, or 23 nucleotides, about 16 to 29 nucleotides, about 18 to 23 nucleotides, or about 21-23 nucleotides. In various embodiments, a device or scaffold comprises one or more RNAi molecules that mediate RNAi of one or more genes that inhibit T cell or dendritic cell suppression. In some embodiments, the target gene is an immune checkpoint gene. In some embodiments, the target gene is an immune suppression gene. In certain embodiments, the target gene encodes a TGF-β, STAT3, IDO, PD-1, PD-1 ligand 1, CTLA-4, LAG-3, or TIM3 protein. Exemplary nucleotide sequences for each of these targets are as follows: TGF-β (GenBank No: M60316.1, SEQ ID NO: 13); STAT3 (NCBI Reference Sequence No: NM_139276.2, SEQ ID NO: 14); IDO1 (NCBI Reference Sequence No: NM_002164.5, SEQ ID NO: 15); PD-1 (NCBI Reference Sequence No: NM_005018.2, SEQ ID NO: 16); PD-L1 (NCBI Reference Sequence No: NM_014143.3, SEQ ID NO: 17); CTLA-4 (NCBI Reference Sequence No: NM_001037631.2, SEQ ID NO: 18); LAG-3 (GenBank No: X51985.3, SEQ ID NO: 19); and TIM3 (GenBank No: AF450242.1, SEQ ID NO: 20). These sequences are not limiting, as additional variants and isoforms of each protein may be targeted.

In various embodiments, an RNAi molecule may be present in a device or scaffold with a transfection agent. For example, the RNAi molecule may be condensed with polyethylimine (PEI), poly-L-lysine (PLL), or a polyamidoamine (PAMAM) dendrimer. See, e.g., Huang et al. (2005) Human Gene Therapy 16:609-617. Additional non-limiting examples of transfection agents include liposomes (e.g., lipofectamine).

Granulocyte Macrophage Colony Stimulating Factor (GM-CSF)

Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages.

Various scaffold devices described herein comprise and release GM-CSF polypeptides to attract host DCs to the device. Contemplated GM-CSF polypeptides are isolated from endogenous sources or synthesized in vivo or in vitro. Endogenous GM-CSF polypeptides are isolated from healthy human tissue. Synthetic GM-CSF polypeptides are synthesized in vivo following transfection or transformation of template DNA into a host organism or cell, e.g. a mammal or cultured human cell line. Alternatively, synthetic GM-CSF polypeptides are synthesized in vitro by polymerase chain reaction (PCR) or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

GM-CSF polypeptides are modified to increase protein stability in vivo. Alternatively, GM-CSF polypeptides are engineered to be more or less immunogenic. Endogenous mature human GM-CSF polypeptides are glycosylated, reportedly, at amino acid residues 23 (leucine), 27 (asparagine), and 39 (glutamic acid) (see U.S. Pat. No. 5,073,627). GM-CSF polypeptides of the present invention are modified at one or more of these amino acid residues with respect to glycosylation state.

GM-CSF polypeptides are recombinant. Alternatively GM-CSF polypeptides are humanized derivatives of mammalian GM-CSF polypeptides. Exemplary mammalian species from which GM-CSF polypeptides are derived include, but are not limited to, mouse, rat, hamster, guinea pig, ferret, cat, dog, monkey, or primate. In a preferred embodiment, GM-CSF is a recombinant human protein (PeproTech, Catalog #300-03). Alternatively, GM-CSF is a recombinant murine (mouse) protein (PeproTech, Catalog #315-03). Finally, GM-CSF is a humanized derivative of a recombinant mouse protein.

Human Recombinant GM-CSF (PeproTech, Catalog #300-03) is encoded by the following polypeptide sequence (SEQ ID NO: 30):

```
MAPARSPSPS TQPWEHVNAI QEARRLLNLS RDTAAEMNET

VEVISEMFDL QEPTCLQTRL ELYKQGLRGS LTKLKGPLTM

MASHYKQHCP PTPETSCATQ IITFESFKEN LKDFLLVIPF

DCWEPVQE
```

Murine Recombinant GM-CSF (PeproTech, Catalog #315-03) is encoded by the following polypeptide sequence (SEQ ID NO: 31):

```
MAPTRSPITV TRPWKHVEAI KEALNLLDDM PVTLNEEVEV
VSNEFSFKKL TCVQTRLKIF EQGLRGNFTK LKGALNMTAS
YYQTYCPPTP ETDCETQVTT YADFIDSLKT FLTDIPFECK KPVQK
```

Human Endogenous GM-CSF is encoded by the following mRNA sequence (NCBI Accession No. NM_000758 and SEQ ID NO: 32):

```
  1  acacagagag aaaggctaaa gttctctgga ggatgtggct gcagagcctg ctgctcttgg 61  gcactgtggc ctgcagcatc tctgcacccg cccgctcgcc cagcccagc acgcagccct 121  gggagcatgt gaatgccatc caggaggccc ggcgtctcct gaacctgagt agagacactg 181  ctgctgagat gaatgaaaca gtagaagtca tctcagaaat gtttgacctc caggagccga 241  cctgcctaca gacccgcctg gagctgtaca gcagggcct gcggggcagc ctcaccaagc 301  tcaagggccc cttgaccatg atggccagcc actacaagca gcactgccct ccaaccccgg 361  aaacttcctg tgcaacccag attatcacct ttgaaagttt caagagaaac ctgaaggact 421  ttctgcttgt catccccttt gactgctggg agccagtcca ggagtgagac cggccagatg 481  aggctggcca agccggggag ctgctctctc atgaaacaag agctagaaac tcaggatggt 541  catcttggag ggaccaaggg gtgggccaca gccatggtgg gagtggcctg gacctgccct
```

```
-continued
601  gggccacact gaccctgata caggcatggc agaagaatgg gaatatttta tactgacaga 661  aatcagtaat atttatatat ttatattttt aaaatattta tttatttatt tatttaagtt 721  catattccat atttattcaa gatgttttac cgtaataatt attattaaaa atatgcttct 781  a
```

Human Endogenous GM-CSF is encoded by the following amino acid sequence (NCBI Accession No. NP 000749.2 and SEQ ID NO: 33):

```
MWLQSLLLLGTVACSISAPARSPSPSTQPWEHVNAIQEARRLLNLSRDTA
AEMNETVEVISEMFDLQEPTCLQTRLELYKQGLRGSLTKLKGPLTMMASH
YKQHCPPTPETSCATQIITFESFKENLKDFLLVIPFDCWEPVQE
```

Immunostimulatory Compounds

As used herein and depending on context, the term "immunostimulatory compound" includes compounds that increase a subject's immune response to an antigen. Examples of immunostimulatory compounds include immune stimulants and immune cell activating compounds. Devices of the present subject matter may contain immunostimulatory compounds that help program the immune cells to recognize ligands and enhance antigen presentation. Immune cell activating compounds include TLR agonists. Such agonists include pathogen associated molecular patterns (PAMPs), e.g., an infection-mimicking composition such as a bacterially-derived immunomodulator (a.k.a., danger signal). TLR agonists include nucleic acid or lipid compositions (e.g., monophosphoryl lipid A (MPLA)). In one example, the TLR agonist comprises a TLR9 agonist such as a cytosine-guanosine oligonucleotide (CpG-ODN), a poly(ethylenimine) (PEI)-condensed oligonucleotide (ODN) such as PEI-CpG-ODN, or double stranded deoxyribonucleic acid (DNA). In another example, the TLR agonist comprises a TLR3 agonist such as polyinosine-polycytidylic acid (poly (I:C)), PEI-poly (I:C), polyadenylic-polyuridylic acid (poly (A:U)), PEI-poly (A:U), or double stranded ribonucleic acid (RNA). Other exemplary vaccine immunostimulatory compounds include lipopolysaccharide (LPS), chemokines/cytokines, fungal beta-glucans (such as lentinan), imiquimod, CRX-527, and OM-174. Additional non-limiting immunostimulatory compounds include immunostimulatory antibodies.

Imiquimod has the following structure:

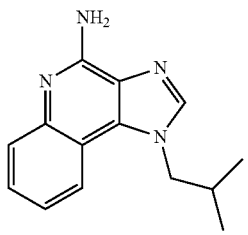 [SMILES: CC(C)Cn1cnc2c(N)nc3ccccc3c21]

This compound is described in U.S. Pat. No. 7,323,568 issued Jan. 29, 2008; U.S. Pat. No. 8,642,616 issued Feb. 4, 2004; Walter et al. (2013) Nat Commun 4: 1560; Bilu and Sauder (2003) Br. J. Dermatol. 149 Suppl 66: 5-8; and Miller et al. (1999) Int J Immunopharmacol 21 (1): 1-14, the entire contents of each of which are incorporated herein by reference.

Additional non-limiting examples of TLR agonists include CRX-527 and OM-174.

CRX-527 is described in Lembo et al., J Immunol. 2008 Jun. 1; 180(11):7574-81; and Hennessy et al., Nature Reviews Drug Discovery 9, 293-307 (April 2010), the entire content of which is hereby incorporated herein by reference. CRX-527 has the chemical name (2S)-2-[[(3R)-3-decanoyloxytetradecanoyl]amino]-3-[(2R,3R,4R,5S,6R)-3-[[(3R)-3-decanoyloxytetradecanoyl]amino]-4-[(3R)-3-decanoyloxytetradecanoyl]oxy-6-(hydroxymethyl)-5-phosphonooxyoxan-2-yl]oxypropanoic acid.

OM-174 has the chemical name [(3R)-1-[[(2R,3R,4R,5S,6R)-2-[[2R,3S,4R,5R,6R)-3,4-dihydroxy-5-[[(3R)-3-hydroxytetradecanoyl]amino]-6-phosphonooxyoxan-2-yl]methoxy]-4-hydroxy-6-(hydroxymethyl)-5-phosphonooxyoxan-3-yl]amino]-1-oxotetradecan-3-yl]dodecanoate. OM-174 is described in Onier et al., Int J Cancer. 1999 May 31; 81(5):755-60; Isambert et al., BMC Cancer (2013) 13:172; and Hennessy et al., Nature Reviews Drug Discovery 9, 293-307 (April 2010), the entire content of each of which is hereby incorporated herein by reference.

Cytosine-Guanosine (CpG) Oligonucleotide (CpG-ODN) Sequences

CpG sites are regions of deoxyribonucleic acid (DNA) where a cysteine nucleotide occurs next to a guanine nucleotide in the linear sequence of bases along its length (the "p" represents the phosphate linkage between them and distinguishes them from a cytosine-guanine complementary base pairing). CpG sites play a pivotal role in DNA methylation, which is one of several endogenous mechanisms cells use to silence gene expression. Methylation of CpG sites within promoter elements can lead to gene silencing. In the case of cancer, it is known that tumor suppressor genes are often silenced while oncogenes, or cancer-inducing genes, are expressed. CpG sites in the promoter regions of tumor suppressor genes (which prevent cancer formation) have been shown to be methylated while CpG sites in the promoter regions of oncogenes are hypomethylated or unmethylated in certain cancers. The TLR-9 receptor binds unmethylated CpG sites in DNA.

Various compositions described herein comprise CpG oligonucleotides. CpG oligonucleotides are isolated from endogenous sources or synthesized in vivo or in vitro. Exemplary sources of endogenous CpG oligonucleotides include, but are not limited to, microorganisms, bacteria, fungi, protozoa, viruses, molds, or parasites. Alternatively, endogenous CpG oligonucleotides are isolated from mammalian benign or malignant neoplastic tumors. Synthetic CpG oligonucleotides are synthesized in vivo following transfection or transformation of template DNA into a host organism. Alternatively, Synthetic CpG oligonucleotides are synthesized in vitro by polymerase chain reaction (PCR) or other art-recognized methods (Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

CpG oligonucleotides are presented for cellular uptake by dendritic cells. For example, naked CpG oligonucleotides are used. The term "naked" is used to describe an isolated endogenous or synthetic polynucleotide (or oligonucleotide) that is free of additional substituents. In another embodiment, CpG oligonucleotides are bound to one or more compounds to increase the efficiency of cellular uptake. Alternatively, or in addition, CpG oligonucleotides are bound to one or more compounds to increase the stability of the oligonucleotide within the scaffold and/or dendritic cell. CpG oligonucleotides are optionally condensed prior to cellular uptake. For example, CpG oligonucleotides are condensed using polyethylimine (PEI), a cationic polymer that increases the efficiency of cellular uptake into dendritic cells to yield cationic nanoparticles. CpG oligonucleotides may also be condensed using other polycationic reagents to yield cationic nanoparticles. Additional non-limiting examples of polycationic reagents that may be used include poly-L-lysine (PLL) and polyamidoamine (PAMAM) dendrimers.

Vector systems that promote CpG internalization into DCs to enhance delivery and its localization to TLR9 have been developed. The amine-rich polycation, polyethylimine (PEI) has been extensively used to condense plasmid DNA, via association with DNA phosphate groups, resulting in small, positively charge condensates facilitating cell membrane association and DNA uptake into cells (Godbey W. T., Wu K. K., and Mikos, A. G. J. of Biomed Mater Res, 1999, 45, 268-275; Godbey W. T., Wu K. K., and Mikos, A. G. Proc Natl Acad Sci USA. 96(9), 5177-81. (1999); each herein incorporated by reference). An exemplary method for condensing CpG-ODN is described in U.S. Patent Application No. US 20130202707 A1 published Aug. 8, 2013, the entire content of which is incorporated herein by reference. Consequently, PEI has been utilized as a non-viral vector to enhance gene transfection and to fabricate PEI-DNA loaded PLG matrices that promoted long-term gene expression in host cells in situ (Huang Y C, Riddle F, Rice K G, and Mooney D J. Hum Gene Ther. 5, 609-17. (2005), herein incorporated by reference).

CpG oligonucleotides can be divided into multiple classes. For example, exemplary CpG-ODNs encompassed by compositions, methods and devices of the present invention are stimulatory, neutral, or suppressive. The term "stimulatory" describes a class of CpG-ODN sequences that activate TLR9. The term "neutral" describes a class of CpG-ODN sequences that do not activate TLR9. The term "suppressive" describes a class of CpG-ODN sequences that inhibit TLR9. The term "activate TLR9" describes a process by which TLR9 initiates intracellular signaling.

Stimulatory CpG-ODNs can further be divided into three types A, B and C, which differ in their immune-stimulatory activities. Type A stimulatory CpG ODNs are characterized by a phosphodiester central CpG-containing palindromic motif and a phosphorothioate 3' poly-G string. Following activation of TLR9, these CpG ODNs induce high IFN-α production from plasmacytoid dendritic cells (pDC). Type A CpG ODNs weakly stimulate TLR9-dependent NF-κB signaling.

Type B stimulatory CpG ODNs contain a full phosphorothioate backbone with one or more CpG dinucleotides. Following TLR9 activation, these CpG-ODNs strongly activate B cells. In contrast to Type A CpG-ODNs, Type B CpG-ODNS weakly stimulate IFN-α secretion.

Type C stimulatory CpG ODNs comprise features of Types A and B. Type C CpG-ODNs contain a complete phosphorothioate backbone and a CpG containing palindromic motif. Similar to Type A CpG ODNs, Type C CpG ODNs induce strong IFN-α production from pDC. Simlar to Type B CpG ODNs, Type C CpG ODNs induce strong B cell stimulation.

Exemplary stimulatory CpG ODNs comprise, but are not limited to, ODN 1585 (5'-ggGGTCAACGTTGAgggggg-3') (SEQ ID NO: 21), ODN 1668 (5'-tccatgacgttcctgatgct-3') (SEQ ID NO: 22), ODN 1826 (5'-tccatgacgttcctgacgtt-3') (SEQ ID NO: 23), ODN 2006 (5'-tcgtcgttttgtcgttttgtcgtt-3') (SEQ ID NO: 24), ODN 2006-G5 (5'-TCGTCGTTTTGTCGTTTTGTCGTTGGGGG-3') (SEQ ID NO: 25), ODN 2216 (5'-ggGGGACGA:TCGTCgggggg-3') (SEQ ID NO: 26), ODN 2336 (5'-gggGACGAC:GTCGTGgggggg-3') (SEQ ID NO: 27), ODN 2395 (5'-tcgtcgttttcggcgc:gcgccg-3') (SEQ ID NO: 28), ODN M362 (5'-tcgtcgtcgttc:gaacgacgttgat-3') (SEQ ID NO: 29) (all InvivoGen). The present invention also encompasses any humanized version of the preceding CpG ODNs. In one preferred embodiment, compositions, methods, and devices of the present invention comprise ODN 1826 (the sequence of which from 5' to 3' is tccatgac<u>g</u>ttcctgac<u>g</u>tt, wherein CpG elements are underlined, SEQ ID NO: 23).

Neutral, or control, CpG ODNs that do not stimulate TLR9 are encompassed by the present invention. These ODNs comprise the same sequence as their stimulatory counterparts but contain GpC dinucleotides in place of CpG dinucleotides.

Exemplary neutral, or control, CpG ODNs encompassed by the present invention comprise, but are not limited to, ODN 1585 control, ODN 1668 control, ODN 1826 control, ODN 2006 control, ODN 2216 control, ODN 2336 control, ODN 2395 control, ODN M362 control (all InvivoGen). The present invention also encompasses any humanized version of the preceding CpG ODNs.

Immunostimulatory Antibodies

Aspects of the present subject matter relate to the use of immunostimulatory antibodies to stimulate or active cells of the immune system. Providing stimulation to immune cells such as T cells and dendritic cells within the tumor microenvironment improves the anti-tumor immune response. In some embodiments, stimulation is provided using an immunostimulatory antibody that binds and agonizes a surface receptor on T cells or dendritic cells. In certain embodiments, T cell function is enhanced using one or more antibodies targeted to one or more co-stimulatory cell surface molecules, such as 4-1BB (CD137) and OX40 (CD134), leading to enhanced T cell proliferation and survival. In some embodiments, dendritic cell activation is facilitated with one or more agonistic CD40 antibodies. In general due to their immunostimulatory nature, these antibodies can lead to off target immune-related toxicities when applied systemically. Application of these antibodies at the site of action using a device or scaffold of the present subject matter circumvents this issue by focusing the dose at the desired site of action. Additionally, the clinical activity of immunostimulatory antibodies is improved by concentrating the dose thereof at the tumor site using a device or scaffold as disclosed herein.

CD137 Antibodies

CD137 is a surface molecule found on activated T cells that provides costimulation to these cells. Stimulation of CD137 results in increased T cell proliferation and protects T cells from activation induced cell death. CD137 has been shown in several preclinical models to lead to anti-tumor activity. BMS-66513 (urelumab), one non-limiting example of an anti-CD137 antibody, has been tested in several clinical trials and shown to lead to partial remissions in disease, but with liver toxicity, among other auto-immune sequalae (Ascierto et al., 2010, Seminars in Oncology). PF-05082566 is another example of an CD137 antibody in clinical development. PF-05082566 is described in Fisher et al. (2012) Cancer Immunol Immunother. 61(10):1721-33, the entire content of which is incorporated herein by reference. As indicated above, a variety of anti-CD137 antibodies, including those that are not be suitable for systemic delivery, may be used in devices and scaffolds of the present subject matter.

An exemplary non-limiting example of an amino acid sequence for CD137 is publically available as GenBank No: AAH06196.1 (SEQ ID NO: 34).

CD134 Antibodies

CD134 is expressed primarily on activated CD4+ and CD8+ T cells and provides co-stimulation when engaged. Engagement of CD134 with a ligand such as and anti-CD134 antibody promotes survival and expansion of T cells. Non-limiting examples of CD134 antibodies, include 9B12 and MEDI6469. 9B12 is described in Curti et al. (2013) Cancer Res 73: 7189, the entire content of which is incorporated by reference. MEDI6469 is described in Leidner et al. Journal of Clinical Oncology, 2015 ASCO Annual Meeting (May 29-Jun. 2, 2015). Vol 33, No 15_suppl (May 20 Supplement), 2015: TPS6083, the entire content of which is incorporated herein by reference.

An exemplary non-limiting example of an amino acid sequence for CD134 is publically available as GenBank No: AAI05071.1 (SEQ ID NO: 35).

CD40 Antibodies

CD40 is a surface receptor found on antigen-presenting cells such as dendritic cells. Engagement of CD40 results in activation of antigen-presenting cells, a process important for their function. This activation of dendritic cells leads to upregulation of co-stimulatory receptors and production of pro-inflammatory cytokines, which lead to an enhanced ability to prime T cells. Agonistic anti-CD40 antibodies have shown limited activity in the clinic (Vonderheide and Glennie, 2013, Clinical Cancer Research). Non-limiting examples of CD40 antibodies include HCD122 (Lucatumumab), CP-870,893, SGN-40 huS2C6 (Dacetuzumab), and Chi Lob 7/4. These antibodies are in clinical development. As explained above, even antibodies that are not suitable for systemic use may be utilized in embodiments of the present subject matter with few or no adverse side effects. Lucatumumab is described in Fanale et al. (2014) Br J Haematol. 164(2):258-65, the entire content of which is incorporated herein by reference. CP-870,893 is described in Glaude et al. (2011) Cancer Immunol. Immunother. 60, 1009-1017 (2011), the entire content of which is incorporated herein by reference. Dacetuzumab is described in de Vos et al. (2014) Journal of Hematology & Oncology 20147:44, the entire content of which is incorporated herein by reference. Chi Lob 7/4 is described in Vonderheide and Glennie (2013) Clin Cancer Res. 19(5): 1035-1043., the entire content of which is incorporated herein by reference.

An exemplary non-limiting example of an amino acid sequence for CD40 is publically available as GenBank No: AAH12419.1 (SEQ ID NO: 36).

Materials Systems

Any type of cryogel or hydrogel is suitable as a delivery device for the immunomodulators described herein.

A hydrogel (also called aquagel) is a network of polymer chains that are hydrophilic, and are sometimes found as a colloidal gel in which water is the dispersion medium. Hydrogels are highly absorbent (they can contain over 99% water) natural or synthetic polymers that possess a degree of flexibility very similar to natural tissue, due to their significant water content. Unlike conventional hydrogels, a unique characteristic of the devices described herein is that when an appropriate shear stress is applied, the deformable hydrogel is dramatically and reversibly compressed (up to 95% of its volume), resulting in injectable macroporous preformed scaffolds. This property allows the devices to be delivered via syringe with high precision to target sites.

Aspects of the present subject matter relate to click-hydrogels and click-cryogels. A click hydrogel or cryogel is a gel in which cross-linking between hydrogel or cryogel polymers is facilitated by click reactions between the polymers. Each polymer may contain one of more functional groups useful in a click reaction. Given the high level of specificity of the functional group pairs in a click reaction, active compounds can be added to the preformed device prior to or contemporaneously with formation of the hydrogel device by click chemistry. Non-limiting examples of click reactions that may be used to form click-hydrogels include Copper I catalyzed azide-alkyne cycloaddition, strain-promoted as size-alkyne cycloaddition, thiol-ene photocoupling, Diels-Alder reactions, inverse electron demand Diels-Alder reactions, tetrazole-alkene photo-click reactions, oxime reactions, thiol-Michael addition, and aldehyde-hydrazide coupling. Non-limiting aspects of click hydrogels are described in Jiang et al. (2014) Biomaterials, 35:4969-4985, the entire content of which is incorporated herein by reference.

In various embodiments, a click alginate is utilized (see, e.g., PCT International Patent Application Publication No. WO 2015/154078 published Oct. 8, 2015, hereby incorporated by reference in its entirety).

Exemplary click-hydrogel devices and scaffold materials include a hydrogel comprising a first polymer and a second polymer, where the first polymer is connected to the second polymer by linkers of formula (A):

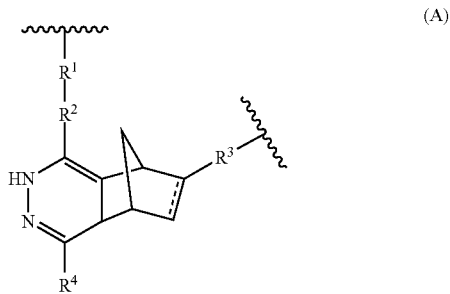

(A)

wherein bond $= = =$ is a single or a double bond;

$R^1$ is $—C_0-C_6\text{alkyl-NR}^{2N}—$, $—C_0-C_6\text{alkyl} —O—$, or $—C_0-C_3\text{alkyl-C(O)}—$;

$R^2$ is a bond, aryl, or heteroaryl, wherein aryl and heteroaryl are optionally substituted with halogen, hydroxy, $C_1-C_6\text{alkyl}$, $C_1-C_6\text{alkoxy}$, $(C_1-C_6\text{alkyl})\text{amino}$, or $\text{di}(C_1-C_6\text{alkyl})\text{amino}$;

$R^3$ is $—C_0-C_6\text{alkyl-NR}^{2N}—$, $—C_0-C_6\text{alkyl-O}—$, or $—C_0-C_3\text{alkyl-C(O)}—$; and R4 is hydrogen, $C_1-C_6\text{alkyl}$, aryl, or heteroaryl, wherein aryl and heteroaryl are optionally substituted with halogen, hydroxy, $C_1-C_6\text{alkyl}$, $C_1-C_6\text{alkoxy}$, $(C_1-C_6\text{alkyl})\text{amino}$, or $\text{di}(C_1-C_6\text{alkyl})\text{amino}$.

$R^{2N}$ is independently hydrogen, $C_1-C_6$ alkyl, aryl, heteroaryl, $R^2N$, or $R^2$, wherein $C_1-C_6$ alkyl, aryl and heteroaryl are optionally substituted with halogen, hydroxy, $C_1-C_6$ alkyl, $C_1-C_6$ alkoxy, $(C_1-C_6 \text{ alkyl})\text{amino}$, or $\text{di}(C_1-C_6 \text{ alkyl})$ amino. In one embodiment, the hydrogel of the disclosure is wherein the linkers of formula (A) are of the form of formula (I):

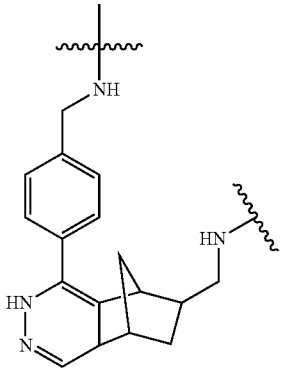

or by formula (II):

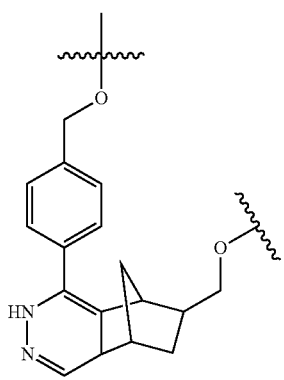

or by formula (III):

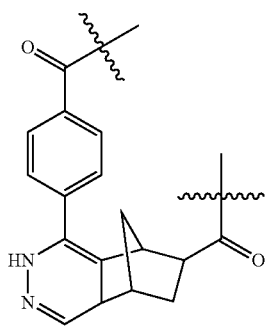

wherein the linkers of formula (I), (II), or (III) are optionally substituted at any suitable position.

Another embodiment provides the linkers of formula (A) according to any preceding embodiment, wherein $R^1$ is
  a. —$NR^{2N}$—, —$C_1$-$C_6$ alkyl-$NR^{2N}$—, —O—, —$C_1$-$C_6$ alkyl —O—, —C(O)—, or —$C_1$-$C_3$ alkyl-C(O)—;
  b. —$C_0$-$C_6$ alkyl-$NR^{2N}$—;
  c. —$C_1$-$C_6$ alkyl-$NR^{2N}$—;
  d. —$C_1$-$C_3$ alkyl-$NR^{2N}$—;
  e. -methyl-NH— or -pentyl-NH—;
  f. —$C_0$-$C_6$ alkyl-O—;
  g. —$C_1$-$C_6$ alkyl-O—;
  h. —$C_1$-$C_3$ alkyl-O—;
  i. -methyl-O— or -pentyl-O—;
  j. —$C_0$-$C_3$ alkyl-C(O)—;
  k. —C(O)—;
  l. -methyl-C(O)—;
  m. the same as $R^3$.

$R^{2N}$ is independently hydrogen, $C_1$-$C_6$ alkyl, aryl, heteroaryl, $R^2N$, or $R^2$, wherein $C_1$-$C_6$ alkyl, aryl and heteroaryl are optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl)amino.

Another embodiment provides the linkers of formula (A) according to any preceding embodiment, wherein $R^2$ is a bond.

In one embodiment, the linkers of formula (A) according to any preceding embodiment are those wherein $R^2$ is
  a. aryl or heteroaryl, each optionally substituted;
  b. optionally substituted aryl;
  c. phenyl;
  d. optionally substituted heteroaryl; or
  e. pyridyl, pyrimidyl, or pyrazinyl.

Another embodiment provides the linkers of formula (A) according to any preceding embodiment, wherein $R^3$ is
  a. —$NR^{2N}$—, —$C_1$-$C_6$ alkyl-$NR^{2N}$—, —O—, —$C_1$-$C_6$ alkyl —O—, —C(O)—, or —$C_1$-$C_3$ alkyl-C(O)—;
  b. —$C_0$-$C_6$ alkyl-$NR^{2N}$—;
  c. —$C_1$-$C_6$ alkyl-$NR^{2N}$—;
  d. —$C_1$-$C_3$ alkyl-$NR^{2N}$—;
  e. -methyl-NH— or -pentyl-NH—;
  f. —$C_0$-$C_6$ alkyl-O—;
  g. —$C_1$-$C_6$ alkyl-O—;
  h. —$C_1$-$C_3$ alkyl-O—;
  i. -methyl-O— or -pentyl-O—;
  j. —$C_0$-$C_3$ alkyl-C(O)—;
  k. —C(O)—;
  l. -methyl-C(O)—; or
  m. the same as $R^1$.

$R^{2N}$ is independently hydrogen, $C_1$-$C_6$ alkyl, aryl, heteroaryl, $R^2N$, or $R^2$, wherein $C_1$-$C_6$ alkyl, aryl and heteroaryl are optionally substituted with halogen, hydroxy, $C_1$-$C_6$ alkyl, $C_1$-$C_6$ alkoxy, ($C_1$-$C_6$ alkyl)amino, or di($C_1$-$C_6$ alkyl)amino. In one embodiment, the linkers of formula (A) according to any preceding embodiment are those wherein $R^4$ is hydrogen.

In one embodiment, the linkers of formula (A) according to any preceding embodiment are those wherein $R^4$ is
  a. $C_1$-$C_6$ alkyl, aryl, or heteroaryl, wherein aryl and heteroaryl are optionally substituted;
  b. aryl or heteroaryl, wherein aryl and heteroaryl are optionally substituted; c. optionally substituted aryl;
  d. phenyl;
  e. optionally substituted heteroaryl; or
  f. pyridyl, pyrimidyl, or pyrazinyl.

Another embodiment provides the linkers of formula (A) according to any preceding embodiment, wherein $R_4$ is $C_1$-$C_6$ alkyl, $C_1$-$C_3$ alkyl, or methyl.

In some embodiments, the hydrogel comprises a plurality of linkers of formula (A); or formula (I), formula (II), or formula (III).

The invention also includes a hydrogel comprising an interconnected network of a plurality of polymers, e.g., including a first polymer and a second polymer. For example, the polymers are connected via a plurality of linkers of formula (A), or of formula (I), formula (II), or formula (III).

Some embodiments of the disclosure provide hydrogels wherein the first polymer and the second polymer are independently soluble polymers. In other embodiments, the first polymer and the second polymer are independently water-soluble polymers.

In some cases, the concentration of crosslinks per hydrogel (e.g., where each crosslink comprises formula I) is at least about 10% (w/w), e.g., at least about 10%, about 15%, about 20%, about 30%, about 40%, about 50%, about 60%, about 70%, about 80%, about 90%, about 95%, about 97%, about 99%, or about 100% (w/w).

The first polymer and the second polymer can be the same or different. In some embodiments, the first polymer and the second polymer are the same type of polymer. In other embodiments, the first polymer and/or the second polymer comprise a polysaccharide. For example, the first polymer and the second polymer can both comprise a polysaccharide. In some embodiments, the first polymer and/or the second polymer are independently selected from the group consisting of alginate, chitosan, polyethylene glycol (PEG), gelatin, hyaluronic acid, collagen, chondroitin, agarose, polyacrylamide, and heparin. In some embodiments, the first polymer and the second polymer are the same polymer independently selected from the group consisting of alginate, chitosan, polyethylene glycol (PEG), gelatin, hyaluronic acid, collagen, chondroitin, agarose, polyacrylamide, and heparin.

Such scaffolds and scaffold materials, as well as methods for producing such scaffolds, are described in PCT International Patent Application Publication No. WO 2015/154078 published Oct. 8, 2015, the entire content of which is incorporated herein by reference. For example, a click hydrogel may be prepared in a process: a) providing a first polymer comprising a first click reaction moiety and a second polymer comprising a second click reaction moiety. In non-limiting examples, the first click reaction moiety and the second click reaction moiety may be react with each other in a copper I catalyzed azide-alkyne cycloaddition, strain-promoted assize-alkyne cycloaddition, thiol-ene photocoupling, a Diels-Alder reaction, a inverse electron demand Diels-Alder reaction, a tetrazole-alkene photo-click reaction, a oxime reaction, a thiol-Michael addition, or via aldehyde-hydrazide coupling. In an embodiment, the first click reaction moiety is a diene moiety and the second click reaction moiety is a dienophile moiety. In an embodiment, the first click reaction moiety is a tetrazine moiety and the second click reaction moiety is a norbornene moiety. As used herein, the terms "tetrazine" and "tetrazine moiety" include molecules that comprise 1,2,4,5-tetrazine substituted with suitable spacer for linking to the polymer (e.g., alkylamines like methylamine or pentylamine), and optionally further substituted with one or more substituents at any available position. Exemplary tetrazine moieties suitable for the compositions and methods of the disclosure are descrived in Karver et al. Bioconjugate Chem. 22(2011): 2263-2270, and WO 2014/065860, both incorporated herein by reference). As used herein, the terms "norbornene" and "norbornene moieties" include but are not limited to norbornadiene and norbornene groups further comprising suitable spacer for linking to the polymer (e.g., alkylamines like methylamine or pentylamine), and optionally further substituted with one or more substituents at any available position. Such moieties include, for example, norbornene-5-methylamine and norbornadienemethylamine.

Accordingly, the invention features a cell-compatible and optionally, cell-adhesive, highly crosslinked hydrogel (e.g., cryogel) polymer composition comprising open interconnected pores, wherein the hydrogel (e.g., cryogel) is characterized by shape memory following deformation by compression or dehydration. The device has a high density of open interconnected pores. Also, the hydrogel (e.g., cryogel) comprises a crosslinked gelatin polymer or a crosslinked alginate polymer.

Examples of polymer compositions from which the cryogel or hydrogel is fabricated include alginate, hyaluronic acid, gelatin, heparin, dextran, carob gum, PEG, PEG derivatives including PEG-co-PGA and PEG-peptide conjugates. The techniques can be applied to any biocompatible polymers, e.g. collagen, chitosan, carboxymethylcellulose, pullulan, polyvinyl alcohol (PVA), Poly(2-hydroxyethyl methacrylate) (PHEMA), Poly(N-isopropylacrylamide) (PNIPAAm), or Poly(acrylic acid) (PAAc). For example, the composition comprises an alginate-based hydrogel/cryogel. In another example, the composition comprises a gelatin-based hydrogel/cryogel.

Cryogels are a class of materials with a highly porous interconnected structure that are produced using a cryotropic gelation (or cryogelation) technique. Cryogels also have a highly porous structure. Typically, active compounds are added to the cryogel device after the freeze-formation of the pore/wall structure of the cryogel. Cryogels are characterized by high porosity, e.g., at least about 50, 55, 60, 65, 70, 75, 80, 85, 90, or 95% pores with thin pore walls that are characterized by high density of polymer crosslinking. The walls of cryogels are typically dense and highly crosslinked, enabling them to be compressed through a needle into a subject without permanent deformation or substantial structural damage. In various embodiments, the pore walls comprise at least about 10, 15, 20, 25, 30, 35, 40, 10-40% or more polymer. In some embodiments, a polymer concentration of about 0.5-4% (before the cryogelation) is used, and the concentration increases substantially by the completion of cryogelation. Non-limiting aspects of cryogel gelation and the increase of polymer concentration after cryogelation are discussed in Béduer et al. (2015) Advanced Healthcare Materials Volume 4, Issue 2, pages 301-312, the entire content of which is incorporated herein by reference. In various implementations, cryogelation comprises a technique in which polymerization-crosslinking reactions are conducted in quasi-frozen reaction solution. Non-limiting examples of cryogelation techniques are described in U.S. Patent Application Publication No. 2014/0227327, published Aug. 14, 2014, the entire content of which is incorporated herein by reference. An advantage of cryogels compared to conventional macroporous hydrogels obtained by phase separation is their high reversible deformability. Cryogels may be extremely soft but can be deformed and reform their shape. They are very tough, and can withstand high levels of deformations, such as elongation and torsion; they can also be squeezed under mechanical force to drain out their solvent content. In various embodiments, improved deformability properties of alginate cryogels originate from the high crosslinking density of the unfrozen liquid channels of the reaction system.

Two exemplary cryogel materials systems are described below.

a) Methacrylated gelatin cryogel (CryoGelMA)—An exemplary cryogel utilized methacrylated gelatin and the results are described in detail in Koshy et al., Biomaterials, 35: 2477-2487; hereby incorporated by reference).

b) Click Alginate cryogel with Laponite nanoplatelets (CryoClick)—The base material is click alginate (PCT International Patent Application Publication No. WO 2015/154078 published Oct. 8, 2015, hereby incorporated by reference in its entirety). In some examples, the base material contains laponite (commercially available silicate clay used in many consumer products such as cosmetics). Laponite has a large surface area and highly negative charge density which allows it to adsorb positively charged moieties on a variety of proteins and other biologically active molecules by an electrostatic interaction, allowing drug loading. When placed in an environment with a low concentration of drug, adsorbed drug releases from the laponite in a sustained manner. This system allows release of a more flexible array of immunomodulators compared to the base material alone.

In various embodiments, a device or scaffold is loaded (e.g., soaked with) with one or more active compounds after polymerization. In certain embodiments, device or scaffold polymer forming material is mixed with one or more active compounds before polymerization. In some embodiments, a device or scaffold polymer forming material is mixed with one or more active compounds before polymerization, and hen is loaded with more of the same or one or more additional active compounds after polymerization.

In some embodiments, pore size or total pore volume of a device or scaffold is selected to influence the release of compounds from the device or scaffold. Exemplary porosities (e.g., nanoporous, microporous, and macroporous scaffolds and devices) and total pore volumes (e.g., about 5, 10, 15, 20, 25, 30, 35, 40, 45, 50, 55, 60, 65, 70, 75, 80, 85, 90, or 95%) are described herein. Increased pore size and total pore volume increases the amount of compounds that can be delivered into or near a tumor. In some embodiments, a pore size or total pore volume is selected to increase the speed at which active ingredients exit the device or scaffold. In various embodiments, an active ingredient may be incorporated into the scaffold material of a hydrogel or cryogel, e.g., to achieve continuous release of the active ingredient from the scaffold or device over a longer period of time compared to active ingredient that may diffuse from a pore cavity.

Porosity influences recruitment the cells into devices and scaffolds and the release of substances from devices and scaffolds. Pores may be, e.g., nanoporous, microporous, or macroporous. For example, the diameter of nanopores is less than about 10 nm. Micropores are in the range of about 100 nm to about 20 μm in diameter. Macropores are greater than about 20 μm (e.g., greater than about 100 μm or greater than about 400 μm). Exemplary macropore sizes include 50 μm, 100 μm, 150 μm, 200 μm, 250 μm, 300 μm, 350 μm, 400 μm, 450 μm, 500 μm, 550 μm, and 600 μm. Macropores are those of a size that permit a eukaryotic cell to traverse into or out of the composition. In one example, a macroporous composition has pores of about 400 μm to 500 μm in diameter. The preferred pore size depends on the application.

Release Data

Release data for CryoGelMA of GM-CSF is shown in FIG. 24B, and CryoGelMA CpG (immunostimulatory compound) release was previously described in U.S. Patent Application Publication No. US 20140227327 A1 published Aug. 14, 2014 entitled "Injectable Cryogel Vaccine Devices and Methods of Use Thereof", hereby incorporated by reference.

Tumor Immunomodulation Using an Injectable Biomaterials Scaffold

Dendritic cells survey tumors and collect tumor antigen from dying cancer cells, but are locally suppressed by the tumor to prevent the generation of anti-tumor T cell responses. This tumor-induced DC suppression is reversed by attracting and accumulating DCs within a biomaterial administered at the tumor that provides sustained release of a pro-maturation stimulus.

Many cancer vaccine strategies rely on ex vivo cell manipulation, the retrieval of tumor-derived material, or knowledge of a defined tumor antigen, which limit their widespread use. An advantage of the device scaffold described herein is that tumor-derived material or knowledge/identification of patient is not required.

A biodegradable polymer was used to create porous scaffolds that could be injected through a conventional needle and provide sustained delivery of granulocyte macrophage colony-stimulating factor (GM-CSF) as a DC accumulation factor, and CpG oligonucleotides (CpG-ODN) as a DC maturation stimulus. Subcutaneous injection of GM-CSF-releasing scaffolds led to massive immune cell infiltration of the scaffold and the enrichment of DCs at the injection site. In vitro tests revealed that CpG-ODN released from these scaffolds could increase expression of surface markers on DCs that are indicative of maturation, and promote their secretion of interleukin 12, a cytokine associated with anti-tumor cytotoxic T cell responses. Deployment of GM-CSF-releasing scaffolds at a tumor resulted in pronounced immune cell accumulation at the scaffold injection site, including DCs, macrophages, and granulocytes.

Immune cell localization was accomplished using delivery of a composition within a tumor using an engineered biomaterial releasing immune-modulating factors. Successful maturation of DCs accumulated using this strategy results in the generation of anti-tumor immunity, without the need for ex vivo cell manipulation or knowledge/availability of defined or purified tumor antigens.

A biomaterial loaded with the factors (e.g., GM-CSF and CpG or poly I:C) further includes an inhibitor of DC suppression and a chemotherapeutic agent (as a source of antigen for vaccination) is administered to a tumor location. Some non-limiting examples of biomaterial devices and scaffolds are loaded only with immune cell localization factors, or only inhibitors of immune suppression, or only chemotherapeutic agents. Non-limiting examples of biomaterial devices and scaffolds do not include immune cell localization factors, or do not include inhibitors of immune suppression, or do not include chemotherapeutic agents. Various combinations of such active compounds are disclosed herein for use in biomaterials. CpG or poly I:C is optionally condensed, e.g., using a cationic condensing agent such as poly(ethylenimine) (PEI) or cationic gelatin. Immune cells come into the biomaterial and acquire and are stimulated by the factors. The tumor itself is the site of vaccination. Rather than using cancer cells that have been collected from the patient, the tumor itself is used as the source of tumor antigen. The chemotherapeutic agent is a means to locally generate antigen. This approach provides an injectable platform that alleviates the need to use any patient-derived material in generating an anti-tumor immune response.

Inhibitors and Immune Checkpoint Blockade

Various implementations of the present subject matter relate to the administration of an inhibitor of T cell or dendritic cell suppression and scaffolds or devices comprising an inhibitor of T cell or dendritic cell suppression. Non-limiting examples of such inhibitors include TGF-β pathway inhibitors, STAT3 pathway inhibitors, and IDO pathway inhibitors, as well as immune checkpoint inhibitors such as PD-1 pathway inhibitors, CTLA-4 pathway inhibitors, LAG-3 pathway inhibitors, CD276 (also known as B7-H3) pathway inhibitors, and TIM3 pathway inhibitors.

Many inhibitory pathways exist within tumors that suppress tumor antigen presentation and the anti-tumor immune response. For example, TGF-β dampens tumor immunosurveillance and polarizes innate immune cells towards an immature differentiation status that prevents optimal anti-tumor immunity. Additionally, the STAT3 pathway promotes the production of immune inhibitory cytokines within the tumor, dampens anti-tumor T-helper 1-mediated immunity, and inhibits dendritic cell maturation. Small molecule inhibitors of these pathways and other immunosuppressive pathways described above are delivered to the tumor using the cryogel or hydrogel devices. Other approaches to alter the tumor microenvironment may also be utilized, e.g., antibodies against immune checkpoint proteins.

Cytotoxic T-lymphocyte associated antigen 4 (CTLA-4) is an immune checkpoint protein that down-regulates pathways of T-cell activation (Fong et al., Cancer Res. 69(2): 609-615, 2009; Weber Cancer Immunol. Immunother, 58:823-830, 2009). Blockade of CTLA-4 has been shown to augment T-cell activation and proliferation. Inhibitors of CTLA-4 include anti-CTLA-4 antibodies. Anti-CTLA-4 antibodies bind to CTLA-4 and block the interaction of CTLA-4 with its ligands CD80/CD86 expressed on antigen presenting cells and thereby blocking the negative down regulation of the immune responses elicited by the interaction of these molecules. Examples of anti-CTLA-4 antibodies are described in U.S. Pat. Nos. 5,811,097; 5,811,097; 5,855,887; 6,051,227; 6,207,157; 6,682,736; 6,984,720; and 7,605,238. One anti-CDLA-4 antibody is tremelimumab, (ticilimumab, CP-675,206). In one embodiment, the anti-CTLA-4 antibody is ipilimumab (also known as 10D1, MDX-D010) a fully human monoclonal IgG antibody that binds to CTLA-4. Ipilimumab is marketed under the name Yervoy™ and has been approved for the treatment of unresectable or metastatic melanoma.

Other immune-checkpoint inhibitors include lymphocyte activation gene-3 (LAG-3) inhibitors, such as IMP321, a soluble Ig fusion protein (Brignone et al., 2007, J. Immunol. 179:4202-4211). Other immune-checkpoint inhibitors include B7 inhibitors, such as B7-H3 and B7-H4 inhibitors. In particular, the anti-B7-H3 antibody MGA271 (Loo et al., 2012, Clin. Cancer Res. July 15 (18) 3834). Also included are TIM3 (T-cell immunoglobulin domain and mucin domain 3) inhibitors (Fourcade et al., 2010, J. Exp. Med. 207:2175-86 and Sakuishi et al., 2010, J. Exp. Med. 207: 2187-94).

A ligand-receptor interaction that has been explored as a target for cancer treatment is the interaction between the transmembrane programmed cell death 1 protein (PDCD1, PD-1; also known as CD279) and its ligand, PD-1 ligand 1 (PD-L1, CD274). In normal physiology PD-L1 on the surface of a cell binds to PD1 on the surface of an immune cell, which inhibits the activity of the immune cell. Upregulation of PD-L1 on the cancer cell surface may allow them to evade the host immune system by inhibiting T cells that might otherwise attack the tumor cell. Antibodies that bind to either PD-1 or PD-L1 and therefore block the interaction may allow the T-cells to attack the tumor. An IgG4 PD1 antibody called Nivolumab has been described (Pardoll, DM, 2012, Nature reviews. Cancer 12 (4): 252-64). Many of the immune checkpoints are initiated by ligand-receptor interactions; thus, hey can be readily blocked by antibodies or modulated by recombinant forms of ligands or receptors.

Other examples of antibody-based blockers include Cytotoxic T-lymphocyte-associated antigen 4 (CTLA4)-specific antibodies.

In various embodiments, the antibody is a polyclonal antibody, a monoclonal antibody, a chimeric antibody, a humanized antibody, or a human antibody.

In some embodiments, the anti-PD-1 antibody is nivolumab, pembrolizumab, or pidilizumab. Nivolumab is described in Johnson et al. (2015) Ther Adv Med Oncol 7 (2): 97-106; and Sundar R et al. (2015) Ther Adv Med Oncol 7 (2): 85-96, the entire content of each of which is incorporated herein by reference. Pembrolizumab is described in Hamid et al. (2013) New England Journal of Medicine 369 (2): 134-44, the entire content of which is incorporated herein by reference. Pidilizumab is described in Westin et al. (2014) "Safety and Activity of PD1 Blockade by Pidilizumab in Combination with Rituximab in Patients with Relapsed Follicular Lymphoma: a Single Group, Open-label, Phase 2 Trial" doi:10.1016/S1470-2045(13)70551-5, the entire content of which is incorporated herein by reference.

In certain embodiments, the anti-PD-L1 antibody is BMS-936559 or MPDL3280A. BMS-936559 is described in Brahmer J R et al. (2012) N Engl J Med. 2012; 366:2455, the entire content of which is incorporated herein by reference. MPDL3280A is described in Herbst R S et al. (2013) J Clin Oncol. 31(suppl; abstr 3000); Soria J C et al. (2013) European Cancer Congress Amsterdam (abstr 3408); Hamid 0 et al. (2013) J Clin Oncol31(suppl; abstr 9010); and Kohrt H et al. (2013) J Immunother Cancer. 2013; 1(suppl 1):012, the entire content of each of which is incorporated herein by reference.

Additional anti-PD1 and anti-PD-L1 antibodies are described in U.S. Pat. No. 8,952,136 issued Feb. 10, 2015, the entire content of which is incorporated herein by reference.

In various embodiments, the anti-CTLA-4 antibody is ipilimumab. Ipilimumab is described in "Yervoy (ipilimumab) (package insert)" Princeton, N.J.: Bristol-Myers Squibb Company; December 2013. Retrieved 29 Oct. 2014, the entire content of which is incorporated herein by reference.

General Definitions

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to 5.0 mg.

A small molecule is a compound that is less than 2000 daltons in mass. The molecular mass of the small molecule is preferably less than 1000 daltons, more preferably less than 600 daltons, e.g., the compound is less than 500 daltons, 400 daltons, 300 daltons, 200 daltons, or 100 daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

As used herein, an "expression vector" is a DNA or RNA vector that is capable of transforming a cell and of effecting expression of one or more specified polynucleotides. Preferably, the expression vector is also capable of replicating within the host cell. Expression vectors may be, e.g., eukaryotic, and are typically viruses or plasmids. Expression vectors of the present invention contain regulatory sequences such as transcription control sequences, translation control sequences, origins of replication, and other regulatory sequences that are compatible with the host cell (e.g., a cell of a subject such as a tumor cell, immune cell, or cells surrounding a device or scaffold after it is administered) and that control the expression of polynucleotides of the present invention. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in a cell or cells of a subject. Such regulatory sequences may be obtained from, e.g., viruses or eukaryotic organisms, or may be chemically synthesized. A variety of such transcription control sequences are known to those skilled in the art. Particularly preferred transcription control sequences are promoters active in directing transcription in the cells of a subject, either constitutively and/or in one or more specific tissues. In various embodiments, an expression vector is expressed transiently.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1. Hydrogels for Immune Modulator Delivery to Tumors Achieve Tumor Regression and Increase Survival of Mammalian Subjects This study provides in vivo proof of concept tumor data relating to the use of hydrogels to deliver immune modulators to tumors.

50 µl nanoporous click alginate hydrogels (3% w/v) were used in this study. Non-limiting structural aspects of click alginate hydrogels are described in PCT International Patent Application Publication No. WO 2015/154078 published Oct. 8, 2015, the entire content of which is hereby incorporated herein by reference. GM-CSF was used as a recruitment/growth factor for immune cells in combination with Imiquimod (an FDA approved TLR7 ligand), which served as a danger signal. These two agents were used to bring immune cells such as dendritic cells into the tumor where the immune cells could be stimulated by the danger signal provided. The GM-CSF and Imiquimod were mixed with a hydrogel that was injected into established tumors in mice. Surprisingly, administration of the hydrogels led to cures (loss of tumor volume and survival 40 days after tumor cell injection) in a proportion of the mice.

Mice injected with $2 \times 10^5$ B16-mOVA cells (B16-F10 melanoma cells expressing inner cell membrane bound ovalbumin as a model antigen) were administered hydrogels 11 and 13 days after tumor cell injection. Click alginate hydrogels having following compositions were injected into the tumors: Blank (hydrogel only), GM-CSF (hydrogel+1 ug GM-CSF), Imiquimod (hydrogel+1 mg Imiquimod), GM-CSF+Imiquimod (hydrogel+1 ug GM-CSF+1 mg Imiquimod). Tumor dimensions were measured using calipers and used to calculate tumor area, which is plotted in FIG. 25A-D.

As shown in FIG. 25A-D, treatment with GM-CSF+Imiquimod hydrogels resulted in a complete regression of tumors in 2 of 5 mice (40% of the treated population). An additional mouse (20% of the treated population) had reduced tumor volume. These results revealed stronger treatment than each of the other conditions. Additionally, neither Blank hydrogels, GM-CSF hydrogels, nor Imiquimod hydrogels achieved complete regression of tumor volume in any treated mouse.

Additionally, the GM-CSF+Imiquimod hydrogel achieved a higher degree of mouse survival than any of the other hydrogels used in this study. Whereas 40% of the mice receiving GM-CSF+Imiquimod hydrogels were alive at least 40 days after tumor injection, every mouse receiving Blank hydrogels, GM-CSF hydrogels, or Imiquimod hydrogels died within 35 days. See FIG. 26.

Further, a stronger T cell response was observed in mice administered GM-CSF+Imiquimod hydrogel compared to the other treatment groups. 21 days after tumor inoculation, peripheral blood was taken from mice that were still alive in each group. The cells were stimulated with a peptide from ovalbumin and the fraction of CD8+ T cells responding to the peptide was quantified using flow cytometry. The data (FIG. 27) indicate that in some mice, large T cell responses are induced by peritumoral injection of hydrogels containing GM-CSF and Imiquimod. The response achieved using GM-CSF+Imiquimod hydrogels was greater than Blank hydrogels, GM-CSF hydrogels, or Imiquimod hydrogels.

FIG. 28 depicts data showing (1) tumor growth in a blank hydrogel treated mouse and (2) regression of growing tumors in mice of the GM-CSF+Imiquimod group. The data show a reduced tumor size in the GM-CSF+Imiquimod group relative to the blank hydrogel group. Additionally, the flow cytometry plots in FIG. 28 show much larger CD8 T cell responses in the surviving GM-CSF+Imiquimod mice than in the lone surviving blank hydrogel mouse at day 21 after inoculation.

These data show that treatment with an exemplary hydrogel comprising GM-CSF and Imiquimod dramatically reduces tumor volume and increases survival in mammalian subjects.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of generating a subject-specific immune response against a solid tumor comprising injecting into a solid tumor or into an anatomical location in the proximity of a solid tumor of a subject a biodegradable porous polymeric device comprising:
   a chemotherapeutic agent that induces immunogenic cell death of a solid tumor cell by directly killing the solid tumor cell; and
   a compound that attracts an antigen presenting cell to or into the device;
   wherein said device lacks a tumor antigen prior to administration to the subject, and wherein said device generates a tumor antigen in situ by the killing of the solid tumor cell by the chemotherapeutic agent released from said device;
   thereby allowing for the generated tumor antigen to be acquired by the antigen presenting cell to generate a subject-specific immune response against the solid tumor.

2. The method of claim 1, wherein the polymeric device further comprises an inhibitor of T cell or dendritic cell suppression,
   (i) wherein said inhibitor comprises a transforming growth factor-beta (TGF-β) pathway inhibitor, or a signal transducer and activator of transcription 3 (STAT3) pathway inhibitor;
   (ii) wherein said inhibitor comprises a small molecule, an aptamer, a protein, an RNAi molecule, an antibody, or an antibody fragment; or
   (iii) wherein said inhibitor comprises an inhibitor of an immune checkpoint.

3. The method of claim 2, wherein the small molecule is an organic compound having a molecular weight less than 1000 Daltons.

4. The method of claim 2, wherein said TGF-β pathway inhibitor is selected from the group consisting of LY2157299 GW788388, LY364947, R268712, RepSox, SB525334, and SD208; and said STAT3 pathway inhibitor is selected from the group consisting of BP-1-102, S3I-M2001, STA-21, S3I-201, Stattic, Galiellalactone, a polypeptide having the sequence PY*LKTK (where Y* represents phosphotyrosine) (SEQ ID NO.: 1), and a polypeptide having the sequence Y*LPQTV (where Y* represents phosphotyrosine) (SEQ ID NO.: 2).

5. The method of claim 2, wherein the inhibitor of an immune checkpoint is a PD-1 pathway inhibitor, a LAG-3 pathway inhibitor, an IDO pathway inhibitor, a B7-H3 pathway inhibitor, or a TIM3 pathway inhibitor.

6. The method of claim 2, wherein said inhibitor is a small molecule, an aptamer, a protein, an RNAi molecule, an antibody, or an antibody fragment.

7. The method of claim 6, wherein the inhibitor is an antibody.

8. The method of claim 7, wherein said antibody comprises an anti-PD-1 antibody, an anti-PD-L1 antibody, or an anti-CTLA-4 antibody.

9. The method of claim 8, wherein (a) the anti-PD-1 antibody is nivolumab, pembrolizumab, or pidilizumab; (b) the anti-PD-L1 antibody is BMS-936559 or MPDL3280A; or (c) the anti-CTLA-4 antibody is ipilimumab.

10. The method of claim 6, wherein the antibody is (a) a Fv, Fab, Fab', Fab'-SH, F (ab')2, diabody, a linear antibody or a scFv or (b) a polyclonal antibody, a monoclonal antibody, a chimeric antibody, a humanized antibody, or a human antibody.

11. The method of claim 6, wherein said inhibitor is an IDO inhibitor.

12. The method of claim 11, wherein said IDO inhibitor is an IDO1 inhibitor.

13. The method of claim 11, wherein the inhibitor is a small molecule that is an organic compound having a molecular weight less than 1000 Daltons.

14. The method of claim 13, wherein the small molecule is INCB24360 or NLG919.

15. The method of claim 1, wherein
   (a) said chemotherapeutic agent comprises a member of the anthracycline class of compounds;
   (b) said chemotherapeutic agent comprises doxorubicin;
   (c) said device comprises a hydrogel;
   (d) said device comprises a cryogel;
   (e) said device comprises a cryogel, wherein said cryogel comprises pores;
   (f) said device comprises a methacrylated gelatin cryogel or a click alginate cryogel;

(g) said device comprises an alginate hydrogel;
(h) said device comprises an alginate hydrogel, wherein the alginate hydrogel is an alginate cryogel;
(i) said device comprises an alginate hydrogel, wherein said alginate hydrogel comprises a click alginate;
(j) the device is injected into the solid tumor;
(k) the device is injected into a site in the subject within about 0.1-10 mm from the solid tumor;
(l) the device further comprises a cytokine or a mRNA or expression vector that encodes a cytokine;
(m) the device further comprises a cytokine or a mRNA or expression vector that encodes a cytokine, wherein the cytokine is granulocyte macrophage colony-stimulating factor (GM-CSF), FMS-like tyrosine kinase 3 ligand (Flt3L), Chemokine (C-C Motif) Ligand 20 (CCL20), Interleukin 15 (IL-15), Chemokine (C Motif) Ligand 1 (XCL1), Chemokine (C-X-C Motif) Ligand 10 (CXCL10), Interferon Alpha 1 (IFN-alpha), Interferon Beta (IFN-beta), or Interleukin 12 (IL-12);
(n) the device has a volume of about 50 µl to about 500 µl;
(o) said device further comprises laponite;
(p) the device does not comprise a hyperthermia-inducing composition; and/or
(q) the device does not comprise a near infrared (NIR) absorbing nanoparticle.

16. The method of claim 1, wherein the device further comprises an immunostimulatory compound.

17. The method of claim 16, wherein the immunostimulatory compound is CpG, polyinosine-polycytidylic acid (poly (I:C)), PEI-poly (I:C), polyadenylic-polyuridylic acid (poly (A:U)), PEI-poly (AU), double stranded ribonucleic acid (RNA), monophosphoryl lipid A (MPLA), or Imiquimod.

18. A method of treating a subject afflicted with a solid tumor, comprising injecting into a solid tumor or into an anatomical location in the proximity of a solid tumor a biodegradable porous polymeric device comprising:
a chemotherapeutic agent that induces immunogenic cell death of a solid tumor cell by directly killing the solid tumor cell; and
a compound that attracts an antigen presenting cell to or into the device,
wherein said device lacks a tumor antigen prior to administration to the subject, and wherein said device generates a tumor antigen in situ by the killing of the solid tumor cell by the chemotherapeutic agent released from said device;
thereby allowing for the generated tumor antigen to be acquired by the antigen presenting cell to generate a a subject-specific immune response against a tumor and treating the subject afflicted with the solid tumor.

19. The method of claim 18, wherein
(a) the device further comprises an inhibitor of T cell or dendritic cell suppression;
(b) the device further comprises an immunostimulatory compound;
(c) one or two biodegradable porous polymeric devices is are administered to the subject;
(d) said device comprises an alginate hydrogel;
(e) said device comprises an alginate hydrogel, wherein said alginate hydrogel comprises a click alginate;
(f) the device is injected into the solid tumor;
(g) the device is injected into a site in the subject within about 0.1-10 mm from the solid tumor;
(h) the device further comprises a cytokine;
(i) the device further comprises a cytokine, wherein the cytokine is granulocyte macrophage colony-stimulating factor (GM-CSF), FMS-like tyrosine kinase 3 ligand (Flt3L), Chemokine (C-C Motif) Ligand 20 (CCL20), Interleukin 15 (IL-15), Chemokine (C Motif) Ligand 1 (XCL1), Chemokine (C-X-C Motif) Ligand 10 (CXCL10), Interferon Alpha 1 (IFN-alpha), Interferon Beta (IFN-beta), or Interleukin 12 (IL-12);
(j) the device has a volume of about 50 µl to about 500 µl;
(k) said subject has been identified as comprising a solid tumor;
(l) the method further comprises contacting the tumor with radiation;
(m) the device does not comprise a hyperthermia-inducing composition;
(n) the device does not comprise a near infrared (NIR) absorbing nanoparticle;
(o) the method does not comprise contacting an incorporated NIR nanoparticle with NIR radiation to induce local hyperthermia in situ; and/or
(p) the method further comprises systemically administering a chemotherapeutic agent to the subject.

20. The method of claim 18, wherein treating the subject comprises
(a) reducing the volume of the solid tumor;
(b) reducing the growth of the solid tumor;
(c) reducing metastasis of the solid tumor;
(d) increasing the survival of the subject;
(e) increasing the progression free survival of the subject;
(f) increasing a T cell response to an antigen within the solid tumor; and/or
(g) vaccinating the subject to an antigen within the solid tumor.

21. The method of claim 20, wherein treating the subject comprises reducing the volume of the solid tumor by at least about 5, 10, 15, 20, 25, 30, 35, 40, 45, 50, 55, 60, 65, 70, 75, 80, 85, 90, 95, 96, 97, 98, 99, or 100% within about 1-12 months.

22. The method of claim 18, wherein the device further comprises an immunostimulatory compound.

23. The method of claim 22, wherein the immunostimulatory compound is CpG, polyinosine-polycytidylic acid (poly (I:C)), PEI-poly (I:C), polyadenylic-polyuridylic acid (poly (A:U)), PEI-poly (AU), double stranded ribonucleic acid (RNA), monophosphoryl lipid A (MPLA), or Imiquimod.

24. The method of claim 1,
wherein the device further comprises an immunostimulatory compound comprising CpG-ODN,
wherein the chemotherapeutic agent comprises doxorubicin,
wherein the compound that attracts an antigen presenting cell to or into the device comprises a GM-CSF, and
wherein the biodegradable porous polymeric device comprises a macroporous alginate hydrogel.

25. The method of claim 18,
wherein the device further comprises an immunostimulatory compound comprising CpG-ODN,
wherein the chemotherapeutic agent comprises doxorubicin,
wherein the compound that attracts an antigen presenting cell to or into the device comprises a GM-CSF, and
wherein the biodegradable porous polymeric device comprises a macroporous alginate hydrogel.

26. The method of claim 1, wherein the tumor antigen is generated in situ without the need for ex vivo cell manipulation.

* * * * *

UNITED STATES PATENT AND TRADEMARK OFFICE
CERTIFICATE OF CORRECTION

| | |
|---|---|
| PATENT NO. | : 11,786,457 B2 |
| APPLICATION NO. | : 15/546852 |
| DATED | : October 17, 2023 |
| INVENTOR(S) | : Sandeep T. Koshy et al. |

It is certified that error appears in the above-identified patent and that said Letters Patent is hereby corrected as shown below:

In the Claims

At Column 91, Line number 33, Claim number 17, delete "(AU)," and replace with -- (A:U), --

At Column 91, Line number 51, Claim number 18, delete "a"

At Column 91, Line number 59, Claim number 19, delete "is"

At Column 92, Line number 46, Claim number 23, delete "(AU)," and replace with -- (A:U), --

Signed and Sealed this
Eighteenth Day of June, 2024

Katherine Kelly Vidal
*Director of the United States Patent and Trademark Office*

SEQUENCE LISTING

```
<160> NUMBER OF SEQ ID NOS: 36

<210> SEQ ID NO 1
<211> LENGTH: 6
<212> TYPE: PRT
<213> ORGANISM: Artificial Sequence
<220> FEATURE:
<223> OTHER INFORMATION: TGF-Beta inhibitor
<220> FEATURE:
<221> NAME/KEY: misc_feature
<222> LOCATION: (1)..(1)
<223> OTHER INFORMATION: Y is phosphotyrosine

<400> SEQUENCE: 1

Pro Tyr Leu Lys Thr Lys
1               5

<210> SEQ ID NO 2
<211> LENGTH: 6
<212> TYPE: PRT
<213> ORGANISM: Artificial Sequence
<220> FEATURE:
<223> OTHER INFORMATION: TGF-Beta inhibitor
<220> FEATURE:
<221> NAME/KEY: misc_feature
<222> LOCATION: (1)..(1)
<223> OTHER INFORMATION: Y is phosphotyrosine

<400> SEQUENCE: 2

Tyr Leu Pro Gln Thr Val
1               5

<210> SEQ ID NO 3
<211> LENGTH: 144
<212> TYPE: PRT
<213> ORGANISM: Homo sapiens

<400> SEQUENCE: 3

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60
```

```
Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
             85                  90                  95

Met Ala Ser His Tyr Lys Gln His Cys Pro Thr Pro Glu Thr Ser
            100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
            130                 135                 140
```

<210> SEQ ID NO 4
<211> LENGTH: 235
<212> TYPE: PRT
<213> ORGANISM: Homo sapiens

<400> SEQUENCE: 4

```
Met Thr Val Leu Ala Pro Ala Trp Ser Pro Thr Thr Tyr Leu Leu Leu
  1               5                  10                  15

Leu Leu Leu Leu Ser Ser Gly Leu Ser Gly Thr Gln Asp Cys Ser Phe
             20                  25                  30

Gln His Ser Pro Ile Ser Ser Asp Phe Ala Val Lys Ile Arg Glu Leu
         35                  40                  45

Ser Asp Tyr Leu Leu Gln Asp Tyr Pro Val Thr Val Ala Ser Asn Leu
 50                  55                  60

Gln Asp Glu Glu Leu Cys Gly Gly Leu Trp Arg Leu Val Leu Ala Gln
 65                  70                  75                  80

Arg Trp Met Glu Arg Leu Lys Thr Val Ala Gly Ser Lys Met Gln Gly
             85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
            130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
                165                 170                 175

Thr Ala Pro Thr Ala Pro Gln Pro Pro Leu Leu Leu Leu Leu Leu Leu
                180                 185                 190

Pro Val Gly Leu Leu Leu Leu Ala Ala Ala Trp Cys Leu His Trp Gln
            195                 200                 205

Arg Thr Arg Arg Arg Thr Pro Arg Pro Gly Glu Gln Val Pro Pro Val
            210                 215                 220

Pro Ser Pro Gln Asp Leu Leu Leu Val Glu His
225                 230                 235
```

<210> SEQ ID NO 5
<211> LENGTH: 95
<212> TYPE: PRT
<213> ORGANISM: Homo sapiens

<400> SEQUENCE: 5

```
Met Cys Cys Thr Lys Ser Leu Leu Leu Ala Ala Leu Met Ser Val Leu
  1               5                  10                  15
```

```
Leu Leu His Leu Cys Gly Glu Ser Ala Ser Asn Phe Asp Cys Cys
            20                  25                  30

Leu Gly Tyr Thr Asp Arg Ile Leu His Pro Lys Phe Ile Val Gly Phe
                35                  40                  45

Thr Arg Gln Leu Ala Asn Glu Gly Cys Asp Ile Asn Ala Ile Ile Phe
 50                  55                  60

His Thr Lys Lys Lys Leu Ser Val Cys Ala Asn Pro Lys Gln Thr Trp
 65                  70                  75                  80

Val Lys Tyr Ile Val Arg Leu Leu Ser Lys Lys Val Lys Asn Met
                85                  90                  95

<210> SEQ ID NO 6
<211> LENGTH: 135
<212> TYPE: PRT
<213> ORGANISM: Homo sapiens

<400> SEQUENCE: 6

Met Val Leu Gly Thr Ile Asp Leu Cys Ser Cys Phe Ser Ala Gly Leu
 1               5                  10                  15

Pro Lys Thr Glu Ala Asn Trp Val Asn Val Ile Ser Asp Leu Lys Lys
                20                  25                  30

Ile Glu Asp Leu Ile Gln Ser Met His Ile Asp Ala Thr Leu Tyr Thr
                35                  40                  45

Glu Ser Asp Val His Pro Ser Cys Lys Val Thr Ala Met Lys Cys Phe
 50                  55                  60

Leu Leu Glu Leu Gln Val Ile Ser Leu Glu Ser Gly Asp Ala Ser Ile
 65                  70                  75                  80

His Asp Thr Val Glu Asn Leu Ile Ile Leu Ala Asn Asn Ser Leu Ser
                85                  90                  95

Ser Asn Gly Asn Val Thr Glu Ser Gly Cys Lys Glu Cys Glu Glu Leu
                100                 105                 110

Glu Glu Lys Asn Ile Lys Glu Phe Leu Gln Ser Phe Val His Ile Val
                115                 120                 125

Gln Met Phe Ile Asn Thr Ser
    130                 135

<210> SEQ ID NO 7
<211> LENGTH: 114
<212> TYPE: PRT
<213> ORGANISM: Homo sapiens

<400> SEQUENCE: 7

Met Arg Leu Leu Ile Leu Ala Leu Leu Gly Ile Cys Ser Leu Thr Ala
 1               5                  10                  15

Tyr Ile Val Glu Gly Val Gly Ser Glu Val Ser Asp Lys Arg Thr Cys
                20                  25                  30

Val Ser Leu Thr Thr Gln Arg Leu Pro Val Ser Arg Ile Lys Thr Tyr
                35                  40                  45

Thr Ile Thr Glu Gly Ser Leu Arg Ala Val Ile Phe Ile Thr Lys Arg
 50                  55                  60

Gly Leu Lys Val Cys Ala Asp Pro Gln Ala Thr Trp Val Arg Asp Val
 65                  70                  75                  80

Val Arg Ser Met Asp Arg Lys Ser Asn Thr Arg Asn Asn Met Ile Gln
                85                  90                  95

Thr Lys Pro Thr Gly Thr Gln Gln Ser Thr Asn Thr Ala Val Thr Leu
                100                 105                 110
```

Thr Gly

<210> SEQ ID NO 8
<211> LENGTH: 107
<212> TYPE: PRT
<213> ORGANISM: Homo sapiens

<400> SEQUENCE: 8

```
Met Ala Arg Ala Ala Leu Ser Ala Ala Pro Ser Asn Pro Arg Leu Leu
1               5                   10                  15
Arg Val Ala Leu Leu Leu Leu Leu Val Ala Ala Gly Arg Arg Ala
                20                  25                  30
Ala Gly Ala Ser Val Ala Thr Glu Leu Arg Cys Gln Cys Leu Gln Thr
            35                  40                  45
Leu Gln Gly Ile His Pro Lys Asn Ile Gln Ser Val Asn Val Lys Ser
        50                  55                  60
Pro Gly Pro His Cys Ala Gln Thr Glu Val Ile Ala Thr Leu Lys Asn
65                  70                  75                  80
Gly Arg Lys Ala Cys Leu Asn Pro Ala Ser Pro Ile Val Lys Lys Ile
                85                  90                  95
Ile Glu Lys Met Leu Asn Ser Asp Lys Ser Asn
            100                 105
```

<210> SEQ ID NO 9
<211> LENGTH: 189
<212> TYPE: PRT
<213> ORGANISM: Homo sapiens

<400> SEQUENCE: 9

```
Met Ala Ser Pro Phe Ala Leu Leu Met Val Leu Val Val Leu Ser Cys
1               5                   10                  15
Lys Ser Ser Cys Ser Leu Gly Cys Asp Leu Pro Glu Thr His Ser Leu
                20                  25                  30
Asp Asn Arg Arg Thr Leu Met Leu Leu Ala Gln Met Ser Arg Ile Ser
            35                  40                  45
Pro Ser Ser Cys Leu Met Asp Arg His Asp Phe Gly Phe Pro Gln Glu
        50                  55                  60
Glu Phe Asp Gly Asn Gln Phe Gln Lys Ala Pro Ala Ile Ser Val Leu
65                  70                  75                  80
His Glu Leu Ile Gln Gln Ile Phe Asn Leu Phe Thr Thr Lys Asp Ser
                85                  90                  95
Ser Ala Ala Trp Asp Glu Asp Leu Leu Asp Lys Phe Cys Thr Glu Leu
            100                 105                 110
Tyr Gln Gln Leu Asn Asp Leu Glu Ala Cys Val Met Gln Glu Glu Arg
        115                 120                 125
Val Gly Glu Thr Pro Leu Met Asn Ala Asp Ser Ile Leu Ala Val Lys
130                 135                 140
Lys Tyr Phe Arg Arg Ile Thr Leu Tyr Leu Thr Glu Lys Lys Tyr Ser
145                 150                 155                 160
Pro Cys Ala Trp Glu Val Val Arg Ala Glu Ile Met Arg Ser Leu Ser
                165                 170                 175
Leu Ser Thr Asn Leu Gln Glu Arg Leu Arg Arg Lys Glu
            180                 185
```

<210> SEQ ID NO 10
<211> LENGTH: 187

```
<212> TYPE: PRT
<213> ORGANISM: Homo sapiens

<400> SEQUENCE: 10

Met Thr Asn Lys Cys Leu Leu Gln Ile Ala Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Cys Gln Cys Gln Lys Leu Leu Trp Gln Leu Asn Gly Arg
            35                  40                  45

Leu Glu Tyr Cys Leu Lys Asp Arg Arg Asn Phe Asp Ile Pro Glu Glu
        50                  55                  60

Ile Lys Gln Leu Gln Gln Phe Gln Lys Glu Asp Ala Ala Val Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Arg Asn His Leu Lys Thr Val Leu Glu Glu Lys Leu Glu
        115                 120                 125

Lys Glu Asp Phe Thr Arg Gly Lys Arg Met Ser Ser Leu His Leu Lys
130                 135                 140

Arg Tyr Tyr Gly Arg Ile Leu His Tyr Leu Lys Ala Lys Glu Asp Ser
145                 150                 155                 160

His Cys Ala Trp Thr Ile Val Arg Val Glu Ile Leu Arg Asn Phe Tyr
                165                 170                 175

Val Ile Asn Arg Leu Thr Gly Tyr Leu Arg Asn
            180                 185

<210> SEQ ID NO 11
<211> LENGTH: 306
<212> TYPE: PRT
<213> ORGANISM: Homo sapiens

<400> SEQUENCE: 11

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160
```

```
Asp Asn Lys Glu Tyr Glu Tyr Ser Val Glu Cys Gln Glu Asp Ser Ala
            165                 170                 175

Cys Pro Ala Ala Glu Glu Ser Leu Pro Ile Glu Val Met Val Asp Ala
        180                 185                 190

Val His Lys Leu Lys Tyr Glu Asn Tyr Thr Ser Ser Phe Phe Ile Arg
    195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305

<210> SEQ ID NO 12
<211> LENGTH: 197
<212> TYPE: PRT
<213> ORGANISM: Homo sapiens

<400> SEQUENCE: 12

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 13
```

<211> LENGTH: 1448
<212> TYPE: DNA
<213> ORGANISM: Homo sapiens

<400> SEQUENCE: 13

| | | | | | |
|---|---|---|---|---|---|
| gtgaccgagc | ggcgcggacg | gccgcctgcc | ccctctgcca | cctggggcgg | tgcgggcccg | 60 |
| gagcccggag | cccgggtagc | gcgtagagcc | ggcgcgatgc | acgtgcgctc | actgcgagct | 120 |
| gcggcgccgc | acagcttcgt | ggcgctctgg | gcacccctgt | tcctgctgcg | ctccgccctg | 180 |
| gccgacttca | gcctggacaa | cgaggtgcac | tcgagcttca | tccaccggcg | cctccgcagc | 240 |
| caggagcggc | gggagatgca | gcgcgagatc | ctctccattt | tgggcttgcc | ccaccgcccg | 300 |
| cgcccgcacc | tccagggcaa | gcacaactcg | gcacccatgt | tcatgctgga | cctgtacaac | 360 |
| gccatggcgg | tggaggaggg | cggcgggccc | ggcggccagg | gcttctccta | cccctacaag | 420 |
| gccgtcttca | gtacccaggg | ccccccctctg | gccagcctgc | aagatagcca | tttcctcacc | 480 |
| gacgccgaca | tggtcatgag | cttcgtcaac | ctcgtggaac | atgacaagga | attcttccac | 540 |
| ccacgctacc | accatcgaga | gttccggttt | gatctttcca | agatcccaga | agggaagct | 600 |
| gtcacggcag | ccgaattccg | gatctacaag | gactacatcc | gggaacgctt | cgacaatgag | 660 |
| acgttccgga | tcagcgttta | tcaggtgctc | caggagcact | gggcaggga | atcggatctc | 720 |
| ttcctgctcg | acagccgtac | cctctgggcc | tcggaggagg | gctggctggt | gtttgacatc | 780 |
| acagccacca | gcaaccactg | ggtggtcaat | ccgcggcaca | acctgggcct | gcagctctcg | 840 |
| gtggagacgc | tggatgggca | gagcatcaac | cccaagttgg | cgggcctgat | tgggcggcac | 900 |
| gggcccagga | acaagcagcc | cttcatggtg | gctttcttca | aggccacgga | ggtccacttc | 960 |
| cgcagcatcc | ggtccacggg | gagcaaacag | cgcagccaga | accgctccaa | gacgcccaag | 1020 |
| aaccaggaag | ccctgcggat | ggccaacgtg | gcagagaaca | gcagcagcga | ccagaggcag | 1080 |
| gcctgtaaga | agcacgagct | gtatgtcagc | ttccgagacc | tgggctggca | ggactggatc | 1140 |
| atcgcgcctg | aaggctacgc | cgcctactac | tgtgaggggg | agtgtgcctt | ccctctgaac | 1200 |
| tcctacatga | acgccaccaa | ccacgccatc | gtgcagacgc | tggtccactt | catcaacccg | 1260 |
| gaaacggtgc | ccaagccctg | ctgtgcgccc | acgcagctca | atgccatctc | cgtcctctac | 1320 |
| ttcgatgaca | gctccaacgt | catcctgaag | aaatacagaa | acatggtggt | ccgggcctgt | 1380 |
| ggctgccact | agctcctccg | agaattcaga | cccttggggg | ccaagttttt | ctggatcctc | 1440 |
| cattgctc | | | | | | 1448 |

<210> SEQ ID NO 14
<211> LENGTH: 4978
<212> TYPE: DNA
<213> ORGANISM: Homo sapiens

<400> SEQUENCE: 14

| | | | | | |
|---|---|---|---|---|---|
| ggtttccgga | gctgcggcgg | cgcagactgg | gaggggagc | cggggggttcc | gacgtcgcag | 60 |
| ccgagggaac | aagccccaac | cggatcctgg | acaggcaccc | cggcttggcg | ctgtctctcc | 120 |
| ccctcggctc | ggagaggccc | ttcggcctga | gggagcctcg | ccgcccgtcc | ccggcacacg | 180 |
| cgcagccccg | gcctctcggc | ctctgccgga | gaaacagttg | ggacccctga | ttttagcagg | 240 |
| atggcccaat | ggaatcagct | acagcagctt | gacacacggt | acctggagca | gctccatcag | 300 |
| ctctacagtg | acagcttccc | aatggagctg | cggcagtttc | tggccccttg | gattgagagt | 360 |
| caagattggg | catatgcggc | cagcaaagaa | tcacatgcca | ctttggtgtt | tcataatctc | 420 |
| ctgggagaga | ttgaccagca | gtatagccgc | ttcctgcaag | agtcgaatgt | tctctatcag | 480 |

```
cacaatctac gaagaatcaa gcagtttctt cagagcaggt atcttgagaa gccaatggag    540
attgcccgga ttgtggcccg gtgcctgtgg aagaatcac gccttctaca gactgcagcc     600
actgcggccc agcaaggggg ccaggccaac caccccacag cagccgtggt gacggagaag    660
cagcagatgc tggagcagca ccttcaggat gtccggaaga gagtgcagga tctagaacag    720
aaaatgaaag tggtagagaa tctccaggat gactttgatt tcaactataa aaccctcaag    780
agtcaaggag acatgcaaga tctgaatgga acaaccagt cagtgaccag gcagaagatg    840
cagcagctgg aacagatgct cactgcgctg gaccagatgc ggagaagcat cgtgagtgag    900
ctggcggggc ttttgtcagc gatggagtac gtgcagaaaa ctctcacgga cgaggagctg    960
gctgactgga agaggcggca acagattgcc tgcattggag gcccgcccaa catctgccta    1020
gatcggctag aaaactggat aacgtcatta gcagaatctc aacttcagac ccgtcaacaa    1080
attaagaaac tggaggagtt gcagcaaaaa gtttcctaca aggggacccc cattgtacag    1140
caccggccga tgctggagga gagaatcgtg gagctgttta aaacttaat gaaaagtgcc     1200 tttgtggtgg agcggcagcc ctgcatgccc atgcatcctg accggcccct cgtcatcaag    1260
accggcgtcc agttcactac taaagtcagg ttgctggtca aattccctga gttgaattat    1320
cagcttaaaa ttaaagtgtg cattgacaaa gactctgggg acgttgcagc tctcagagga    1380
tcccggaaat ttaacattct gggcacaaac acaaaagtga tgaacatgga agaatccaac    1440
aacggcagcc tctctgcaga attcaaacac ttgaccctga gggagcagag atgtgggaat    1500
gggggccgag ccaattgtga tgcttccctg attgtgactg aggagctgca cctgatcacc    1560
tttgagaccg aggtgtatca ccaaggcctc aagattgacc tagagaccca ctccttgcca    1620
gttgtggtga tctccaacat ctgtcagatg ccaaatgcct gggcgtccat cctgtggtac    1680
aacatgctga ccaacaatcc caagaatgta aactttttta ccaagccccc aattggaacc    1740
tgggatcaag tggccgaggt cctgagctgg cagttctcct ccaccaccaa gcgaggactg    1800
agcatcgagc agctgactac actggcagag aaactcttgg acctggtgt gaattattca     1860 gggtgtcaga tcacatgggc taaattttgc aaagaaaaca tggctggcaa gggcttctcc    1920
ttctgggtct ggctggacaa tatcattgac cttgtgaaaa agtacatcct ggcccttggg    1980
aacgaagggt acatcatggg ctttatcagt aaggagcggg agcgggccat cttgagcact    2040
aagcctccag gcaccttcct gctaagattc agtgaaagca gcaaagaagg aggcgtcact    2100
ttcacttggg tggagaagga catcagcggt aagacccaga tccagtccgt ggaaccatac    2160
acaaagcagc agctgaacaa catgtcattt gctgaaatca tcatgggcta taagatcatg    2220
gatgctacca atatcctggt gtctccactg gtctatctct atcctgacat tcccaaggag    2280
gaggcattcg gaaagtattg tcggccagag agccaggagc atcctgaagc tgacccaggt    2340
agcgctgccc catacctgaa gaccaagttt atctgtgtga caccaacgac ctgcagcaat    2400
accattgacc tgccgatgtc cccccgcact ttagattcat tgatgcagtt tggaaataat    2460
ggtgaaggtg ctgaaccctc agcaggaggg cagtttgagt ccctcacctt tgacatggag    2520
ttgacctcgg agtgcgctac ctcccccatg tgaggagctg agaacggaag ctgcagaaag    2580
atacgactga ggcgcctacc tgcattctgc caccctcac acagccaaac cccagatcat     2640
ctgaaactac taactttgtg gttccagatt ttttttaatc tcctacttct gctatctttg    2700
agcaatctgg gcacttttaa aaatagagaa atgagtgaat gtgggtgatc tgcttttatc    2760
taaatgcaaa taaggatgtg ttctctgaga cccatgatca ggggatgtgg cggggggtgg    2820
```

```
ctagagggag aaaaaggaaa tgtcttgtgt tgttttgttc ccctgccctc ctttctcagc    2880
agcttttttgt tattgttgtt gttgttctta gacaagtgcc tcctggtgcc tgcggcatcc   2940
ttctgcctgt ttctgtaagc aaatgccaca ggccacctat agctacatac tcctggcatt   3000
gcactttta accttgctga catccaaata gaagatagga ctatctaagc cctaggtttc    3060
tttttaaatt aagaaataat aacaattaaa gggcaaaaaa cactgtatca gcatagcctt   3120
tctgtattta agaaacttaa gcagccgggc atggtggctc acgcctgtaa tcccagcact   3180
ttgggaggcc gaggcggatc ataaggtcag gagatcaaga ccatcctggc taacacggtg   3240
aaacccgtc tctactaaaa gtacaaaaaa ttagctgggt gtggtggtgg gcgcctgtag    3300
tcccagctac tcgggaggct gaggcaggag aatcgcttga acctgagagg cggaggttgc   3360
agtgagccaa aattgcacca ctgcacactg cactccatcc tgggcgacag tctgagactc   3420
tgtctcaaaa aaaaaaaaa aaaaagaaa cttcagttaa cagcctcctt ggtgctttaa     3480
gcattcagct tccttcaggc tggtaattta tataatccct gaaacgggct tcaggtcaaa   3540
cccttaagac atctgaagct gcaacctggc ctttggtgtt gaaataggaa ggtttaagga   3600
gaatctaagc attttagact tttttttata aatagactta ttttcctttg taatgtattg   3660
gccttttagt gagtaaggct gggcagaggg tgcttacaac cttgactccc tttctccctg   3720
gacttgatct gctgtttcag aggctaggtt gtttctgtgg gtgccttatc agggctggga   3780
tacttctgat tctggcttcc ttcctgcccc accctcccga ccccagtccc cctgatcctg   3840
ctagaggcat gtctccttgc gtgtctaaag gtccctcatc ctgtttgttt taggaatcct   3900
ggtctcagga cctcatggaa gaagaggggg agagagttac aggttggaca tgatgcacac   3960
tatggggccc cagcgacgtg tctggttgag ctcagggaat atggttctta gccagtttct   4020
tggtgatatc cagtggcact tgtaatggcg tcttcattca gttcatgcag ggcaaaggct   4080
tactgataaa cttgagtctg ccctcgtatg agggtgtata cctggcctcc ctctgaggct   4140
ggtgactcct ccctgctggg gccccacagg tgaggcagaa cagctagagg gcctccccgc   4200
ctgcccgcct tggctggcta gctcgcctct cctgtgcgta tgggaacacc tagcacgtgc   4260
tggatgggct gcctctgact cagaggcatg gccggatttg gcaactcaaa accaccttgc   4320
ctcagctgat cagagtttct gtggaattct gtttgttaaa tcaaattagc tggtctctga   4380
attaaggggg agacgacctt ctctaagatg aacagggttc gccccagtcc tcctgcctgg   4440
agacagttga tgtgtcatgc agagctctta cttctccagc aacactcttc agtacataat   4500
aagcttaact gataaacaga atatttagaa aggtgagact tgggcttacc attgggttta   4560
aatcataggg acctagggcg agggttcagg gcttctctgg agcagatatt gtcaagttca   4620
tggccttagg tagcatgtat ctggtcttaa ctctgattgt agcaaaagtt ctgagaggag   4680
ctgagccctg ttgtggccca ttaaagaaca gggtcctcag gccctgcccg cttcctgtcc   4740
actgcccct cccatcccc agcccagccg agggaatccc gtgggttgct tacctaccta    4800
taaggtggtt tataagctgc tgtcctggcc actgcattca aattccaatg tgtacttcat   4860
agtgtaaaaa tttatattat tgtgaggttt tttgtctttt tttttttttt tttttttgg   4920
tatattgctg tatctacttt aacttccaga aataaacgtt atataggaac cgtaaaaa    4978
```

<210> SEQ ID NO 15
<211> LENGTH: 1944
<212> TYPE: DNA
<213> ORGANISM: Homo sapiens

<400> SEQUENCE: 15

```
aatttctcac tgcccctgtg ataaactgtg gtcactggct gtggcagcaa ctattataag      60
atgctctgaa aactcttcag acactgaggg gcaccagagg agcagactac aagaatggca     120
cacgctatgg aaaactcctg gacaatcagt aaagagtacc atattgatga agaagtgggc     180
tttgctctgc caaatccaca ggaaaatcta cctgattttt ataatgactg gatgttcatt     240
gctaaacatc tgcctgatct catagagtct ggccagcttc gagaaagagt tgagaagtta     300
aacatgctca gcattgatca tctcacagac cacaagtcac agcgccttgc acgtctagtt     360
ctgggatgca tcaccatggc atatgtgtgg ggcaaaggtc atggagatgt ccgtaaggtc     420
ttgccaagaa atattgctgt tccttactgc caactctcca agaaactgga actgcctcct     480
attttggttt atgcagactg tgtcttggca aactggaaga aaaggatcc taataagccc     540 ctgacttatg agaacatgga cgttttgttc tcatttcgtg atggagactg cagtaaagga     600
ttcttcctgg tctctctatt ggtggaaata gcagctgctt ctgcaatcaa agtaattcct     660
actgtattca aggcaatgca aatgcaagaa cgggacactt gctaaaggc gctgttggaa     720 atagcttctt gcttggagaa agcccttcaa gtgtttcacc aaatccacga tcatgtgaac     780
ccaaaagcat ttttcagtgt tcttcgcata tatttgtctg gctggaaagg caaccccag     840 ctatcagacg gtctggtgta tgaagggttc tgggaagacc caaggagtt tgcagggggc     900 agtgcaggcc aaagcagcgt cttttcagtgc tttgacgtcc tgctgggcat ccagcagact     960
gctggtggag gacatgctgc tcagttcctc caggacatga aagatatat gccaccagct    1020 cacaggaact tcctgtgctc attagagtca aatccctcag tccgtgagtt tgtcctttca    1080
aaaggtgatg ctggcctgcg ggaagcttat gacgcctgtg tgaaagctct ggtctccctg    1140
aggagctacc atctgcaaat cgtgactaag tacatcctga ttcctgcaag ccagcagcca    1200
aaggagaata agacctctga agacccttca aaactggaag ccaaaggaac tggaggcact    1260
gatttaatga atttcctgaa gactgtaaga agtacaactg agaaatccct tttgaaggaa    1320
ggttaatgta acccaacaag agcacatttt atcatagcag agacatctgt atgcattcct    1380
gtcattaccc attgtaacag agccacaaac taatactatg caatgtttta ccaataatgc    1440
aatacaaaag acctcaaaat acctgtgcat ttcttgtagg aaaacaacaa aaggtaatta    1500
tgtgtaatta tactagaagt tttgtaatct gtatcttatc attggaataa aatgacattc    1560
aataaataaa aatgcataag atatattctg tcggctgggc gcggtggctc acgcctgtaa    1620
tcccagcact ttgggaggcc gaggcgggcg gatcacaagg tcaggagatc gagaccatct    1680
tggctaacac ggtgaaaccc cgtctctact aaaaatacaa aaaattagcc gggcgcggtg    1740
gcgggcacct gtagtcccag ctactcggga ggctgaggca ggagaatggc gtgaacctgg    1800
gaggcggagc ttgcagtgag ccaagattgt gccactgcaa tccggcctgg gctaaagagc    1860
gggactccgt ctcaaaaaaa aaaaaaaaa gatatattct gtcataataa ataaaaatgc    1920
ataagatata aaaaaaaaaa aaaa                                          1944
```

<210> SEQ ID NO 16
<211> LENGTH: 2115
<212> TYPE: DNA
<213> ORGANISM: Homo sapiens

<400> SEQUENCE: 16

```
agtttccctt ccgctcacct ccgcctgagc agtggagaag gcggcactct ggtggggctg      60
ctccaggcat gcagatccca caggcgccct ggccagtcgt ctgggcggtg ctacaactgg     120
```

```
gctggcggcc aggatggttc ttagactccc cagacaggcc ctggaacccc cccaccttct    180
ccccagccct gctcgtggtg accgaagggg acaacgccac cttcacctgc agcttctcca    240
acacatcgga gagcttcgtg ctaaactggt accgcatgag ccccagcaac cagacggaca    300
agctggccgc cttccccgag gaccgcagcc agcccggcca ggactgccgc ttccgtgtca    360
cacaactgcc caacgggcgt gacttccaca tgagcgtggt cagggcccgg cgcaatgaca    420
gcggcaccta cctctgtggg gccatctccc tggcccccaa ggcgcagatc aaagagagcc    480
tgcgggcaga gctcagggtg acagagagaa gggcagaagt gcccacagcc caccccagcc    540
cctcacccag gccagccggc cagttccaaa ccctggtggt tggtgtcgtg ggcggcctgc    600
tgggcagcct ggtgctgcta gtctgggtcc tggccgtcat ctgctcccgg gccgcacgag    660
ggacaatagg agccaggcgc accggccagc ccctgaagga ggaccctca gccgtgcctg    720 tgttctctgt ggactatggg gagctggatt ccagtggcg agagaagacc ccggagcccc    780
ccgtgccctg tgtccctgag cagacggagt atgccaccat tgtctttcct agcggaatgg    840
gcacctcatc ccccgcccgc aggggctcag ctgacgccct cggagtgcc cagccactga    900 ggcctgagga tggacactgc tcttggcccc tctgaccggc ttccttggcc accagtgttc    960
tgcagaccct ccaccatgag cccggtcag cgcatttcct caggagaagc aggcagggtg   1020
caggccattg caggccgtcc aggggctgag ctgcctgggg cgaccgggg ctccagcctg   1080 cacctgcacc aggcacagcc ccaccacagg actcatgtct caatgcccac agtgagccca   1140
ggcagcaggt gtcaccgtcc cctacaggga gggccagatg cagtcactgc ttcaggtcct   1200
gccagcacag agctgcctgc gtccagctcc ctgaatctct gctgctgctg ctgctgctgc   1260
tgctgctgcc tgcggcccgg ggctgaaggc ccgtggccc tgcctgacgc cccggagcct   1320
cctgcctgaa cttgggggct ggttggagat ggccttggag cagccaaggt gcccctggca   1380
gtggcatccc gaaacgccct ggacgcaggg cccaagactg gcacaggag tgggaggtac   1440 atggggctgg ggactcccca ggagttatct gctccctgca ggcctagaga agtttcaggg   1500
aaggtcagaa gagctcctgg ctgtggtggg cagggcagga aaccctcca cctttacaca   1560 tgcccaggca gcacctcagg ccctttgtgg ggcaggaag ctgaggcagt aagcgggcag   1620
gcagagctgg aggcctttca ggcccagcca gcactctggc ctcctgccgc cgcattccac   1680
cccagcccct cacaccactc gggagaggga catcctacgg tcccaaggtc aggagggcag   1740
ggctggggtt gactcaggcc cctcccagct gtggccacct gggtgttggg agggcagaag   1800
tgcaggcacc tagggccccc catgtgccca cctgggagc tctccttgga acccattcct   1860
gaaattattt aaaggggttg gccgggctcc caccagggcc tgggtgggaa ggtacaggcg   1920 ttccccccggg gcctagtacc cccgccgtgg cctatccact cctcacatcc acacactgca   1980
cccccactcc tggggcaggg ccaccagcat ccaggcggcc agcaggcacc tgagtggctg   2040
ggacaaggga tccccctccc ctgtggttct attatattat aattataatt aaatatgaga   2100
gcatgctaag gaaaa                                                   2115
```

<210> SEQ ID NO 17
<211> LENGTH: 3691
<212> TYPE: DNA
<213> ORGANISM: Homo sapiens

<400> SEQUENCE: 17

```
ggcgcaacgc tgagcagctg gcgcgtcccg cgcggcccca gttctgcgca gcttcccgag    60
gctccgcacc agccgcgctt ctgtccgcct gcagggcatt ccagaaagat gaggatattt   120
```

```
gctgtcttta tattcatgac ctactggcat tgctgaacg catttactgt cacggttccc      180
aaggacctat atgtggtaga gtatggtagc aatatgacaa ttgaatgcaa attcccagta      240
gaaaaacaat tagacctggc tgcactaatt gtctattggg aaatggagga taagaacatt      300
attcaatttg tgcatggaga ggaagacctg aaggttcagc atagtagcta cagacagagg      360
gcccggctgt tgaaggacca gctctccctg ggaaatgctg cacttcagat cacagatgtg      420
aaattgcagg atgcaggggt gtaccgctgc atgatcagct atggtggtgc cgactacaag      480
cgaattactg tgaaagtcaa tgccccatac aacaaaatca accaaagaat tttggttgtg      540
gatccagtca cctctgaaca tgaactgaca tgtcaggctg agggctaccc caaggccgaa      600
gtcatctgga caagcagtga ccatcaagtc ctgagtggta agaccaccac caccaattcc      660
aagagagagg agaagctttt caatgtgacc agcacactga gaatcaacac aacaactaat      720
gagattttct actgcacttt taggagatta gatcctgagg aaaaccatac agctgaattg      780
gtcatcccag aactacctct ggcacatcct ccaaatgaaa ggactcactt ggtaattctg      840
ggagccatct tattatgcct tggtgtagca ctgacattca tcttccgttt aagaaaaggg      900
agaatgatga atgtgaaaaa atgtggcatc caagatacaa actcaaagaa gcaaagtgat      960
acacatttgg aggagacgta atccagcatt ggaacttctg atcttcaagc agggattctc     1020
aacctgtggt ttaggggttc atcggggctg agcgtgacaa gaggaaggaa tgggcccgtg     1080
ggatgcaggc aatgtgggac ttaaaaggcc caagcactga aaatggaacc tggcgaaagc     1140
agaggaggag aatgaagaaa gatggagtca acaggagc ctggagggag accttgatac     1200
tttcaaatgc ctgaggggct catcgacgcc tgtgacaggg agaaaggata cttctgaaca     1260
aggagcctcc aagcaaatca tccattgctc atcctaggaa gacgggttga gaatccctaa     1320
tttgagggtc agttcctgca gaagtgccct tgcctccac tcaatgcctc aatttgtttt     1380
ctgcatgact gagagtctca gtgttggaac gggacagtat ttatgtatga gttttccta     1440 tttattttga gtctgtgagg tcttcttgtc atgtgagtgt ggttgtgaat gatttctttt     1500
gaagatatat tgtagtagat gttacaattt tgtcgccaaa ctaaacttgc tgcttaatga     1560
tttgctcaca tctagtaaaa catggagtat ttgtaaggtg cttggtctcc tctataacta     1620
caagtataca ttggaagcat aaagatcaaa ccgttggttg cataggatgt caccttиатt     1680 taacccatta atactctggt tgacctaatc ttattctcag acctcaagtg tctgtgcagt     1740
atctgttcca tttaaatatc agctttacaa ttatgtggta gcctacacac ataatctcat     1800
ttcatcgctg taaccaccct gttgtgataa ccactattat tttacccatc gtacagctga     1860
ggaagcaaac agattaagta acttgcccaa accagtaaat agcagacctc agactgccac     1920
ccactgtcct tttataatac aatttacagc tatattttac tttaagcaat tcttttattc     1980
aaaaaccatt tattaagtgc ccttgcaata tcaatcgctg tgccaggcat tgaatctaca     2040
gatgtgagca agacaaagta cctgtcctca aggagctcat agtataatga ggagattaac     2100
aagaaaatgt attattacaa tttagtccag tgtcatagca taaggatgat gcgagggaa     2160 aacccgagca gtgttgccaa gaggaggaaa taggccaatg tggtctggga cggttggata     2220
tacttaaaca tcttaataat cagagtaatt ttcatttaca aagagaggtc ggtacttaaa     2280
ataaccctga aaaataacac tggaattcct tttctagcat tatatttatt cctgatttgc     2340
ctttgccata taatcaatg cttgtttata tagtgtctgg tattgtttaa cagttctgtc     2400
ttttctattt aaatgccact aaattttaaa ttcatacctt tccatgattc aaaattcaaa     2460
```

| | | | | |
|---|---|---|---|---|
| agatcccatg | ggagatggtt | ggaaaatctc | cacttcatcc | tccaagccat tcaagtttcc | 2520 |
| tttccagaag | caactgctac | tgcctttcat | tcatatgttc | ttctaaagat agtctacatt | 2580 |
| tggaaatgta | tgttaaaagc | acgtattttt | aaaatttttt | tcctaaatag taacacattg | 2640 |
| tatgtctgct | gtgtactttg | ctattttttat | ttattttagt | gtttcttata tagcagatgg | 2700 |
| aatgaatttg | aagttcccag | ggctgaggat | ccatgccttc | tttgtttcta agttatcttt | 2760 |
| cccatagctt | ttcattatct | ttcatatgat | ccagtatatg | ttaaatatgt cctacatata | 2820 |
| catttagaca | accaccattt | gttaagtatt | tgctctagga | cagagtttgg atttgtttat | 2880 |
| gtttgctcaa | aaggagaccc | atgggctctc | cagggtgcac | tgagtcaatc tagtcctaaa | 2940 |
| aagcaatctt | attattaact | ctgtatgaca | gaatcatgtc | tggaactttt gttttctgct | 3000 |
| ttctgtcaag | tataaacttc | actttgatgc | tgtacttgca | aaatcacatt ttctttctgg | 3060 |
| aaattccggc | agtgtacctt | gactgctagc | taccctgtgc | cagaaaagcc tcattcgttg | 3120 |
| tgcttgaacc | cttgaatgcc | accagctgtc | atcactacac | agccctccta agaggcttcc | 3180 |
| tggaggtttc | gagattcaga | tgccctggga | gatcccagag | tttcctttcc ctcttggcca | 3240 |
| tattctggtg | tcaatgacaa | ggagtacctt | ggctttgcca | catgtcaagg ctgaagaaac | 3300 |
| agtgtctcca | acagagctcc | ttgtgttatc | tgtttgtaca | tgtgcatttg tacagtaatt | 3360 |
| ggtgtgacag | tgttctttgt | gtgaattaca | ggcaagaatt | gtggctgagc aaggcacata | 3420 |
| gtctactcag | tctattccta | agtcctaact | cctccttgtg | gtgttggatt tgtaaggcac | 3480 |
| tttatccctt | ttgtctcatg | tttcatcgta | aatggcatag | gcagagatga tacctaattc | 3540 |
| tgcatttgat | tgtcacttt | tgtacctgca | ttaatttaat | aaaatattct tatttatttt | 3600 |
| gttacttggt | acaccagcat | gtccattttc | ttgtttattt | tgtgtttaat aaaatgttca | 3660 |
| gtttaacatc | ccagtggaga | aagttaaaaa | a | | 3691 |

<210> SEQ ID NO 18
<211> LENGTH: 1923
<212> TYPE: DNA
<213> ORGANISM: Homo sapiens

<400> SEQUENCE: 18

| | | | | |
|---|---|---|---|---|
| cttctgtgtg | tgcacatgtg | taatacatat | ctgggatcaa | agctatctat ataaagtcct | 60 |
| tgattctgtg | tgggttcaaa | cacatttcaa | agcttcagga | tcctgaaagg ttttgctcta | 120 |
| cttcctgaag | acctgaacac | cgctcccata | aagccatggc | ttgccttgga tttcagcggc | 180 |
| acaaggctca | gctgaacctg | gctaccagga | cctggccctg | cactctcctg tttttcttc | 240 |
| tcttcatccc | tgtcttctgc | aaagcaatgc | acgtggccca | gctgctgtg gtactggcca | 300 |
| gcagccgagg | catcgccagc | tttgtgtgtg | agtatgcatc | tccaggcaaa gcccactgagg | 360 |
| tccgggtgac | agtgcttcgg | caggctgaca | gccaggtgac | tgaagtctgt gcggcaacct | 420 |
| acatgatggg | gaatgagttg | accttcctag | atgattccat | ctgcacgggc acctccagtg | 480 |
| gaaatcaagt | gaacctcact | atccaaggac | tgagggccag | gacacggga ctctacatct | 540 |
| gcaaggtgga | gctcatgtac | ccaccgccat | actacctggg | cataggcaac ggaacccaga | 600 |
| tttatgtaat | tgctaaagaa | aagaagccct | cttacaacag | gggtctatgt gaaaatgccc | 660 |
| ccaacagagc | cagaatgtga | aaagcaattt | cagccttatt | ttattcccat caattgagaa | 720 |
| accattatga | agaagagagt | ccatatttca | atttccaaga | gctgaggcaa ttctaacttt | 780 |
| tttgctatcc | agctattttt | atttgtttgt | gcatttgggg | ggaattcatc tctctttaat | 840 |
| ataaagttgg | atgcggaacc | caaattacgt | gtactacaat | ttaaagcaaa ggagtagaaa | 900 |

-continued

```
gacagagctg ggatgtttct gtcacatcag ctccactttc agtgaaagca tcacttggga      960
ttaatatggg gatgcagcat tatgatgtgg gtcaaggaat taagttaggg aatggcacag     1020
cccaaagaag gaaaggcag ggagcgaggg agaagactat attgtacaca ccttatattt     1080
acgtatgaga cgtttatagc cgaaatgatc ttttcaagtt aaattttatg cctttattt     1140 cttaaacaaa tgtatgatta catcaaggct tcaaaatac tcacatggct atgttttagc     1200
cagtgatgct aaaggttgta ttgcatatat acatatatat atatatatat atatatatat     1260
atatatatat atatatatat atatatattt taatttgata gtattgtgca tagagccacg     1320
tatgtttttg tgtatttgtt aatggtttga atataaacac tatatggcag tgtctttcca     1380
ccttgggtcc cagggaagtt ttgtggagga gctcaggaca ctaatacacc aggtagaaca     1440
caaggtcatt tgctaactag cttggaaact ggatgaggtc atagcagtgc ttgattgcgt     1500
ggaattgtgc tgagttggtg ttgacatgtg ctttgggggct tttacaccag ttccttcaa     1560 tggtttgcaa ggaagccaca gctggtggta tctgagttga cttgacagaa cactgtcttg     1620
aagacaatgg cttactccag gagacccaca ggtatgacct tctaggaagc tccagttcga     1680
tgggcccaat tcttacaaac atgtggttaa tgccatggac agaagaaggc agcaggtggc     1740
agaatggggt gcatgaaggt ttctgaaaat taacactgct tgtgttttta actcaatatt     1800
ttccatgaaa atgcaacaac atgtataata ttttaatta aataaaaatc tgtggtggtc     1860
gttttaaaaa aaaaaaaaaa aaaaaaaaaa aaaaaaaaaa aaaaaaaaaa aaaaaaaaaa     1920
aaa                                                                  1923

<210> SEQ ID NO 19
<211> LENGTH: 1872
<212> TYPE: DNA
<213> ORGANISM: Homo sapiens

<400> SEQUENCE: 19
tcaggctgcc tgatctgccc agcttttccag cttcctctg gattccggcc tctggtcatc       60
cctccccacc ctctctccaa ggccctctcc tggtctccct tcttctagaa ccccttcctc      120
cacctccctc tctgcagaac ttctccttta ccccccaccc ccaccactg cccccttcc       180 ttttctgacc tccttttgga gggctcagcg ctgcccagac cataggagag atgtgggagg      240
ctcagttcct gggcttgctg tttctgcagc cgctttgggt ggctccagtg aagcctctcc      300
agccaggggc tgaggtcccg gtggtgtggg cccaggaggg ggctcctgcc cagctcccct      360
gcagccccac aatccccctc caggatctca gccttctgcg aagagcaggg gtcacttggc      420
agcatcagcc agacagtggc ccgcccgctg ccgcccccgg ccatcccctg gccccggcc       480 ctcacccggc ggcgccctcc tcctgggggc ccaggccccg ccgctacacg gtgctgagcg      540
tgggtcccgg aggcctgcgc agcgggaggc tgccctgca gccccgcgtc cagctggatg       600
agcgcggccg gcagcgcggg gacttctcgc tatggctgcg cccagcccgg cgcgcggacg      660
ccggcgagta ccgcgccgcg gtgcacctca gggaccgcgc cctctcctgc cgcctccgtc      720
tgcgcctggg ccaggcctcg atgactgcca gcccccagg atctctcaga gcctccgact      780
gggtcatttt gaactgctcc ttcagccgcc ctgaccgcc agcctctgtg cattggttcc      840
ggaaccgggg ccagggccga gtccctgtcc gggagtcccc ccatcaccac ttagcggaaa     900
gcttcctctt cctgccccaa gtcagcccca tggactctgg gccctgggc tgcatcctca      960 cctacagaga tggcttcaac gtctccatca tgtataacct cactgttctg ggtctggagc    1020
```

-continued

```
ccccaactcc cttgacagtg tacgctggag caggttccag ggtggggctg ccctgccgcc      1080
tgcctgctgg tgtggggacc cggtctttcc tcactgccaa gtggactcct cctgggggag      1140
gccctgacct cctggtgact ggagacaatg gcgactttac ccttcgacta gaggatgtga      1200
gccaggccca ggctgggacc tacacctgcc atatccatct gcaggaacag cagctcaatg      1260
ccactgtcac attggcaatc atcacagtga ctcccaaatc ctttgggtca cctggatccc      1320
tggggaagct gctttgtgag gtgactccag tatctggaca agaacgcttt gtgtggagct      1380
ctctggacac cccatcccag aggagtttct caggaccttg gctggaggca caggaggccc      1440
agctcctttc ccagccttgg caatgccagc tgtaccaggg ggagaggctt cttggagcag      1500
cagtgtactt cacagagctg tctagcccag gtgcccaacg ctctgggaga gccccaggtg      1560
ccctcccagc aggccacctc ctgctgtttc tcacccttgg tgtcctttct ctgctccttt      1620
tggtgactgg agcctttggc tttcaccttt ggagaagaca gtgcgaccaa agacgatttt      1680
ctgccttaga gcaagggatt caccctccgc aggctcagag caagatagag gagctggagc      1740
aagaaccgga gccggagccg gagccggaac cggagcccga gcccgagccc gagccggagc      1800
agctctgacc tggagctgag gcagccagca gatctcagca gcccagtcca aataaacgtc      1860
ctgtctagca gc                                                         1872

<210> SEQ ID NO 20
<211> LENGTH: 1116
<212> TYPE: DNA
<213> ORGANISM: Homo sapiens

<400> SEQUENCE: 20
ggagagttaa aactgtgcct aacagaggtg tcctctgact tttcttctgc aagctccatg        60
ttttcacatc ttccctttga ctgtgtcctg ctgctgctgc tgctactact tacaaggtcc       120
tcagaagtgg aatacagagc ggaggtcggt cagaatgcct atctgccctg cttctacacc       180
ccagccgccc cagggaacct cgtgcccgtc tgctggggca aggagcctg tcctgtgttt       240 gaatgtggca acgtggtgct caggactgat gaaagggatg tgaattattg acatccaga       300 tactggctaa atggggattt ccgcaaagga gatgtgtccc tgaccataga gaatgtgact       360
ctagcagaca gtgggatcta ctgctgccgg atccaaatcc caggcataat gaatgatgaa       420
aaatttaacc tgaagttggt catcaaacca gccaaggtca cccctgcacc gactctgcag       480
agagacttca ctgcagcctt tccaaggatg cttaccacca ggggacatgg cccagcagag       540
acacagacac tggggagcct ccctgatata aatctaacac aaatatccac attggccaat       600
gagttacggg actctagatt ggccaatgac ttacgggact ctggagcaac catcagaata       660
ggcatctaca tcggagcagg gatctgtgct gggctggctc tggctcttat cttcggcgct       720
ttaattttca atggtattc tcatagcaaa gagaagatac agaatttaag cctcatctct       780
ttggccaacc tccctccctc aggattggca aatgcagtag cagagggaat tcgctcagaa       840
gaaaacatct ataccattga agagaacgta tatgaagtgg aggagcccaa tgagtattat       900
tgctatgtca gcagcaggca gcaaccctca caacctttgg gttgtcgctt tgcaatgcca       960
tagatccaac cacctatttt ttgagcttgg tgttttgtct ttttcagaaa ctatgagctg      1020
tgtcacctga ctggttttgg aggttctgtc cactgctatg gagcagagtt ttcccatttt      1080
cagaagataa tgactcacat gggaattgaa ctggga                                1116

<210> SEQ ID NO 21
<211> LENGTH: 20
```

<212> TYPE: DNA
<213> ORGANISM: Artificial Sequence
<220> FEATURE:
<223> OTHER INFORMATION: ODN 1585

<400> SEQUENCE: 21
ggggtcaacg ttgagggggg                                                    20

<210> SEQ ID NO 22
<211> LENGTH: 20
<212> TYPE: DNA
<213> ORGANISM: Artificial Sequence
<220> FEATURE:
<223> OTHER INFORMATION: ODN 1668

<400> SEQUENCE: 22
tccatgacgt tcctgatgct                                                    20

<210> SEQ ID NO 23
<211> LENGTH: 20
<212> TYPE: DNA
<213> ORGANISM: Artificial Sequence
<220> FEATURE:
<223> OTHER INFORMATION: ODN 1826

<400> SEQUENCE: 23
tccatgacgt tcctgacgtt                                                    20

<210> SEQ ID NO 24
<211> LENGTH: 24
<212> TYPE: DNA
<213> ORGANISM: Artificial Sequence
<220> FEATURE:
<223> OTHER INFORMATION: ODN 2006

<400> SEQUENCE: 24
tcgtcgtttt gtcgttttgt cgtt                                               24

<210> SEQ ID NO 25
<211> LENGTH: 29
<212> TYPE: DNA
<213> ORGANISM: Artificial Sequence
<220> FEATURE:
<223> OTHER INFORMATION: ODN 2006-G5

<400> SEQUENCE: 25
tcgtcgtttt gtcgttttgt cgttggggg                                          29

<210> SEQ ID NO 26
<211> LENGTH: 20
<212> TYPE: DNA
<213> ORGANISM: Artificial Sequence
<220> FEATURE:
<223> OTHER INFORMATION: ODN 2216

<400> SEQUENCE: 26
gggggacgat cgtcgggggg                                                    20

<210> SEQ ID NO 27
<211> LENGTH: 21
<212> TYPE: DNA
<213> ORGANISM: Artificial Sequence
<220> FEATURE:
<223> OTHER INFORMATION: ODN 2336

<400> SEQUENCE: 27

-continued

```
ggggacgacg tcgtggggggg g                                                  21
```

<210> SEQ ID NO 28
<211> LENGTH: 22
<212> TYPE: DNA
<213> ORGANISM: Artificial Sequence
<220> FEATURE:
<223> OTHER INFORMATION: ODN 2395

<400> SEQUENCE: 28

```
tcgtcgtttt cggcgcgcgc cg                                                  22
```

<210> SEQ ID NO 29
<211> LENGTH: 25
<212> TYPE: DNA
<213> ORGANISM: Artificial Sequence
<220> FEATURE:
<223> OTHER INFORMATION: ODN M362

<400> SEQUENCE: 29

```
tcgtcgtcgt tcgaacgacg ttgat                                               25
```

<210> SEQ ID NO 30
<211> LENGTH: 128
<212> TYPE: PRT
<213> ORGANISM: Homo sapiens

<400> SEQUENCE: 30

Met Ala Pro Ala Arg Ser Pro Ser Pro Ser Thr Gln Pro Trp Glu His
1               5                   10                  15

Val Asn Ala Ile Gln Glu Ala Arg Arg Leu Leu Asn Leu Ser Arg Asp
            20                  25                  30

Thr Ala Ala Glu Met Asn Glu Thr Val Glu Val Ile Ser Glu Met Phe
        35                  40                  45

Asp Leu Gln Glu Pro Thr Cys Leu Gln Thr Arg Leu Glu Leu Tyr Lys
    50                  55                  60

Gln Gly Leu Arg Gly Ser Leu Thr Lys Leu Lys Gly Pro Leu Thr Met
65                  70                  75                  80

Met Ala Ser His Tyr Lys Gln His Cys Pro Pro Thr Pro Glu Thr Ser
                85                  90                  95

Cys Ala Thr Gln Ile Ile Thr Phe Glu Ser Phe Lys Glu Asn Leu Lys
            100                 105                 110

Asp Phe Leu Leu Val Ile Pro Phe Asp Cys Trp Glu Pro Val Gln Glu
        115                 120                 125

<210> SEQ ID NO 31
<211> LENGTH: 125
<212> TYPE: PRT
<213> ORGANISM: Mus musculus

<400> SEQUENCE: 31

Met Ala Pro Thr Arg Ser Pro Ile Thr Val Thr Arg Pro Trp Lys His
1               5                   10                  15

Val Glu Ala Ile Lys Glu Ala Leu Asn Leu Leu Asp Asp Met Pro Val
            20                  25                  30

Thr Leu Asn Glu Glu Val Glu Val Val Ser Asn Glu Phe Ser Phe Lys
        35                  40                  45

Lys Leu Thr Cys Val Gln Thr Arg Leu Lys Ile Phe Glu Gln Gly Leu
    50                  55                  60

Arg Gly Asn Phe Thr Lys Leu Lys Gly Ala Leu Asn Met Thr Ala Ser

```
                65                  70                  75                  80
Tyr Tyr Gln Thr Tyr Cys Pro Pro Thr Pro Glu Thr Asp Cys Glu Thr
                    85                  90                  95

Gln Val Thr Thr Tyr Ala Asp Phe Ile Asp Ser Leu Lys Thr Phe Leu
                100                 105                 110

Thr Asp Ile Pro Phe Glu Cys Lys Lys Pro Val Gln Lys
                115                 120                 125

<210> SEQ ID NO 32
<211> LENGTH: 781
<212> TYPE: DNA
<213> ORGANISM: Homo sapiens

<400> SEQUENCE: 32
acacagagag aaaggctaaa gttctctgga ggatgtggct gcagagcctg ctgctcttgg      60
gcactgtggc ctgcagcatc tctgcacccg cccgctcgcc cagccccagc acgcagccct     120
gggagcatgt gaatgccatc caggaggccc ggcgtctcct gaacctgagt agagacactg     180
ctgctgagat gaatgaaaca gtagaagtca tctcagaaat gtttgacctc aggagccga      240 cctgcctaca gacccgcctg gagctgtaca agcagggcct gcggggcagc ctcaccaagc     300
tcaagggccc cttgaccatg atggccagcc actacaagca gcactgccct ccaaccccgg     360
aaacttcctg tgcaacccag attatcacct ttgaaagttt caagagaaac ctgaaggact     420
ttctgcttgt catcccctt gactgctggg agccagtcca ggagtgagac cggccagatg      480
aggctggcca agccggggag ctgctctctc atgaaacaag agctagaaac tcaggatggt     540
catcttggag ggaccaaggg gtgggccaca gccatggtgg gagtggcctg acctgccct      600 gggccacact gaccctgata caggcatggc agaagaatgg gaatatttta tactgacaga     660
aatcagtaat atttatatat ttatattttt aaaatattta tttatttatt tatttaagtt     720
catattccat atttattcaa gatgttttac cgtaataatt attattaaaa atatgcttct     780
a                                                                    781

<210> SEQ ID NO 33
<211> LENGTH: 144
<212> TYPE: PRT
<213> ORGANISM: Homo sapiens

<400> SEQUENCE: 33

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125
```

```
Asp Phe Leu Leu Val Ile Pro Phe Asp Cys Trp Glu Pro Val Gln Glu
    130                 135                 140
```

<210> SEQ ID NO 34
<211> LENGTH: 255
<212> TYPE: PRT
<213> ORGANISM: Homo sapiens

<400> SEQUENCE: 34

```
Met Gly Asn Ser Cys Tyr Asn Ile Val Ala Thr Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

<210> SEQ ID NO 35
<211> LENGTH: 277
<212> TYPE: PRT
<213> ORGANISM: Homo sapiens

<400> SEQUENCE: 35

```
Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60
```

```
Arg Pro Cys Gly Pro Gly Phe Tyr Asn Asp Val Ser Ser Lys Pro
 65                  70                  75                  80

Cys Lys Pro Cys Thr Trp Cys Asn Leu Arg Ser Gly Ser Glu Arg Lys
                 85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
            130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
            195                 200                 205

Val Pro Gly Gly Arg Ala Val Ala Ala Ile Leu Gly Leu Gly Leu Val
210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
            275

<210> SEQ ID NO 36
<211> LENGTH: 277
<212> TYPE: PRT
<213> ORGANISM: Homo sapiens

<400> SEQUENCE: 36

Met Val Arg Leu Pro Leu Gln Cys Val Leu Trp Gly Cys Leu Leu Thr
 1               5                  10                  15

Ala Val His Pro Glu Pro Pro Thr Ala Cys Arg Glu Lys Gln Tyr Leu
                20                  25                  30

Ile Asn Ser Gln Cys Cys Ser Leu Cys Gln Pro Gly Gln Lys Leu Val
            35                  40                  45

Ser Asp Cys Thr Glu Phe Thr Glu Thr Glu Cys Leu Pro Cys Gly Glu
 50                 55                  60

Ser Glu Phe Leu Asp Thr Trp Asn Arg Glu Thr His Cys His Gln His
 65                 70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
            115                 120                 125

Phe Gly Val Lys Gln Ile Ala Thr Gly Val Ser Asp Thr Ile Cys Glu
            130                 135                 140

Pro Cys Pro Val Gly Phe Phe Ser Asn Val Ser Ser Ala Phe Glu Lys
145                 150                 155                 160
```

```
Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg Ala Leu Val Val Ile Pro Ile Ile Phe Gly Ile Leu Phe Ala Ile
        195                 200                 205

Leu Leu Val Leu Val Phe Ile Lys Lys Val Ala Lys Lys Pro Thr Asn
        210                 215                 220

Lys Ala Pro His Pro Lys Gln Glu Pro Gln Glu Ile Asn Phe Pro Asp
225                 230                 235                 240

Asp Leu Pro Gly Ser Asn Thr Ala Ala Pro Val Gln Glu Thr Leu His
                245                 250                 255

Gly Cys Gln Pro Val Thr Gln Glu Asp Gly Lys Glu Ser Arg Ile Ser
                260                 265                 270

Val Gln Glu Arg Gln
            275
```